United States Patent
Jayyosi et al.

(10) Patent No.: US 6,635,655 B1
(45) Date of Patent: Oct. 21, 2003

(54) THERAPEUTIC USES OF DI-ARYL ACID DERIVATIVES

(75) Inventors: Zaid Jayyosi, Collegeville, PA (US); Gerard M. McGeehan, Chester Springs, PA (US); Michael F. Kelley, West Chester, PA (US); Richard F. Labaudiniere, Collegeville, PA (US); Litao Zhang, Collegeville, PA (US); Robert D. Groneberg, Collegeville, PA (US); Daniel G. McGarry, King of Prussia, PA (US); Thomas J. Caulfield, Phoenixville, PA (US); Anne Minnich, Montgomeryville, PA (US); Mark Bobko, Exton, PA (US)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/662,649

(22) Filed: Sep. 14, 2000

Related U.S. Application Data

(63) Continuation of application No. PCT/US00/11833, filed on Apr. 28, 2000.
(60) Provisional application No. 60/131,455, filed on Apr. 28, 1999.

(51) Int. Cl.$^7$ ............ A61K 31/47; A61K 31/421; C07D 215/00; C07D 263/02; C07D 263/30
(52) U.S. Cl. .......... 514/311; 514/374; 514/824; 514/866; 514/884; 546/152; 548/215; 548/235
(58) Field of Search ............ 514/374, 824, 514/866, 311, 880, 884; 546/152; 548/215, 235

(56) References Cited

U.S. PATENT DOCUMENTS

| | | | | |
|---|---|---|---|---|
| 4,794,188 A | * | 12/1988 | Musser et al. | 546/152 |
| 6,290,973 B1 | * | 9/2001 | Hawkins et al. | 424/278.1 |
| 6,376,512 B1 | | 4/2002 | Jayyosi et al. | 514/311 |

FOREIGN PATENT DOCUMENTS

| | | | |
|---|---|---|---|
| CS | 248922 | * | 3/1987 |
| EP | 0 520 723 | | 12/1992 |
| EP | 0 657 422 | | 6/1995 |
| EP | 0 845 451 | | 6/1998 |
| WO | 8705510 | * | 9/1987 |
| WO | WO 97/27847 | | 8/1997 |
| WO | WO 97/27857 | | 8/1997 |
| WO | WO 97/28137 | | 8/1997 |
| WO | WO 97/28149 | | 8/1997 |
| WO | WO 98/27974 | | 7/1998 |
| WO | WO 99/08501 | | 2/1999 |
| WO | WO 99/11255 | | 3/1999 |
| WO | WO 99/15520 | | 4/1999 |
| WO | WO 99/16758 | | 4/1999 |
| WO | WO 99/20275 | | 4/1999 |
| WO | WO 00/64876 | | 11/2000 |

OTHER PUBLICATIONS

Kozikowski et al, Tetrahedron Lett.28/43,5125–8(1987), also cited as Chem.Abstract 110:56678.*
Picard et al(PuBMed Abstr.:12055342:"PPAR gamma and Glucose Homeostasis", Annu Rev Nutr, 167–197 (2002).*
Molavi et al,PubMed Abstr.:12000972:"PPAR Ligands as . . . another pandora's Box"; J.Cardiov.Pharm.Ther.Jan.7, 7/1,1–8(2002).*
Kozikowski et al(Chem.Abstr. 110:56678; also cited as Tetrahedron Lett.,28/43,5125–28(1987).*
Kahovcova et al(Chem. Abstr. 111:115036; also cited as CS 248922 dated Mar. 12, 1987).*
Co-pending U.S. Application No. 09/724,496, filed Nov. 28, 2000.

* cited by examiner

*Primary Examiner*—Mukund J. Shah
*Assistant Examiner*—Sudhaker B. Patel
(74) *Attorney, Agent, or Firm*—Finnegan, Henderson, Farabow, Garrett & Dunner, LLP

(57) ABSTRACT

The use of diaryl acid derivatives of formula (I)

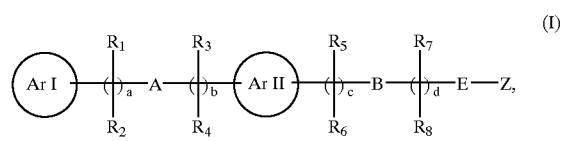

or pharmaceutically acceptable salts, N-oxides, hydrates or solvates thereof, wherein the variables shown are defined in the disclosure, and their pharmaceutical compositions as PPAR ligand receptor binders. The PPAR ligand receptor binders of this invention are useful as agonists or antagonists of the PPAR receptor.

25 Claims, No Drawings

THERAPEUTIC USES OF DI-ARYL ACID DERIVATIVES

This application is continuation of international application no. PCT/US00/11833, filed on Apr. 28, 2000, the contents of which are incorporated by reference herein. This application also claims the benefit of priority under 35 U.S.C. §119(e) to U.S. Provisional Application No. 60/131,455, filed on Apr. 28, 1999.

BACKGROUND OF THE INVENTION

This invention is directed to the use of diaryl acid derivatives and their pharmaceutical compositions as PPAR ligand receptor binders. The PPAR ligand receptor binders of this invention are useful as agonists or antagonists of the PPAR receptor.

FIELD OF THE INVENTION

Peroxisome proliferator-activated receptors (PPAR) can be subdivided into three subtypes, namely: PPARα, PPARδ, and PPARγ. These are encoded by different genes (Motojima, Cell Structure and Function, 18:267–277, 1993). Moreover, 2 isoforms of PPARγ also exist, PPARγ$_1$ and γ$_2$. These 2 proteins differ in their NH$_2$-terminal-30 amino acids and are the result of alternative promoter usage and differential mRNA splicing (Vidal-Puig, Jimenez, Linan, Lowell, Hamann, Hu, Spiegelman, Flier, Moller, J. Clin. Invest., 97:2553–2561, 1996).

Biological processes modulated by PPAR are those modulated by receptors, or receptor combinations, which are responsive to the PPAR receptor ligands described herein. These processes include, for example, plasma lipid transport and fatty acid catabolism, regulation of insulin sensitivity and blood glucose levels, which are involved in hypoglycemia/hyperinsulinism (resulting from, for example, abnormal pancreatic beta cell function, insulin secreting tumors and/or autoimmune hypoglycemia due to autoantibodies to insulin, the insulin receptor, or autoantibodies that are stimulatory to pancreatic beta cells), macrophage differentiation which lead to the formation of atherosclerotic plaques, inflammatory response, carcinogenesis, hyperplasia, adipocyte differentiation.

Obesity is an excessive accumulation of adipose tissue. Recent work in this area indicates that PPARγ plays a central role in the adipocyte gene expression and differentiation. Excess adipose tissue is associated with the development of serious medical conditions, for example, non-insulin-dependent diabetes mellitus (NIDDM), hypertension, coronary artery disease, hyperlipidemia obesity and certain malignancies. The adipocyte may also influence glucose homeostasis through the production of tumor necrosis factor α (TNFα) and other molecules.

Non-insulin-dependent diabetes mellitus (NIDDM), or Type II diabetes, is the more common form of diabetes, with 90–95% of hyperglycemic patients experiencing this form of the disease. In NIDDM there appears to be a reduction in the pancreatic β-cell mass, several distinct defects in insulin secretion or a decrease in tissue sensitivity to insulin. The symptoms of this form of diabetes include fatigue, frequent urination, thirst, blurred vision, frequent infections and slow healing of sores, diabetic nerve damage and renal disease.

Resistance to the metabolic actions of insulin is one of the key features of non-insulin dependent diabetes (NIDDM). Insulin resistance is characterised by impaired uptake and utilization of glucose in insulin-sensitive target organs, for example, adipocytes and skeletal muscle, and by impaired inhibition of hepatic glucose output. The functional insulin deficiency and the failure of insulin to supress hepatic glucose output results in fasting hyperglycemia. Pancreatic β-cells compensate for the insulin resistance by secreting increased levels of insulin. However, the β-cells are unable to maintain this high output of insulin, and, eventually, the glucose-induced insulin secretion falls, leading to the deterioration of glucose homeostasis and to the subsequent development of overt diabetes.

Hyperinsulinemia is also linked to insulin resistance, hypertriglyceridaemia and increased plasma concentration of low density lipoproteins. The association of insulin resistance and hyperinsulinemia with these metabolic disorders has been termed "Syndrome X" and has been strongly linked to an increased risk of hypertension and coronary artery disease.

Metformin is known in the art to be used in the treatment of diabetes in humans (U.S. Pat. No. 3,174,901). Metformin acts primarily to decrease liver glucose production. Troglitazone® is known to work primarily on enhancing the ability of skeletal muscle to respond to insulin and take up glucose. It is known that combination therapy comprising metformin and troglitazone can be used in the treatment of abnormalities associated with diabetes (DDT 3:79–88, 1998).

PPAR γ activators, in particular Troglitazone®, have been found to convert cancerous tissue to normal cells in liposarcoma, a tumor of fat (PNAS 96:3951–3956, 1999). Furthermore, it has been suggested that PPAR γ activators may be useful in the treatment of breast and colon cancer (PNAS 95:8806–8811, 1998, Nature Medicine 4:1046–1052, 1998).

Moreover, PPARγ activators, for example Troglitazone®, have been implicated in the treatment of polycystic ovary syndrome (PCO). This is a syndrome in women that is characterized by chronic anovulation and hyperandrogenism. Women with this syndrome often have insulin resistance and an increased risk for the development of noninsulin-dependent diabetes mellitus. (Dunaif, Scott, Finegood, Quintana, Whitcomb, J. Clin. Endocrinol. Metab., 81:3299, 1996.

Furthermore, PPARγ activators have recently been discovered to increase the production of progesterone and inhibit steroidogenesis in granulosa cell cultures and therefore may be useful in the treatment of climacteric. (U.S. Pat. No. 5,814,647 Urban et al. Sep. 29, 1998; B. Lohrke et al. Journal of Edocrinology, 159, 429–39, 1998). Climacteric is defined as the syndrome of endocrine, somatic and psychological changes occurring at the termination of the reproductive period in the female.

Peroxisomes are cellular organelles which play a role in controlling the redox potential and oxidative stress of cells by metabolizing a variety of substrates such as hydrogen peroxide. There are a number of disorders associated with oxidative stress. For example, inflammatory response to tissue injury, pathogenesis of emphysema, ischemia-associated organ injury (shock), doxorubicin-induced cardiac injury, drug-induced hepatotoxicity, atherosclerosis, and hyperoxic lung injuries, are each associated with the production of reactive oxygen species and a change in the reductive capacity of the cell. Therefore, it is envisaged that PPARα activators, among other things, regulate the redox potential and oxidative stress in cells, would be effective in the treatment of these disorders (Poynter et al, J. Biol. Chem. 273, 32833–41, 1998).

It has also been discovered that PPARα agonists inhibit NFκB-mediated transcription thereby modulating various inflammatory responses such as the inducible nitric oxide synthase (NOS) and cyclooxygenase-2 (COX-2) enzyme pathways (Pineda-Torra, I. T al, 1999, Curr. Opinion in Lipidology, 10,151–9) and thus can be used in the therapeutic intervention of a wide variety of inflammatory diseases and other pathologies (Colville-Nash, et al., Journal of Immunology, 161, 978–84, 1998; Staels et al, Nature, 393, 790–3, 1998).

Peroxisome proliferators activate PPAR, which in turn, acts as a transcription factor, and causes differentiation, cell growth and proliferation of peroxisomes. PPAR activators are also thought to play a role in hyperplasia and carcinogenesis as well as altering the enzymatic capability of animal cells, such as rodent cells, but these PPAR activators appear to have minimal negative effects in human cells (Green, Biochem. Pharm. 43(3):393, 1992). Activation of PPAR results in the rapid increase of gamma glutamyl transpeptidase and catalase.

PPARα is activated by a number of medium and long-chain fatty acids and is involved in stimulating β-oxidation of fatty acids in tissues such as liver, heart, skeletal muscle, and brown adipose tissue (Isseman and Green, supra; Beck et al., Proc. R. Soc. Lond. 247:83–87, 1992; Gottlicher et al., Proc. Natl. Acad. Sci. USA 89:4653–4657, 1992). Pharmacological PPARα activators, for example fenofibrate, clofibrate, genfibrozil, and bezafibrate, are also involved in substantial reduction in plasma triglycerides along with moderate reduction in LDL cholesterol, and they are used particularly for the treatment of hypertriglyceridemia, hyperlipidemia and obesity. PPARα is also known to be involved in inflammatory disorders. (Schoonjans, K., Current Opinion in Lipidology, 8, 159–66, 1997).

The human nuclear receptor PPARδ has been cloned from a human osteosarcoma cell cDNA library and is fully described in A. Schmidt et al., Molecular Endocrinology, 6:1634–1641 (1992), the contents of which are hereby incorporated herein by reference. It should be noted that PPARδ is also referred to in the literature as PPARβ and as NUC1, and each of these names refers to the same receptor. For example, in A. Schmidt et al., Molecular Endocrinology, 6: pp. 1634–1641, 1992, the receptor is referred to as NUC1. PPARδ is observed in both embryo and adult tissues. This receptor has been reported to be involved in regulating the expression of some fat-specific genes, and plays a role in the adipogenic process (Amri, E. et al., J. Biol. Chem. 270, 2367–71, 1995).

Atherosclerotic disease is known to be caused by a number of factors, for example, hypertension, diabetes, low levels of high density lipoprotein (HDL), and high levels of low density lipoprotein (LDL). In addition to risk reduction via effects on plasma lipid concentrations and other risk factors, PPARα agonists exert direct atheroprotective effects (Frick, M. H.,et al. 1997.. Circulation 96:2137–2143, de Faire, et al. 1997. Cardiovasc. Drugs Ther. 11 Suppl 1:257–63:257–263).

It has recently been discovered that PPARδ agonists are useful in raising HDL levels and therefore useful in treating atherosclerotic diseases. (Leibowitz et al.; WO/9728149). Atherosclerotic diseases include vascular disease, coronary heart disease, cerebrovascular disease and peripheral vessel disease. Coronary heart disease includes CHD death, myocardial infarction, and coronary revascularization. Cerebrovascular disease includes ischemic or hemorrhagic stroke and transient ischemic attacks.

PPARγ subtypes are involved in activating adipocyte differentiation, and are not involved in stimulating peroxisome proliferation in the liver. Activation of PPARγ is implicated in adipocyte differentiation through the activation of adipocyte-specific gene expression (Lehmann, Moore, Smith-Oliver, Wilkison, Willson, Kliewer, J. Biol. Chem., 270:12953–12956, 1995). The DNA sequences for the PPARγ receptors are described in Elbrecht et al., BBRC 224;431–437 (1996). Although peroxisome proliferators, including fibrates and fatty acids, activate the transcriptional activity of PPAR's, only prostaglandin $J_2$ derivatives such as the arachidonic acid metabolite 15-deoxy-delta$^{12}$, 14-prostaglandin $J_2$ (15d-PGJ$_2$) have been identified as natural ligands specific for the PPARγ subtype, which also binds thiazolidinediones. This prostaglandin activates PPARγ-dependent adipogenesis, but activates PPARα only at high concentrations (Forman, Tontonoz, Chen, Brun, Spiegelman, Evans, Cell, 83:803–812, 1995; Kliewer, Lenhard, Wilson, Patel, Morris, Lehman, Cell, 83:813–819, 1995). This is further evidence that the PPAR family subtypes are distinct from one another in their pharmacological response to ligands.

It has been suggested that compounds activating both PPARα and PPARγ should be potent hypotriglyceridemic drugs, which could be used in the treatment of dyslipidemia associated with atherosclerosis, non-insulin dependent diabetes mellitus,Syndrome X,. (Staels, B. et al., Curr. Pharm. Des., 3 (1), 1–14 (1997)) and familial combined hyperlipidemia (FCH). Syndrome X is the syndrome characterized by an initial insulin resistant state, generating hyperinsulinaemia, dyslipidaemia and impaired glucose tolerance, which can progress to non-insulin dependent diabetes mellitus (Type II diabetes), characterized by hyperglycemia. FCH is characterized by hypercholesterolemia and hypertriglyceridemia within the same patient and family.

The present invention is directed to a series of compounds that are useful in modulating PPAR receptors, as well as to a number of other pharmaceutical uses associated therewith.

SUMMARY OF THE INVENTION

This invention provides new aromatic compounds and pharmaceutical compositions prepared therewith that are PPAR ligand receptor binders, and which are useful as agonists or antagonists of the PPAR receptors. The invention also includes the discovery of new uses for previously known compounds.

The compounds for use according to the invention, including the new compounds of the present invention, are of Formula I

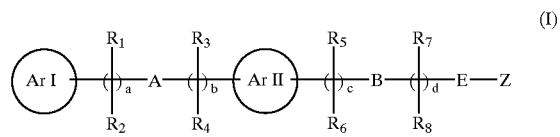

wherein:

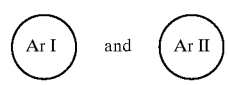

are independently aryl, fused arylcycloalkenyl, fused arylcycloalkyl, fused arylheterocyclenyl, fused arylheterocyclyl, heteroaryl, fused heteroarylcycloalkenyl, fused heteroarylcycloalkyl, fused heteroarylheterocyclenyl, or fused heteroarylheterocyclyl;

A is —O—, —S—, —SO—, —SO$_2$—, —NR$_{13}$—, —C(O)—, —N(R$_{14}$)C(O)—, —C(O)N(R$_{15}$)—, —N(R$_{14}$)C(O)N(R$_{15}$)—, —C(R$_{14}$)=N—,

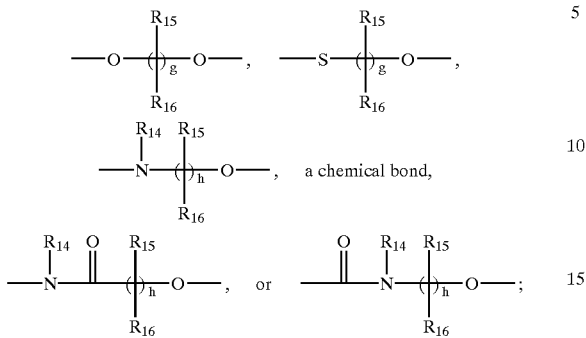

a chemical bond, or

B is —O—, —S—, —NR$_9$—, a chemical bond, —C(O)—, —N(R$_{20}$)C(O)—, or —C(O)N(R$_{20}$)—;

E is a chemical bond or an ethylene group;

a is 0–6;

b is 0–4;

c is 0–4;

d is 0–6;

g is 1–5;

h is 1–4;

R$_1$, R$_3$, R$_5$ and R$_7$, are independently hydrogen, halogen, alkyl, carboxyl, alkoxycarbonyl or aralkyl;

R$_2$, R$_4$, R$_6$ and R$_8$, are independently —(CH$_2$)$_q$—X;

q is 0–3;

X is hydrogen, halogen, alkyl, alkenyl, cycloalkyl, heterocyclyl, aryl, heteroaryl, aralkyl, heteroaralkyl, hydroxy, alkoxy, aralkoxy, heteroaralkoxy, carboxyl, alkoxycarbonyl, tetrazolyl, acyl, acylHNSO$_2$—, —SR$_{23}$, Y$^1$Y$^2$N— or Y$^3$Y$^4$NCO—;

Y$^1$ and Y$^2$ are independently hydrogen, alkyl, aryl, aralkyl or heteroaralkyl, or one of Y$^1$ and Y$^2$ is hydrogen or alkyl and the other of Y$^1$ and Y$^2$ is acyl or aroyl;

Y$^3$ and Y$^4$ are independently hydrogen, alkyl, aryl, aralkyl or heteroaralkyl;

Z is R$_{21}$O$_2$C—, R$_{21}$OC—, cyclo-imide, —CN, R$_{21}$O$_2$SHNCO—, R$_{21}$O$_2$SHN—, (R$_{21}$)$_2$NCO—, R$_{21}$O—2,4-thiazolidinedionyl, or tetrazolyl; and R$_{19}$ and R$_{21}$ are independently hydrogen, alkyl, aryl, cycloalkyl, or aralkyl;

R$_{13}$, R$_{17}$, R$_{19}$ and R$_{23}$ are independently R$_{22}$OC—, R$_{22}$NHOC—, hydrogen, alkyl, aryl, heteroaryl, cycloalkyl, heterocyclyl, heteroaralkyl, or aralkyl;

R$_{14}$, R$_{15}$, R$_{16}$, R$_{18}$ and R$_{20}$ are independently hydrogen, alkyl, aralkyl, carbonyl, or alkoxycarbonyl;

or R$_{14}$, and R$_{15}$ taken together with the carbon and nitrogen atoms through which they are linked form a 5 or 6-membered azaheterocyclyl group; or when a is 2–6, then at least one pair of vicinal R$_1$ radicals taken together with the carbon atoms to which the R$_1$ radicals are linked form a

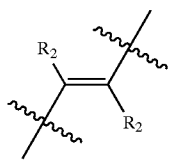

group; or when b is 2–4, then at least one pair of vicinal R$_3$ radicals taken together with the carbon atoms to which the R$_3$ radicals are linked form a

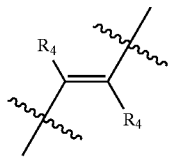

group; or when c is 2–4, then at least one pair of vicinal R$_5$ radicals taken together with the carbon atoms to which the R$_5$ radicals are linked form a

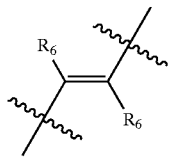

group; or when d is 2–6, then at least one pair of vicinal R$_7$ radicals taken together with the carbon atoms to which the R$_7$ radicals are linked form a

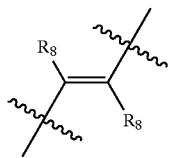

group, or a 5-membered cycloalkyl group; or when d is 2–6, then at least one pair of non-vicinal R$_7$ radicals taken together with the carbon atoms to which the R$_7$ radicals are linked form a 5-membered cycloalkyl group; or geminal R$_5$ and R$_6$ radicals taken together with the carbon atom through which these radicals are linked form a 5 membered cycloalkyl group; or geminal R$_7$ and R$_8$ radicals taken together with the carbon atom through which these radicals are linked form a 5 membered cycloalkyl group; and R$_{22}$ is hydrogen, alkyl, aryl, heteroaryl, cycloalkyl, heterocyclyl, heteroaralkyl, or aralkyl; or a pharmaceutically acceptable salt thereof, an N-oxide thereof, a hydrate thereof or a solvate thereof.

DETAILED DESCRIPTION OF THE INVENTION

As employed above and throughout the disclosure, the following terms, unless otherwise indicated, shall be understood to have the following meanings:

Definitions

In the present specification, the term "compounds for use according to the invention", and equivalent expressions, are meant to embrace compounds of general Formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

"Prodrug" means a compound which is convertible in vivo by metabolic means (e.g. by hydrolysis) to a compound of Formula (I), including N-oxides thereof. For example an ester of a compound of Formula (I) containing a hydroxy group may be convertible by hydrolysis in vivo to the parent molecule. Alternatively an ester of a compound of Formula (I) containing a carboxy group may be convertible by hydrolysis in vivo to the parent molecule.

"Patient" includes both human and other mammals.

In the present invention, the moiety

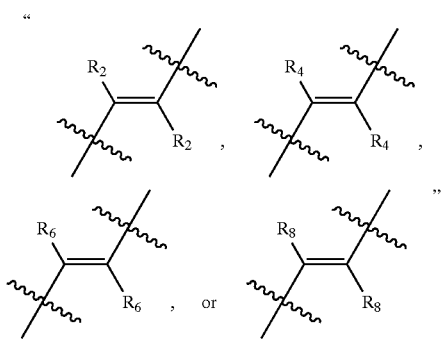

encompasses both the syn and anti configurations.

"Chemical bond" means a direct single bond between atoms.

"Acyl" means an H—CO— or alkyl-CO— group wherein the alkyl group is as herein described. Preferred acyls contain a lower alkyl. Exemplary acyl groups include formyl, acetyl, propanoyl, 2-methylpropanoyl, butanoyl and palmitoyl.

"Alkenyl" means an aliphatic hydrocarbon group containing a carbon-carbon double bond and which may be a straight or branched chain having about 2 to about 15 carbon atoms in the chain. Preferred alkenyl groups have 2 to about 12 carbon atoms in the chain and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain, which may be straight or branched. The alkenyl group is optionally substituted by one or more halo groups. Exemplary alkenyl groups include ethenyl, propenyl, n-butenyl, i-butenyl, 3-methylbut-2-enyl, n-pentenyl, heptenyl, octenyl and decenyl.

"Alkoxy" means an alkyl-O— group wherein the alkyl group is as herein described. Exemplary alkoxy groups include methoxy, ethoxy, n-propoxy, i-propoxy, n-butoxy and heptoxy.

"Alkoxycarbonyl" means an alkyl-O—CO— group, wherein the alkyl group is as herein defined. Exemplary alkoxycarbonyl groups include methoxycarbonyl, ethoxycarbonyl, or t-butyloxycarbonyl.

"Alkyl" means an aliphatic hydrocarbon group which may be straight or branched having about 1 to about 20 carbon atoms in the chain. Preferred alkyl groups have 1 to about 13 carbon atoms in the chain. Branched means that one or more lower alkyl groups such as methyl, ethyl or propyl are attached to a linear alkyl chain. "Lower alkyl" means about 1 to about 4 carbon atoms in the chain, which may be straight or branched. The alkyl is optionally substituted with one or more "alkyl group substituents" which may be the same or different, and include halo, carboxy, cycloalkyl, cycloalkenyl, heterocyclyl, heterocyclenyl, aryl, alkoxy, alkoxycarbonyl, aralkoxycarbonyl, heteroaralkoxycarbonyl, $Y^1Y^2NCO$—, wherein $Y^1$ and $Y^2$ are independently hydrogen, alkyl, aryl, aralkyl or heteroaralkyl, or $Y^1$ and $Y^2$ taken together with the nitrogen atom to which $Y^1$ and $Y^2$ are attached form heterocyclyl. Exemplary alkyl groups include methyl, trifluoromethyl, ethyl, n-propyl, i-propyl, n-butyl, t-butyl, n-pentyl, and 3-pentyl. Preferably, the alkyl group substituent is selected from acyl, carboxy, carboxymethyl, methoxycarbonylethyl, benzyloxycarbonylmethyl, and pyridylmethyloxycarbonylmethyl and alkoxycarbonyl.

"Alkylsulfinyl" means an alkyl-SO— group wherein the alkyl group is as defined above. Preferred groups are those wherein the alkyl group is lower alkyl.

"Alkylsulfonyl" means an alkyl-$SO_2$— group wherein the alkyl group is as defined above. Preferred groups are those wherein the alkyl group is lower alkyl.

"Alkylthio" means an alkyl-S— group wherein the alkyl group is as defined above. Exemplary alkylthio groups include methylthio, ethylthio, i-propylthio and heptylthio.

"Aralkoxy" means an aralkyl-O— group wherein the aralkyl group is as defined herein. Exemplary aralkoxy groups include benzyloxy and 1- and 2-naphthalenemethoxy.

"Aralkoxycarbonyl" means an aralkyl-O—CO— group wherein the aralkyl group is as defined herein. An exemplary aralkoxycarbonyl group is benzyloxycarbonyl.

"Aralkyl" means an aryl-alkyl- group wherein the aryl and alkyl groups are as defined herein. Preferred aralkyls contain a lower alkyl moiety. Exemplary aralkyl groups include benzyl, 2-phenethyl and naphthalenemethyl.

"Aralkylsulfonyl" means an aralkyl-$SO_2$— group wherein the aralkyl group is as defined herein.

"Aralkylsulfinyl" means an aralkyl-SO— group wherein the aralkyl group is as defined herein.

"Aralkylthio" means an aralkyl-S— group wherein the aralkyl group is as defined herein. An exemplary aralkylthio group is benzylthio.

"Aroyl" means an aryl-CO— group wherein the aryl group is as defined herein. Exemplary aroyl groups include benzoyl and 1- and 2-naphthoyl.

"Aryl" means an aromatic monocyclic or multicyclic ring system of about 6 to about 14 carbon atoms, preferably of about 6 to about 10 carbon atoms. The aryl is optionally substituted with one or more "ring system substituents" which may be the same or different, and are as defined herein. Exemplary aryl groups include phenyl, naphthyl, substituted phenyl, and substituted naphthyl.

"Aryldiazo" means an aryl-diazo- group wherein the aryl and diazo groups are as defined herein.

"Fused arylcycloalkenyl" means a fused aryl and cycloalkenyl as defined herein. Preferred fused arylcycloalkenyls are those wherein the aryl thereof is phenyl and the cycloalkenyl consists of about 5 to about 6 ring atoms. A fused arylcycloalkenyl group may be bonded to the rest of the compound through any atom of the fused system capable of such bondage. The fused arylcycloalkenyl may be optionally substituted by one or more ring system substituents, wherein the "ring system substituent" is as defined herein. Exemplary fused arylcycloalkenyl groups include 1,2-dihydronaphthylenyl; indenyl; 1,4-naphthoquinonyl, and the like.

"Fused arylcycloalkyl" means a fused aryl and cycloalkyl as defined herein. Preferred fused arylcycloalkyls are those wherein the aryl thereof is phenyl and the cycloalkyl consists of about 5 to about 6 ring atoms. A fused arylcycloalkyl group may be bonded to the rest of the compound through any atom of the fused system capable of such bonding. The fused arylcycloalkyl may be optionally substituted by one or more ring system substituents, wherein the "ring system substituent" is as defined herein. Exemplary fused arylcycloalkyl groups include 1,2,3,4-tetrahydronaphthylenyl; 1,4-dimethyl-2,3-dihydronaphthalenyl; 2,3-dihydro-1,4-naphthoquinonyl, α-tetralonyl, and the like.

"Fused arylheterocyclenyl" means a fused aryl and heterocyclenyl wherein the aryl and heterocyclenyl groups are as defined herein. Preferred fused arylheterocyclenyl groups are those wherein the aryl thereof is phenyl and the heterocyclenyl consists of about 5 to about 6 ring atoms. A fused arylheterocyclenyl group may be bonded to the rest of the compound through any atom of the fused system capable of such bonding. The designation of aza, oxa or thia as a prefix before the heterocyclenyl portion of the fused arylheterocyclenyl means that a nitrogen, oxygen or sulfur atom respectively, is present as a ring atom. The fused arylheterocyclenyl may be optionally substituted by one or more ring system substituents, wherein the "ring system substituent" is as defined herein. The nitrogen atom of a fused arylheterocyclenyl may be a basic nitrogen atom. The nitrogen or sulphur atom of the heterocyclenyl portion of the fused arylheterocyclenyl is also optionally oxidized to the corresponding N-oxide, S-oxide or S,S-dioxide. Exemplary fused arylheterocyclenyl include 3H-indolinyl, 2(1H) quinolinonyl, 2H-1-oxoisoquinolyl, 1,2-dihydroquinolinyl, (2H)quinolinyl N-oxide, 3,4-dihydroquinolinyl, 1,2-dihydroisoquinolinyl, 3,4-dihydroisoquinolinyl, chromonyl, 3,4-dihydroisoquinoxalinyl, 4-(3H)quinazolinonyl, 4H-chromen-2yl, and the like. Preferably, 2(1H) quinolinonyl, 1,2-dihydroquinolinyl, (2H)quinolinyl N-oxide, or 4-(3H)quinazolinonyl.

"Fused arylheterocyclyl" means a fused aryl and heterocyclyl wherein the aryl and heterocyclyl groups are as defined herein. Preferred fused arylheterocyclyls are those wherein the aryl thereof is phenyl and the heterocyclyl consists of about 5 to about 6 ring atoms. A fused arylheterocyclyl may be bonded to the rest of the compound through any atom of the fused system capable of such bonding. The designation of aza, oxa or thia as a prefix before the heterocyclyl portion of the fused arylheterocyclyl means that a nitrogen, oxygen or sulphur atom respectively is present as a ring atom. The fused arylheterocyclyl group may be optionally substituted by one or more ring system substituents, wherein the "ring system substituent" is as defined herein. The nitrogen atom of a fused arylheterocyclyl may be a basic nitrogen atom. The nitrogen or sulphur atom of the heterocyclyl portion of the fused arylheterocyclyl is also optionally oxidized to the corresponding N-oxide, S-oxide or S,S-dioxide. Exemplary fused arylheterocyclyl ring systems include indolinyl, 1,2,3,4-tetrahydroisoquinolinyl, 1,2,3,4-tetrahydroquinolinyl, 1H-2,3-dihydroisoindol-2-yl, 2,3-dihydrobenz[f]isoindol-2-yl, 1,2,3,4-tetrahydrobenz[g]isoquinolin-2-yl, chromanyl, isochromanonyl, 2,3-dihydrochromonyl, 1,4-benzodioxan, 1,2,3,4-tetrahydroquinoxalinyl, and the like. Preferably, 1,2,3,4-tetrahydroisoquinolinyl, 1,2,3,4-tetrahydroquinoxalinyl, and 1,2,3,4-tetrahydroquinolinyl.

"Aryloxy" means an aryl-O— group wherein the aryl group is as defined herein. Exemplary groups include phenoxy and 2-naphthyloxy.

"Aryloxycarbonyl" means an aryl-O—CO— group wherein the aryl group is as defined herein. Exemplary aryloxycarbonyl groups include phenoxycarbonyl and naphthoxycarbonyl.

"Arylsulfonyl" means an aryl-SO$_2$— group wherein the aryl group is as defined herein.

"Arylsulfinyl" means an aryl-SO— group wherein the aryl group is as defined herein.

"Arylthio" means an aryl-S— group wherein the aryl group is as defined herein. Exemplary arylthio groups include phenylthio and naphthylthio.

"Carbamoyl" is an NH$_2$—CO— group.

"Carboxy" means a HO(O)C— (carboxylic acid) group.

"Compounds of the invention," and equivalent expressions, are meant to embrace compounds of general Formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

"Cycloalkoxy" means an cycloalkyl-O— group wherein the cycloalkyl group is as defined herein. Exemplary cycloalkoxy groups include cyclopentyloxy and cyclohexyloxy.

"Cycloalkyl-alkoxy" means an cycloalkyl-alkylene-O— group wherein the cycloalkyl group and alkylene group are as defined herein. Exemplary cycloalkyl-alkoxy groups include cyclopentylmethylene-oxy and cyclohexylmethylene-oxy.

"Cycloalkenyl" means a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. The cycloalkenyl is optionally substituted with one or more "ring system substituents" which may be the same or different, and are as defined herein. Exemplary monocyclic cycloalkenyl include cyclopentenyl, cyclohexenyl, cycloheptenyl, and the like. An exemplary multicyclic cycloalkenyl is norbornylenyl.

"Cycloalkyl" means a non-aromatic mono- or multicyclic ring system of about 3 to about 10 carbon atoms, preferably of about 5 to about 10 carbon atoms. Preferred ring sizes of rings of the ring system include about 5 to about 6 ring atoms. The cycloalkyl is optionally substituted with one or more "ring system substituents" which may be the same or different, and are as defined herein. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

"Cycloalkylene" means a bivalent, saturated carbocyclic group having about 3 to about 6 carbon atoms. Preferred cycloalkylene groups include 1,1-, 1,2-, 1,3-, and 1,4-cis or trans-cyclohexylene, and 1,1-, 1,2-, and 1,3-cyclopentylene.

"Cyclo-imide" means a compound of formulae

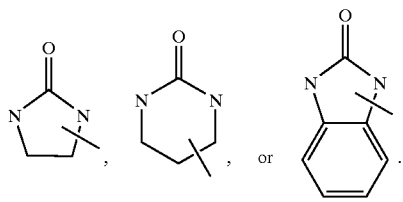

The cyclo-imide moiety may be attached to the parent molecule through either a carbon atom or nitrogen atom of the carbamoyl moiety. An exemplary imide group is N-phthalimide.

"Diazo" means a bivalent —N=N— radical.

"Halo" means fluoro, chloro, bromo, or iodo. Preferred are fluoro, chloro and bromo, more preferably fluoro and chloro.

"Halo" means fluoro, chloro, bromo, or iodo. Preferred are fluoro, chloro and bromo, more preferably fluoro and chloro.

"Heteroaralkyl" means a heteroaryl-alkyl- group wherein the heteroaryl and alkyl groups are as defined herein. Preferred heteroaralkyls contain a lower alkyl moiety. Exemplary heteroaralkyl groups include thienylmethyl, pyridylmethyl, imidazolylmethyl and pyrazinylmethyl.

"Heteroaralkylthio" means a heteroaralkyl-S— group wherein the heteroaralkyl group is as defined herein. An exemplary heteroaralkylthio group is 3-pyridinepropanthiol.

"Heteroaralkoxy" means an heteroaralkyl-O— group wherein the heteroaralkyl group is as defined herein. An exemplary heteroaralkoxy group is 4-pyridylmethyloxy.

"Heteroaroyl" means an means an heteroaryl-CO— group wherein the heteroaryl group is as defined herein. Exemplary heteroaryl groups include thiophenoyl, nicotinoyl, pyrrol-2-ylcarbonyl and 1- and 2-naphthoyl and pyridinoyl.

"Heteroaryldiazo" means an heteroaryl-diazo- group wherein the heteroaryl and diazo groups are as defined herein.

"Heteroaryl" means an aromatic monocyclic or multicyclic ring system of about 5 to about 14 carbon atoms, preferably about 5 to about 10 carbon atoms, in which at least one of the carbon atoms in the ring system is replaced by a hetero atom, i.e., other than carbon, for example nitrogen, oxygen or sulfur. Preferred ring sizes of rings of the ring system include about 5 to about 6 ring atoms. The heteroaryl ring is optionally substituted by one or more "ring system substituents" which may be the same or different, and are as defined herein. The designation of aza, oxa or thia as a prefix before the heteroaryl means that a nitrogen, oxygen or sulfur atom is present, respectively, as a ring atom. A nitrogen atom of an heteroaryl may be a basic nitrogen atom and also may be optionally oxidized to the corresponding N-oxide. Exemplary heteroaryl and substituted heteroaryl groups include pyrazinyl, thienyl, isothiazolyl, oxazolyl, pyrazolyl, cinnolinyl, pteridinyl, benzofuryl, furazanyl, pyrrolyl, 1,2,4-thiadiazolyl, pyridazinyl, indazolyl, quinoxalinyl, phthalazinyl, imidazo [1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, naphthyridinyl, benzoazaindole, 1,2,4-triazinyl, benzothiazolyl, furyl, imidazolyl, indolyl, isoindolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl. Preferred heteroaryl and substituted heteroaryl groups include quinolinyl, indazolyl, indolyl, quinazolinyl, pyridyl, pyrimidinyl, furyl, benzothiazolyl, quinoxalinyl, benzimidazolyl, benzothienyl, and isoquinolinyl.

"Fused heteroarylcycloalkenyl" means a fused heteroaryl and cycloalkenyl wherein the heteroaryl and cycloalkenyl groups are as defined herein. Preferred fused heteroarylcycloalkenyls are those wherein the heteroaryl thereof is phenyl and the cycloalkenyl consists of about 5 to about 6 ring atoms. A fused heteroarylcycloalkenyl may be bonded to the rest of the compound through any atom of the fused system capable of such bonding. The designation of aza, oxa or thia as a prefix before the heteroaryl portion of the fused heteroarylcycloalkenyl means that a nitrogen, oxygen or sulfur atom is present, respectively, as a ring atom. The fused heteroarylcycloalkenyl may be optionally substituted by one or more ring system substituents, wherein the "ring system substituent" is as defined herein. The nitrogen atom of a fused heteroarylcycloalkenyl may be a basic nitrogen atom. The nitrogen atom of the heteroaryl portion of the fused heteroarylcycloalkenyl may also be optionally oxidized to the corresponding N-oxide. Exemplary fused heteroarylcycloalkenyl groups include 5,6-dihydroquinolyl; 5,6-dihydroisoquinolyl; 5,6-dihydroquinoxalinyl; 5,6-dihydroquinazolinyl; 4,5-dihydro-1H-benzimidazolyl; 4,5-dihydrobenzoxazolyl; 1,4-naphthoquinolyl, and the like.

"Fused heteroarylcycloalkyl" means a fused heteroaryl and cycloalkyl wherein the heteraryl and cycloalkyl groups are as defined herein. Preferred fused heteroarylcycloalkyls are those wherein the heteroaryl thereof consists of about 5 to about 6 ring atoms and the cycloalkyl consists of about 5 to about 6 ring atoms. A fused heteroarylcycloalkyl may be bonded to the rest of the compoun through any atom of the fused system capable of such bonding. The designation of aza, oxa or thia as a prefix before the heteroaryl portion of the fused heteroarylcycloalkyl means that a nitrogen, oxygen or sulfur atom is present respectively as a ring atom. The fused heteroarylcycloalkyl may be optionally substituted by one or more ring system substituents, wherein the "ring system substituent" is as defined herein. The nitrogen atom of a fused heteroarylcycloalkyl may be a basic nitrogen atom. The nitrogen atom of the heteroaryl portion of the fused heteroarylcycloalkyl may also be optionally oxidized to the corresponding N-oxide. Exemplary fused heteroarylcycloalkyl include 5,6,7,8-tetrahydroquinolinyl; 5,6,7,8-tetrahydroisoquinolyl; 5,6,7,8-tetrahydroquinoxalinyl; 5,6,7,8-tetrahydroquinazolyl; 4,5,6,7-tetrahydro-1H-benzimidazolyl; 4,5 ,6,7-tetrahydrobenzoxazolyl; 1H-4-oxa-1,5-diazanaphthalen-2-only; 1,3-dihydroimidizole-[4,5]-pyridin-2-onyl, 2,3-dihydro-1,4-dinaphthoquinonyl and the like, preferably, 5,6,7,8-tetrahydroquinolinyl or 5,6,7,8-tetrahydroisoquinolyl.

"Fused heteroarylheterocyclenyl" means a fused heteroaryl and heterocyclenyl wherein the heteraryl and heterocyclenyl groups are as defined herein. Preferred fused heteroarylheterocyclenyls are those wherein the heteroaryl thereof consists of about 5 to about 6 ring atoms and the heterocyclenyl consists of about 5 to about 6 ring atoms. A fused heteroarylheterocyclenyl may be bonded to the rest of the compound through any atom of the fused system capable of such bonding. The designation of aza, oxa or thia as a prefix before the heteroaryl or heterocyclenyl portion of the fused heteroarylheterocyclenyl means that a nitrogen, oxygen or sulfur atom is present respectively as a ring atom. The fused heteroarylheterocyclenyl may be optionally substituted by one or more ring system substituent, wherein the "ring system substituent" is as defined herein. The nitrogen atom of a fused heteroarylazaheterocyclenyl may be a basic nitrogen atom. The nitrogen or sulphur atom of the heteroaryl or heterocyclenyl portion of the fused heteroarylheterocyclenyl may also be optionally oxidized to the corresponding N-oxide, S-oxide or S,S-dioxide. Exemplary fused heteroarylheterocyclenyl groups include 7,8-dihydro[1,7]naphthyridinyl; 1,2-dihydro[2,7]naphthyridinyl; 6,7-dihydro-3H-imidazo[4,5-c]pyridyl; 1,2-dihydro-1,5-naphthyridinyl; 1,2-dihydro-1,6-naphthyridinyl; 1,2-dihydro-1,7-naphthyridinyl; 1,2-dihydro-1,8-naphthyridinyl; 1,2-dihydro-2,6-naphthyridinyl, and the like.

"Fused heteroarylheterocyclyl" means a fused heteroaryl and heterocyclyl wherein the heteroaryl and heterocyclyl groups are as defined herein. Preferred fused heteroarylheterocyclyls are those wherein the heteroaryl thereof consists of about 5 to about 6 ring atoms and the heterocyclyl consists of about 5 to about 6 ring atoms. A fused heteroarylheterocyclyl may be bonded to the rest of the compound through any atom of the fused system capable of such bonding. The designation of aza, oxa or thia as a prefix before the heteroaryl or heterocyclyl portion of the fused heteroarylheterocyclyl means that a nitrogen, oxygen or sulfur atom is present respectively as a ring atom. The fused heteroarylheterocyclyl may be optionally substituted by one or more ring system substituent, wherein the "ring system substituent" is as defined herein. The nitrogen atom of a fused heteroarylheterocyclyl may be a basic nitrogen atom. The nitrogen or sulphur atom of the heteroaryl or heterocyclyl portion of the fused heteroarylheterocyclyl may also be optionally oxidized to the corresponding N-oxide, S-oxide or S,S-dioxide. Exemplary fused heteroarylheterocyclyl groups include 2,3-dihydro-1H pyrrol[3,4-b]quinolin-2-yl; 1,2,3,4-tetrahydrobenz[b][1,7]naphthyridin-2-yl; 1,2,3,4-tetrahydrobenz[b][1,6]naphthyridin-2-yl; 1,2,3,4-tetrahydro-9H-pyrido[3,4-b]indol-2yl; 1,2,3,4-tetrahydro-9H-pyrido[4,3-b]indol-2yl, 2,3,-dihydro-1H-pyrrolo[3,4-b]indol-2-yl; 1H-2,3,4,5-tetrahydroazepino[3,4-b]indol-2-yl; 1H-2,3,4,5-tetrahydroazepino[3,4-b]indol-3-yl; 1H-2,3,4,5-tetrahydroazepino[4,5-b]indol-2yl, 5,6,7,8-tetrahydro[1,7]napthyridinyl; 1,2,3,4-tetrhydro[2,7]naphthyridyl; 2,3-dihydro[1,4]dioxino[2,3-b]pyridyl; 2,3-dihydro[1,4]dioxino[2,3-b]pryidyl; 3,4-dihydro-2H-1-oxa[4,6]diazanaphthalenyl; 4,5,6,7-tetrahydro-3H-imidazo[4,5-c]pyridyl; 6,7-dihydro[5,8]diazanaphthalenyl; 1,2,3,4-tetrahydro[1,5]napthyridinyl; 1,2,3,4-tetrahydro[1,6]napthyridinyl; 1,2,3,4-tetrahydro[1,7]napthyridinyl; 1,2,3,4-tetrahydro[1,8]napthyridinyl; 1,2,3,4-tetrahydro[2,6]napthyridinyl, and the like.

"Heteroarylsulfonyl" means an heteroaryl-SO$_2$— group wherein the heteroaryl group is as defined herein. An exemplary heterarylsulfonyl groups is 3-pyridinepropansulfonyl.

"Heteroarylsulfinyl" means an heteroaryl-SO— group wherein the heteroaryl group is as defined herein.

"Heteroarylthio" means an heteroaryl-S— group wherein the heteroaryl group is as defined herein. Exemplary heteroaryl thio groups include pyridylthio and quinolinylthio.

"Heterocyclenyl" means a non-aromatic monocyclic or multicyclic hydrocarbon ring system of about 3 to about 10 carbon atoms, preferably about 5 to about 10 carbon atoms, in which at least one or more of the carbon atoms in the ring system is replaced by a hetero atom, for example a nitrogen, oxygen or sulfur atom, and which contains at least one carbon-carbon double bond or carbon-nitrogen double bond. Preferred ring sizes of rings of the ring system include about 5 to about 6 ring atoms. The designation of aza, oxa or thia as a prefix before the heterocyclenyl means that a nitrogen, oxygen or sulfur atom is present respectively as a ring atom. The heterocyclenyl may be optionally substituted by one or more ring system substituents, wherein the "ring system substituent" is as defined herein. The nitrogen atom of an heterocyclenyl may be a basic nitrogen atom. The nitrogen or sulphur atom of the heterocyclenyl is also optionally oxidized to the corresponding N-oxide, S-oxide or S,S-dioxide. Exemplary monocyclic azaheterocyclenyl groups include 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Exemplary oxaheterocyclenyl groups include 3,4-dihydro-2H-pyran, dihydrofuryl, and fluorodihydrofuryl An exemplary multicyclic oxaheterocyclenyl group is 7-oxabicyclo[2.2.1]heptenyl. Exemplary monocyclic thiaheterocycleny rings include dihydrothiophenyl and dihydrothiopyranyl.

"Heterocyclyl" means a non-aromatic saturated monocyclic or multicyclic ring system of about 3 to about 10 carbon atoms, preferably about 5 to about 10 carbon atoms, in which at least one of the carbon atoms in the ring system is replaced by a hetero atom, for example nitrogen, oxygen or sulfur. Preferred ring sizes of rings of the ring system include about 5 to about 6 ring atoms. The designation of aza, oxa or thia as a prefix before the heterocyclyl means that a nitrogen, oxygen or sulfur atom is present respectively as a ring atom. The heterocyclyl may be optionally substituted by one or more "ring systenm substituents" which may be the same or different, and are as defined herein. The nitrogen atom of an heterocyclyl may be a basic nitrogen atom. The nitrogen or sulphur atom of the heterocyclyl is also optionally oxidized to the corresponding N-oxide, S-oxide or S,S-dioxide. Exemplary monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuryl, tetrahydrothiophenyl, tetrahydrothiopyranyl, and the like. Exemplary multicyclic heterocyclyl rings include 1,4diazabicyclo-[2.2.2]octane and 1,2-cyclohexanedicarboxylic acid anhydride.

"Ring system substituent" includes hydrogen, alkyl, cycloalkyl, heterocyclyl, aryl, heteroaryl, aralkyl, heteroaralkyl, hydroxy, alkoxy, aryloxy, aralkoxy, cycloalkylalkyloxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, fused cycloalkyl, fused cycloalkenyl, fused heterocyclyl, fused heterocyclenyl, arylazo, heteroarylazo, $R^a R^b N$—, $R^c R^d NCO$—, $R^c O_2 CN$—, and $R^c R^d NSO_2$— wherein $R^a$ and $R^b$ are independently hydrogen, alkyl, aryl, aralkyl or heteroaralkyl, or one of $R^a$ and $R^b$ is hydrogen or alkyl and the other of $R^a$ and $R^b$ is aroyl or heteroaroyl. $R^c$ and $R^d$ are independently hydrogen, alkyl, aryl, heteroaryl, cycloalkyl, cycloalkenyl, heterocyclyl, heterocyclenyl, aralkyl or heteroaralkyl. Where the ring is cycloalkyl, cycloalkenyl, heterocyclyl or heterocyclenyl, the ring system substituent may also include methylene ($H_2C$=), oxo (O=), thioxo (S=), on carbon atom(s) thereof. Preferably, the ring substituents are selected from oxo (O=), alkyl, aryl, alkoxy, aralkoxy, halo, carboxy, alkoxycarbonyl, and $R^c O_2 CN$—, wherein $R^c$ is cycloalkyl.

"Tetrazolyl" means a group of formula

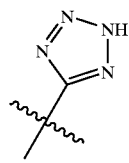

wherein the hydrogen atom thereof is optionally replaced by alkyl, carboxyalkyl or alkoxycarbonylalkyl.

"PPAR ligand receptor binder" means a ligand which binds to the PPAR receptor. PPAR ligand receptor binders of this invention are useful as agonists or antagonists of the PPAR-α, PPAR-δ, or PPAR-γ receptor.

The term "pharmaceutically acceptable salt" refers to a relatively non-toxic, inorganic or organic acid addition salt of a compound of the present invention. A salt can be prepared in situ during the final isolation and purification of a compound or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts, and the like. (See, for example S. M. Berge, et al., "Pharmaceutical Salts," J. Pharm. Sci., 66: 1–19, 1977, the contents of which are hereby incorporated herein by reference.)

"Treating" means the partial or complete relieving or preventing of one or more physiological or biochemical parameters associated with PPAR activity.

The term "modulate" refers to the ability of a compound to either directly (by binding to the receptor as a ligand) or indirectly (as a precursor for a ligand or an inducer which promotes production of a ligand from a precursor) induce expression of gene(s) maintained under hormone control, or to repress expression of gene(s) maintained under such control.

The term "obesity" refers generally to individuals who are at least about 20–30% over the average weight for the person's age, sex and height. Technically, "obese" is defined, for males, as individuals whose body mass index is greater than 27.3 kg/m². Those skilled in the art readily recognize that the invention method is not limited to those who fall within the above criteria. Indeed, the invention method can also be advantageously practiced by individuals who fall outside of these traditional criteria, for example by those who are prone to obesity.

The phrase "amount effective to lower blood glucose levels" refers to levels of a compound sufficient to provide circulating concentrations high enough to accomplish the desired effect. Such a concentration typically falls in the range of about 10 nM up to 2 μM, with concentrations in the range of about 100 nm up to about 500 nM being preferred.

The phrase "amount effective to lower triglyceride levels" refers to levels of a compound sufficient to provide circulating concentrations high enough to accomplish the desired effect. Such a concentration typically falls in the range of about 10 nM up to 2 μM; with concentrations in the range of about 100 nm up to about 500 nM being preferred.

PREFERRED EMBODIMENTS

Preferred embodiments according to the invention includes the use of compounds of Formula I (and their pharmaceutical compositions) as binders for PPAR receptors.

More particularly, the use of compounds of Formula I that bind to the PPAR-α receptor, compounds of Formula I that bind to the PPAR-δ receptor, compounds of Formula I that bind to the PPAR-γ receptor, compounds of Formula I that bind to the PPAR-α and the PPAR-γ receptor, compounds of Formula I that bind to the PPAR-α and the PPAR-δ receptor, compounds of Formula I that bind to the PPAR-γ and the PPAR-δ receptor, compounds of Formula I that act as PPAR receptor agonists, compounds of Formula I that act as PPAR-α receptor agonists, compounds of Formula I that act as PPAR-δ receptor agonists, compounds of Formula I that act as PPAR-γ receptor agonists, compounds of Formula I that act as both PPAR-α and PPAR-γ receptor agonists, compounds of Formula I that act as both PPAR-α and PPAR-δ receptor agonists, compounds of Formula I that act as both PPAR-γ and PPAR-δ receptor agonists, compounds of Formula I that act as both PPAR-α receptor antagonists and PPAR-γ receptor agonists, compounds of Formula I that act as both PPAR-α receptor antagonists and PPAR-δ receptor agonists, compounds of Formula I and act as both PPAR-γ receptor antagonists and PPAR-δ receptor agonists, compounds of Formula I that act as both PPAR-α receptor agonists and PPAR-γ receptor antagonists, compounds of Formula I that act as both PPAR-α receptor agonists and PPAR-δ receptor antagonists, compounds of Formula I that act as both PPAR-γ receptor agonists and PPAR-δ receptor antagonists, compounds of Formula I that act as PPAR receptor antagonists, compounds of Formula I that act as PPAR-α receptor antagonists, compounds of Formula I that act as PPAR-δ receptor antagonists, compounds of Formula I that act as PPAR-γ receptor antagonists, compounds of Formula I that act as both PPAR-α and PPAR-γ receptor antagonists, compounds of Formula I that act as both PPAR-α and PPAR-δ receptor antagonists, and compounds of Formula I that act as both PPAR-γ and PPAR-δ receptor antagonists.

An embodiment according to the invention is directed to treating a patient suffering from a physiological disorder capable of being modulated by a compound of Formula I having PPAR ligand binding activity, comprising administering to the patient a pharmaceutically effective amount of the compound, or a pharmaceutically acceptable salt thereof. Physiological disorders capable of being so modulated include, for example, cell differentiation to produce lipid accumulating cells, regulation of insulin sensitivity and blood glucose levels, which are involved in hypoglycemia/hyperinsulinism (resulting from, for example, abnormal pancreatic beta cell function, insulin secreting tumors and/or autoimmune hypoglycemia due to autoantibodies to insulin, autoantibodies to the insulin receptor, or autoantibodies that are stimulatory to pancreatic beta cells), macrophage differentiation which leads to the formation of atherosclerotic plaques, inflammatory response, carcinogenesis, hyperplasia, adipocyte gene expression, adipocyte differentiation, reduction in the pancreatic β-cell mass, insulin secretion, tissue sensitivity to insulin, liposarcoma cell growth, chronic anovulation, hyperandrogenism, progesterone production, steroidogenesis, redox potential and oxidative stress in cells, nitric oxide synthase (NOS) production, increased gamma glutamyl transpeptidase, catalase, plasma triglycerides, HDL and LDL cholesterol levels and the like.

Another embodiment according to the invention is directed to a method of treating a disease state in a patient with a pharmaceutically effective amount of a compound of Formula I, or a pharmaceutically acceptable salt thereof, wherein the disease is associated with a physiological detrimental blood level of insulin, glucose, free fatty acids (FFA), or triclycerides.

An embodiment according to the invention is directed to treating a patient suffering from a physiological disorder associated with physiologically detrimental levels of triclycerides in the blood, by administering to the patient a pharmaceutically effective amount of the compound, or of a pharmaceutically acceptable salt thereof.

An embodiment according to the invention is the use of compounds of Formula I and their pharmaceutical compositions as anti-diabetic, anti-lipidemic, anti-hypertensive or anti-arteriosclerotic agents, or in the treatment of obesity.

Another embodiment according to the invention is directed to a method of treating hyperglycemia in a patient, by administering to the patient a pharmaceutically effective amount to lower blood glucose levels of a compound of Formula I, or a pharmaceutically acceptable salt thereof. Preferably, the form of hyperglycemia treated in accordance with this invention is Type II diabetes.

Another embodiment according to the invention is directed to a method of reducing triglyceride levels in a patient, comprising administering to the patient a therapeutically effective amount (to lower triglyceride levels) of a compound of Formula I, or a pharmaceutically acceptable salt thereof.

Another embodiment according to the invention is directed to a method of treating hyperinsulinism in a patient, comprising administering to the patient a therapeutically effective amount of a compound of Formula I, or a pharmaceutically acceptable salt thereof.

Another embodiment according to the invention is directed to a method of treating insulin resistance in a patient, comprising administering to the patient a therapeutically effective amount of a compound of Formula I, or a pharmaceutically acceptable salt thereof.

Another embodiment according to the invention is directed to a method of treating cardiovascular disease, such as atherosclerosis in a patient, comprising administering to the patient a therapeutically effective amount of a compound of Formula I, or a pharmaceutically acceptable salt thereof.

Another embodiment according to the invention is directed to treating of hyperlipidemia in a patient, comprising administering to the patient a therapeutically effective amount of a compound of Formula I, or a pharmaceutically acceptable salt thereof.

Another embodiment according to the invention is directed to treating of hypertension in a patient, comprising administering to the patient a therapeutically effective amount of a compound of Formula I, or a pharmaceutically acceptable salt thereof.

Another embodiment according to the invention is directed to treating eating disorders in a patient, comprising administering to the patient a therapeutically effective amount of a compound of Formula I, or a pharmaceutically acceptable salt thereof. Treatment of eating disorders includes the regulation of appetite andor food intake in patients suffering from under-eating disorders such as anorexia nervosa as well as over-eating disorders such as obesity and anorexia bulimia.

Another embodiment according to the invention is directed to treating a disease state associated with low levels of HDL comprising administering to the patient a therapeutically effective amount of a compound of Formula I, or a pharmaceutically acceptable salt thereof. Diseases associated with low levels of HDL include atherosclerotic diseases.

Another embodiment according to the invention is directed to treating polycystic ovary syndrome comprising administering to the patient a therapeutically effective amount of a compound of Formula I, or a pharmaceutically acceptable salt thereof.

Another embodiment according to the invention is directed to treating climacteric comprising administering to the patient a therapeutically effective amount of a compound of Formula I, or a pharmaceutically acceptable salt thereof.

Another embodiment according to the invention is directed to treating inflammatory diseases such as rheumatoid arthritis, chronic obstructive pulmonary disease (emphysema or chronic bronchitis), or asthma comprising administering to the patient a therapeutically effective amount of a compound of Formula I, or a pharmaceutically acceptable salt thereof.

Another aspect of the invention is to provide a novel pharmaceutical composition which is effective, in and of itself, for utilization in a beneficial combination therapy because it includes a plurality of active ingredients which may be utilized in accordance with the invention.

In another aspect, the present invention provides a method for treating a disease state in a patient, wherein the disease is associated with a physiological detrimental level of insulin, glucose, free fatty acids (FFA), or triglycerides, in the blood, comprising administering to the patient a therapeutically effective amount of a compound of Formula I, and also administering a therapeutically effective amount of an additional hypoglycemic agent.

In another aspect, the present invention provides a method for treating a disease state in a patient, wherein the disease is associated with a physiological detrimental level of insulin, glucose, free fatty acids (FFA), or triglycerides, in the blood, comprising administering to the patient a therapeutically effective amount of a compound of Formula I, and also administering a therapeutically effective amount of a biguanidine compound.

In another aspect, the present invention provides a method for treating a disease state in a patient, wherein the disease is associated with a physiological detrimental level of insulin, glucose, free fatty acids (FFA), or triglycerides, in the blood, comprising administering to the patient a therapeutically effective amount of a compound of Formula I, and also administering a therapeutically effective amount of metformin.

The invention also provides kits or single packages combining two or more active ingredients useful in treating the disease. A kit may provide (alone or in combination with a pharmaceutically acceptable diluent or carrier), a compound of Formula (I) and an additional hypoglycaemic agent (alone or in combination with diluent or carrier).

There are many known hypoglycemic agents in the art, for example, insulin; biguanidines, such as metformin and buformin; sulfonylureas, such as acetohexamide, chloropropamide, tolazamide, tolbutamide, glyburide, glypizide and glyclazide; thiazolidinediones, such as troglitazone; α-glycosidase inhibitors, such as acarbose and miglatol; and $B_3$ adrenoreceptor agonists such as CL-316,243.

Since sulfonylureas are known to be capable of stimulating insulin release, but are not capable of acting on insulin resistance, and compounds of Formula I are able to act on insulin resistance, it is envisaged that a combination of these medicaments could be used as a remedy for conditions associated with both deficiency in insulin secretion and insulin-resistance.

Therefore, the invention also provides a method of treating diabetes mellitus of type II in a patient comprising administering a compound of Formula I and one or more additional hypoglycemic agents selected from the group consisting of sulfonylureas, biguanidines, thiazolidinediones, $B_3$-adrenoreceptor agonists, α-glycosidase inhibitors and insulin.

The invention also provides a method of treating diabetes mellitus of type II in a patient comprising administering a compound of Formula I and a sulfonylurea selected from the group consisting of acetohexamide, chlorpropamide, tolazamide, tolbutamide, glyburide, glypizide and glyclazide.

The invention also provides a method of treating diabetes mellitus of type II in a patient comprising administering a compound of Formula I and a biguanidine selected from the group consisting of metformin and buformin.

The invention also provides a method of treating diabetes mellitus of type II in a patient comprising administering a compound of Formula I and an α-glycosidase inhibitor selected from the group consisting acarbose and miglatol.

The invention also provides a method of treating diabetes mellitus of type II in a patient comprising administering a compound of Formula I and an thiazolidinedione, for example, troglitazone.

As indicated above, a compound of Formula I may be administered alone or in combination with one or more additional hypoglycemic agents. Combination therapy includes administration of a single pharmaceutical dosage formulation which contains a compound of Formula I and one or more additional hypoglycemic agent, as well as administration of the compound of Formula I and each additional hypoglycemic agents in its own separate pharmaceutical dosage formulation. For example, a compound of Formula I and hypoglycemic agent can be administered to the patient together in a single oral dosage composition such as a tablet or capsule, or each agent administered in separate oral dosage formulations. Where separate dosage formulations are used, the compound of Formula I and one or more additional hypoglycemic agents can be administered at essentially the same time, i.e., concurrently, or at separately staggered times, i.e., sequentially.

For example, the compound of Formula I may be administered in combination with one or more of the following additional hypoglycemic agents: insulin; biguanidines such as metformin or buformin; sulfonylureas such as acetohexamide, chloropropamide, tolazamide, tolbutamide, glyburide, glypizide or glyclazide; thiazolidinediones such as troglitazone; α-glycosidase inhibitors such as acarbose or miglatol; or $B_3$ adrenoreceptor agonists such as CL-316,243.

The compound of Formula I is preferably administered with a biguanidine, in particular, metformin.

The compounds of Formula I contain at least two aromatic or hetero-aromatic rings, which may be designated as shown in Formula II below, and for which their substitution pattern along the chain with respect to each other also is shown below.

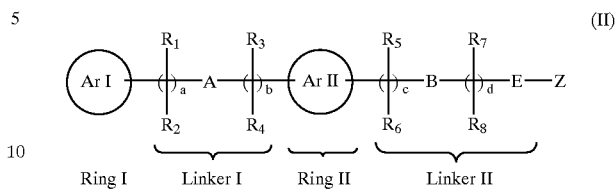

(II)

A preferred aspect of the compounds of Formula II, is a compound wherein

is selected from quinolinyl, benzothiophenyl, benzoimidazolyl, quinazolinyl, benzothiazolyl, quinoxalinyl, naphthyl, pyridyl, 1H-indazolyl, 1,2,3,4-tetrahydroquinolinyl, benzofuranyl, thienyl, or indolyl, and one end of the linker, Linker I, is attached to

preferably at the 2-position of the ring moiety.

Another aspect of the compounds of Formula II is a compound wherein

is a 6-membered aryl or heteroaryl group and Linker I and Linker II are attached to

at positions 1,3-, or 1,4- to each other.

Another aspect of the compounds of Formula II is a compound wherein

is a naphthyl group, Linker I and Linker II are attached to

at positions 1,4-, or 2,4- to each other on the naphthyl moiety.

A further preferred aspect of the compound of Formula II is described by Formula V below:

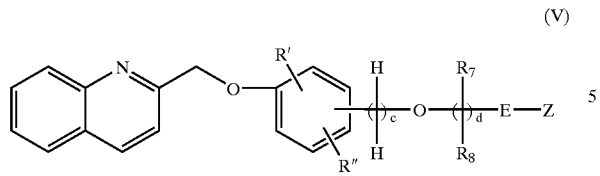
(V)

where $R_7$, $R_8$, c, d, E and Z are as defined above, c+d=1–3, and R' and R" are ring system substituents.

Another aspect of this invention is a compound of the invention wherein

is optionally substituted aryl, optionally substituted azaheteroaryl, or optionally substituted fused arylheterocyclenyl or fused arylheterocyclyl; and

is optionally substituted phenyl or optionally substituted naphthyl, optionally substituted heteroaryl, or optionally substituted fused arylheterocyclenyl.

Another aspect of this invention is a compound of the invention wherein a=1 or 2; $R_1$ and $R_2$ is hydrogen; A is a chemical bond; and b=0.

Another aspect of this invention is a compound of the invention wherein a=0, 1, or 2, A is —C(O)N($R^{15}$)— or —N($R^{14}$)C(O)—, and b=0 or 1.

Another more preferred aspect of this invention is a compound of the invention wherein $R_1$ and $R_2$ are both hydrogen, a=1, A is —O— and b=0.

Another more preferred aspect of this invention is a compound of the invention wherein $R_1$ and $R_2$ are both hydrogen, a=2, A is —O— and b=0.

Another more preferred aspect of this invention is a compound of the invention wherein a=0, A is —O— or —$NR_{13}$—; $R_{13}$ is hydrogen or alkyl; $R_3$ and $R_4$ are both independently hydrogen; and b=1.

Another aspect of this invention is a compound of the invention wherein a=0; A is

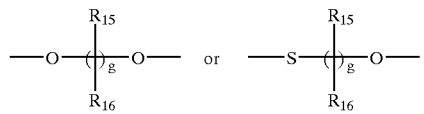

$R_{15}$ and $R_{16}$ are hydrogen; g is 1, 2, 3 or 4; and b=0.

Another aspect of this invention is a compound of the invention wherein a=0; A is —$NR_{13}$—, b=1, $R_3$ and $R_4$ are hydrogen, and $R_{13}$ is hydrogen, alkyl, or $R_{22}$(O=)C—.

Another aspect of this invention is a compound of the invention wherein a=2; then the vicinal $R_1$ radicals taken together with the carbon atoms through which these radicals are linked form a

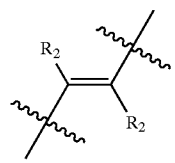

group; $R_2$ is hydrogen; A is a chemical bond or —O—; and b=0.

Another aspect of this invention is a compound of the invention wherein a=6; then at least one pair of vicinal $R_1$ radicals taken together with the carbon atoms through which these radicals are linked form a

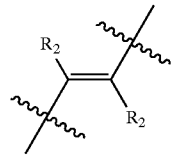

group; $R_2$ is hydrogen or alkyl; A is —O—; and b=0.

Another aspect of this invention is a compound of the invention wherein a=1, 2 or 3; $R_1$ and $R_2$ are hydrogen; A is —O—; and b=0.

Another aspect of this invention is a compound of the invention wherein a=1; $R_1$, $R_2$, $R_3$ and $R_4$ are hydrogen; A is —O—; and b=1.

Another aspect of this invention is a compound of the invention wherein a=2; A is

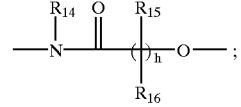

h=1 or 2; and b=0.

Another aspect of this invention is a compound of the invention wherein c=0; d=0; B and E is a chemical bond; Z is $R_{21}O_2SHNCO$—, and $R_{21}$ is phenyl.

Another aspect of this invention is a compound of the invention wherein c=0; d=2; B is —C(O)N($R_{20}$)—, E is a chemical bond; Z is a tetrazolyl group or —$CO_2R_{21}$; $R_{20}$ is hydrogen, alkyl, alkoxycarbonyl.

Another aspect of this invention is a compound of the invention wherein c=0 or 4; d=0 or 1; B and E is a chemical bond; Z is tetrazolyl, $NH_2CO$— or —$CO_2R_{21}$; and $R_{21}$ is hydrogen or lower alkyl.

Another aspect of this invention is a compound of the invention wherein c=0 or 1; d=0 or 1; B is —O— or a chemical bond; E is a chemical bond; and Z is tetrazolyl, $NH_2CO$— or —$CO_2R_{21}$; and $R_{21}$ is hydrogen or lower alkyl.

Another aspect of this invention is a compound of the invention wherein c=0; d=1; B is —O— or a chemical bond; E is a chemical bond; $R_7$ and $R_8$ are hydrogen or alkyl; and Z is tetrazolyl, $NH_2CO$— or —$CO_2R_{21}$; and $R_{21}$ is hydrogen or lower alkyl.

Another aspect of this invention is a compound of the invention wherein c=2 or 4, then at least one pair of vicinal $R_5$ radicals taken together with the carbon atoms to which the $R_5$ radicals are linked form a

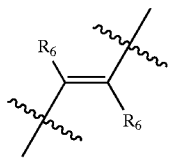

group; d=0; D and E is a chemical bond; and Z is a tetrazolyl group or —$CO_2R_{21}$; and $R_{21}$ is hydrogen.

Another aspect of this invention is a compound of the invention wherein c=0; d=3 or 4; B is —O—; E is a chemical bond; $R_7$ and $R_8$ are hydrogen or alkyl, or at least one of $R_7$ is carboxyl or alkoxycarbonyl; Z is tetrazolyl, —$CO_2R_{21}$ or $(R_{21})_2NC(O)$—; and $R_{21}$ is hydrogen or lower alkyl.

Another aspect of this invention is a compound of the invention wherein c=0; d=1, 2, or 3; B is —C(O)—; E is a chemical bond; $R_7$ and $R_8$ are hydrogen or alkyl; Z is tetrazolyl or —$CO_2R_{21}$; and $R_{21}$ is hydrogen or lower alkyl.

Another aspect of this invention is a compound of the invention wherein c=4; d=0; B and E are a chemical bond; $R_7$ and $R_8$ are hydrogen or alkyl; Z is tetrazolyl or —$CO_2R_{21}$; and $R_{21}$ is hydrogen or lower alkyl.

Another aspect of this invention is a compound of the invention wherein c=0, 1 or 2; d=1, 2 or 3; B is —S— or $NR_{19}$, E are a chemical bond; $R_5$, $R_6$, $R_7$ and $R_8$ are hydrogen; Z is tetrazoly or —$CO_2R_{21}$; and $R_{21}$ is hydrogen or lower alkyl.

Another aspect of this invention is a compound of the invention wherein $R_6$ and $R_8$ are —$(CH_2)_q$—X; q is 0, 1 or 2; and X is independently hydrogen, aralkyl or lower alkyl.

Another aspect of this invention is a compound of the invention wherein at least one pair of geminal $R_5$ and $R_6$ radicals taken together with the carbon atom through which these radicals are linked form a 5-membered cycloalkyl group.

Another aspect of this invention is a compound of the invention wherein at least one pair of geminal $R_7$ and $R_8$ radicals taken together with the carbon atom through which these radicals are linked form a 5-membered cycloalkyl group.

Another aspect of this invention is a compound of the invention wherein Z is —$CO_2H$, —CN or a tetrazolyl group.

A preferred aspect of this invention is a compound of the invention wherein (Ar I)

is an optionally substituted quinolinyl, quinoxalinyl, quinazolinyl, isoquinolinyl, N-alkyl-quinolin-4-onyl, quinazolin-4-onyl, benzoxazolyl, benzimidazolyl, benzothiazolyl, benzofuranyl, benzothiophenyl, indolinyl oxazolyl, thiazolyl, oxadiazolyl isoxazolyl, imidazolyl, pyrazol-yl, thiadiazolyl, triazolyl, pyridyl pyrimidinyl, pyrazinyl, pyridazinyl, phenyl, or napthalenyl group, wherein the substituent is a ring system substituent as defined herein, more preferably a substituent selected from the group consisting of phenyl, substituted-phenyl, thienyl, substituted thienyl, cycloalkyl, lower alkyl, branched alkyl, fluoro, chloro, alkoxy, aralkyloxy, trifluoromethyl and trifluoromethyloxy.

A more preferred aspect of this invention is a compound of the invention wherein (Ar I)

is unsubstituted quinolin-2-yl, 3-substituted quinolin-2-yl, 4-substituted quinolin-2-yl, 6-substituted quinolin-2-yl or 7 substituted quinolin-2-yl; an unsubstituted quinozalin-2-yl, 3-substituted quinozalin-2-yl, 6-substituted quinozalin-2-yl or 3,6-disubstituted quinozalin-2-yl; unsubstituted quinazolin-2-yl, 4-substituted quinazolin-2-yl or 6-substituted quinazolin-2-yl; unsubstituted isoquinolin-3-yl, 6-substituted isoquinolin-3-yl or 7-substituted isoquinolin-3-yl; 3-substituted-quinazolin-4-on-2-yl; N-substituted quinolin-4-on-2-yl; 2-substituted-oxazol-4-yl or 2,5 disubstituted-oxazol-4-yl; 4-substituted oxazol-2-yl or 4,5-disubstituted-oxazol-2-yl; 2-substituted thiazol-4-yl or 2,5-disubstituted thiazol-4-yl; 4-substituted thiazol-2-yl or 4,5-disubstituted-thiazol-2-yl; 5-substituted-[1,2,4] oxadiazol-3-yl; 3-substituted-[1,2,4]oxadiazol-5-yl; 5-substituted-imidazol-2-yl or 3,5-disubstituted-imidazol-2-yl; 2-substituted-imidazol-5-yl or 2,3-disubstituted-imidazol-5-yl; 3-substituted-isoxazol-5-yl; 5-substituted-isoxazol-3-yl; 5-substituted-[1,2,4]thiadiazol-3-yl; 3-substituted-[1,2,4]-thiadiazol-5-yl; 2-substituted-[1,3,4]-thiadiazol-5-yl; 2-substituted-[1,3,4]-oxadiazol-5-yl; 1-substituted-pyrazol-3-yl; 3-substituted-pyrazol-5-yl; 3-substituted-[1,2,4]-triazol-5-yl; 1-substituted-[1,2,4]-triazol-3-yl; 3-substituted pyridin-2-yl, 5-substituted pyridin-2-yl, 6-substituted pyridin-2-yl or 3,5-disubstituted pyridin-2-yl; 3-substituted pyrazin-2-yl, 5-substituted pyrazin-2-yl, 6-substituted pyrazin-2-yl or 3,5 disubstituted-pyrazin-2-yl; 5-substituted pyrimidin-2-yl or 6-substituted-pyrimidin-2-yl; 6-substituted-pyridazin-3-yl or 4,6-disubstituted-pyridazin-3-yl; unsubstituted napthalen-2-yl, 3-substituted napthalen-2-yl, 4-substituted napthalen-2-yl, 6-substituted napthalen-2-yl or 7 substituted napthalen-2-yl; 2-substituted phenyl, 4-substituted phenyl or 2,4-disubstituted phenyl; unsubstituted-benzothiazol-2-yl or 5-substituted-benzothiazol-2-yl; unsubstituted benzoxazol-2yl or 5-substituted-benzoxazol-2yl; unsubstituted-benzimidazol-2-yl or 5-substituted-benzimidazol-2-yl; unsubstituted-thiophen-2yl, 3-substituted-thiophen-2yl, 6-substituted-thiophen-2yl or 3,6-disubstituted-thiophen-2yl; unsubstituted-benzofuran-2-y, 3-substituted-benzofuran-2-yl, 6-substituted-benzofuran-2-yl or 3,6-disubstituted-benzofuran-2-yl; 3-substituted-benzofuran-6-yl or 3,7-disubstituted-benzofuran-6-yl, wherein the substituent is a ring system substituent as defined herein, more preferably a substituent selected from the group consisting of phenyl, substituted-phenyl, thienyl, substituted thienyl, cycloalkyl, lower alkyl, branched alkyl, fluoro, chloro, alkoxy, aralkyloxy, trifluoromethyl and trifluoromethyloxy.

Another more preferred aspect of this invention is a compound of the invention wherein a=0, A is —O— or —$NR_{13}$—; $R_{13}$ is hydrogen or alkyl; $R_3$ and $R_4$ are both independently hydrogen; b=1; and ArI is 3-substituted quinolin-2-yl, 4-substituted quinolin-2-yl, 6-substituted quinolin-2-yl, 7 substituted quinolin-2-yl, unsubstituted quinoxalin-2-yl, 3-substituted quinoxalin-2-yl, 6-substituted quinoxalin-2-yl, 3,6-disubstituted quinoxalin-2-yl, unsubstituted quinazolin-2-yl, 4-substituted quinazolin-2-yl, 6-substituted quinazolin-2-yl, unsubstituted isoquinolin-3-yl, 6-substituted isoquinolin-3-yl, 7-substituted isoquinolin-3-yl, 4-substituted oxazol-2-yl, 4,5-disubstituted-oxazol-2-yl, 4-substituted-thiazol-2-yl, 4,5-disubstituted-thiazol-2-yl, 5-substituted-imidazol-2-yl, 3,5-disubstituted-imidazol-2-yl, 1-substituted-pyrazol-3-yl, 3-substituted-pyrazol-5-yl, 3-substituted pyridin-2-yl, 5-substituted pyridin-2-yl, 6-substituted pyridin-2-yl or 3,5-disubstituted pyridin-2-yl, 3-substituted pyrazin-2-yl, 5-substituted pyrazin-2-yl, 6-substituted pyrazin-2-yl, 3,5 disubstituted-pyrazin-2-yl, 5-substituted pyrimidin-2-yl, 6-substituted-pyrimidin-2-yl, 6-substituted-pyridazin-3-yl, 4,6-disubstituted-pyridazin-3-yl, unsubstituted-benzothiazol-2-yl, 5-substituted-benzothiazol-2-yl, unsubstituted-benzoxazol-2-yl, 5-substituted-benzoxazol-2-yl, unsubstituted benzimidazol-2-yl, 5-substituted-benzimidazol-2-yl, 3-substituted-benzofuran-6-yl or 3,7-disubstituted-benzofuran-6-yl.

Another aspect of this invention is a compound of formula I as described by formula (Ia) below:

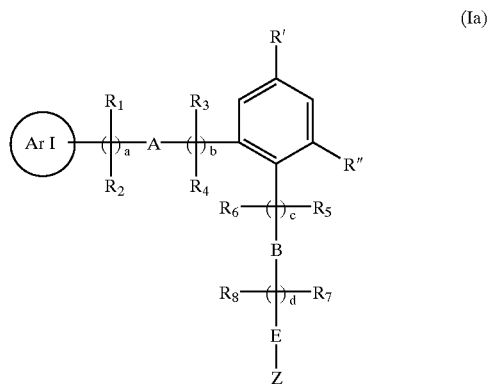

wherein

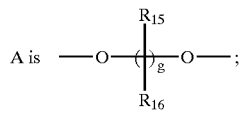

is independently aryl, fused arylcycloalkenyl, fused arylcycloalkyl, fused arylheterocyclenyl, fused arylheterocyclyl, heteroaryl, fused heteroarylcycloalkenyl, fused heteroarylcycloalkyl, fused heteroarylheterocyclenyl, or fused heteroarylheterocyclyl;

a=1;

b=0;

$R_1$ and $R_2$ are hydrogen

A is —O—;

$R_5$, $R_6$, $R_7$, $R_8$ are hydrogen;

c=0;

B and E are a chemical bond;

Z is $R_{21}O_2C$—, $R_{21}OC$—, cyclo-imide, —CN, $R_{21}O_2SHNCO$—, $R_{21}O_2SHN$—, $(R_{21})_2NCO$—, $R_{21}O$—2,4-thiazolidinedionyl, or tetrazolyl;

R' and R" are ring system substituents as defined herein, more preferably, R' is hydrogen, lower alkyl, halo, alkoxy, aryloxy or aralkyloxy; and R" is lower alkyl, hydrogen, aralkyloxy, alkoxy, cycloalkylalkyloxy or halo.

Another aspect of this invention is a compound of formula I as described by formula (Ia) wherein

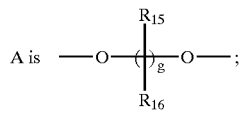

is independently aryl, fused arylcycloalkenyl, fused arylcycloalkyl, fused arylheterocyclenyl, fused arylheterocyclyl, heteroaryl, fused heteroarylcycloalkenyl, fused heteroarylcycloalkyl, fused heteroarylheterocyclenyl, or fused heteroarylheterocyclyl;

a=1;

A is 

g=2, 3, 4 or 5;

$R_1$, $R_2$, $R_3$, $R_4$, $R_{15}$ and $R_{16}$ are hydrogen;

b=0 or 1;

c=0;

d=0;

B and E are a chemical bond;

Z is —CO$_2$H;

R' and R" are ring system substituents as defined herein, more preferably, R' is hydrogen, lower alkyl, halo, alkoxy, aryloxy or aralkyloxy; and R" is lower alkyl, alkoxy, aralkoxy, cycloalkylalkoxy or halo.

Another aspect of this invention is a compound of formula I as described by formula (Ia) wherein

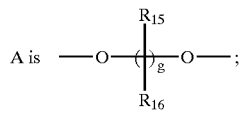

is independently aryl, fused arylcycloalkenyl, fused arylcycloalkyl, fused arylheterocyclenyl, fused arylheterocyclyl, heteroaryl, fused heteroarylcycloalkenyl, fused heteroarylcycloalkyl, fused heteroarylheterocyclenyl, or fused heteroarylheterocyclyl;

a=1;

A is 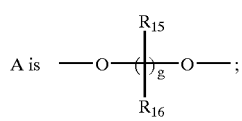

g=2, 3, 4 or 5;

$R_1$, $R_2$, $R_3$, $R_4$, $R_{15}$ and $R_{16}$ are hydrogen;

b=0 or 1;

c=0;

d=0;

B and E are a chemical bond;

Z is —CO$_2$H;

R' is hydrogen; and R" is lower alkyl.

Another aspect of this invention is a compound of formula I as described by formula (Ia) wherein (Ar I)

is independently aryl, fused arylcycloalkenyl, fused arylcycloalkyl, fused arylheterocyclenyl, fused arylheterocyclyl, heteroaryl, fused heteroarylcycloalkenyl, fused heteroarylcycloalkyl, fused heteroarylheterocyclenyl, or fused heteroarylheterocyclyl;

a=1;

A is —O—$\overset{R_{15}}{\underset{R_{16}}{(C)_g}}$—O—;

g=2, 3, 4 or 5;
$R_1$, $R_2$, $R_3$, $R_4$, $R_{15}$ and $R_{16}$ are hydrogen;
$R_7$ and $R_8$ are independently hydrogen;
b=0 or 1;
c=0;
d=1;
B and E are a chemical bond;
Z is —$CO_2H$;
R' and R" are ring system substituents as defined herein, more preferably, R' is hydrogen, lower alkyl, halo, alkoxy, aryloxy or aralkyloxy; and R" is lower alkyl, alkoxy, aralkoxy, cycloalkylalkoxy or halo.

Another aspect of this invention is a compound of formula I as described by formula (Ia) wherein (Ar I)

is independently aryl, fused arylcycloalkenyl, fused arylcycloalkyl, fused arylheterocyclenyl, fused arylheterocyclyl, heteroaryl, fused heteroarylcycloalkenyl, fused heteroarylcycloalkyl, fused heteroarylheterocyclenyl, or fused heteroarylheterocyclyl;

a=1;

A is —O—$\overset{R_{15}}{\underset{R_{16}}{(C)_g}}$—O—;

g=2, 3, 4 or 5;
$R_1$, $R_2$, $R_3$, $R_4$, $R_{15}$ and $R_{16}$ are independently hydrogen;
$R_7$ and $R_8$ are hydrogen
b=0 or 1;
c=0;
d=1;
B and E are a chemical bond;
Z is —$CO_2H$;
R' is hydrogen; and R" is lower alkyl.

Another aspect of this invention is a compound of formula I as described by formula (Ia) wherein:
a=0–2;
b=0–1;
A is —O— or —$NR_{13}$—;
$R_1$, $R_2$, $R_3$ and $R_4$ are independently hydrogen;
$R_{13}$ is hydrogen, $R_{22}OC$—, or alkyl;
c=0;
d=0;
B and E are a chemical bond;
Z is —$CO_2H$;
R' and R" are ring system substituents as defined herein, more preferably, R' is lower alkyl, halo, alkoxy, aryloxy or aralkyl; and R" is lower alkyl or halo.

A more preferred aspect of this invention is a compound of formula I as described by formula (Ia) wherein:
a 1 or 2;
A is —O—;
b=0;
$R_1$, $R_2$, $R_7$ and $R_8$ are independently hydrogen;
c=0;
d=1;
B and E are a chemical bond;
R' is hydrogen, halo or benzyloxy;
R" is lower alkyl, preferably methyl;
Z is —$CO_2H$.

A more preferred aspect of this invention is a compound of formula I as described by formula (Ia) wherein:
a=1 or 2;
A is —O—;
b=0;
$R_1$, $R_2$, $R_7$ and $R_8$ are independently hydrogen;
c=0;
d=1;
B and E are a chemical bond;
R' is hydrogen, halo or benzyloxy;
R" is lower alkyl, preferably methyl;
Z is —$CO_2H$.

A more preferred aspect of this invention is a compound of formula I as described by formula (Ia) wherein:
a=1 or 2;
A is —O—;
b=0;
$R_1$, $R_2$, $R_7$, $R_8$ are independently hydrogen;
c=0;
B is —O—;
d=1;
B and E are a chemical bond;
R' is halo;
R" is lower alkyl, preferably methyl;
Z is —$CO_2H$.

A more preferred aspect of this invention is a compound of formula I as described by formula (Ia) wherein:
a=1;
$R_1$ and $R_2$ are hydrogen
A is —O—;
b=0;
c=0;
d=0;
B and E are a chemical bond;
R' is hydrogen, aralkoxy, or halo;
R" is lower alkyl, preferably methyl;
Z is —$CO_2H$.

A more preferred aspect of this invention is a compound of formula I as described by formula (Ia) wherein:
a=1;
A is —O—;
b=0;
c=0;
d=0;
B and E are a chemical bond;
R' is hydrogen;
R" is lower alkyl;
Z is —CO$_2$H.

A more preferred aspect of this invention is a compound of formula I as described by formula (Ia) wherein:

(Ar I)

is aryl or heteroaryl;
a=1;
A is —O—;
b=0;
c=0;
d=0;
B and E are a chemical bond;
R' is hydrogen;
R" is lower alkyl;
Z is —CO$_2$H.

A more preferred aspect of this invention is a compound of formula I as described by formula (Ia) wherein:

(Ar I)

is optionally substituted azaheteroaryl;
a=1;
A is —O—;
b=0;
c=0;
d=0;
B and E are a chemical bond;
R' is hydrogen;
R" is lower alkyl;
Z is CO$_2$H.

A more preferred aspect of this invention is a compound of formula I as described by formula (Ia) wherein:

(Ar I)

is optionally substituted quinolinyl, or a 5-membered heteroaryl group wherein the heteroaryl group is substituted by optionally substituted phenyl or optionally substituted cyclohexyl;
a=1;
A is —O—;

b=0;
c=0;
d=0;
B and E are a chemical bond;
R' is hydrogen;
R" is lower alkyl;
Z is CO$_2$H.

A preferred compound according to the invention is selected from the group consisting of

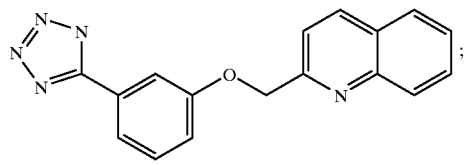

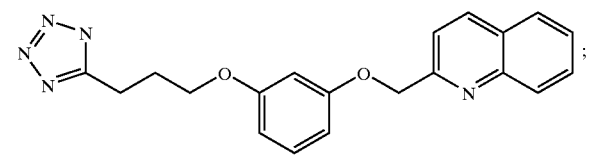

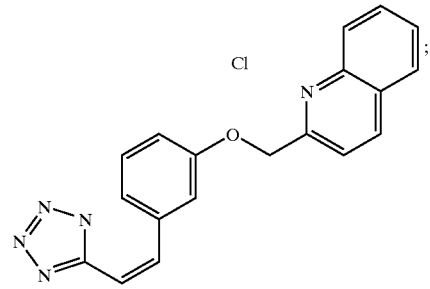

180° C.

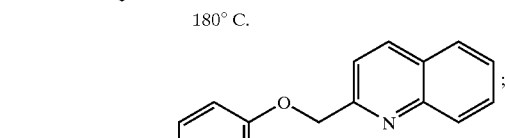

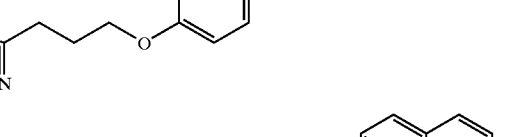

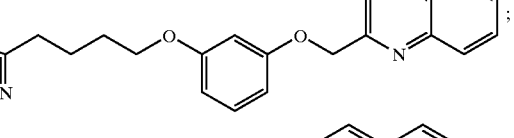

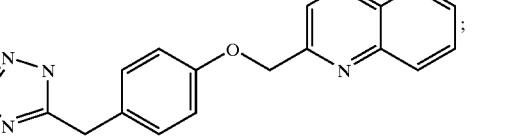

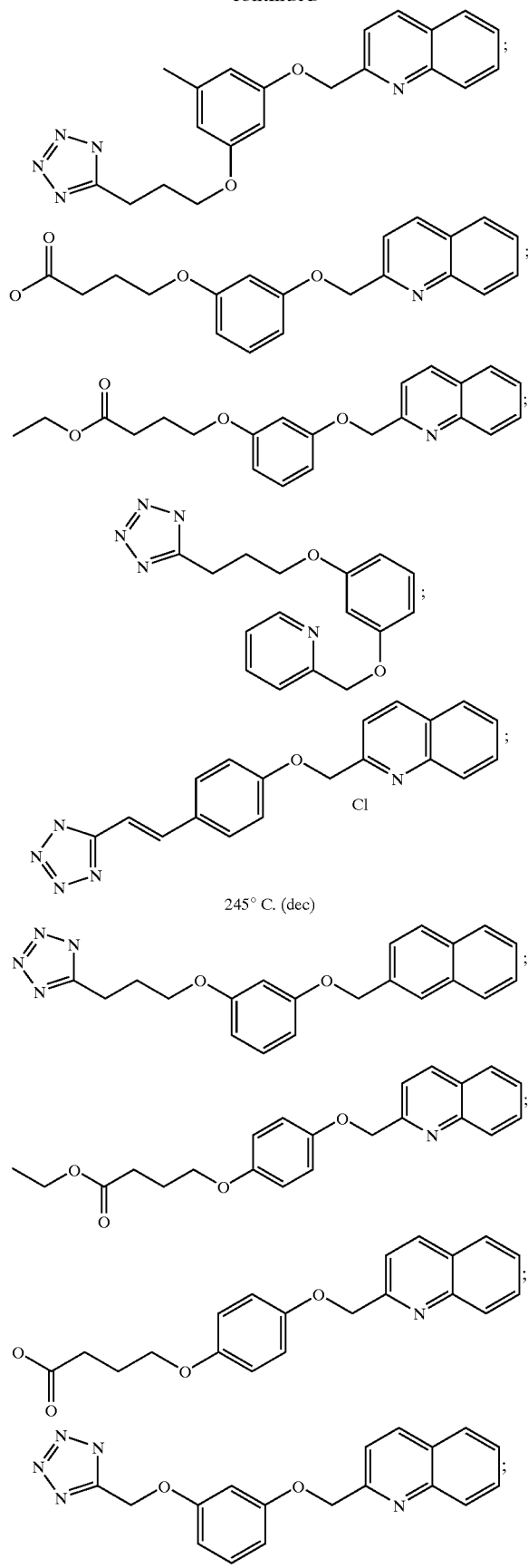
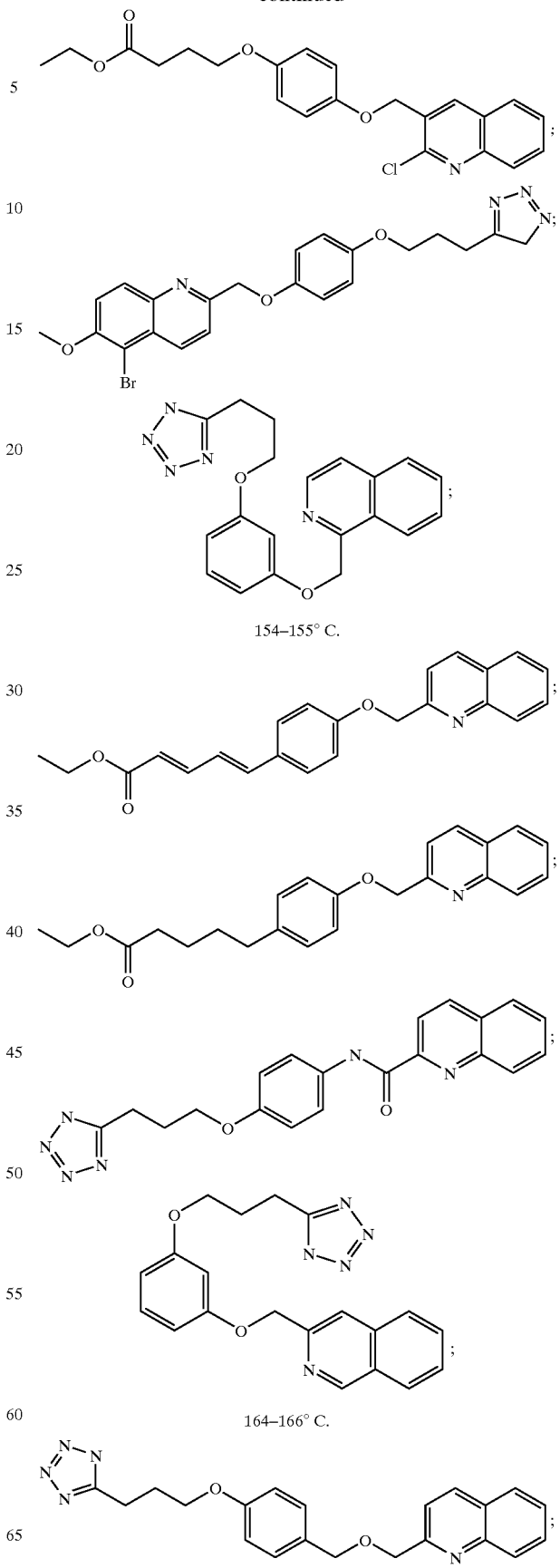
154–155° C.
245° C. (dec)
164–166° C.

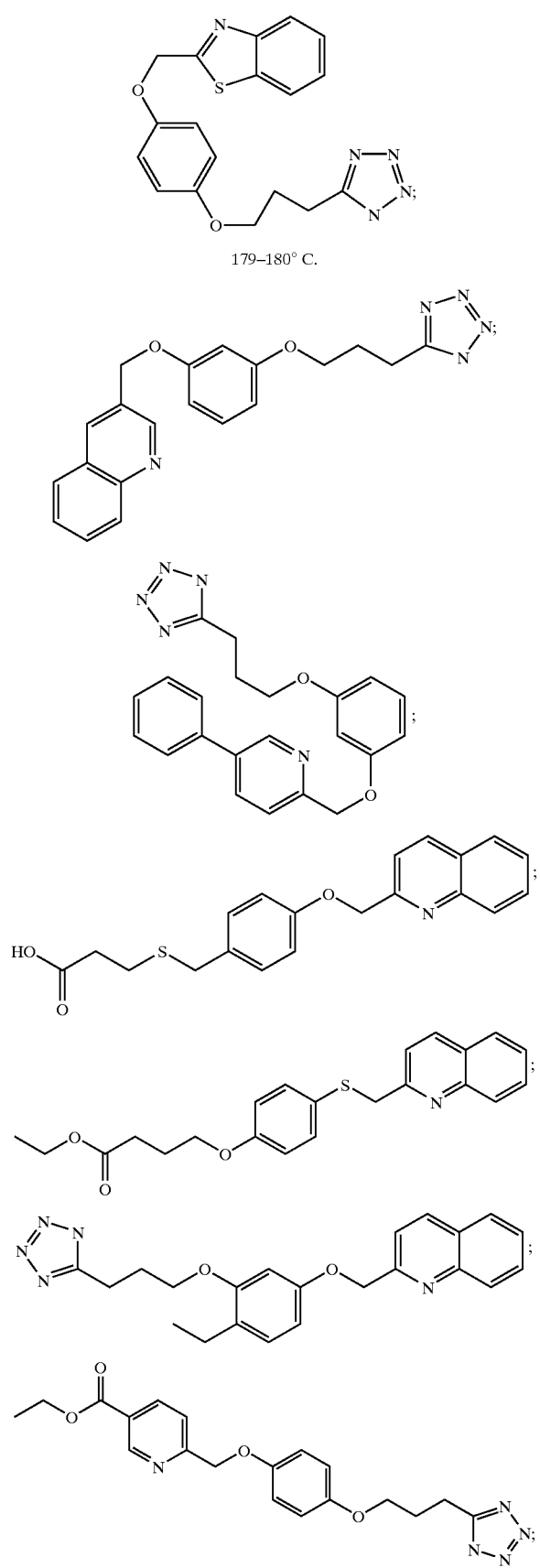

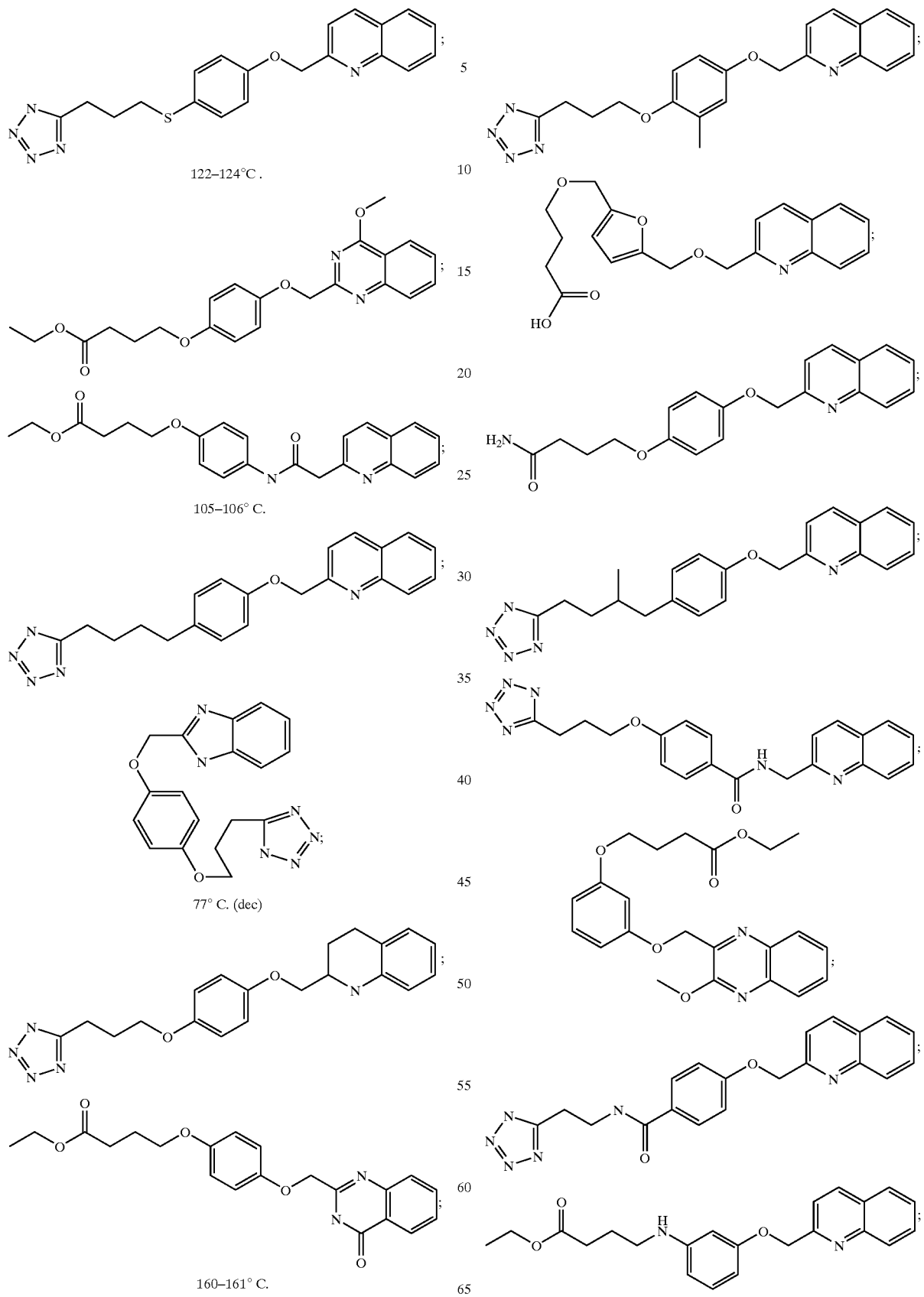

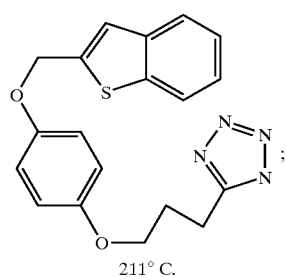
211° C.
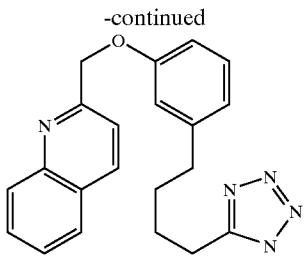
149–150° C.
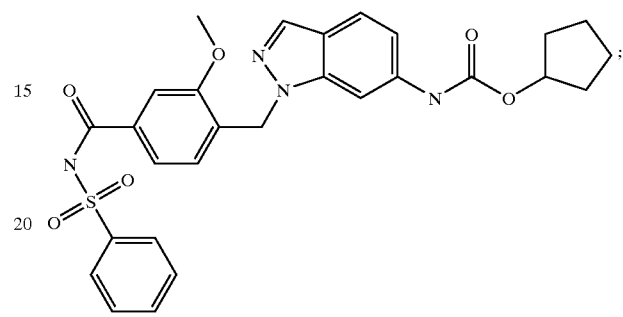
187° C.
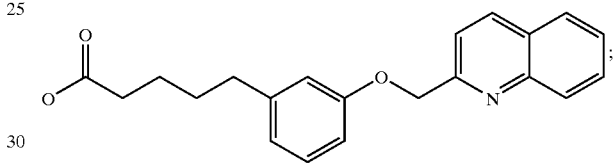
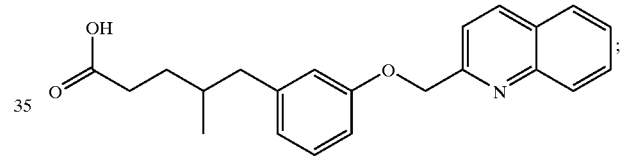
171–173° C.
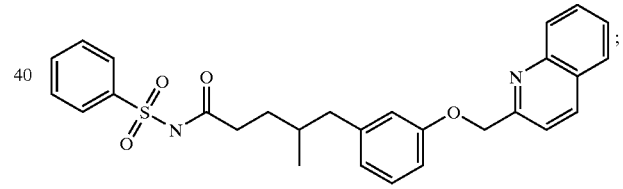
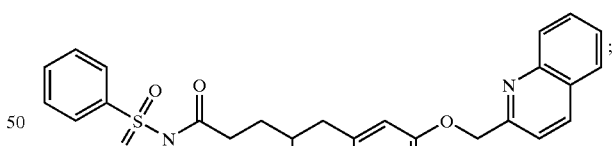
80–82° C.
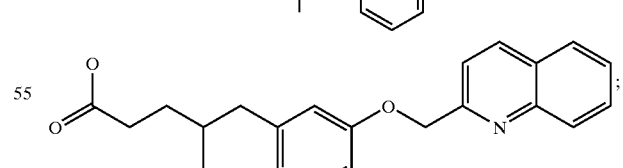
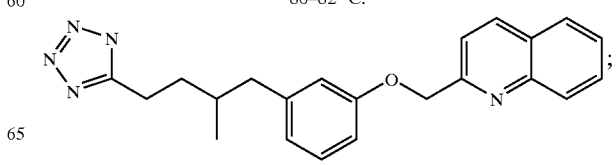
89–91° C.

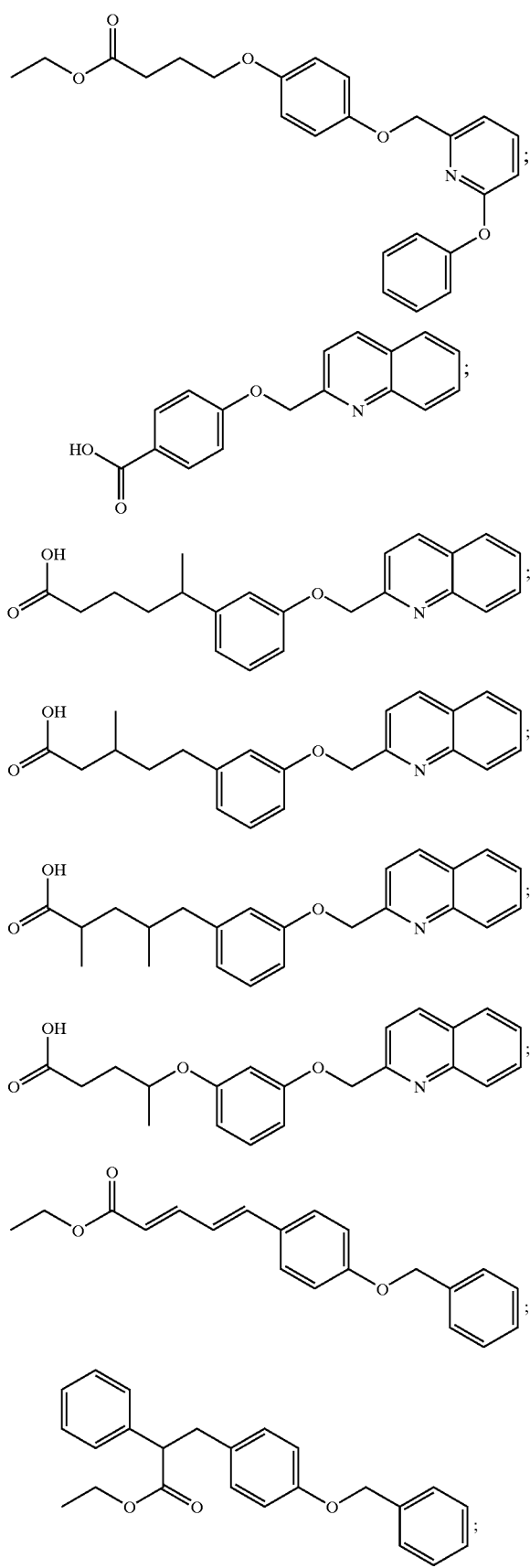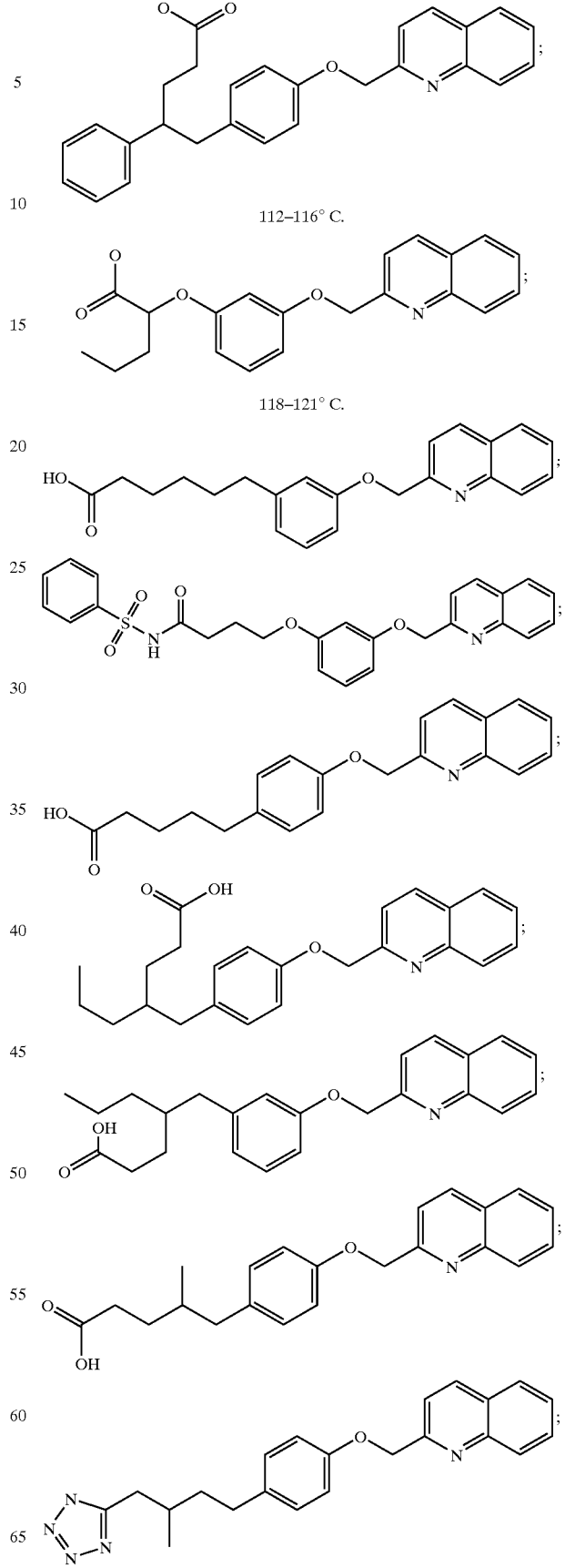
112–116° C.
118–121° C.

-continued

129–133° C.

138° C.

177–179° C.

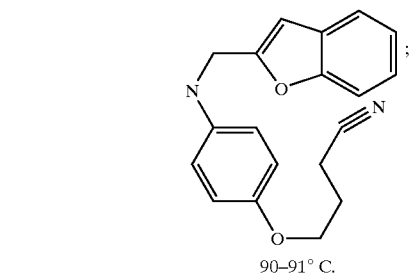
90–91° C.
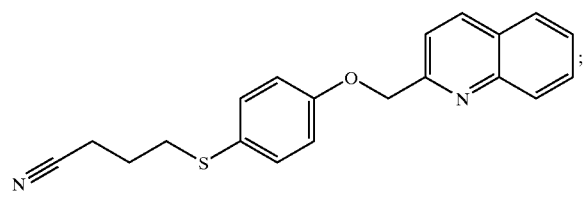
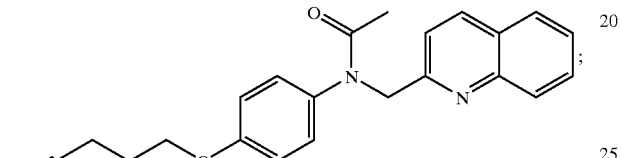
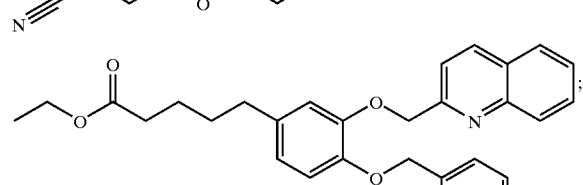
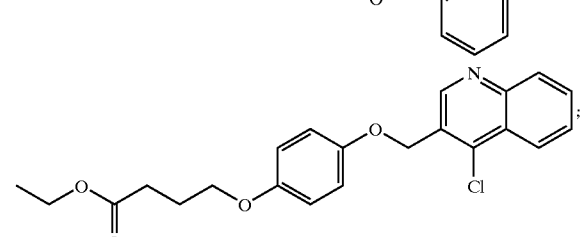
90–91° C.
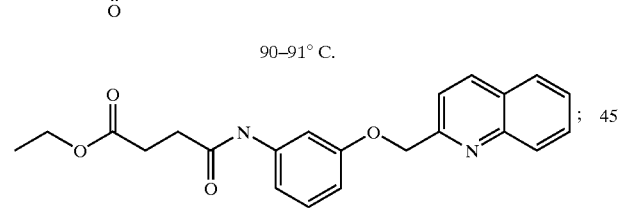
98–100° C.
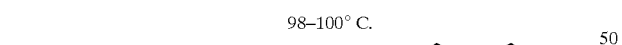
123–126° C.
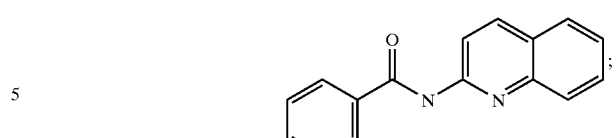
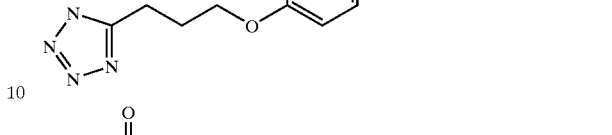
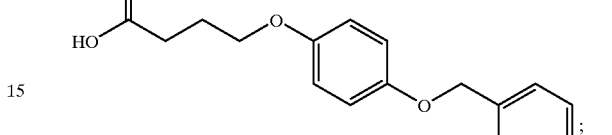
262° C. (dec)
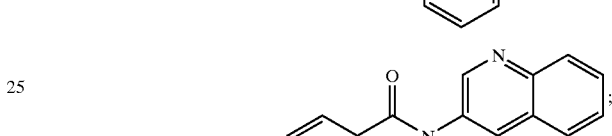
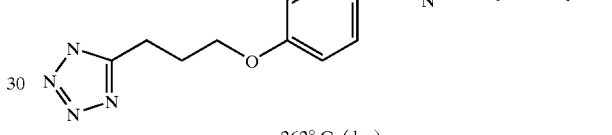
176–181° C.
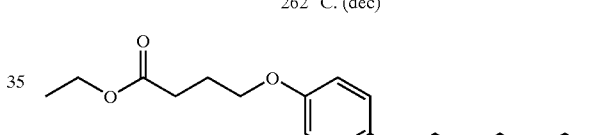
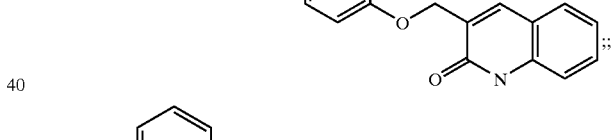

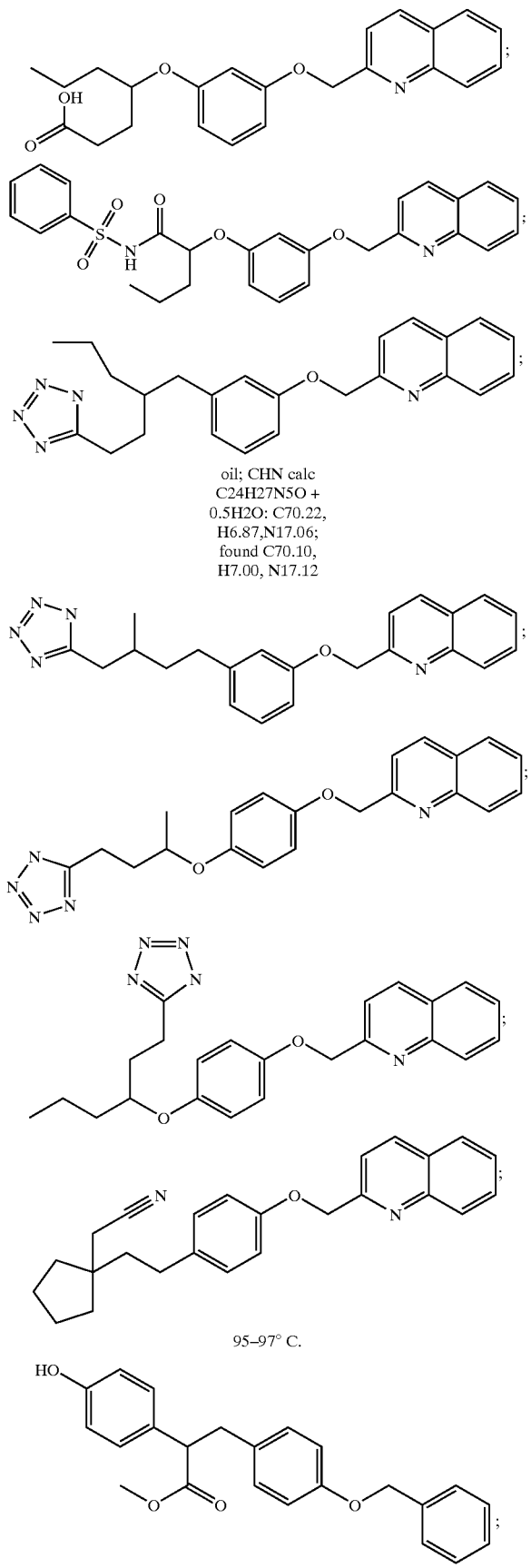
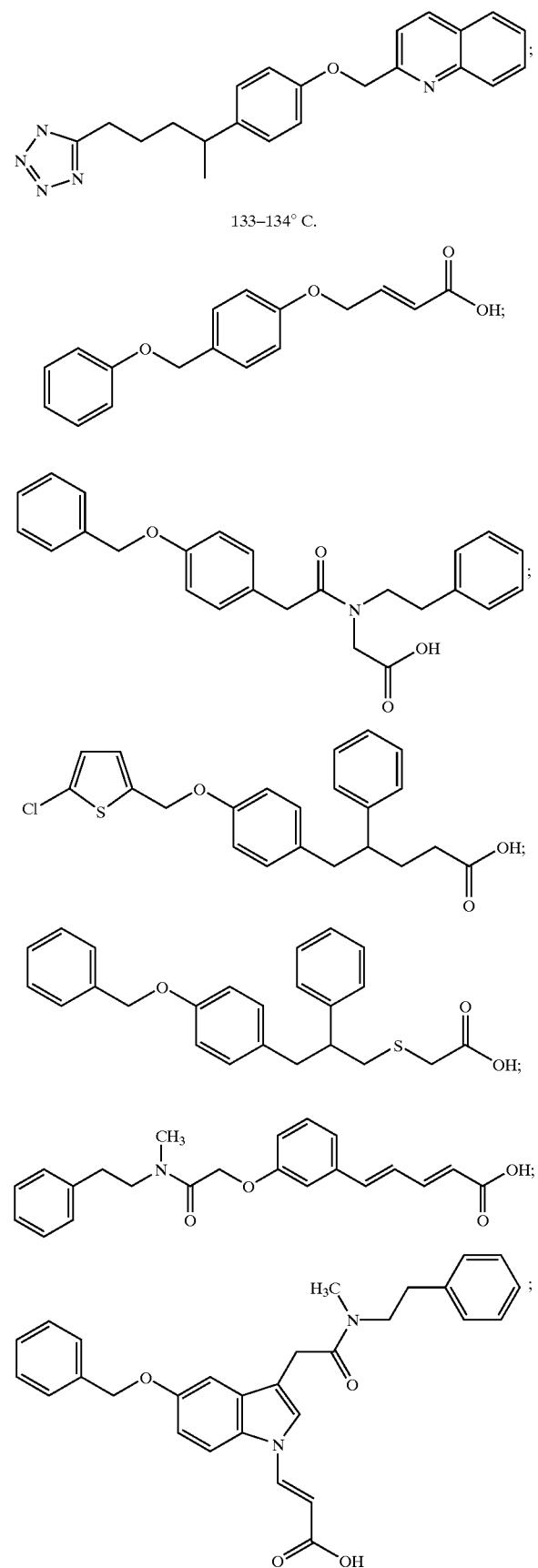

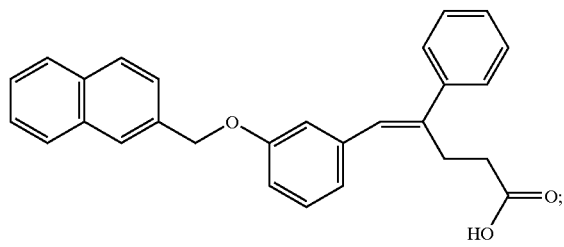
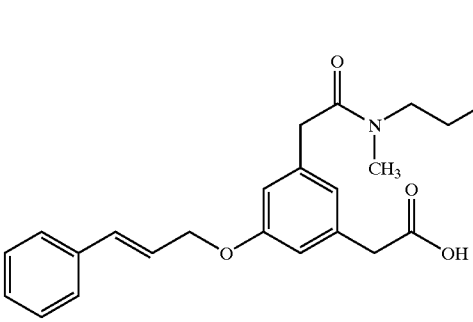
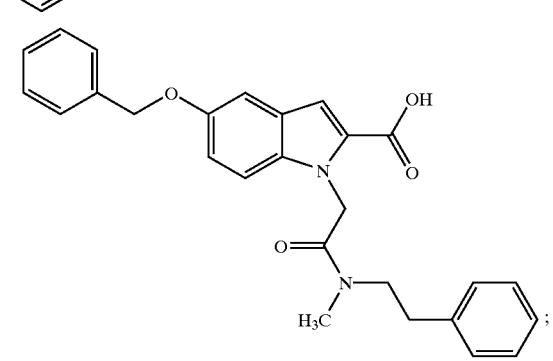
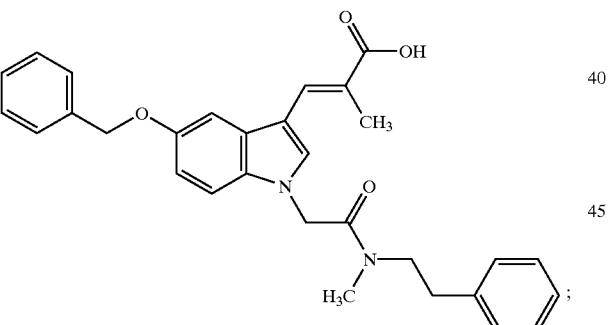
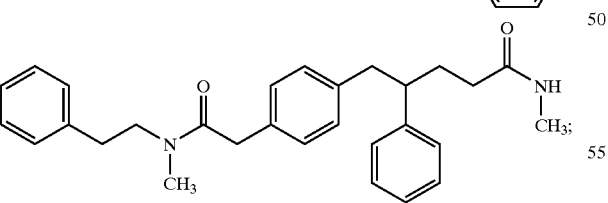
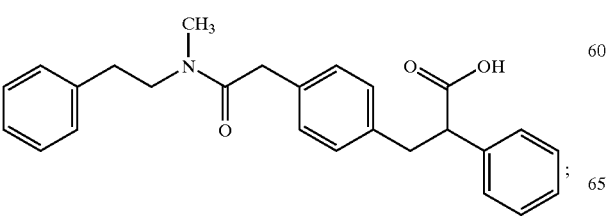
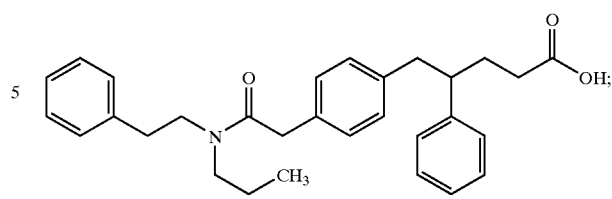
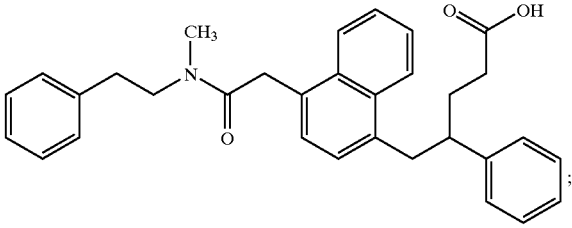
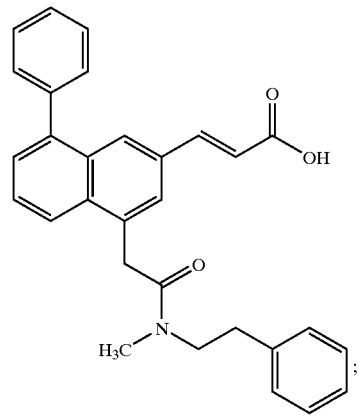
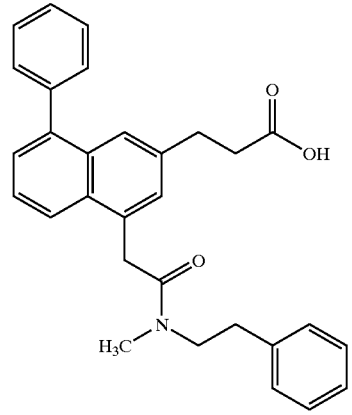
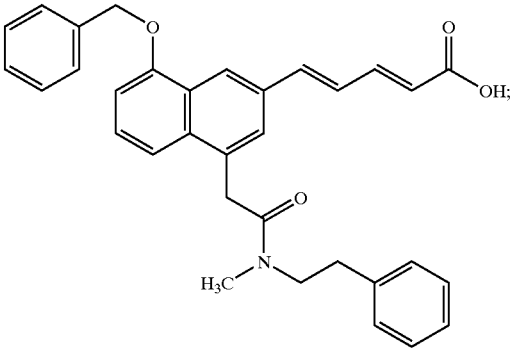

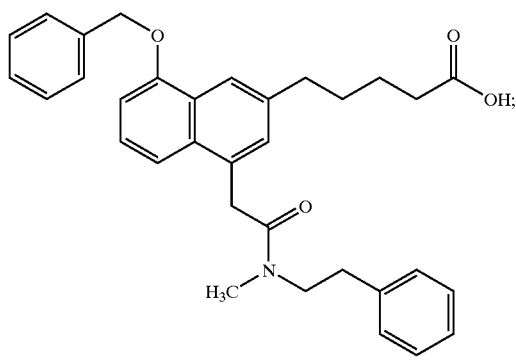
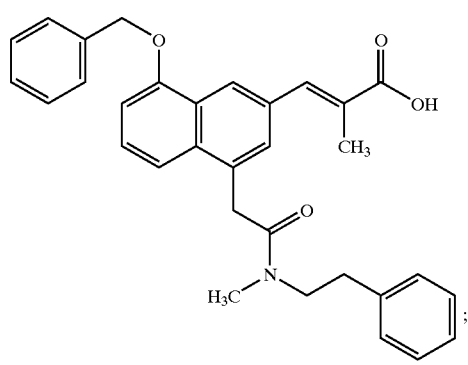
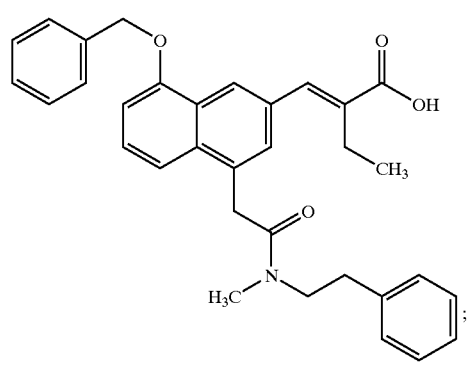
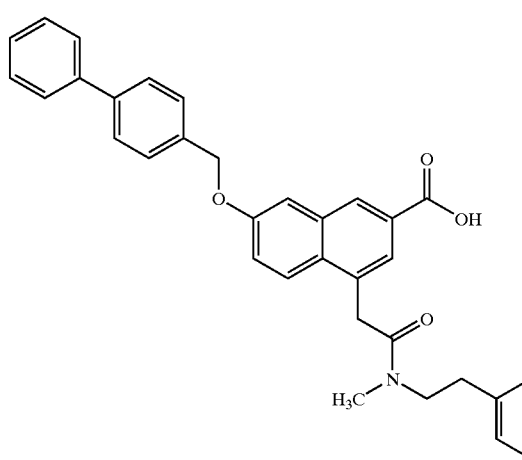
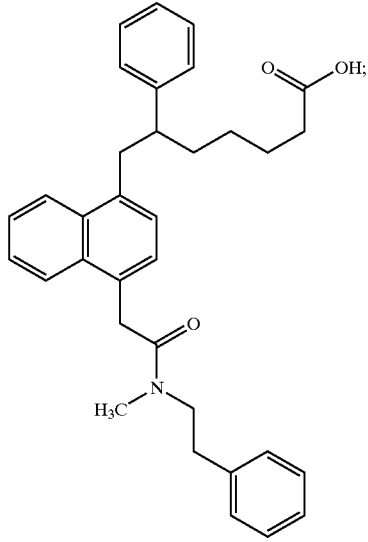
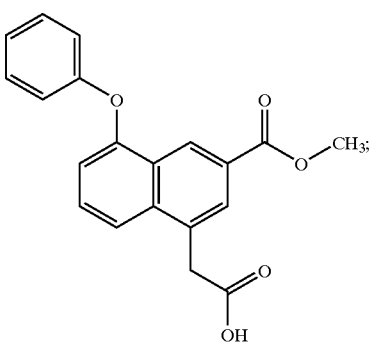
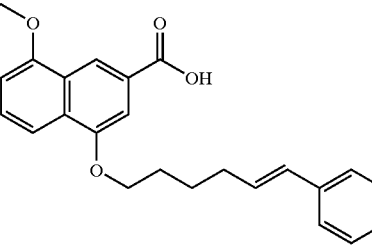
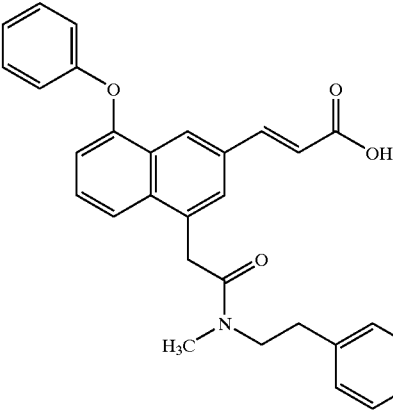

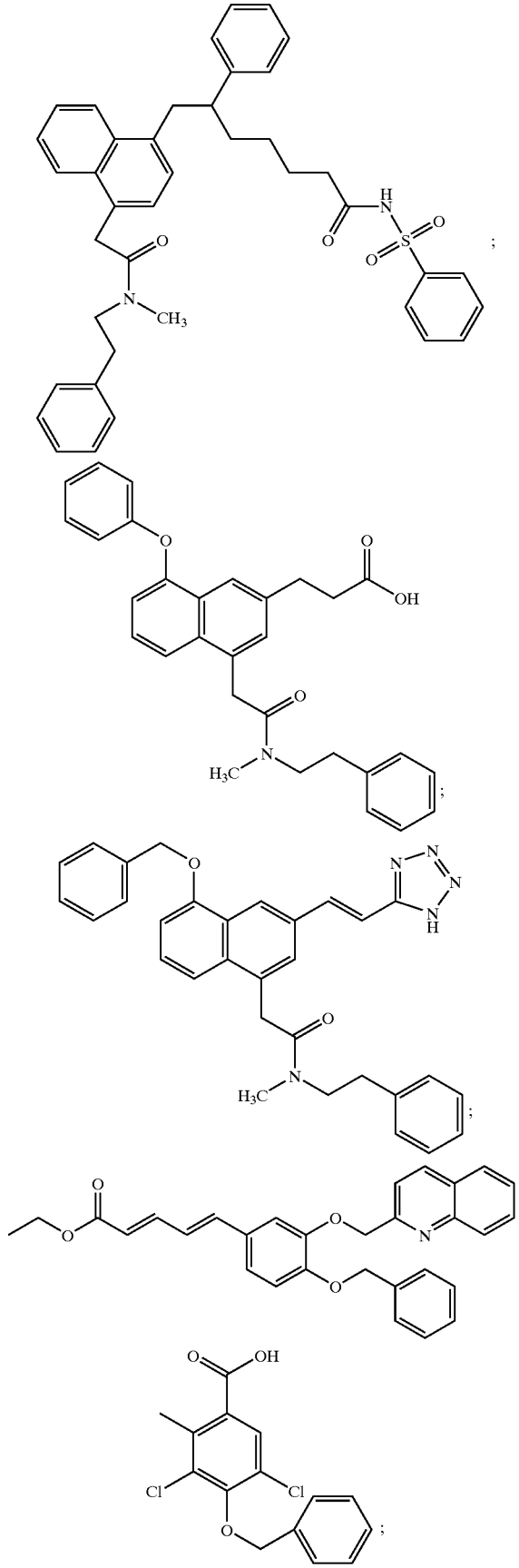
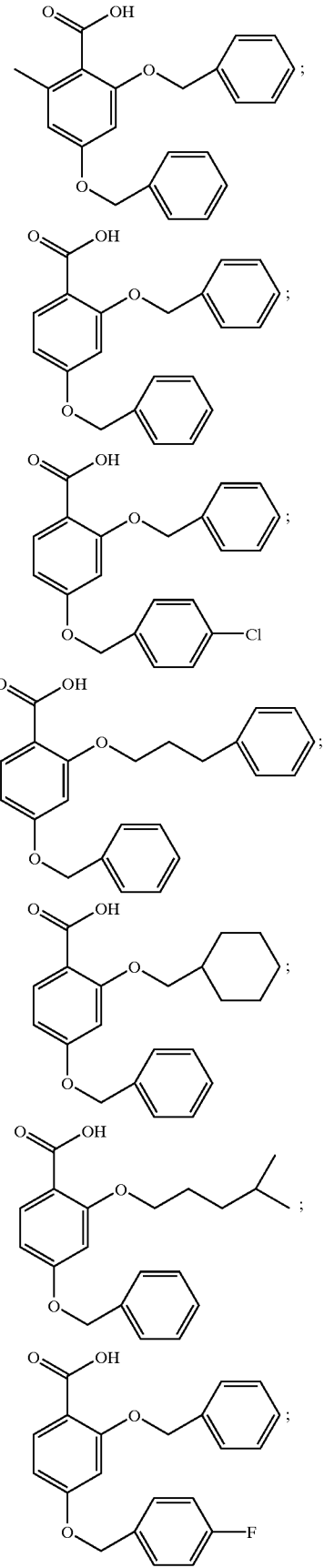

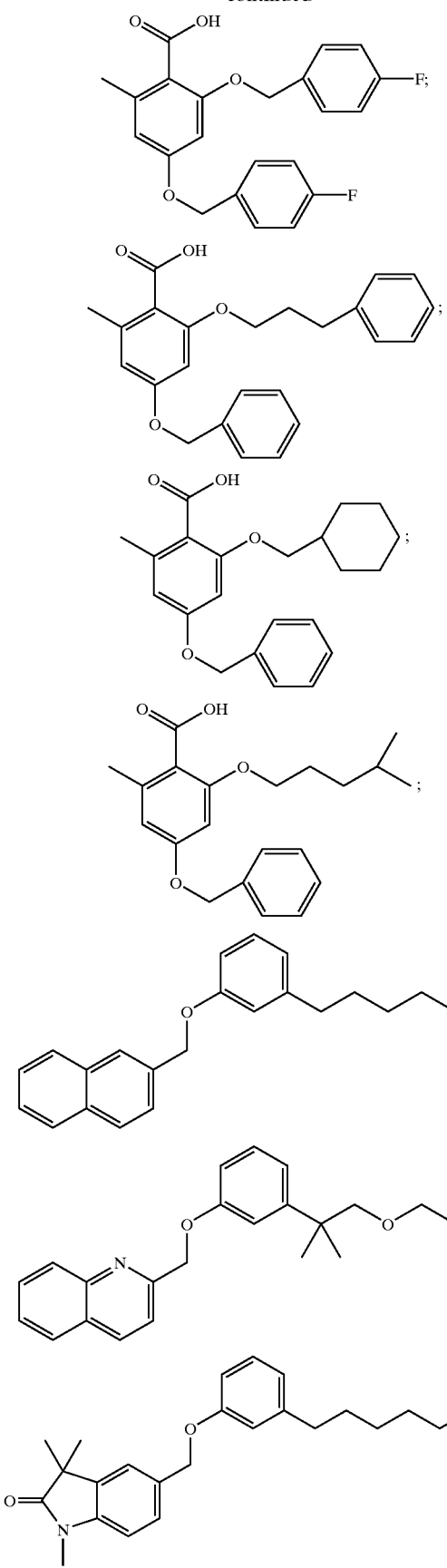
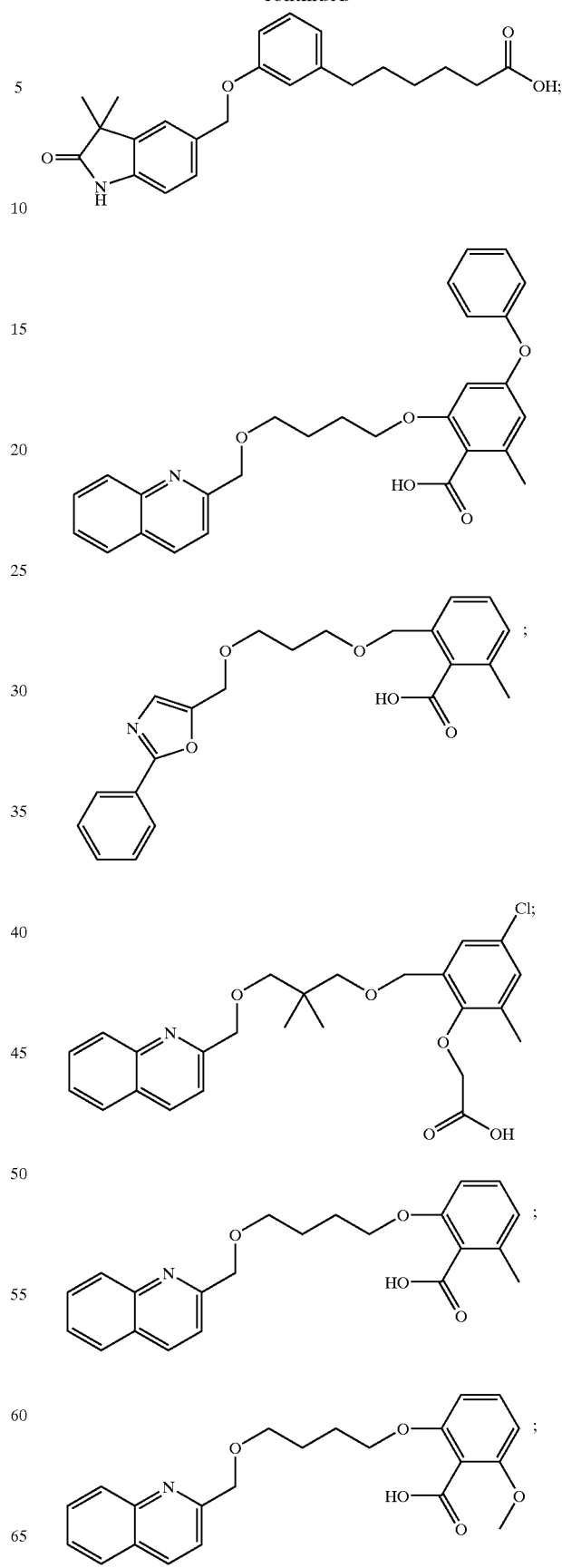

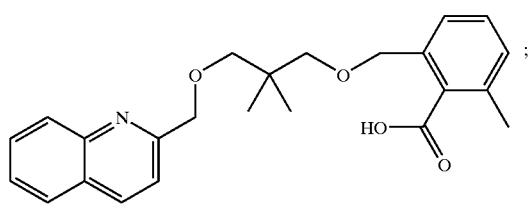
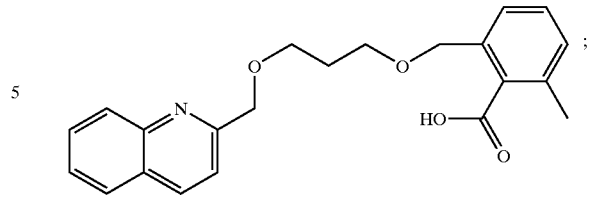
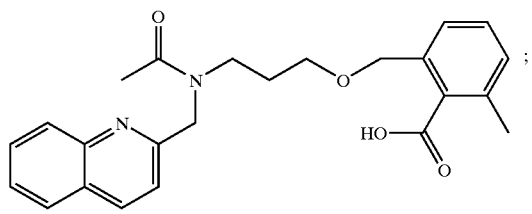
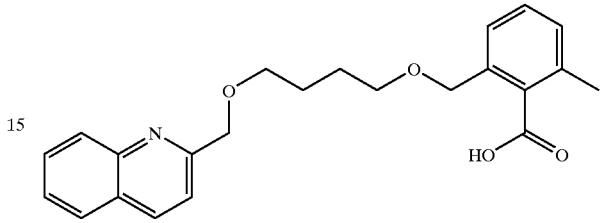
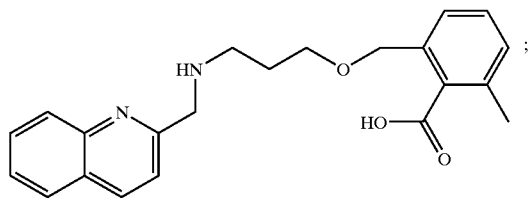
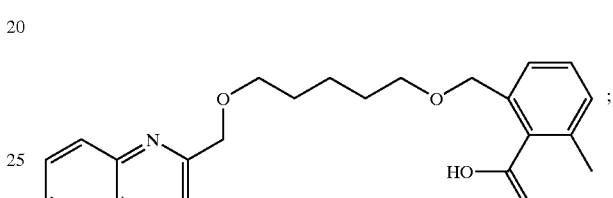
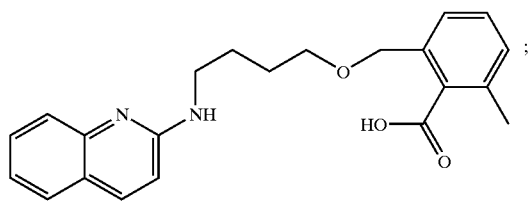
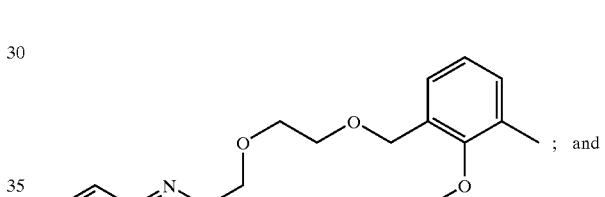
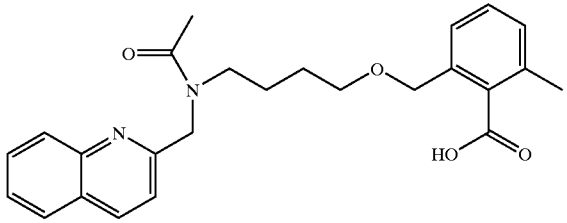
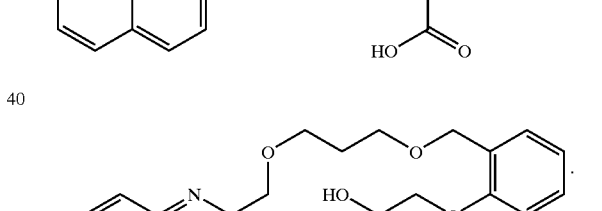
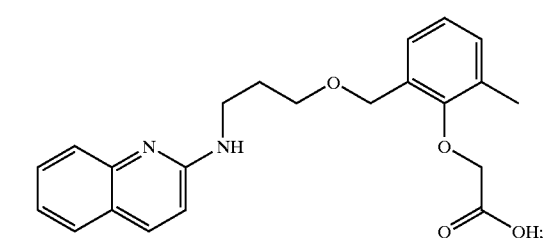
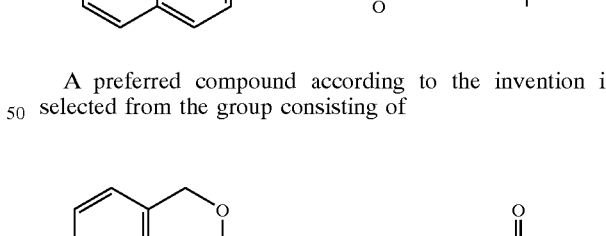
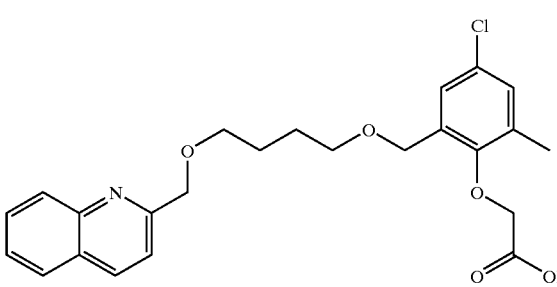
A preferred compound according to the invention is selected from the group consisting of
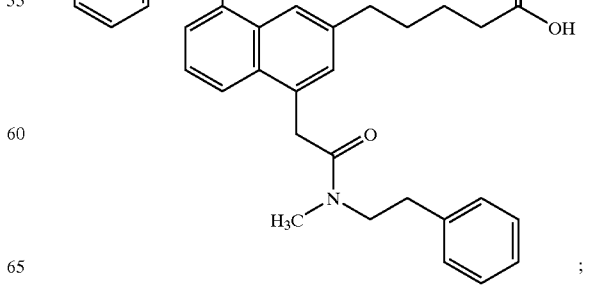

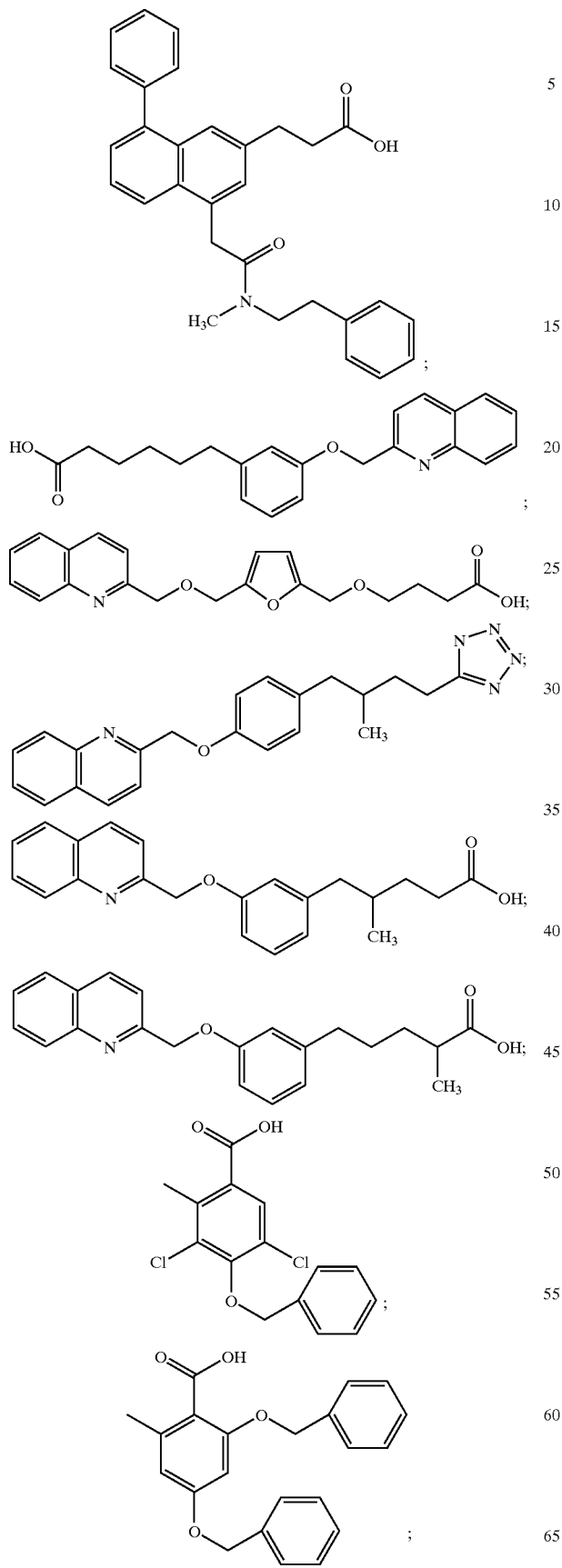
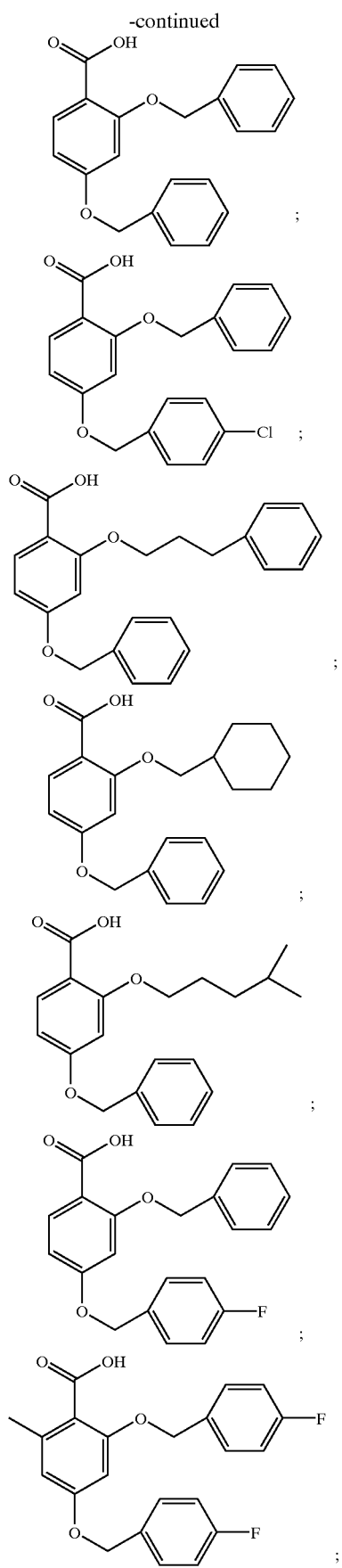

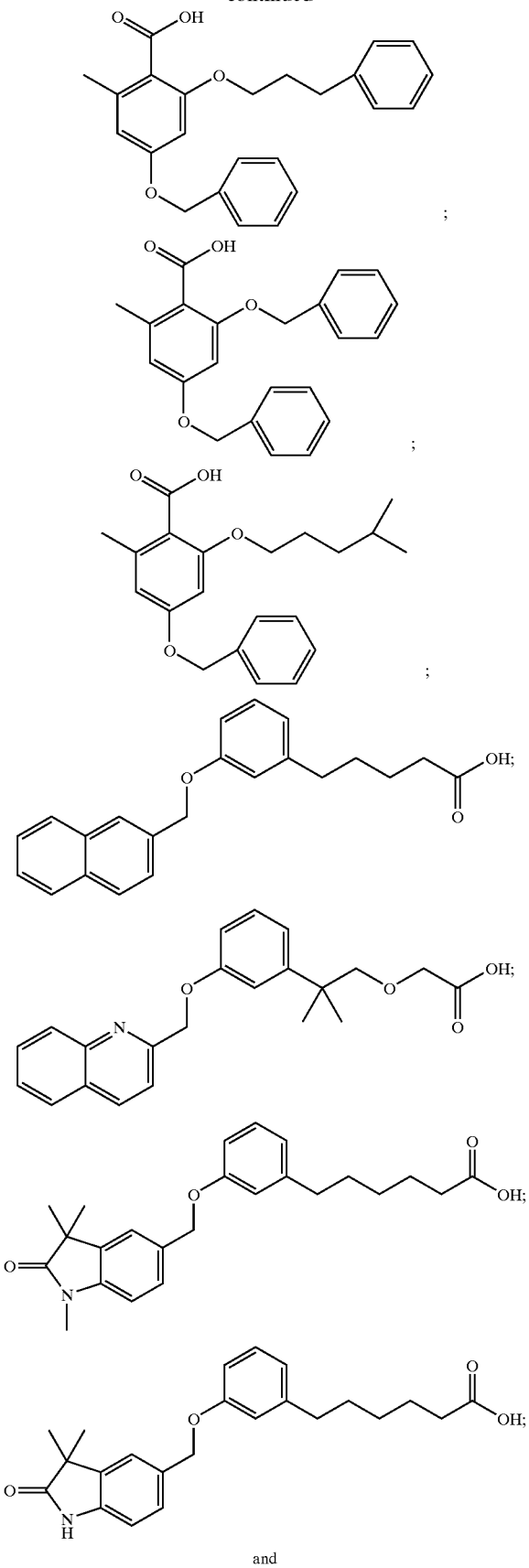
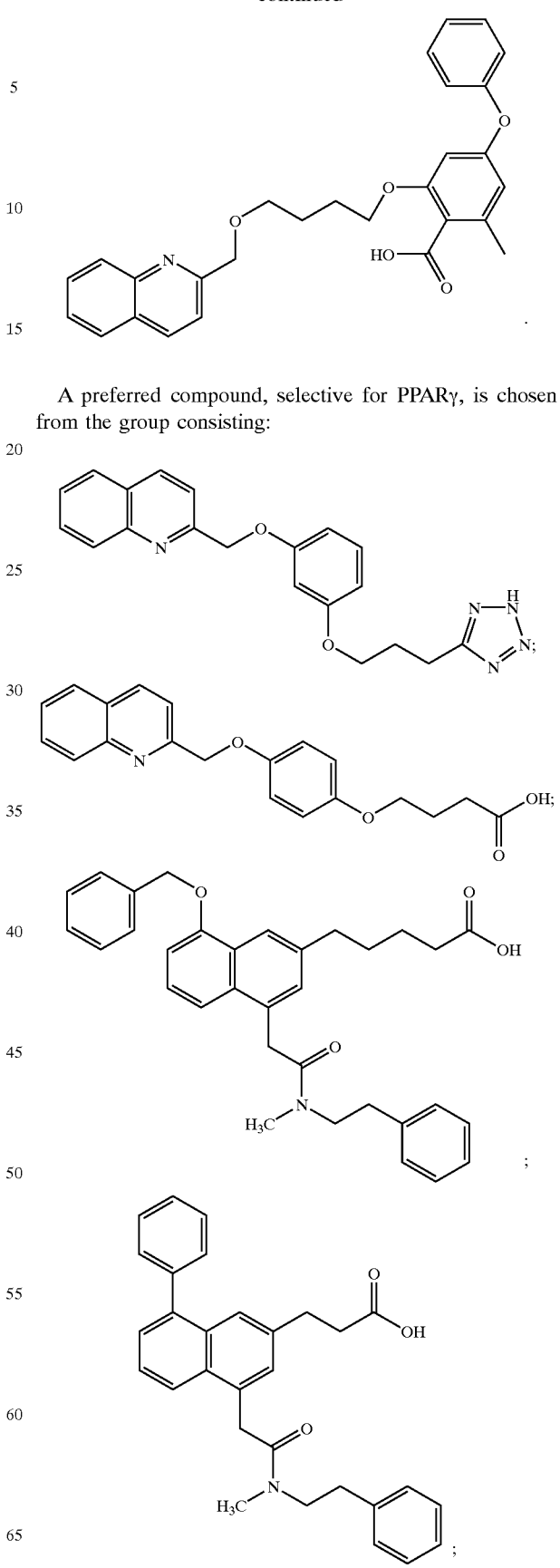
A preferred compound, selective for PPARγ, is chosen from the group consisting:

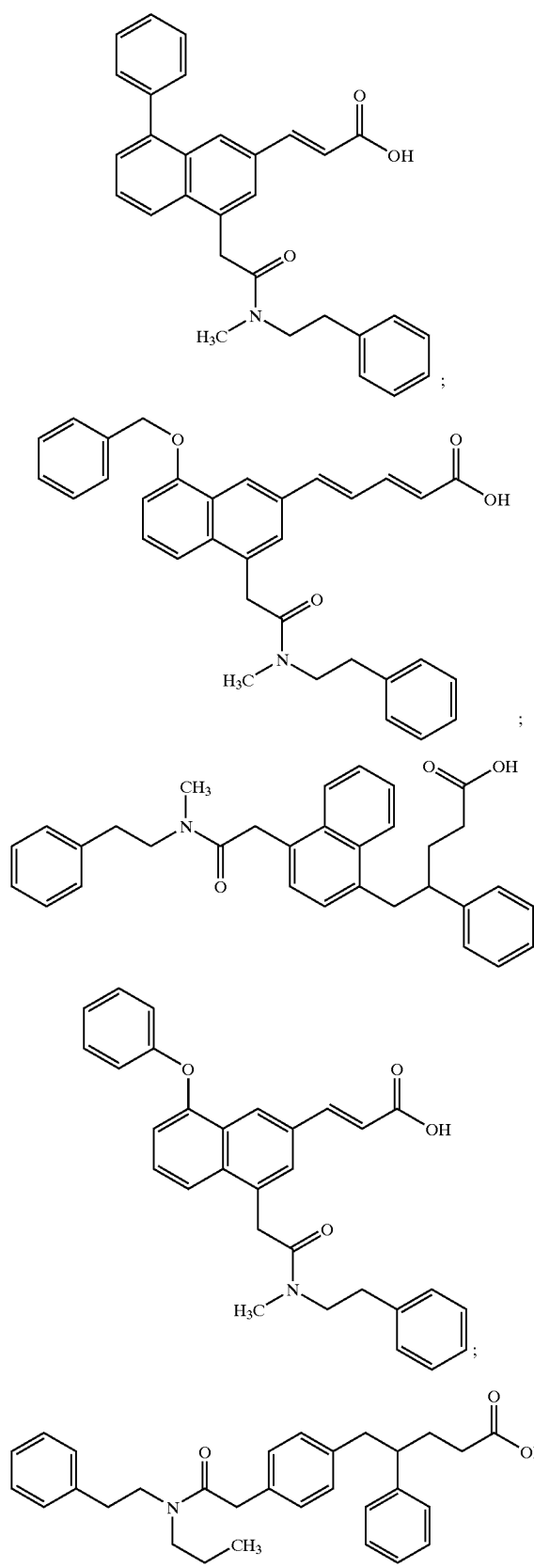
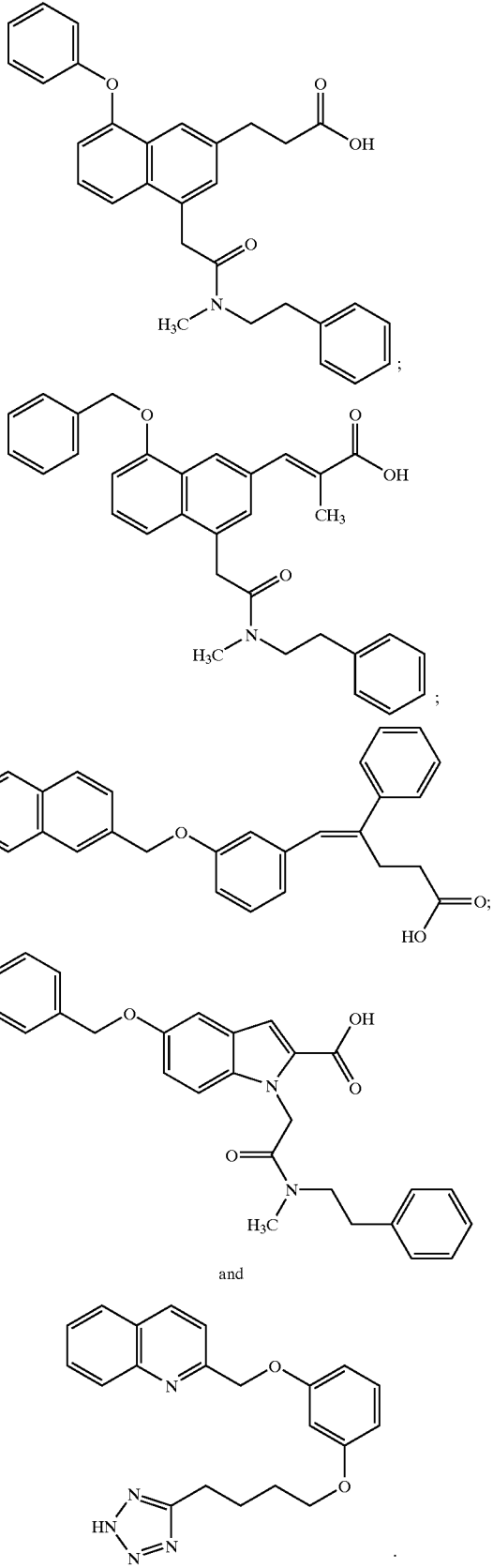
and

A preferred compound, selective for PPARα, is chosen from the group consisting:

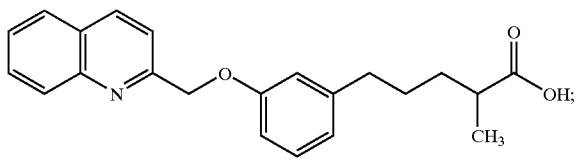

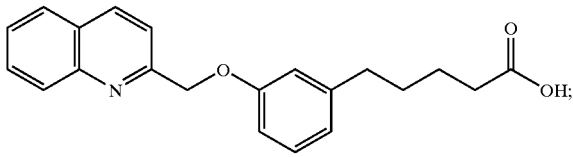

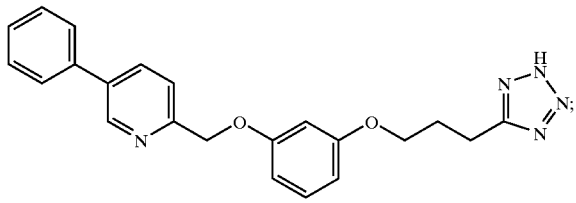

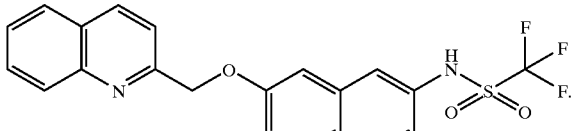

and

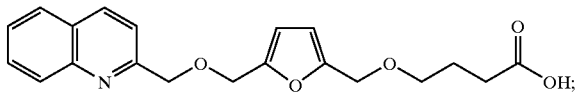

A preferred compound having PPARα and PPARδ activity is selected from the group consisting:

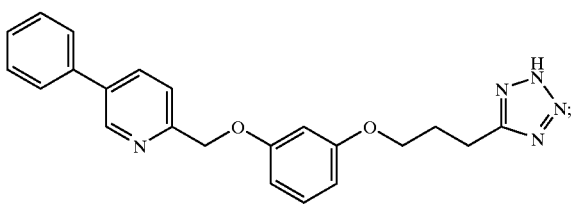

and

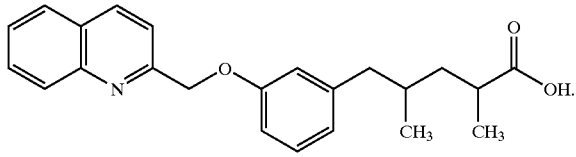

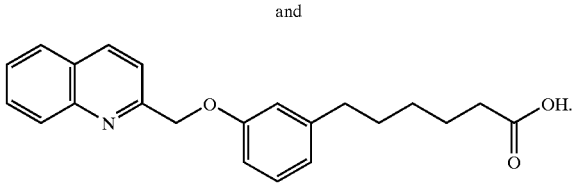

A preferred compound having PPARα and PPARγ activity is selected from the group consisting:

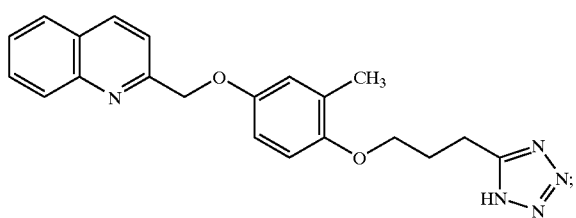

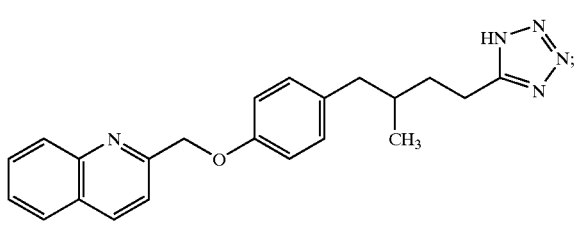

This invention also encompasses all combinations of preferred aspects of the invention described herein.

Compounds useful according to this invention can be prepared by the methods disclosed herein as well as the specific examples and in the following references which are incorporated herein by reference: Galemmo, Robert A., Jr et. al, J. Med. Chem. (1990), 33(10), 2828–41; Youssefyeh, Raymond D. et al, J. Med. Chem. (1990), 33(4), 1186–94; Youssefyeh, Raymond et. al, International patent publication no. WO 8705510; Astles, Peter Charles et. al., International patent publication no. WO 9513262, Jayossi et al, International patent application Ser. No. PCT/US00/11490 in the name of Aventis Pharmeuticals Products Inc, filed on Apr. 28$^{th}$ 2000; and Jayossi et al, U.S. non-provisional patent application titled "Therapeutic uses of Tri-Aryl Acid Derivatives" in the name of Jayossi et al., Ser. No. 50/131,454 filed on Apr. 28$^{th}$ 1999, incorporated herein in their entirety.

Compounds useful according to this invention can be prepared in segments, as is common to a long chain molecule. Thus, it is convenient to synthesize these molecules by employing condensation reactions at the A and B sites of the molecule. Compounds of Formula I can be prepared by the application or adaptation of known methods, by which is meant methods used heretofore or described in the literature.

For example, the synthetic methodology described in the following publications, the contents of which are incorporated herein by reference may be employed: "Development of a novel series of (2-quinolinylmethoxy)phenyl-containing compounds as high-affinity leukotriene receptor antagonists. 1. Initial structure-activity relationships." *J. Med. Chem.* (1990), 33(4), 1186–1194; "The development of a novel series of (quinolin-2-ylmethoxy)phenyl-containing compounds as high-affinity leukotriene receptor antagonists. 3. Structural variation of the acidic side chain to give antagonists of enhanced potency." *J. Med. Chem.* (1990), 33(10), 2828–41; "A Novel Series of [2-(Methylphenethylamino)-2-oxoethyl]benzene-Containing Leukotriene B4 Antagonists: Initial Structure-Activity Relationships." *J. Med. Chem.* (1996), 39(19), 3748–3755; and 'Structure-Activity Relationships Study of Two Series of Leukotriene B4 Antagonists: Novel Indolyl and Naphthyl Compounds Substituted with a 2-[Methyl(2-phenethyl)amino]-2-oxoethyl Side Chain." *J. Med. Chem.* (1996), 39(19), 3756–3768.

Additional methodologies which can be used to synthesize construct compounds of this invention are described below. The coupling of an aryl-halide with a terminal alkyne using a Pd(0) catalyst (the Sonikashira coupling) or a variant thereof can be used to assemble molecules as described in Scheme 100.

Partial reduction using mild hydrogenation conditions, for example with a catalyst poison such as quinoline, can provide the cis olefin. Isomerization of the olefin can be accomplished, if desired, to provide the trans olefin. Either of these olefins can be used as intermediates for further elaboration. They also are compounds which, themselves, can act as PPAR modulators.

Reduction of the olefin can be accomplished by hydrogenation, for example $H_2$, Pd/C.

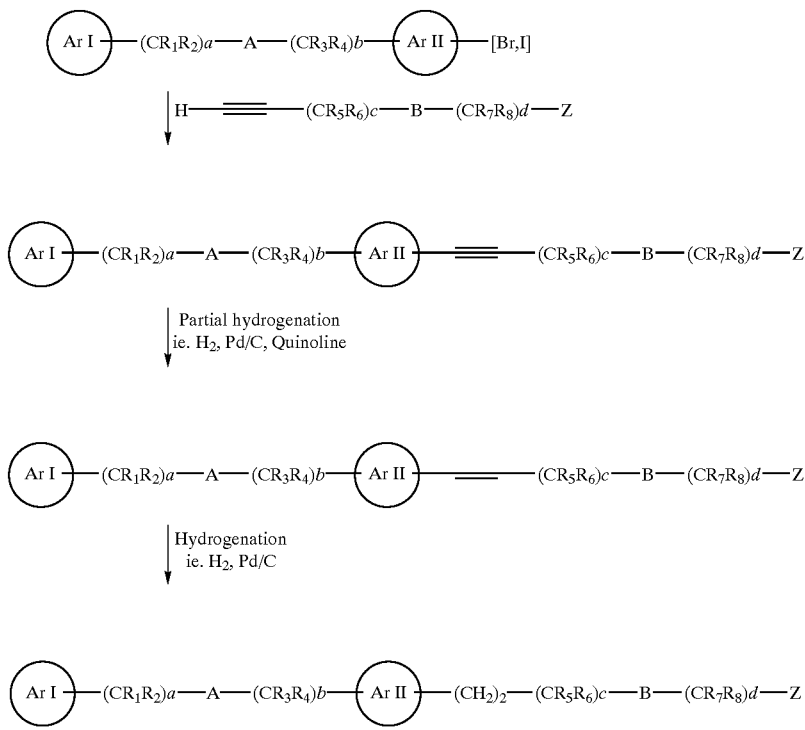

An example of an analog which can be prepared by using this chemistry is shown:

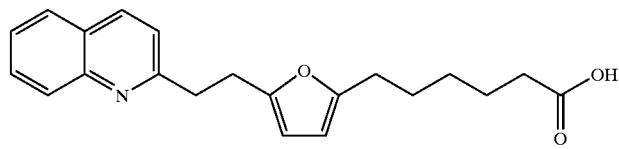

A modification of this chemistry is shown in Scheme 101 below. Coupling of the aryl halide and terminal alkyne provides an intermediate which can be subsequently reduced as above and then coupled with an intermediate having a leaving group L as described in earlier sections. Alternatively, each alkyne or alkene intermediate can be coupled with a fragment which contains a leaving group L to provide the corresponding alkynyl and alkenyl analogs.

Scheme 101

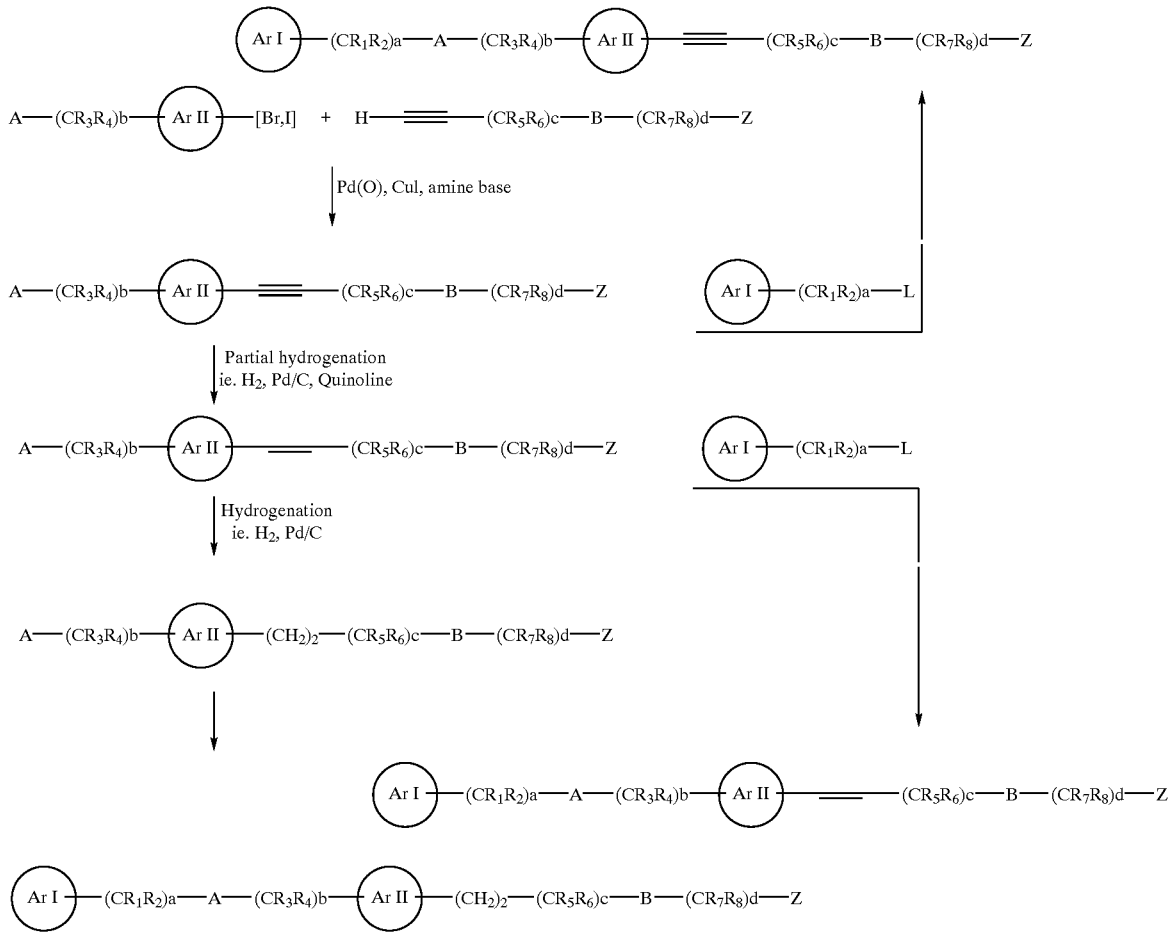

An example of an analog which can be prepared by using this chemistry is shown:

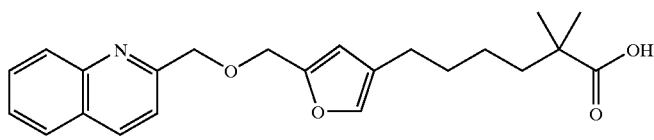

Additional chemistry which can be employed is shown in Scheme 102. Heteroaromatic systems which have an acidic C—H bond can be deprotonated with a base such as BuLi or a grignard reagent, and the resulting anion can be reacted with an electrophile such as an aldehyde, ketone, carboxylic acid derivative, epoxide, etc. as shown.

Scheme 102

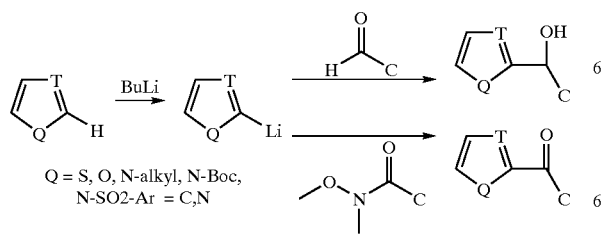

-continued

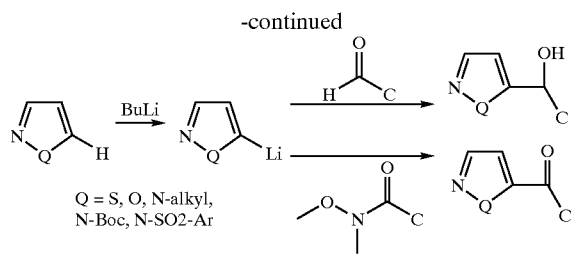

A further elaboration of this chemistry is shown in scheme 103, wherein a heteroaromatic ring is deprotonated with a base such as BuLi and the anion is condensed with an aldehyde. The resulting alcohol can be deoxygenated using conditions such as Barton's tin hydride mediated reduction of a thiono carbamate or zanthate or by using conditions for the reduction of benzylic alcohols such as Et3SiH, TFA. A representative example of the condensation product is shown.

Scheme 103

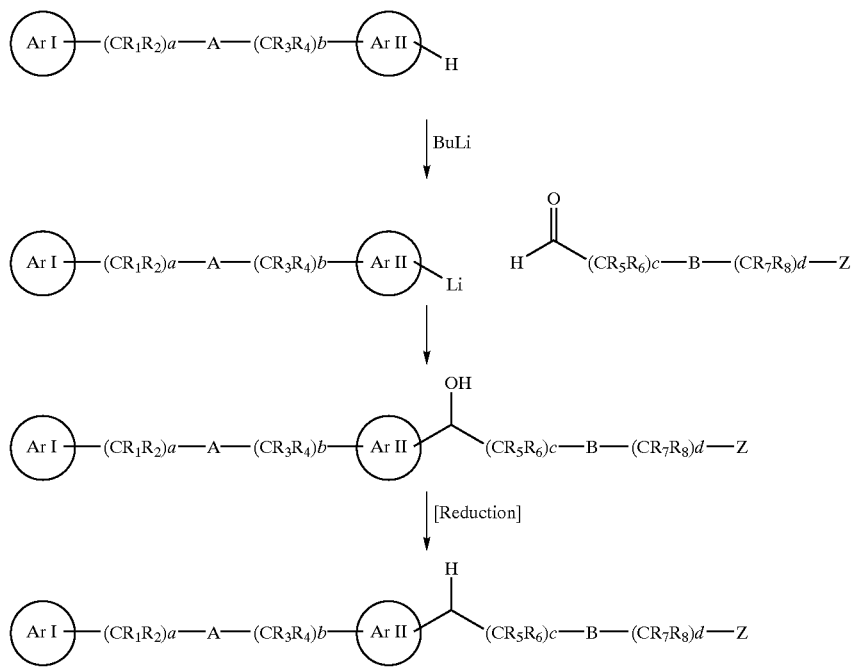

An example of an condensation product which can be prepared by using this chemistry is shown

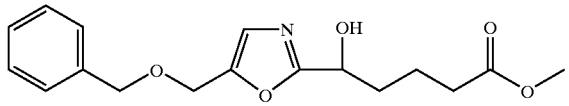

In another embodiment of this invention Ar I or Ar II is defined as a benzofuran. This type of ring system can be assembled in various ways using literature methods (for examples, see Friedlichsen, W. in *Comprehensive Heterocyclic Chemstry II*, Vol 2. Katritzky, A. R.; Rees, C. W.; Scriven, E. F. V. Eds. Elsevier Science 1996). A particularly suitable method with regard to this invention involves formation of a 2-methoxycarbonyl substituted benzofuran from a bromo substituted-ortho-hydroxy benzaldehyde, (Foster, R. T.; Robertson, A.; Bushra, A.; *J. Chem Soc.*, 1948, 2254) as illustrated in scheme 104. Ring closure is carried out in the presence of base such as sodium methoxide in methanol or lithium hexamethyldisilazide in a solvent such as THF, DME, DMPU or a mixture thereof, generally at a temperature between −78° C. and reflux. The resulting 2-methoxycarbonyl benzofuran can then be further derivatized, as illustrated in scheme 104 or as described elsewhere in this experimental section, to provide a variety of appositely substituted benzofurans.

Scheme 104

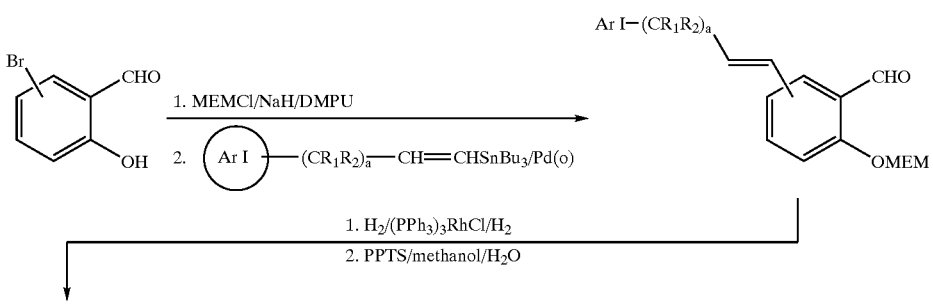

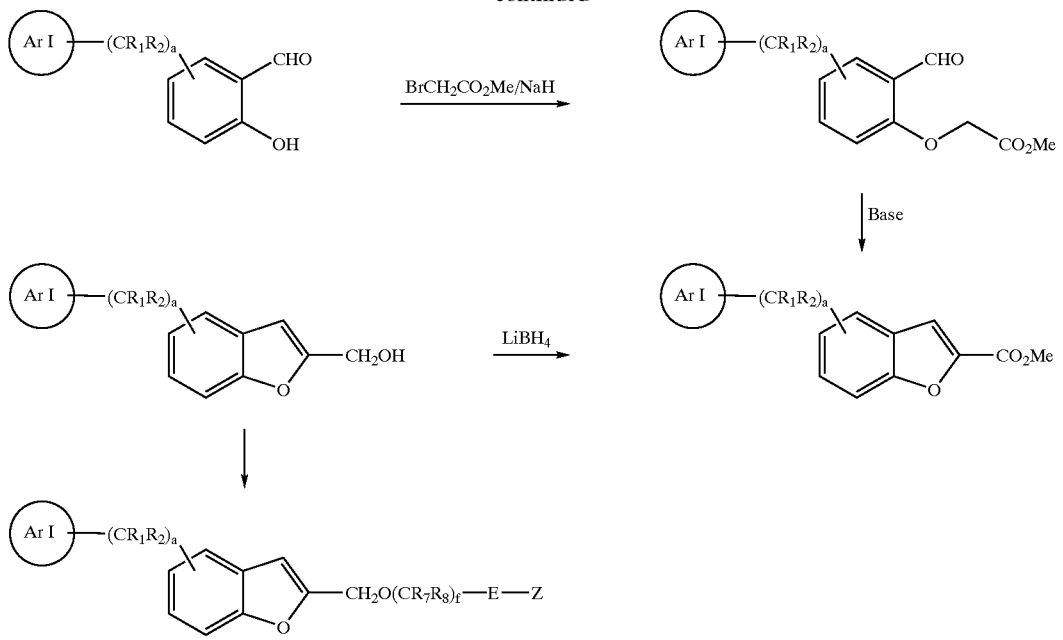

In one particular embodiment of this invention, AR I or Ar II is defined as a heterocycle such as pyridine, pyrimidine and pyridazine. In principle, appropriately functionalized ring systems of this kind can be prepared by functionalization of specific precursors followed by ring synthesis or by derivatization of a preformed ring system. There are numerous approaches to the synthesis and functionalization of the aforementioned heterocyclic frameworks in the chemical literature (for examples, see (a) Katritzky, A. R.; Rees, C. W.; Scriven, E. F. V. Eds. *Comprehensive Heterocyclic Chemstry II*, Vol 5 and Vol 6. Elsevier Science 1996 and references therein). A particularly useful protocol with regard to the current invention involves Mitsunobu etherification of hydroxyl substituted heterocycles such as outlined in Scheme A. Treatment of 5-bromo-pyridin-2-one (1, G, J=CH), 5-bromo-pyrimidin-2-one (2, G=N, J=CH) or bromo-pyrazin-3-one (3, G=CH, J=N) with an alcohol under Mitsunobu's conditions provides the corresponding bromo-substituted heterocyclic ethers (4) (for typical procedures see Mitsunobu. O., *Synthesis*, 1981, 1).

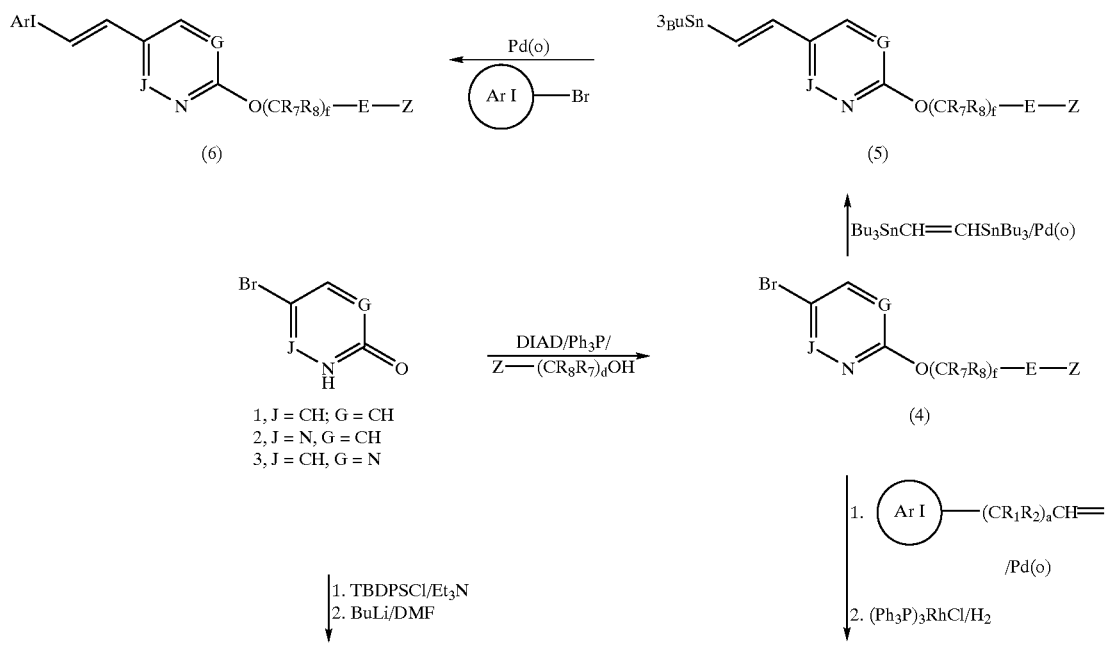

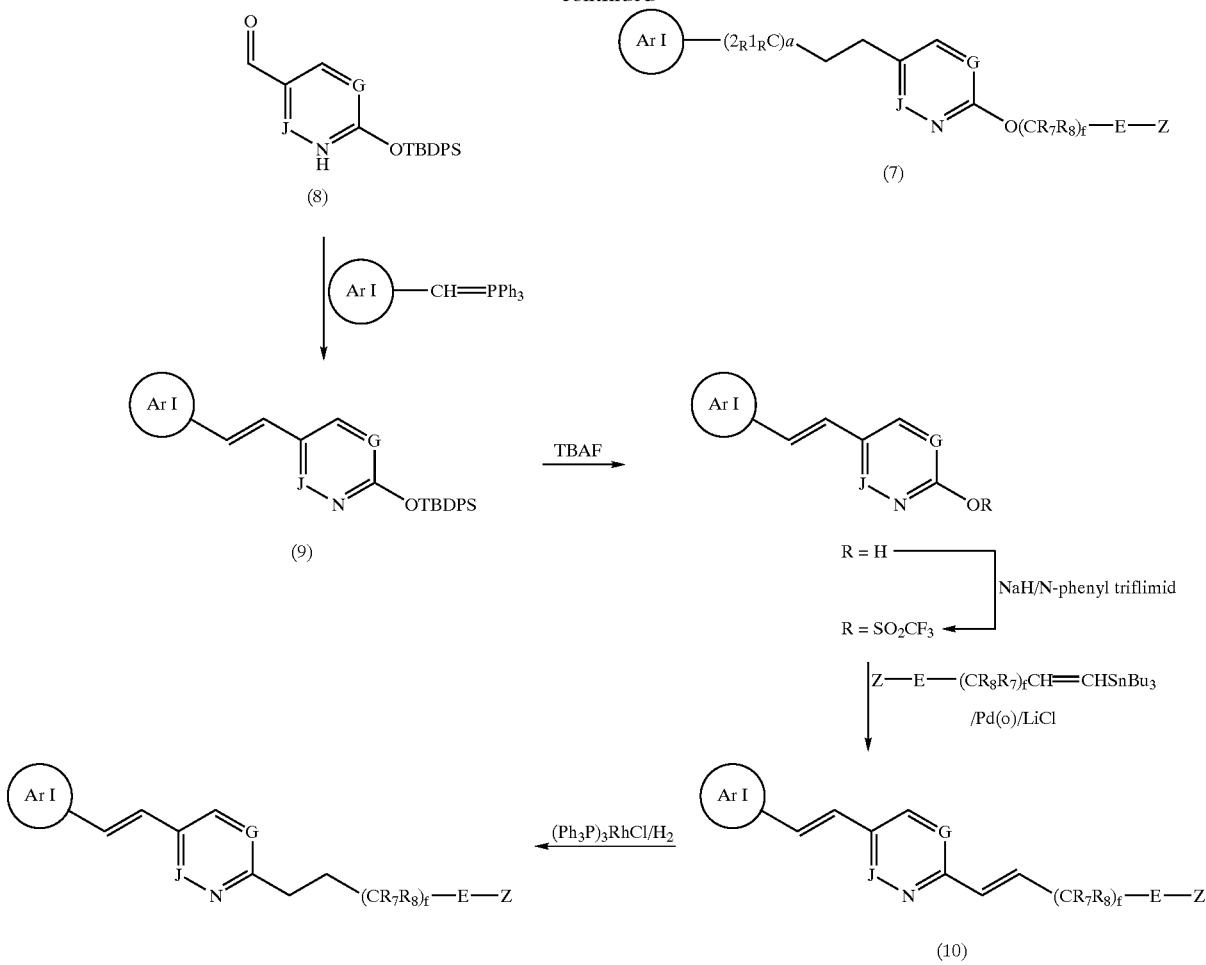

These heterocyclic bromides can be further functionalized in a number of ways. For example, coupling with a vinyl stannane can be effected under palladium(0) catalysis to provide systems with an alkenyl side chain (5 and 6). The choice of catalyst and reaction temperature depends on the substrate employed but is most commonly tetrakistriphenylphosphine palladium, bis(triphenylphosphine) palladium chloride, 1,1'-bis(diphenylphosphino)ferrocene/bis-dibenzylideneacetone palladium or 1,2 bis-(diphenylphosphino)ethane/bis(acetonitrile) dichloropalladium at a temperature between 50 and 150° C. Suitable solvents include DMF, DMPU, HMPA, DMSO, toluene, and DME. (for examples see Farina, V. Krishnamurthy, V.; Scott, W. J. *Organic Reactions*, 1997, 50, 1). Reduction of the olefin using, for example Wilkinson's catalyst in a solvent such as toluene, THF or an alcohol at a temperature between about 20 and 80° C. provides the corresponding alkane (7). Heterocyclic bromides such as (1) can also be metalated (after protection of the carbonyl functionality as a O-silyl ether by reaction with an appropriate silyl chloride or triflate in the presence of a base such as triethylamine or imidazole in a solvent such as dichloromethane or DMF) with an alkyl lithium reagent generally at low temperature (below −50° C.) Suitable solvents for this process include THF or diethyl ether, either alone or as mixtures with additives such as HMPA, TMEDA or DABCO. The resulting aryl lithium species can then be reacted with a variety of electrophiles such as aldehydes, alkyl halides, oxiranes, aziridines or ab-unaturated carbonyls to provide heterocycles substituted with a variety of functionalized side chains. In particular, by using DMF as the electrophile, this procedure can be used to install an aldehyde functional group on the heterocycle (8). The aldehyde can then be further functionalized by Wittig or Horner Emons reaction to produce olefin substituted heterocyclic silyl ethers (9). (For examples see Cadogan, J. I. G. *Organophosphorus Reagents in Organic Synthesis*, Academic Press, 1979 and references therein). The silyl ether can be cleaved using tetrabutyl ammonium fluoride in THF at room temperature or above (For examples see *Protective Groups in Organic Synthesis*, T. W. Greene and P. G. M. Wuts; John Wiley Publications 1998 and references therein). The resulting hydroxyl functionality can be converted to the corresponding triflate using N-phenyl triflimide and a base such as sodium hydride or sodium hexamethyldisilazide in a solvent such as THF or DME at or below room temperature. Coupling of the resulting triflate with a vinyl (or alkynyl ) stannane in the presence of lithium chloride and a Pd(0) catalyst as described above produces the corresponding bisalkenyl substituted heterocycles (10).

Bromo substituted heterocycles such as (11 and 12 scheme B) can be converted into the analogous hydroxyl substituted system by first, conversion to the borate ester (13) then oxidative cleavage of the carbon boron bond with an oxidant such as aqueous hydrogen peroxide in the presence of acid or base (such as acetic acid, sodium carbonate or sodium hydroxide) or oxone in the presence of a base (such as sodium carbonate) at or above 0° C. (For examples see Webb, K. S.; Levy, D. *Tetrahedron Letts.*, 1995, 36, 5117. and Koster, R.; Morita, Y. *Angew. Chem.*, 1966, 78, 589).

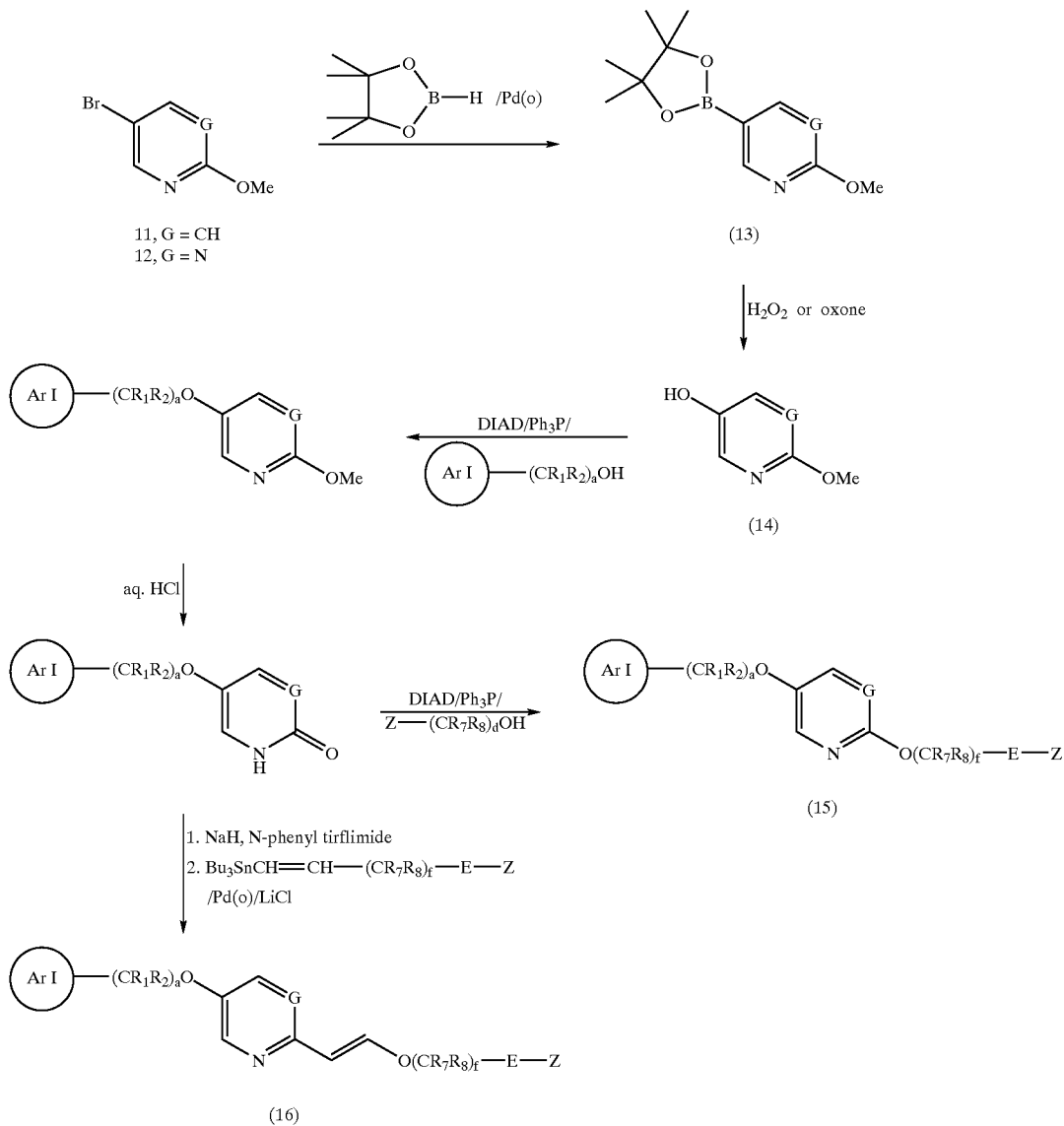

The resulting hydroxy substituted heterocycles (14) can be further derivatized as already described above to give ether (15) or alkenyl (16) substituted side chains. Certain heterocyclic bromides or chlorides situated ortho or para to a ring nitrogen can be readily displaced with an alcohol in the presence of base such as sodium hydride in a solvent such as Toluene, DMSO, THF, DMPU or HMPA at or above room temperature (For examples see Kelly, T. R. et al. *J. Amer. Chem. Soc.*, 1994, 116, 3657 and Newkome, G. R. et al. *J. Org. Chem.*, 1977, 42, 1500). In particular, alcoholysis of a 2,6-dibromo-pyridine using a controlled stoichiometric amount of alcohol reagent provides the alkoxy substituted-bromo-pyridine. Subsequent reaction of this product with a further equivalent of another alcohol provides the unsymmetrically dialkoxy-substituted heterocycle.

Scheme C

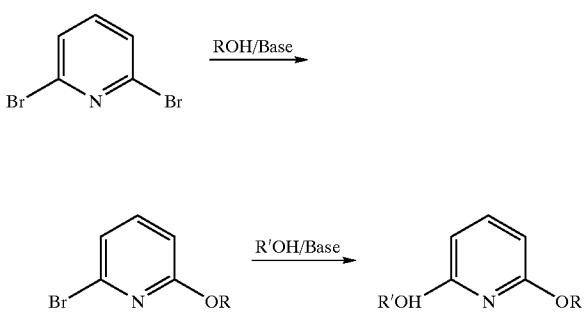

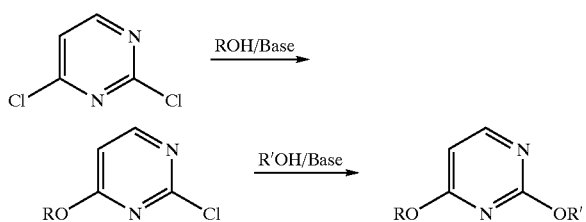

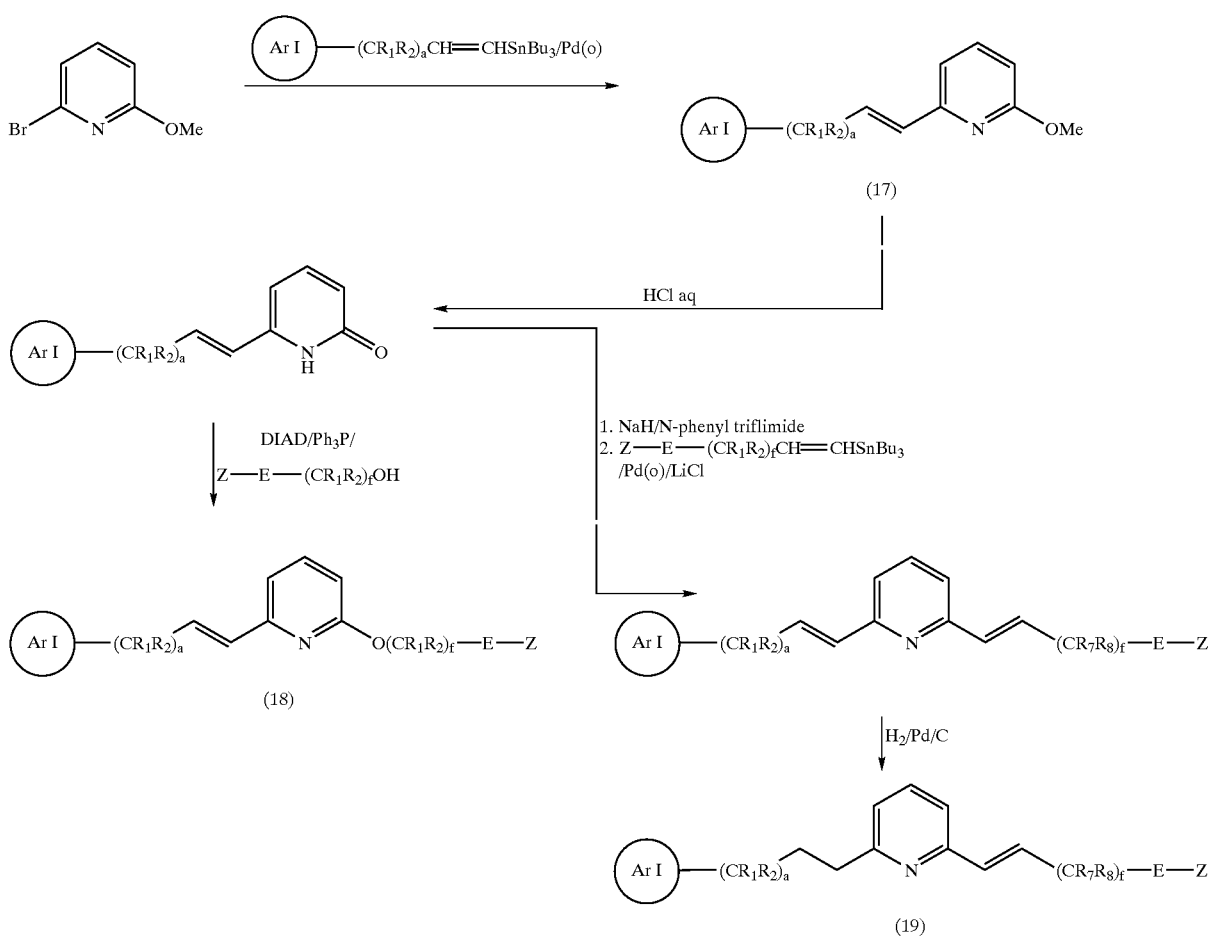

Similar procedures using 2,4-dichloro-pyrimidine or 2,6-dibromo-pyridazine provides the corresponding dialkoxy-substituted pyrimidines and pyridazines. A simple alkoxy group positioned ortho to a nitrogen in these heterocyclic systems can be hydrolyzed to the corresponding hydroxy substituent using aqueous hydrochloric acid normally at or above room temperature (Scheme D).

For example, treatment of the 2-methoxy-6-alkenyl-substituted pyridine (17) with hydrochloric acid provides the 6-alkenyl substituted pyridin-2-one. This intermediate, in turn, can be further derivatized to the corresponding 2-alkoxy (18) or 2-alkyl (19) substituted systems as previously described. A methyl, methylene or methine group positioned ortho to a ring nitrogen in these heterocyclic systems can be deprotonated with a base such as an alkyl lithium or LDA in a solvent such as THF ether or LIMPA, generally at low temperature (below 0° C.) and the resulting anion reacted with electrophiles such as aldehydes epoxides alkyl halides or a,b-unsaturated carbonyl compounds to provide a variety of functionalized side chain substituents.

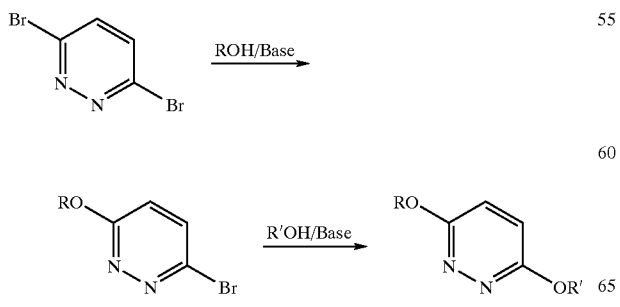

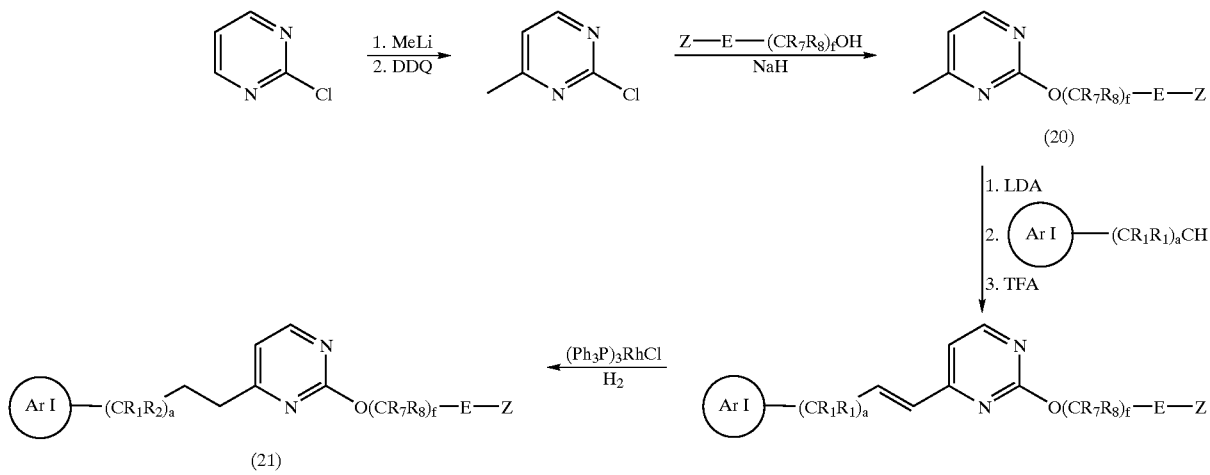

(20)

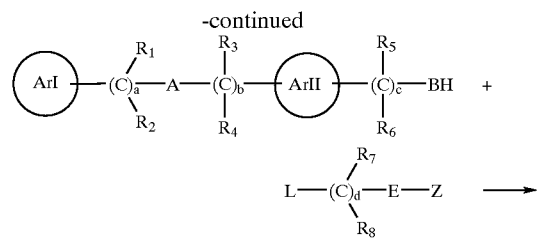

(21)

For example (Scheme E), 2-alkoxy-4-methyl-pyrimidine (20) is treated with LDA at −78° C. followed by an aldehyde to give the corresponding hydroxy adduct. Subsequent dehydration with trifluoroacetic acid in a solvent such as dichloromethane followed by hydrogenation of the resulting olefin provides the 4-alkyl-2-alkoxy-pyrimidine (21).

As illustrated above, compounds of Formula I can be prepared by art recognized procedures from known compounds or readily preparable intermediates. Thus, in order to prepare a compound of the formula:

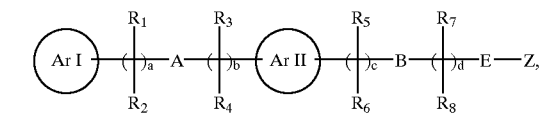

the following reactions or combinations of reactions can be employed:

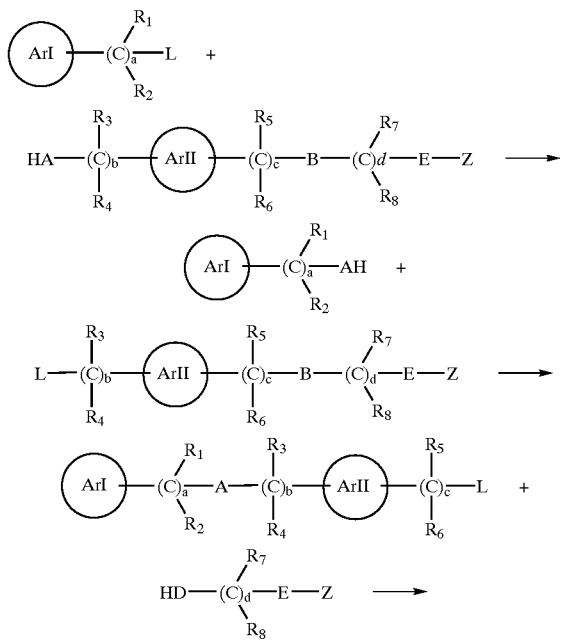

-continued wherein:

$R_1$, $R_2$, $R_3$, $R_4$, $R_5$, $R_6$, $R_7$, $R_8$, a, b, c, d, A, and B are as defined above; E is a chemical bond; Z is —CN, —COOR$_3$ or tetrazol, and L is a leaving group, such as halo, tosylate, or mesylate. Where A or B is O or S, any base normally employed to deprotonate an alcohol or thiol may be used, such as sodium hydride, sodium hydroxide, triethylamine, sodium bicarbonate or diisopropylethylamine.

Reaction temperatures are in the range of about room temperature to reflux, and reaction times vary from about 2 to about 96 hours. The reactions are usually carried out in a solvent that will dissolve both reactants and is inert to both as well. Suitable solvents include, but are not limited to, diethyl ether, tetrahydrofuran, N,N-dimethylformamide, dimethylsulfoxide, dioxane and the like.

In the case where B is SO or $SO_2$ treatment of the thio compound with m-chlorobenzoic acid or sodium periodate results in the sulfinyl compound. Preparation of the sulfonyl compound may be accomplished by known procedures such as dissolving the sulfinyl compound in acetic acid and treating with 30% $H_2O_2$.

Those compounds where B is —C(=O)— may be prepared by the following reaction sequence:

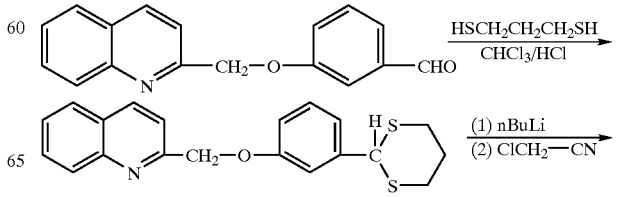

-continued

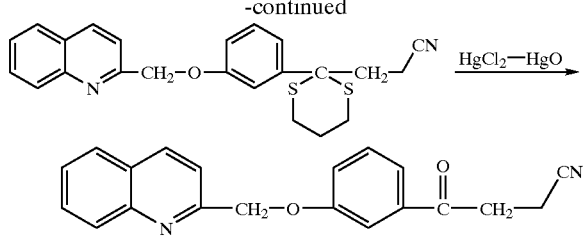

Condensation of the aldehyde with 1,3-propanedithiol results in the dithiane compound. This may be carried out in chloroform at reduced temperatures of about −20° C., while bubbling HCl gas into the reaction mixture. The dithiane compound is then treated with N-butyl lithium in nonpolar solvent at about −78° C. and then reacted with the substituted benzyl chloride. This results in addition of Ring III to the molecule. The dithiane moiety is then treated with a mercuric chloride-mercuric oxide mixture to form the complex which is then split off leaving the desired compound.

Those compounds where A is a chemical bond may be prepared by known coupling methods, for example, the reaction of an appropriate alkyl halide with an appropriate organometallic reagent such as a lithium organocopper reagent (See Posner, Org. React. 22, 235–400 (1975), Normant, Synthesis 63–80 (1972), Posner, "An introduction to Synthesis Using Organocopper Reagents" p. 68–81, Wiley, New York, 1980); coupling of an appropriate lithium organocopper reagent, or Grignard reagent, with a suitable ester of sulfuric or sulfonic acid (see "An introduction to Synthesis Using Organocopper Reagents" p. 68–81, Wiley, New York, 1980, Kharasch and Reinmuth "Grignard Reactions of Non Metallic Substances", pp1277–1286, Prentice-Hall, Englewood Cliffs, N.J., 1954); or other known reactions for forming alkyl bonds (See March "Advanced Organic Chemistry" p. 1149, Third Edition, Wiley, NY, 1985).

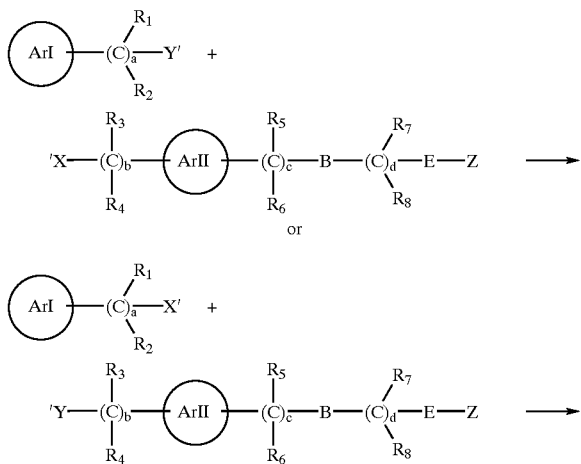

where X' is halide, an ester of a sulfuric acid, or a sulfonic acid ester, and Y' is a lithium organocopper reagent or a Grignard reagent.

There is no particular restriction on the nature of the reagent or solvent to be employed, provided that it has no adverse effect on the reaction or on the reagents involved.

Alternatively, compounds where A is a chemical bond may be prepared by reduction of appropriate compounds, wherein A is an ethylene moiety, with a suitable reducing agent, for example $H_2/Pd/C$.

There is no particular restriction on the solvent or nature of the reducing agent to be used in this reaction, and any solvent and reducing agent conventionally used in reactions of this type may equally be used here, provided that it has no adverse effect on other parts of the molecule. An example of a suitable reducing agent is $H_2/Pd/C$. Other reducing reagents are known in the art. For example, see: Mitsui and Kasahara, in Zabicky, "The Chemistry of Alkenes", vol. 2, pp. 175–214, Interscience, NY, 1970; and Rylander "Catalytic Hydrogenation over Platinum Metals," pp. 59–120, Academic Press, NY, 1967.

Those compounds wherein E is an ethylene moiety are prepared by reacting the appropriate aldehyde or ketone with a substituted Wittig reagent of the formula

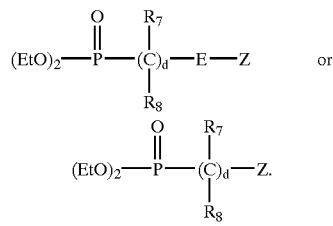

Condensation results in formation of the double bond. The Wittig reagent is prepared by known art recognized procedure, such as reaction of triphenyl phosphine or diethylphosphone with a suitable substituted alkyl/aryl bromide followed by treatment with a strong organometallic base such as n-BuLi or NaOH, resulting in the desired ylide. Conventional Wittig reaction conditions may be used in accordance with standard practice, for examples see Bestmann and Vostrowsky, Top. Curr. Chem. 109, 85–164 (1983), and Pommer and Thieme, Top. Curr. Chem. 109, 165–188 (1983).

There is no particular restriction on the nature of the solvent to be employed, provided that it has no adverse effect on the reaction or on the reagents involved.

Of course this Wittig condensation may also take place when the Wittig reagent is formed on Ring II position of the molecule, which is then condensed with an aldehyde.

There is no particular restriction on the nature of the solvent to be employed, provided that it has no adverse effect on the reaction or on the reagents involved.

There is no particular restriction on the solvent or nature of the reducing agent to be used in this reaction, and any solvent and reducing agent conventionally used in reactions of this type may equally be used here, provided that it has no adverse effect on other parts of the molecule. An Example of a suitable reducing agent is $H_2/Pd/C$. Other reducing reagents are known in the art. For example, see: Mitsui and Kasahara, in Zabicky, "The Chemistry of Alkenes", vol. 2, p. 175–214, Interscience, NY, 1970; and Rylander "Catalytic Hydrogenation over Platinum Metals", p. 59–120, Academic Press, NY, 1967.

The tetrazole may be formed from the nitrile at various stages of the synthesis by treatment with hydrazoic acid formed in situ from sodium azide and an acid.

When B is $-N(R_{20})C(O)-$, or $-C(O)N(R_{20})-$ then condensation of the acid halide with the appropriate amine will give the desired compound as shown below in the following scheme.

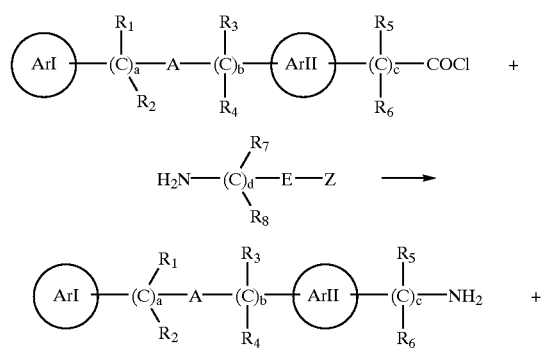
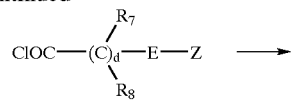
Those compounds where B and/or E are a chemical bond may also be synthesized by coupling methods analogous to those for compounds where A is a chemical bond as described above.
Furthermore, compounds of the invention may be easily synthesized by solid phase methods, as outlined below, using imputs (XI)–(XVII) as listed in schemes 105 and Table 3 below:
Scheme 105
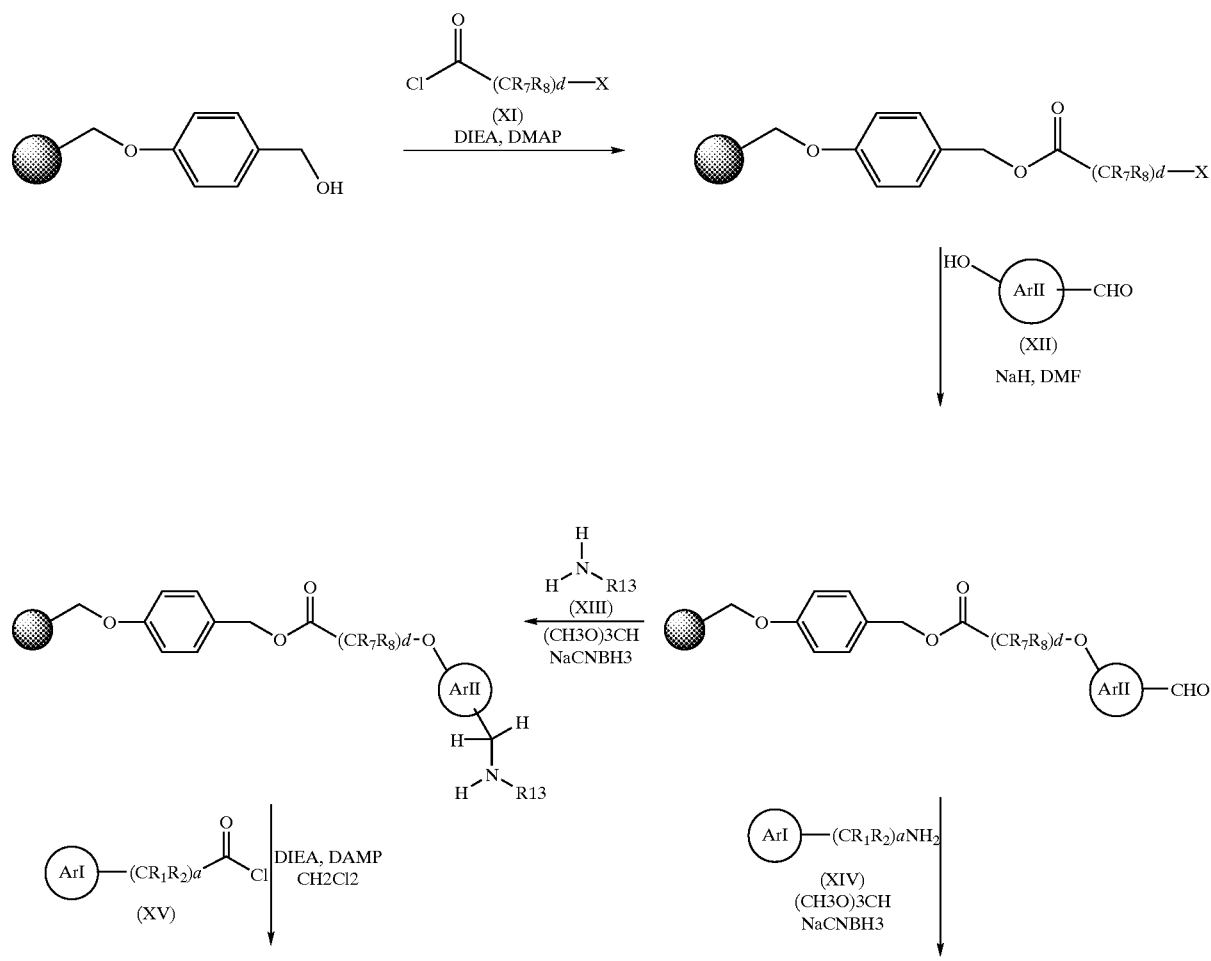

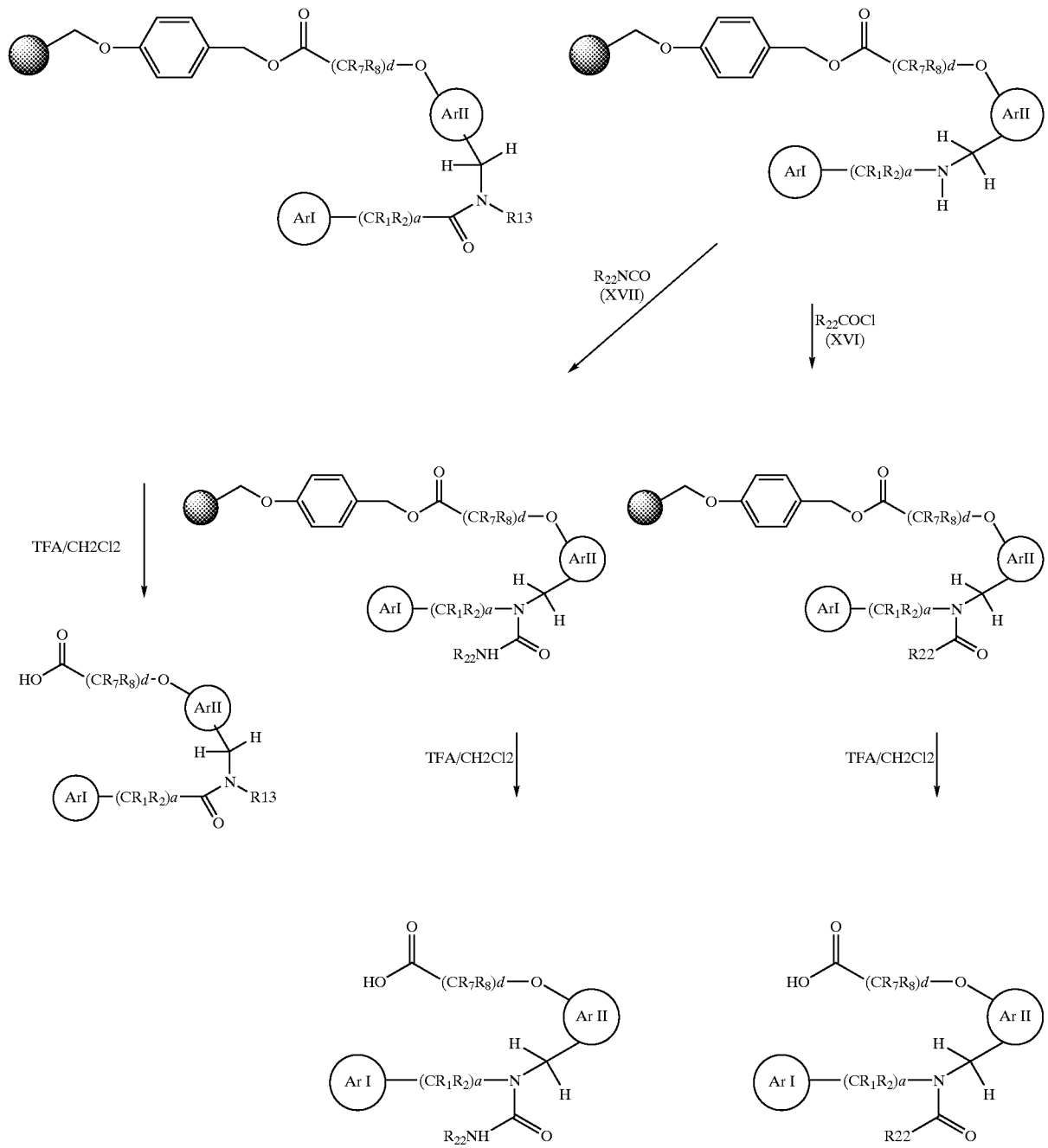

TABLE 3

TABLE 3-continued

Similarly, other compounds of the invention can be made by a skilled person using the above mentioned methodology.

Compounds useful according to the invention also may be prepared by the application or adaptation of other known methods, by which is meant methods used heretofore or described in the literature, for example those described by R. C. Larock in Comprehensive Organic Transformations, VCH publishers, 1989.

In the reactions described hereinafter, it may be necessary to protect reactive functional groups, for example, hydroxy, amino, imino, thio or carboxy groups, where these are desired in the final product, so as to avoid their unwanted participation in the reactions. Conventional protecting groups may be used in accordance with standard practice. For examples, see T. W. Green and P. G. M. Wuts in "Protective Groups in Organic Chemistry" John Wiley and Sons, 1991; and J. F. W. McOmie in "Protective Groups in Organic Chemistry" Plenum Press, 1973.

According to a further feature of the present invention, compounds useful according to the invention may be prepared by interconversion of other compounds of the invention.

A compound of the invention that includes a group containing at least one nitrogen ring atom, preferably imine (=N—), may be converted to the corresponding compound wherein at least one nitrogen ring atom of the group is oxidized to an N-oxide, preferably by reacting with a peracid, for example, peracetic acid in acetic acid or m-chloroperoxybenzoic acid in an inert solvent such as dichloromethane, at a temperature from about room temperature to reflux, preferably at elevated temperature.

The products of this invention may be obtained as racemic mixtures of their dextro and levorotatory isomers, since at least one asymmetric carbon atom may be present. When two asymmetric carbon atoms are present, the product may exist as a mixtures of diastereomers based on syn and anti configurations. These diastereomers may be separated by fractional crystallization. Each diastereomer may then be resolved into dextro and levorotatory optical isomers by conventional methods.

It will also be apparent to those skilled in the art that certain compounds of Formula I may exhibit geometrical isomerism. Geometrical isomers include the cis and trans forms of compounds of the invention having an alkenyl moiety. The present invention comprises the individual geometrical isomers and stereoisomers and mixtures thereof.

Such isomers can be separated from their mixtures, by the application or adaptation of known methods, for example chromatographic techniques and recrystallization techniques, or they are separately prepared from the appropriate isomers of their intermediates, for example, by the application or adaptation of methods described herein.

Resolution may best be carried out in the intermediate stage where it is convenient to combine the racemic compound with an optically active compound by salt formation, ester formation, or amide formation to form two diastereomeric products. If an acid is added to an optically active base, then two diastereomeric salts are produced which possesses different properties and different solubilities and can be separated by fractional crystallization. When the salts have been completely separated by repeated crystallization, the base is split off by acid hydrolysis, and enantiomerically purified acids are obtained.

Compounds useful according to the invention are useful in the form of the free base or acid or in the form of a pharmaceutically acceptable salt thereof. All forms are within the scope of the invention.

Where a compound useful according to the invention is substituted with a basic moiety, acid addition salts are formed and are simply a more convenient form for use; in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial pharmaceutical effects of these compounds in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as an intermediate in preparing a pharmaceutically acceptable salt by ion exchange procedures. Pharmaceutically acceptable salts useful within the scope of the invention are those derived from the following acids: mineral acids, such as hydrochloric acid, trifluoroacetic acid, sulfuric acid, phosphoric acid and sulfamic acid; and organic acids, such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise: hydrohalides, e.g., hydrochloride and hydrobromide, trifluoroacetates, sulfates, phosphates, nitrates, sulfamates, acetates, citrates, lactates, tartarates, malonates, oxalates, salicylates, propionates, succinates, fumarates, maleates, methylene-bis-β-hydroxynaphthoates, gentisates, mesylates, isothionates, di-p-toluyltartrates, methanesulfonates, ethanesulfonates, benzenesulfonates, p-toluenesulfonates, cyclohexylsulfamates and quinates, respectively.

The acid addition salts of the compounds useful according to the invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid, and isolating the salt by evaporating the solution, or by reacting the free base and acid in an organic solvent, in which case the salt separates directly or can be obtained by concentration of the solution.

The compounds useful according to the invention may be regenerated from the acid addition salts by the application or adaptation of known methods. For example, parent compounds useful according to the invention can be regenerated from their acid addition salts by treatment with an alkali, e.g., aqueous sodium bicarbonate solution or aqueous ammonia solution.

Where a compound useful according to the invention is substituted with an acidic moiety, base addition salts may be formed, and are simply a more convenient form for use; in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial pharmaceutical effects on the activity of the compounds of the present invention in the free acid are not vitiated by side effects ascribable to the cations. Pharmaceutically acceptable salts useful according to the invention, include for example alkali and alkaline earth metal salts, including those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, omithine, choline, N,N'-dibenzylethylenediamine, chloroprocaine, diethanolamine, procaine, diethylamine, N-benzylphenethylamine, piperazine, tris(hydroxymethyl)aminomethane, tetramethylammonium hydroxide, and the like.

Metal salts of compounds useful according to the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds useful according to the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitrites such as acetonitrile, or ketones such as acetone. Amino acid salts may be similarly prepared.

The base addition salts of the compounds useful according to the invention can be regenerated from the salts by the application or adaptation of known methods. For example, parent compounds useful according to the invention can be regenerated from their base addition salts by treatment with an acid, e.g. hydrochloric acid.

Salt forms useful according to the invention also include compounds having a quarternarized nitrogen. The quarternarized salts are formed by methods such as by alkylation of $sp^3$ or $sp^2$ hybridized nitrogen in the compounds.

As will be self-evident to those skilled in the art, some of the compounds useful according to the invention do not form stable salts. However, acid addition salts are most likely to be formed by compounds useful according to the invention having a nitrogen-containing heteroaryl group and/or wherein the compounds contain an amino group as a substituent. Preferable acid addition salts of the compounds useful according to the invention are those wherein there is not an acid labile group.

As well as being useful in themselves as active compounds, the salts of the compounds useful according to the invention are useful for the purposes of purification of the compounds, for example by exploitation of the solubility differences between the salts and the parent compounds, side products and/or starting materials by techniques well known to those skilled in the art.

Various substituents on the compounds useful according to the invention, e.g., as defined in R, $R_1$ and $R_2$, can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art may be employed. Examples of many of these possible groups may be found in "Protective Groups in Organic Synthesis" by T. W. Green, John Wiley and Sons, 1981. For example, nitro groups can be added to the aromatic ring by nitration, and the nitro groups then converted to other groups, such as amino, by reduction, and halo, by diazotization of the amino group and replacement of the diazo group. Acyl groups can be substituted onto the aryl groups by Friedel-Crafts acylation. The acyl groups then can be transformed to the corresponding alkyl groups by various methods, including the Wolff-Kishner reduction and Clemmenson reduction. Amino groups can be alkylated to form mono and dialkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

The starting materials and intermediates are prepared by the application or adaptation of known methods, for example methods as described in the Reference Examples or their obvious chemical equivalents.

The present invention is further exemplified but not limited by the following examples, which illustrate the preparation of the compounds according to the invention.

EXAMPLE 1

3-(2-Quinolinylmethyloxy)benzyl Alcohol

A mixture of 12.8 g (0.06 mol) of 2-quinolinylmethyl chloride HCl, 7.5 g (0.06 mol) of 3-hydroxybenzyl alcohol, and 18 g of potassium carbonate in 50 ml of DMF is heated at 70° C. overnight. The reaction mixture is poured into water, and the precipitated product is collected, filtered and dried to give 3-(2-quinolinylmethyloxy)benzyl alcohol.

EXAMPLE 2

When 2-quinolinylmethyl chloride of Example 1 above is replaced by the quinoline compounds of Table 1 below, then the corresponding product is obtained.

TABLE I

| |
|---|
| 2-chloromethylquinoline |
| 2-bromomethylquinoline |
| 2-(1-chloroethyl)quinoline |
| 2-(2-chloroethyl)quinoline |
| 2-bromoethylquinoline |
| 3-chloromethylquinoline |
| 4-chloromethylquinoline |
| 2-(β-chloroethyl)quinoline |
| 2-(β-chloropropyl)quinoline |
| 2-(β-chloro-β-phenethyl)quinoline |
| 2-chloromethyl-4-methylquinoline |
| 2-chloromethyl-6-methylquinoline |
| 2-chloromethyl-8-methylquinoline |
| 2-chloromethyl-6-methoxyquinoline |
| 2-chloromethyl-6-nitroquinoline |
| 2-chloromethyl-6,8-dimethylquinoline |

EXAMPLE 3

When 3-hydroxybenzyl alcohol of Example 1 above is replaced by the compounds of Table II below, then the corresponding product is obtained.

TABLE II 1,2-benzenediol
1,3-benzenediol
1,4-benzenediol
2-mercaptophenol
3-mercaptophenol
4-mercaptophenol
1,3-dimercaptobenzene
1,4-dimercaptobenzene
3-hydroxybenzyl alcohol
3-hydroxyethylphenol
4-hydroxybenzyl alcohol
4-hydroxyethylphenol
2-methylresorsinol
5-methylresorsinol
5-methoxyresorsinol
5-methyl-1,4-dihydroxybenzene
3-(N-acetylamino)phenol
3-(N-acetylamino)benzyl alcohol
2-hydroxy-α-methylbenzyl alcohol
2-hydroxy-α-ethylbenzyl alcohol
2-hydroxy-α-propylbenzyl alcohol
3-hydroxy-α-methylbenzyl alcohol
3-hydroxy-α-ethylbenzyl alcohol
3-hydroxy-α-propylbenzyl alcohol
4-hydroxy-α-methylbenzyl alcohol
4-hydroxy-α-ethylbenzyl alcohol
4-hydroxy-α-propylbenzyl alcohol

EXAMPLE 4

When the compounds of Table I, Example 2, are reacted with the compounds of Table II, Example 3, under the conditions of Example 1, then the corresponding products are obtained.

EXAMPLE 5

3-(2-Quinolinylmethyloxy)benzyl Chloride

To a stirred solution of 14.5 g of 3-(2-quinolinylmethyloxy)benzyl alcohol in 150 ml of CHCl$_3$ is added dropwise 7.5 ml of thionyl chloride during 10 min. The reaction mixture is stirred for 4 hours at room temperature, and then washed with NaHCO$_3$ solution. The organic solution is separated, dried, and evaporated to give 3-(2-quinolinylmethyloxy)benzyl chloride, which is used without further purification in the next step.

EXAMPLE 6

When the compounds prepared by Examples 2–4 are used in place of 3-(2-quinolinylmethyloxy)benzyl alcohol in Example 5, then the corresponding chloride is prepared.

EXAMPLE 7

α-(3-Hydroxymethylphenoxy)acetonitrile

A mixture of 3-hydroxymethyl phenol (0.081 mol), bromoacetonitrile (0.081 mol) and anhydrous potassium carbonate (0.081 mol) in acetone (160 ml) and dimethylformamide (20 ml) is heated at reflux for 48 hrs. The reaction mixture is filtered and evaporated. The residue is diluted with ethyl acetate (150 ml), washed with 10% aqueous sodium hydroxide solution (3×100 ml) and then with brine (3×100 ml). The ethyl acetate solution is dried (magnesium sulfate) and chromatographed using a silica gel column (ca. 100 g) and eluted with 1:1 petroleum ether:ethylacetate (2 1). The resultant oil is used directly in the next step.

EXAMPLE 8

α-(3-Chloromethylphenoxy)acetonitrile

α-(3-Hydroxymethylphenoxy)acetonitrile (0.055 mol) in diethylether (150 ml) is stirred with thionyl chloride (0.060 mol) and a few drops of dimethylformamide at 40° C. for 1 hr. Then the solution is washed with water and brine, and then evaporated to give α-(3-chloromethylphenoxy) acetonitrile as a yellow oil.

EXAMPLE 9

When bromoacetonitrile of Example 7 is replaced by the nitriles of Table XII below then the corresponding product is prepared:

TABLE XII

α-bromo-α-methylacetonitrile
α-bromo-β-ethylacetonitrile
α-bromopropionitrile
β-bromopropionitrile
β-bromo-β-methylpropionitrile-bromobutyronitrile
β-bromobutyronitrile
α-bromobutyronitrile

EXAMPLE 10

When 3-hydroxymethylphenol of Example 7 is replaced by the compounds of Table XIIIa below, then the corresponding products are prepared.

TABLE XIIIa 2-hydroxymethylphenol
4-hydroxymethylphenol
3-mercaptobenzylalcohol
4-mercaptobenzylalcohol
3-hydroxymethyl-N-acetylamidine
4-hydroxymethyl-N-acetylamidine
4-hydroxymethylamidine
4-methyl-2-hydroxymethylphenol
2-methyl-5-hydroxymethylphenol
4-methyl-3-hydroxymethylphenol
5-methyl-3-hydroxymethylphenol
3-methyl-4-hydroxymethylphenol
2-methyl-4-hydroxymethylphenol
3-methyl-5-hydroxymethylphenol
4-methoxy-3-hydroxymethylphenol
3-methoxy-4-hydroxymethylphenol
2-methoxy-4-hydroxymethylphenol
5-methoxy-3-hydroxymethylphenol
3-methoxy-5-hydroxymethylphenol
2-methoxy-5-hydroxymethylphenol
2-(1'-hydroxyethyl)phenol
3-(1'-hydroxyethyl)phenol
4-(1'-hydroxyethyl)phenol
2-(2'-hydroxyethyl)phenol
3-(2'-hydroxyethyl)phenol
4-(2'-hydroxyethyl)phenol
2-(3'-hydroxypropyl)phenol
3-(3'-hydroxypropyl)phenol
4-(3'-hydroxypropyl)phenol
2-(2'-hydroxypropyl)phenol
3-(2'-hydroxypropyl)phenol
4-(2'-hydroxypropyl)phenol
2-(1'-hydroxypropyl)phenol
3-(1'-hydroxypropyl)phenol
4-(1'-hydroxypropyl)phenol
3-(4'-hydroxybutyl)phenyl
4-(4'-hydroxybutyl)phenyl

EXAMPLE 11

5-(3-Chloropropyl)tetrazole

A mixture of 3.5 g of 4-chlorobutyronitrile, 2.3 g of sodium azide and 1.9 g of ammonium chloride in 50 ml of dimethyl-formamide is stirred at 140° C. for 20 hours. The reaction mixture is poured onto ice, basified with 1N sodium hydroxide and extracted twice with ethyl acetate. The aqueous fraction is acidified with acetic acid and extracted with ethylacetate. Evaporation of the ethyl acetate gives 5-(3-chloropropyl)-tetrazole, which is used directly in the next step.

EXAMPLE 12

When 4-chlorobutyronitrile of Example 11 above is replaced by the nitriles of Table XIX below then the corresponding tetrazole product is obtained.

TABLE XIX chloroacetonitrile
bromoacetonitrile
3-chloropropionitrile
4-chlorobutyronitrile
5-chloropentanonitrile
6-chlorohexanonitrile
2-chloropropionitrile
2-methyl-3-chloropropionitrile
2-chlorobutyronitrile
3-chlorobutyronitrile
4-methyl-5-chloropentanonitrile
2-methyl-3-chloropropionitrile
3-benzyl-4-chlorobutyronitrile
3-carbethoxymethyl-4-chlorobutyronitrile
3-methoxymethyl-4-chlorobutyronitrile
2,3-dimethyl-4-chloropentanonitrile
3,3-dimethyl-4-chloropentanonitrile
spiro-(3,3-cyclopropane)-4-chlorobutyronitrile
1-chloromethyl-2-cyanomethylcyclobutane
1-chloromethyl-2-cyanomethylcyclohexane
3-cyclopropylmethyl-4-chlorobutyronitrile
3-dimethylaminomethyl-4-chlorobutyronitrile
3-methylene-4-chlorobutyronitrile
3-propylidene-4-chlorobutyronitrile

EXAMPLE 13

Ethyl-4-benzyloxy-2-hydroxy-6-methyl-benzoate

Ethyl-2,4-dihydroxy-6-methyl benzoate (4 g, 21 mmol) is dissolved in acetone (80 mL) and to this solution is added potassium carbonate (2.9 g, 21 mmol) and benzyl bromide (2.5 mL, 21 mmol). This mixture is heated at reflux for 16 hours. To the cooled reaction is added ethyl acetate (100 mL) and water (100 mL). The organic layer is washed with water (2×80 mL) and brine (2×80 mL), then dried over magnesium sulfate and the solvent removed in vacuo. The crude is purified by column chromatography (silica, 10% ethyl acetate in hexanes) to give the title compound: $^1$H NMR (300 MHz, CDCl$_3$) δ 7.38 (m, 5H), 6.41 (d, 1H), 6.38 (d, 1H), 5.05 (s, 2H), 4.40 (q, 2H), 2.51 (s, 3H), 1.40 (t, 3H).

EXAMPLE 13a

Ethyl 2,4-bis-(4-Fluoro-benzyloxy)-6-methyl-benzoate

The title compound is prepared using essentially the same procedure used in EXAMPLE 13 except using the twice the amount of 4-fluorobenzyl bromide in place of benzyl bromide.

EXAMPLE 14

Ethyl-4-benzyloxy-2-methyl-6-(3-phenyl-propoxy)-benzoate

Ethyl-4-benzyloxy-2-hydroxy-6-methyl-benzoate (0.5 g, 1.8 mmol) is dissolved in DMF (10 mL) and 60% sodium hydride (0.07 g, 1.8 mmol) is added and stirred 20 minutes, forming a clear solution. Then 1-bromo-3-phenyl propane (0.27 mL, 1.8 mol) is added and this mixture is heated at 100° C. for 4 hours and stirred at room temperature overnight. The solvent is removed in vacuo and the residue purified by flash chromatography (silica, 5% ethyl acetate in hexanes) to give the title compound: $^1$H NMR (300 MHz, CDCl$_3$) δ 7.17–7.40 (m, 10H), 6.39 (d, 1H), 6.33 (d, 1H), 5.03 (s, 2H), 4.38 (q, 2H), 3.91 (t, 2H), 2.77 (t, 2H), 2.30 (s, 3H), 2.05 (m, 2H), 1.38 (t, 3H); MS (EI) 404 (M)$^+$.

The following compounds are prepared using essentially the same procedure used in EXAMPLE 14 except using the cited bromide in place of 1-bromo-3-phenyl propane.

EXAMPLE 14a

Ethyl-4-benzyloxy-2-cyclohexylmethoxy-6-methyl-benzoate $^1$H NMR (300 MHz, CDCl$_3$) δ 7.32–7.41 (m, 5H), 6.36 (m, 2H), 5.04 (s, 2H), 4.35 (q, 2H), 3.71 (d, 2H), 2.28 (s, 3H), 1.71 (m, 5H), 1.34 (t, 3H), 0.88–1.24 (m, 6H); MS (EI) 383 (M)$^+$. Prepared from cyclohexyl methyl bromide.

EXAMPLE 14b

Ethyl-4-benzyloxy-2-methyl-6-(4-methylpentyloxy)-benzoate $^1$H NMR (300 MHz, CDCl$_3$) δ 7.32–7.41 (m, 5H), 6.37 (d, 2H), 5.04 (s, 2H), 4.35 (q, 2H), 3.90 (t, 2H), 2.28 (s, 3H), 1.68–1.78 (m, 2H), 1.55–1.59 (m, 2H), 1.26–1.39 (m, 5H), 0.89 (d, 4H); MS (EI) 370 (M)$^+$. Prepared from 1-bromo-4-methylpentane.

EXAMPLE 15

4-Benzyloxy-2-methyl-6-(3-phenyl-propoxy)-benzoic Acid

Ethyl-4-benzyloxy-2-methyl-6-(3-phenyl-propoxy)-benzoate (0.57 g, 1.4 mmol) and 10 N sodium hydroxide (1.4 mL, 14 mmol) are combined in ethanol (6 mL) and heated at reflux for 6 hours. The solvent is removed in vacuo and dichloromethane is added to the residue. Then 1 N hydrochloric acid is added to acidify the mixture to pHl. The aqueous layer is extracted once with dichloromethane and the combined organic layers washed once with water. The organic layer is dried over magnesium sulfate and the solvent removed in vacuo to give the title compound as a tan solid. The solid is recrystallized from ethyl acetate/petroleum ether to provide an analytically pure sample; m.p. 109–111° C., $^1$H NMR (300 MHz, CDCl$_3$) δ 7.18–7.41 (m, 10H), 6.55 (d, 1H), 6.41 (d, 1H), 5.07 (s, 2H), 4.10 (t, 2H), 2.81 (t, 2H), 2.62 (s, 3H), 2.16–2.21 (m, 2H); MS (EI) 376 (M)$^+$.

The following compounds are prepared using essentially the same procedure used in EXAMPLE 12 except using the cited ester in place of ethyl-4-benzyloxy-2-(1-phenyl-3-propoxy)-6-methyl benzoate.

EXAMPLE 15a

4-Benzyloxy-2-cyclohexylmethoxy-6-methyl-benzoic Acid

M.p. 127–8° C. (ethyl acetate/petroleum ether); $^1$H NMR (300 MHz, CDCl$_3$) δ 7.35–7.42 (m, 5H), 6.55 (d, 1H), 6.46 (d, 1H), 5.09 (s, 2H), 3.91 (d, 2H), 2.63 (s, 3H), 1.75–1.86

(m, 6H), 1.05–1.32 (m, 5H); MS (EI) 354 (M)+. Prepared from ethyl-4-benzyloxy-2-cyclohexylmethoxy-6-methyl-benzoate.

EXAMPLE 15b

4-Benzyloxy-2-methyl-6-(4-methyl-pentyloxy)-benzoic Acid

M.p. 83–5° C. (ethyl acetate/petroleum ether); $^1$H NMR (300 MHz, CDCl$_3$) δ 7.35–7.42 (m, 5H), 6.55 (d, 1H), 6.47 (d, 1H), 5.09 (s, 2H), 4.10 (t, 2H), 2.63 (s, 3H), 1.83–1.89 (m, 2H), 1.58–1.63 (m, 1H), 1.32–1.37 (m, 2H), 0.92 (d, 4H); MS (EI) 342 (M)+. Prepared from ethyl-4-benzyloxy-2-methyl-6-(4-methyl-pentyloxy)-benzoate.

EXAMPLE 15c 2,4-bis-(4-Fluoro-benzyloxy)-6-methyl-benzoic Acid $^1$H NMR (300 MHz, CDCl$_3$) δ 7.39–7.35 (m, 4H), 7.11–7.03 (m, 4H), 6.49 (d, 2H), 5.10 (s, 2H), 5.02 (s, 2H), 2.54 (s, 3H); MS (EI) 384 (M)+. Prepared from ethyl 2,4-bis-(4-fluoro-benzyloxy)-6-methyl-benzoate.

EXAMPLE 16

2-(3-Iodophenoxymethyl)-naphthalene

To a solution of 3-iodophenol (4.0 g, 18 mmol) in ethanol (40 mL) is added potassium hydroxide (1.0 g, 18 mmol) and 2-(bromomethyl) naphthalene (4.0 g, 18 mmol) and this mixture is refluxed overnight. The hot reaction is filtered and the filtrate is chilled in ice. The ensuing precipitate is collected by filtration to give the title compound. $^1$H NMR (300 MHz, CDCl$_3$) δ 7.84–7.89 (m, 4H), 7.48–7.53 (m, 3H), 7.40 (d, 1H), 7.29–7.32 (m, 1H), 6.95–7.04 (m, 2H), 5.20 (s, 2H); MS (EI) 360 (M)+.

EXAMPLE 17

6-[3-(Naphthalen-2-ylmethoxy)-phenyl]-hex-5-ynoic Acid

A solution of 2-(3-iodophenoxymethyl)-naphthalene (0.5 g, 1.4 mmol) and hexynoic acid (0.19 g, 1.7 mmol) in piperidine (5 mL) is purged with Argon for 20 minutes. Then bis(triphenylphosphine)palladium dichloride (0.01 g, 0.014 mmol) and cuprous iodide (0.005 g, 0.028 mmol) are added and this mixture heated in an oil bath at 75° C. for 1.5 hours and then allowed to come to room temperature overnight. The solvent was removed in vacuo and the residue purified by flash chromatography (silica, 4% methanol in dichloromethane) to give the title compound. $^1$H NMR (300 MHz, CDCl$_3$) δ 7.83–7.88 (m, 4H), 7.48–7.54 (m, 3H), 7.19 (t, 1H), 6.98–7.05 (m, 3H), 5.21 (s, 2H), 2.47 (t, 2H), 1.80–1.91 (m, 4H); MS (EI) 344 (M)+.

EXAMPLE 18

6-[3-(Naphthalen-2-ylmethoxy)-phenyl]-hexanoic Acid

To a solution of 6-[3-(naphthalen-2-ylmethoxy)-phenyl]-hex-5-ynoic acid (0.54 g, 1.4 mmol) in methanol (15 mL) is added 10% Pd/C (0.10 g) and this mixture is placed on a Parr apparatus and pressurized to 43 psi with hydrogen. This reaction is allowed to shake overnight. The reaction is filtered and the solvent removed in vacuo. The residue is purified by flash chromatography (silica, 5% methanol in dichloromethane) to give the title compound. $^1$H NMR (300 MHz, CDCl$_3$) δ 7.83–7.89 (m, 4H), 7.46–7.56 (m, 3H), 7.17–7.22 (m, 1H), 6.77–6.85 (m, 3H), 5.21 (s, 2H), 2.59 (t, 2H), 2.31 (t, 2H), 1.58–1.70 (m, 6H); MS (EI) 348 (M)+.

EXAMPLE 19 t-Butyl-diphenyl(3-iodo-benzyloxy)silane

To a solution of 3-iodo-benzyl alcohol (4.68 g, 20 mmol) in CH$_2$Cl$_2$ (40 mL) is added imidazole (1.49 g, 22 mmol) and t-butyldiphenylsilyl chloride (5.74 g, 22 mmol). The resulting mixture is stirred for 1 h diluted with ether washed with water and brine, dried over MgSO$_4$ and concentrated to give the title compound as an oil (9.41 g). MS (EI) 472 (M)+.

EXAMPLE 20

6-[3-(t-Butyldiphenylsilyloxymethyl)-phenyl]-hex-5-ynol

To a solution of t-Butyl-diphenyl(3-iodo-benzyloxy) silane (8.49 g, 18 mmol) in THF (70 mL) is added hex-5-ynol (2.5 mL, 22 mmol) and (Ph$_3$P)$_4$Pd (990 mg, 0.85 mmol) and CuI (171 mg, 0.9 mmol). This solution is degassed and placed under an argon atmosphere. To this solution is added piperidine (5.4 mL, 54 mmol) and stirring continued for 4 h. The reaction mixture is diluted with ether, washed with water and brine, dried over MgSO$_4$ and concentrated. The residue is purified by flash chromatography (silica, 30% ethyl acetate in hexanes) to give the title compound as an oil (6.84 g). $^1$H NMR (300 MHz, CDCl$_3$): δ 7.70 (m, 4H), 7.40 (m, 6H), 7.27 (m, 4H), 4.71 (s, 2H), 3.71 (t, 2H), 2.47 (t, 2H), 1.74 (m, 4H), 1.10 (s, 9H).

EXAMPLE 21

6-[3-(t-Butyldiphenylsilyloxymethyl)-phenyl]-hexanol

To a solution of 6-[3-(t-Butyldiphenylsilyloxymethyl)-phenyl]-hex-5-ynol (880 mg, 2 mmol) in ethyl acetate (10 mL) is added Pd on Carbon (120 mg, 10% Pd by wt.). The mixture is stirred under a hydrogen atmosphere for 17 h, purged with argon filtered through celite concentrated to give the title compound (5.9 g) as an oil. MS (EI) 389 (M–tBu)+.

EXAMPLE 22

6-[3-(t-Butyldiphenylsilyloxymethyl)-phenyl]-hexanoic Acid

To a solution of 6-[3-(t-Butyldiphenylsilyloxymethyl)-phenyl]-hexanol (5.9 g, 13.2 mmol) in acetonitrile (28 mL) is added CCl$_4$ (28 mL) and water (43 mL). To this mixture is added NaIO4 (11.7 g, 54 mmol) and RuCl3(H2O) (100 mg, 0.5 mmol). The resulting mixture is stirred for 2 h then diluted with ethyl acetate, washed with water and brine, dried over MgSO$_4$ and activated charcoal, filtered through celite and concentrated. The residue is purified by flash chromatography (silica, 20% ethyl acetate/5% dichloromethane in hexanes) to give the title compound (3.46 g) as an oil. MS (ESI) 461 (M+H)+.

EXAMPLE 23

6-[3-(tert-Butyl-diphenyl-silanyloxymethyl)-phenyl]-hexanoic Acid Methyl Ester

To a solution of 6-[3-(tert-butyl-diphenyl-silanyloxymethyl)-phenyl]-hexanoic acid (3.3 g, 7.2 mmol)

in DMF (15 mL) is added potassium carbonate (1.09 g, 7.9 mmol) and iodomethane (500 μL, 7.9 mmol). The mixture is stirred for 6 hrs then diluted with ether. The organic layer is washed with water, brine, dried over MgSO$_4$ and concentrated. The residue is purified by flash chromatography (eluting with 10% ether/hexanes) to give 2.42 g of title compound. $^1$H NMR (300 MHz, CDCl$_3$) δ 7.70 (m, 4H), 7.38 (m, 6H), 7.20 (m, 2H), 7.12 (s, 1H), 7.06 (d, 1H), 4.76 (s, 2H), 3.65 (s, 3H), 2.59 (t, 2H), 2.30 (t, 2H), 1.64 (m, 4H), 1.37 (m, 2H), 1.10 (s, 9H).

EXAMPLE 24

6-(3-Hydroxymethyl-phenyl)-hexanoic Acid Methyl Ester

To a solution of 6-[3-(tert-butyl-diphenyl-silanyloxymethyl)-phenyl]-hexanoic acid methyl ester (2.37 g, 5 mmol) in THF (10 mL) is added acetic acid (283 μL, 5 mmol) and 1M TBAF (5 mL). The solution is stirred for 2 hrs then diluted with EtOAc/ether (1:1). The organic layer is washed with water, brine, dried over MgSO$_4$ and concentrated. The residue is purified by flash chromatography (eluting with 35% ethyl acetate/hexanes) to give 1.12 g of title compound. MS (EI) 236 (M$^+$).

EXAMPLE 25

6-(3-Bromomethyl-phenyl)-hexanoic Acid Methyl Ester

To a solution of 6-(3-hydroxymethyl-phenyl)-hexanoic acid methyl ester (587 mg, 2.48 mmol) in THF (10 mL) is added triphenylphosphine (716 mg, 2.73 mmol), stirred until homogeneous then cooled to 0° C. NBS (486 mg, 2.73 mmol) is added portionwise and the reaction mixture stirred for 45 min. The mixture is concentrated and the residue is purified by flash chromatography (eluting with 10% ethyl acetate/hexanes) to give 682 mg of title compound. $^1$H NMR (300 MHz, CDCl$_3$) δ 7.23 (m, 3H), 7.10 (m, 1H), 4.48 (s, 2H), 3.66 (s, 3H), 2.60 (t, 2H), 2.31 (t, 2H), 1.63 (m, 4H), 1.37 (m, 2H).

EXAMPLE 26

6-Methoxy-3-methyl-1,3-dihydro-indol-2-one

To a cooled solution (−78° C.) of 6-methoxy-1,3-dihydro-indol-2-one (840 mg, 5.2 mmol, see Quallich, G. J.; Morrissey, P. M. *Synthesis* 1993, 51–53) in THF (20 mL) is added dropwise TMEDA (1.57 mL, 10.4 mL) followed by dropwise addition of 2.5M n-BuLi (4.16 mL, 10.4 mmol). The mixture is stirred for 15 min then warmed to −25° C. Add dropwise iodomethane (405 μL, 6.5 mmol) and let stir for 20 min. The reaction is quenched with sat NH$_4$Cl soln, warmed to room temp and diluted with EtOAc. The organic layer is washed with sat NH$_4$Cl soln, brine, dried over MgSO$_4$ and concentrated. The residue is purified by flash chromatography (eluting with 45% ethyl acetate/hexanes) to give 679 mg of title compound.
MS (ESI) 178 (M+H)$^+$.

EXAMPLE 27

6-Methoxy-3,3-dimethyl-1,3-dihydro-indol-2-one

To a cooled solution (−78° C.) of 6-methoxy-3-methyl-1,3-dihydro-indol-2-one (679 mg, 3.83 mmol) in THF (13 mL) is added TMEDA (1.16 mL, 7.66 mmol) followed by dropwise addition of 2.5M n-BuLi (3.06 mL, 7.66 mmol). The mixture is stirred for 15 min then warmed to −25° C. Add dropwise iodomethane (275 μL, 4.40 mmol) and let stir for 30 min. The reaction is quenched with sat NH$_4$Cl soln, warmed to room temp and diluted with EtOAc. The organic layer is washed with sat NH$_4$Cl soln, brine, dried over MgSO$_4$ and concentrated. The residue is purified by flash chromatography (eluting with 35% ethyl acetate/hexanes) to give 601 mg of title compound as a white crystalline solid. MS (ESI) 192 (M+H)$^+$.

EXAMPLE 28

6-Methoxy-1,3,3-trimethyl-1,3-dihydro-indol-2-one

To a cooled solution (−5°–0° C.) of 6-methoxy-3,3-dimethyl-1,3-dihydro-indol-2-one (600 mg, 3.14 mmol) in THF (10.5 mL) is added 60% NaH (132 mg, 3.30 mmol) and the mixture stirred for 15 min. Add dropwise to the reaction mixture iodomethane (215 μL, 3.45 mmol), the cold bath is removed and stirred for 2 hrs. The reaction is quenched with sat NH$_4$Cl soln, warmed to room temp and diluted with EtOAc.

The organic layer is washed with sat NH$_4$Cl soln, brine, dried over MgSO$_4$ and concentrated. The residue is purified by flash chromatography (eluting with 30% ethyl acetate/hexanes) to give 601 mg of title compound as a white crystalline solid. MS (ESI) 206 (M+H)$^+$.

EXAMPLE 29

6-Hydroxy-1,3,3-trimethyl-1,3-dihydro-indol-2-one

To a solution of 6-methoxy-1,3,3-trimethyl-1,3-dihydro-indol-2-one (601 mg, 2.93 mmol) in acetic acid (880 μL) is added hydrobromic acid (48% in H$_2$O) (8.8 mL). The resulting solution is heated to reflux (105°–110° C.), stirred 2 hrs, then cooled to room temp and concentrated under reduced pressure. The residue is dissolved in EtOAc and the organic layer washed with water, brine, dried over MgSO$_4$ and concentrated. The residue is purified by triturating with a small volume of ether to give 495 mg of title compound as an off white solid. MS (ESI) 192 (M+H)$^+$.

EXAMPLE 30

6-[3-(1,3,3-Trimethyl-2-oxo-2,3-dihydro-1H-indol-6-yloxymethyl)-phenyl]-hexanoic Acid Methyl Ester To a solution of 6-hydroxy-1,3,3-trimethyl-1,3-dihydro-indol-2-one (396 mg, 2.07 mmol) in DMF (7.6 mL) is added 6-(3-Bromomethyl-phenyl)-hexanoic acid methyl ester (682 mg, 2.28 mmol) and potassium carbonate (315 mg, 2.28 mmol). The resulting mixture is heated to 60° C., stirred for 2 hrs. then cooled to room temp and diluted with EtOAc. The organic layer is washed with water, brine, dried over MgSO$_4$ and concentrated. The residue is purified by flash chromatography (eluting with 30% ethyl acetate/hexanes) to give 352 mg of title compound. MS (ESI) 410 (M+H)$^+$.

EXAMPLE 31

6-[3-(1,3,3-Trimethyl-2-oxo-2,3-dihydro-1H-indol-6-yloxymethyl)-phenyl]-hexanoic Acid To a solution of 6-[3-(1,3,3-trimethyl-2-oxo-2,3-dihydro-1H-indol-6-yloxymethyl)-phenyl]-hexanoic acid methyl ester (110 mg, 0.27 mmol) in (1:1) THF/CH$_3$OH (1 mL) is added 250 μL water and 10N NaOH soln (270 μL). The mixture is stirred for 16 hrs, cooled to 5° C., adjusted to pH 4 with 2N HCl soln. and diluted with EtOAc. The organic layer is washed with brine, dried over MgSO$_4$ and concentrated. The residue is purified by flash chromatography (eluting with 50% ethyl acetate/5% methanol/hexanes) to give 67 mg of title compound. $^1$H NMR (300 MHz, CDCl$_3$) δ 7.29 (m, 3H), 7.14 (d, 1H), 7.09 (d, 1H), 6.63 (dd, 1H), 6.52 (d, 1H), 5.04 (s, 2H), 3.18 (s, 3H), 2.64 (t, 2H), 2.36 (t, 2H), 1.66 (m, 4H), 1.40 (m, 2H), 1.34 (s, 6H). MS (ESI) 396 (M+H)$^+$.

EXAMPLE 32a

Methyl 2,6-Dimethyl-benzoate

To a cooled (0° C.) solution of 2,6-dimethylbenzoic acid (20.2 g, 134 mmol) in dichloromethane (200 mL) is added DMF (1 mL) followed by oxalyl chloride (14 mL, 162 mmol). On complete addition, the cold bath is removed and stirring continued for 3 h. The resulting solution is concentrated under vacuum and the residue added slowly to a cooled (0° C.) solution comprising methanol (200 mL) and triethylamine (40 mL). On complete addition the reaction mixture is stirred for 30 min. then poured into hydrochloric acid solution (400 mL, 2N) which is then extracted with ether. The ether extract is washed with hydrochloric acid solution (1N), sokium bicarbonate solution and brine; then dried over MgSO$_4$ and concentrated to give the title compound which is used without further purification. MS (EI) 164 (M)$^+$.

The following compound is prepared using essentially the same procedure used in EXAMPLE 32a, except using the cited alcohol in place of methanol.

EXAMPLE 32b

Isobutyl 2,6-Dimethyl-benzoate

MS (EI) 206 (M)$^+$. Prepared from 2-methyl-1-propanol

EXAMPLE 33a

Methyl 2-Bromomethyl-6-methyl-benzoate

To a solution of methyl 2,6-dimethyl-benzoate (22.0 g, 134 mmol, EXAMPLE 1) in CCl$_4$ (250 mL) is added N-bromo-succinimide (19 g, 107 mmol) followed by benzoyl peroxide (1.0 g, 4.0 mmol). The resulting solution is warmed to reflux and stirred at this temperature for 20 min. The reaction mixture is then allowed to cool before being diluted with ether (200 mL), filtered and concentrated. The residue is purified by flash chromatography (silica, 4% acetone in hexanes) to give the title compound. This product (approx. 85% purity, remainder is methyl 2,6-dimethyl-benzoate) is used without further purification. MS (EI) 242, 244 (M$^+$ Br pattern).

The following compound is prepared using essentially the same procedure used in EXAMPLE 33a, 20 except using the cited ester in place of methyl 2,6-dimethyl-benzoate.

EXAMPLE 33b

Isobutyl 2-Bromomethyl-6-methyl-benzoate

MS (EI) 286, 288 (M$^+$ Br pattern). Prepared from isobutyl 2,6-dimethyl-benzoate (EXAMPLE 32b).

EXAMPLE 34a 3-(Quinolin-2-ylmethoxy)-propan-1-ol 1,3-Propanediol (6.0 mL, 85 mmol) is dissolved in 20% DMPU in THF (80 mL) and cooled to 0° C. Sodium hydride (60%, 3.6 mg, 90 mmol) is added portionwise, and the contents are allowed to stir for 15 min. at 0° C. 2-Chloromethylquinoline (7.64 g, 42.7 mmol) is added and the reaction is allowed to stir overnight. The reaction is poured into water (700 mL) and extracted with ethyl acetate (1×200 mL). Sodium chloride is added to the aqueous layer and extracted again with ethyl acetate (2×200 mL). The organic layers are pooled and washed with water (2×300 mL) and brine (2×300 mL), dried over MgSO$_4$, filtered and reduced under vacuum to an oil. The crude material is purified by flash chromatography (silica, 2.5% methanol in dichloromethane) to give the title compound. MS (ESI) 218 (M+H)$^+$.

The following compounds are prepared using essentially the same procedure used in EXAMPLE 34a, except using the cited diol in place of 1,3-propanediol.

EXAMPLE 34b 4-(Quinolin-2-ylmethoxy)-butan-1-ol

MS (ESI) 232 (M+H)$^+$. Prepared from 1,4-butanediol.

EXAMPLE 34c 5-(Quinolin-2-ylmethoxy)-pentan-1-ol

MS (ESI) 246 (M+H)$^+$. Prepared from 1,5-pentanediol.

EXAMPLE 34d 2-(Quinolin-2-ylmethoxy)-ethanol

MS (ESI) 204 (M+H)$^+$. Prepared from ethylene glycol.

EXAMPLE 34e 2,2-Dimethyl-3-(quinolin-2-ylmethoxy)-propan-1-ol

MS (ESI) 246 (M+H)$^+$. Prepared from neopentyl glycol.

EXAMPLE 35a

Methyl 2-Methyl-6-[3-(quinolin-2-ylmethoxy)-propoxymethyl]-benzoate 3-(Quinolin-2-ylmethoxy)-propan-1-ol (4.6 g, 21.2 mmol, EXAMPLE 3a) is dissolved in 20% DMPU in THF (50 mL) and cooled to 0° C. Sodium hydride (60%, 920 mg, 23 mmol) is added portionwise, and the contents are allowed to stir for 15 min. at 0° C. Methyl 2-bromomethyl-6-methyl-benzoate (77%, 7.25 g, 23 mmol, EXAMPLE 2a) is added and the reaction is allowed to warm to r.t. and continue to stir overnight. The reaction is poured into water (600 mL) and extracted with ethyl acetate (3×200 mL). The organic fractions are pooled and washed with water (3×250 mL) and brine (2×300 mL), dried over MgSO$_4$, filtered and reduced under vacuum to an oil. The crude material is purified by flash chromatography (silica, 2% methanol in dichloromethane) to give the title compound. MS (ESI) 380 (M+H)$^+$.

The following compounds are prepared using essentially the same procedure used in EXAMPLE 35a, except using the cited alcohol in place of 3-(quinolin-2-ylmethoxy)-propan-1-ol.

EXAMPLE 35b

Methyl 2-Methyl-6-[4-(quinolin-2-ylmethoxy)-butoxymethyl]-benzoate

MS (ESI) 394 (M+H)$^+$. Prepared from 4-(quinolin-2-ylmethoxy)-butan-1-ol (EXAMPLE 34b).

EXAMPLE 35c

Methyl 2-Methyl-6-[5-(quinolin-2-ylmethoxy)-pentoxymethyl]-benzoate

MS (ESI) 408 (M+H)+. Prepared from 5-(quinolin-2-ylmethoxy)-pentan-1-ol (EXAMPLE 34c).

EXAMPLE 35d

Methyl 2-[2,2-Dimethyl-3-(quinolin-2-ylmethoxy)-propoxymethyl]-6-methyl-benzoate MS (ESI) 408 (M+H)+. Prepared from 2,2-dimethyl-3-(quinolin-2-ylmethoxy)-propan-1-ol (EXAMPLE 34e).

EXAMPLE 36a

2-Methyl-6-[3-(quinolin-2-ylmethoxy)-propoxymethyl]-benzoic Acid

Methyl 2-methyl-6-[3-(quinolin-2-ylmethoxy)-propoxymethyl]-benzoate (3.3 g, 8.7 mmol, EXAMPLE 35a) is dissolved in ethanol (81 mL). 10 N NaOH (9 mL, 90 mmol) is added and the contents are heated to 90° C. overnight. The reaction is cooled to r.t., and the volume reduced under vacuum. 2 N HCl (45 mL, 90 mmol) is added, and the pH is adjusted to ~4. The contents are poured into water (400 mL) and extracted with dichloromethane (3×200 mL). The organic layers are combined, washed with brine (2×300 mL), dried over $MgSO_4$, filtered and reduced under vacuum to dryness. The crude material is purified by flash chromatography (silica, 3% methanol in dichloromethane) to give the title compound. $^1$H NMR (300 MHz, $CDCl_3$) δ 8.27 (d, 2H), 7.86 (d, 1H), 7.73 (dd, 1H), 7.60–7.50 (m, 2H), 7.26–7.11 (m, 3H), 5.01 (s, 2H), 4.70 (s, 2H), 3.84 (t, 2H), 3.73 (t, 2H), 2.50 (s, 3H), 1.89 (quintet, 2H). MS (ESI) 366 (M+H)+.

The following compounds are prepared using essentially the same procedure used in EXAMPLE 36a, except using the cited ester in place of methyl 2-methyl-6-[3-(quinolin-2-ylmethoxy)-propoxymethyl]-benzoate.

EXAMPLE 36b

2-Methyl-6-[4-(quinolin-2-ylmethoxy)-butoxymethyl]-benzoic Acid $^1$H NMR (300 MHz, $CDCl_3$) δ 8.29–8.22 (m, 2H), 7.83 (d, 1H), 7.77–7.71 (m, 1H), 7.62–7.54 (m, 2H), 7.28–7.15 (m, 3H), 4.93 (s, 2H), 4.63 (s, 2H), 3.66 (t, 2H), 3.55 (t, 2H), 2.52 (s, 3H), 1.84–1.70 (m, 4H), MS (ESI) 380 (M+H)+. Prepared from methyl 2-methyl-6-[4-(quinolin-2-ylmethoxy)-butoxymethyl]-benzoate.

EXAMPLE 36c

2-Methyl-6-[5-(quinolin-2-ylmethoxy)-pentoxymethyl]-benzoic Acid $^1$H NMR (300 MHz, $CDCl_3$) δ 8.22 (d, 2H), 7.84 (d, 1H), 7.75–7.64 (m, 2H), 7.58–7.53 (m, 1H), 7.25–7.13 (m, 3H), 4.93 (s, 2H), 4.62 (s, 2H), 3.68 (t, 2H), 3.53 (t, 2H), 2.41 (s, 3H), 1.72–1.63 (m, 6H); MS (ESI) 394 (M+H)+. Prepared from methyl 2-methyl-6-[5-(quinolin-2-ylmethoxy)-pentoxymethyl]-benzoate (EXAMPLE 35c).

EXAMPLE 36d

2-[2,2-Dimethyl-3-(quinolin-2-ylmethoxy)-propoxymethyl]-6-methyl-benzoic Acid $^1$H NMR (300 MHz, $CDCl_3$) δ 8.25 (d, 2H), 7.85 (d, 1H), 7.72 (t, 1H), 7.59–7.48 (m, 2H), 7.23–7.10 (m, 3H), 4.94 (s, 2H), 4.64 (s, 2H), 3.46 (s, 2H), 3.34 (s, 2H), 2.49 (s, 3H), 0.96 (s, 6H). MS (ESI) 3.94 (M+H)+. Prepared from methyl 2-[2,2-dimethyl-3-(quinolin-2-ylmethoxy)-propoxymethyl]-6-methyl-benzoate (EXAMPLE 35d).

The following compounds are prepared using essentially the same procedure used in EXAMPLE 35a, except without DMPU as a co-solvent; using the cited alcohol in place of 3-(quinolin-2-ylmethoxy)-propan-1-ol, the cited alkylating reagent in place of methyl 2-bromomethyl-6-methyl-benzoate.

EXAMPLE 37a

{2-Methyl-6-[3-(quinolin-2-ylmethoxy)-propoxymethyl]-phenoxy}-acetonitrile

MS (ESI) 377 (M+H)+. Prepared from 3-(quinolin-2-ylmethoxy)-propan-1-ol (EXAMPLE 34a) and (2-bromomethyl-6-methyl-phenoxy)-acetonitrile.

EXAMPLE 37b

{2-Methyl-6-[4-(quinolin-2-ylmethoxy)-butoxymethyl]-phenoxy}-acetonitrile

MS (ESI) 391 (M+H)+. Prepared from 4-(quinolin-2-ylmethoxy)-butan-1-ol (EXAMPLE 34b) and (2-bromomethyl-6-methyl-phenoxy)-acetonitrile.

EXAMPLE 37c

{2-Methyl-6-[2-(quinolin-2-ylmethoxy)-ethoxymethyl]-phenoxy}-acetonitrile

MS (ESI) 363 (M+H)+. Prepared from 2-(quinolin-2-ylmethoxy)-ethanol (EXAMPLE 34d) and (2-bromomethyl-6-methyl-phenoxy)-acetonitrile.

EXAMPLE 37d

{4-Chloro-2-methyl-6-[4-(quinolin-2-ylmethoxy)-butoxymethyl]-phenoxy}-acetonitrile MS (ESI) 424 (M+H)+. Prepared from 4-(quinolin-2-ylmethoxy)-butan-1-ol (EXAMPLE-34b) and (2-bromomethyl-4-chloro-6-methyl-phenoxy)-acetonitrile.

EXAMPLE 37e

{4-Chloro-2-[2,2-dimethyl-3-(quinolin-2-ylmethoxy)-propoxymethyl]-6-methyl-phenoxyl}-acetonitrile MS (ESI) 439 (M+H)+. Prepared from 2,2-dimethyl-3-(quinolin-2-ylmethoxy)-propan-1-ol (EXAMPLE 34e) and (2-bromomethyl-4-chloro-6-methyl-phenoxy)-acetonitrile.

EXAMPLE 38a

{2-Methyl-6-[3-(quinolin-2-ylmethoxy)-propoxvmethyl]-phenoxy}-acetic Acid

{2-Methyl-6-[3-(quinolin-2-ylmethoxy)-propoxymethyl]-phenoxy}-acetonitrile (333 mg, 0.89 mmol, EXAMPLE 6a) is dissolved in ethanol (8 mL). 10 N NaOH (900 μL, 9.0 mmol) is added and the contents heated to 60° C. for 2 hrs. The reaction is cooled to r.t. and the pH adjusted to ~4 with 2 N HCl. The contents are partioned between aq. $NH_4Cl$ (10%, 100 mL) and ethyl acetate (100 mL). The aqueous layer is further extracted with ethyl acetate (2×75 mL). The organic fractions are combined and washed with sat. aq. $NH_4Cl$ (2×125 mL), dried over $MgSO_4$, filtered and reduced under vacuum to an oil. The crude material is purified by flash chromatography (silica, 6% methanol in dichloromethane) to give the title compound. $^1$H NMR (300 MHz, CDCl$_3$) δ 8.29–8.21 (m, 2H), 7.82 (d, 1H), 7.75 (t, 1H), 7.56 (dd, 1H), 7.50 (d, 1H), 7.15 (dd, 2H), 7.00 (dd, 1H), 4.79 (s, 2H), 4.61 (s, 2H), 4.55 (s, 2H), 3.70–3.47 (m, 4H), 2.31 (s, 3H), 1.95 (m, 2H). MS (ESI) 396 (M+H)$^+$.

The following compounds are prepared using essentially the same procedure used in EXAMPLE 38a, except using the cited nitrile in place of {2-methyl-6-[3-(quinolin-2-ylmethoxy)-propoxymethyl]-phenoxy}-acetonitrile.

EXAMPLE 38b

{2-Methyl-6-[4-(quinolin-2-ylmethoxy)-butoxymethyl]-phenoxy}-acetic Acid $^1$H NMR (300 MHz, CDCl$_3$) δ 8.22–8.19 (m, 2H), 7.81 (d, 1H), 7.73 (dd, 1H), 7.55–7.50 (m, 2H), 7.17–7.13 (m, 2H), 7.01 (dd, 1H), 4.85 (s, 2H), 4.60 (s, 2H), 4.56 (s, 2H), 3.64–3.59 (m, 4H), 2.32 (s, 3H), 1.75 (m, 4H). MS (ESI) 410 (M+H)$^+$. Prepared from {2-methyl-6-[4-(quinolin-2-ylmethoxy)-butoxymethyl]phenoxy}-acetonitrile (EXAMPLE 37b).

EXAMPLE 38c

{2-Methyl-6-[2-(quinolin-2-ylmethoxy)-ethoxymethyl]-phenoxy}-acetic Acid $^1$H NMR (300 MHz, CDCl$_3$) δ 8.18–8.11 (m, 2H), 7.79 (d, 1H), 7.75–7.68 (m, 1H), 7.55–7.50 (m, 1H), 7.44 (d, 1H), 7.12–7.08 (m, 2H), 6.99–6.94 (m, 1H), 4.81 (s, 2H), 4.59 (s, 2H), 4.54 (s, 2H), 3.76–3.70 (m, 4H), 2.22 (s, 3H). MS (ESI) 382 (M+H)$^+$. Prepared from {2-methyl-6-[2-(quinolin-2-ylmethoxy)-ethoxymethyl]-phenoxy}-acetonitrile (EXAMPLE 37c).

EXAMPLE 38d

{4-Chloro-2-methyl-6-[4-(quinolin-2-ylmethoxy)-butoxymethyl]-phenoxy}-acetic Acid $^1$H NMR (300 MHz, CDCl$_3$) δ 8.26–8.22 (m, 2H), 7.84 (d, 1H), 7.76–7.70 (m, 1H), 7.60–7.50 (m, 2H), 7.17–7.14 (m, 2H), 4.87 (s, 2H), 4.61 (s, 2H), 4.51 (s, 2H), 3.68–3.59 (m, 4H), 2.31 (s, 3H), 1.76 (s (broad), 4H). MS (ESI) 444 (M+H)$^+$. Prepared from {4-chloro-2-methyl-6-[4-(quinolin-2-ylmethoxy)-butoxymethyl]-phenoxy}-acetonitrile (EXAMPLE 37d).

EXAMPLE 38e

{4-Chloro-2-[2,2-dimethyl-3-(quinolin-2-ylmethoxy)-propoxymethyl]-6-methyl-phenoxyl}-acetic Acid $^1$H NMR (300 MHz, CDCl$_3$) δ 8.33–8.15 (m, 1H), 8.15–7.98 (m, 1H), 7.97–7.30 (m, 4H), 7.20–7.00 (m, 2H), 4.78 (s, 2H), 4.55 (s, 2H), 3.37 (s, 2H), 3.27 (s, 2H), 2.31 (s, 3H), 0.94 (s, 6H). MS (ESI) 459 (M+H)$^+$. Prepared from {4-chloro-2-[2,2-dimethyl-3-(quinolin-2-ylmethoxy)-propoxymethyl]-6-methyl-phenoxy}-acetonitrile (EXAMPLE 37e).

EXAMPLE 39a

N-(4-Hydroxy-butyl)-N-quinolin-2-ylmethyl-acetamide

To a solution of 4-amino-1-butanol (943 μL, 10 mmol) in anhyd. methanol (20 mL) is added 2-quinoline-carboxaldehyde (1.57 g, 10 mmol). The solution is allowed to stir at r.t. for 20 min. Solid NaBH$_4$ (380 mg, 10 mmol) is added portionwise, and the contents are stirred at r.t. for 1 hr. A solution of acetyl chloride (704 μL, 10 mmol) in dichloromethane (10 mL) is added dropwise over 15 min., and the contents are stirred at r.t. for another 2 hrs. Water (100 mL) is added, and the contents are extracted with dichloromethane (3×100 mL). The organic fractions are pooled and washed with brine (2×150 mL), dried over MgSO$_4$, filtered and reduced under vacuum to an oil. The crude material is purified by flash chromatography (silica, 3% methanol in dichloromethane) to give the title compound. MS (ESI) 273 (M+H)$^+$.

The following compound is prepared using essentially the same procedure used in EXAMPLE 39a, except using the cited amino alcohol in place of 4-amino-1-butanol.

EXAMPLE 39b

N-(3-Hydroxy-propyl)-N-quinolin-2-ylmethyl-acetamide

MS (ESI) 259 (M+H)$^+$. Prepared from 3-amino-1-propanol.

EXAMPLE 40a

Methyl 2-[4-(Acetyl-quinolin-2-ylmethyl-amino)-butoxymethyl]-6-methyl-benzoate

N-(3-Hydroxy-propyl)-N-quinolin-2-ylmethyl-acetamide (410 mg, 1.5 mmol, EXAMPLE 39a) is dissolved in 20% DMPU in THF (3 mL) and cooled to 0° C. Sodium hydride (60%, 66 mg, 1.65 mmol) is added and the contents are stirred for 10 min. Methyl 2-bromomethyl-6-methyl-benzoate (77%, 365 mg, 1.5 mmol, EXAMPLE 2a) is added. The contents are allowed to come to r.t., and are stirred overnight. The contents are poured into water (100 mL) and extracted with ethyl acetate (3×75 mL). The organic fractions are pooled and washed with water (2×100 mL) and brine (2×100 mL), dried over MgSO$_4$, filtered and reduced under vacuum to an oil. The crude material is purified by flash chromatography (silica, 3% methanol in dichloromethane) to give the title compound. MS (ESI) 435 (M+H)$^+$.

The following compound is prepared using essentially the same procedure used in EXAMPLE 40a, except using the cited alcohol in place of N-(3-hydroxy-propyl)-N-quinolin-2-ylmethyl-acetamide.

EXAMPLE 40b

Methyl 2-[3-(Acetyl-quinolin-2-ylmethyl-amino)-propoxymethyl]-6-methyl-benzoate

MS (ESI) 421 (M+H)$^+$. Prepared from N-(3-hydroxy-propyl)-N-quinolin-2-ylmethyl-acetamide (EXAMPLE 39b).

EXAMPLE 41a

2-[4-(Acetyl-quinolin-2-ylmethyl-amino)-butoxymethyl]-6-methyl-benzoic Acid

Methyl 2-[4-(acetyl-quinolin-2-ylmethyl-amino)-butoxymethyl]-6-methyl-benzoate (375 mg, 0.86 mmol, EXAMPLE 40a) is dissolved in ethanol (7.5 mL). 10 N NaOH (860 μL, 8.6 mmol) is added, and the contents are heated to 90° C. overnight. The reaction is cooled to r.t. and 2 N HCl (4.3 mL) is added, followed by dropwise addition of 2 N HCl to adjust the pH to ~4–6. The contents are poured into water (100 mL) and extracted with dichloromethane (3×75 mL). The organic fractions are pooled and washed with brine (3×100 mL), dried over MgSO$_4$, filtered and reduced under vacuum to dryness. The crude material is purified by flash chromatography (silica, 6% methanol in dichloromethane) to give the title compound. $^1$H NMR (300 MHz, CDCl$_3$) Rotamers 2:1 δ 8.37 (d, 0.5H), 8.28–8.15 (m, 1.5H), 7.88–7.83 (m, 1.25H), 7.80–7.73 (m, 1.75H), 7.65–7.57 (m, 1.25H), 7.43 (d, 0.25H), 7.33–7.10 (m, 3H), 5.24 (s, 1.33H), 5.01 (s, 0.66H), 4.67 (s, 1.33H), 4.63 (s, 0.66H), 3.55–3.45 (m, 2.66), 3.39–3.32 (m, 1.33), 2.58 (s, 2H), 2.55 (s, 1H), 2.31 (s, 1H), 1.95–1.82 (m, 2H), 1.77–1.62 (m, 2H). MS (ESI) 421 (M+H)$^+$.

The following compound is prepared using essentially the same procedure used in EXAMPLE 41a, except using the cited ester in place of methyl 2-[4-(acetyl-quinolin-2-ylmethyl-amino)-butoxymethyl]-6-methyl-benzoate.

EXAMPLE 41b

2-[3-(Acetyl-quinolin-2-ylmethyl-amino)-propoxymethyl]-6-methyl-benzoic Acid $^1$H NMR (300 MHz, CDCl$_3$) Rotamers 9:1 δ 8.32–8.22 (m, 2H), 7.88–7.84 (m, 2H), 7.81–7.75 (m, 1H), 7.62–7.57 (m, 1H), 7.26–7.18 (m, 2H), 7.11–7.08 (m, 1H), 7.11–7.08 (m, 1H), 5.05 (s, 1.8H), 4.95 (s, 0.2H), 4.66 (s, 1.8H), 4.61 (s, 0.2H), 3.65–3.47 (m, 4H), 2.58 (s, 2.7), 2.51 (s, 0.3H), 2.31 (s, 0.3H), 2.14 (s, 2.7H), 2.00–1.92 (quintet, 2H). MS (ESI) 407 (M+H)$^+$. Prepared from methyl 2-[3-(acetyl-quinolin-2-ylmethyl-amino)-propoxymethyl]-6-methyl-benzoate (EXAMPLE 40b).

EXAMPLE 42a 4-(Quinolin-2-ylamino)-butan-1-ol

2-Chloroquinoline (3.26 g, 20 mmol) and 4-amino-1-butanol are dissolved in anhyd. DMSO (10 mL) and heated to 140° C. for 4 hrs. The reaction is cooled to r.t., poured into water (250 mL) and extracted with ethyl acetate (3×100 mL). The organic fractions are pooled and washed with brine (3×150 mL), dried over MgSO$_4$, filtered and reduced under vacuum to dryness. The crude material is purified by flash chromatography (silica, 7% methanol in dichloromethane) to give the title compound. MS (ESI) 217 (M+H)$^+$.

The following compound is prepared using essentially the same procedure used in EXAMPLE 42a, except using the cited amino alcohol in place of 4-amino-1-butanol.

EXAMPLE 42b 3-(Quinolin-2-ylamino)-propan-1-ol

MS (ESI) 203 (M+H)$^+$. Prepared from 3-amino-1-propanol.

EXAMPLE 43a

Methyl 2-Methyl-6-[4-(quinolin-2-ylamino)-butoxymethyl]-benzoate 4-(Quinolin-2-ylamino)-butan-1-ol (432 mg, 2.0 mmol, EXAMPLE 42a) is dissolved in 20% DMPU in THF (5 mL) and cooled to 0° C. Sodium hydride (60%, 88 mg, 2.2 mmol) is added portionwise, and the contents are stirred for 10 min. Methyl 2-bromomethyl-6-methyl-benzoate (77%, 631 mg, 2.0 mmol, EXAMPLE 2a) is added and the contents are allowed to warm to r.t. and continue to stir overnight. The reaction contents are poured into water (100 mL) and extracted with ethyl acetate (3×75 mL). Sodium chloride is added to the aqueous layer on the second and third extractions. The organic fractions are pooled, washed with brine (2×150 mL), dried over MgSO$_4$, filtered and reduced under vacuum to an oil. The crude material is purified by flash chromatography (silica, 3% methanol in dichloromethane) to give the title compound. MS (ESI) 379 (M+H)$^+$.

The following compound is prepared using essentially the same procedure used in EXAMPLE 43a, except using the cited alcohol in place of 4-(quinolin-2-ylamino)-butan-1-ol.

EXAMPLE 43b

Methyl 2-Methyl-6-[3-(quinolin-2-ylamino)-propoxymethyl]-benzoate

MS (ESI) 365 (M+H)$^+$. Prepared from 3-(quinolin-2-ylamino)-propan-1-ol (EXAMPLE 42b). The following compounds are prepared using essentially the same procedure used in EXAMPLE 41a, except using the cited ester in place of methyl 2-[4-(acetyl-quinolin-2-ylmethyl-amino)-butoxymethyl]-6-methyl-benzoate.

EXAMPLE 44a

2-Methyl-6-[4-(quinolin-2-ylamino)-butoxymethyl]-benzoic Acid $^1$H NMR (300 MHz, DMSO) δ 7.79 (d, 1H), 7.56 (d, 1H), 7.48–7.39 (m, 2H), 7.25–7.00 (m, 4H), 6.72 (d, 1H), 4.46 (s, 2H), 3.42–3.36 (m, 4H), 2.27 (s, 3H), 1.67–1.59 (m, 4H). MS (ESI) 365 (M+H)$^+$. Prepared from methyl 2-methyl-6-[4-(quinolin-2-ylamino)-butoxymethyl]-benzoate (EXAMPLE 43a).

EXAMPLE 44b

2-Methyl-6-[3-(quinolin-2-ylamino)-propoxymethyl]-benzoic Acid $^1$H NMR (300 MHz, CDCl$_3$) δ 7.85 (d, 1H), 7.65–7.60. (m, 1H), 7.48–7.45 (m, 1H), 7.27 (d, 1H), 7.19–7.06 (m, 3H), 6.70 (d, 1H), 4.70 (s, 2H), 3.78 (t, 2H), 3.57–3.51 (m, 2H), 2.54 (s, 3H), 2.14–2.06 (quintet, 2H). MS (ESI) 351 (M+H)$^+$. Prepared from methyl 2-methyl-6-[3-(quinolin-2-ylamino)-propoxymethyl]-benzoate (EXAMPLE 43b).

The following compound is prepared using essentially the same procedure used in EXAMPLE 35a, except using the cited alcohol in place of 3-(quinolin-2-ylmethoxy)-propan-1-ol and the cited alkylating reagent in place of methyl 2-bromomethyl-6-methyl-benzoate.

EXAMPLE 45

{2-Methyl-6-[3-(quinolin-2-ylamino)-propoxymethyl]-phenoxy}-acetonitrile

MS (ESI) 362 (M+H)$^+$. Prepared from 3-(quinolin-2-ylamino)-propan-1-ol and (2-bromomethyl-6-methyl-phenoxy)-acetonitrile.

EXAMPLE 46

{2-Methyl-6-[3-(quinolin-2-ylamino)-propoxymethyl]-phenoxy}-acetic Acid

{2-Methyl-6-[3-(quinolin-2-ylamino)-propoxymethyl]-phenoxy}-acetonitrile (270 mg, 0.75 mmol) is dissolved in ethanol (6 mL). 10 N NaOH (750 μL, 7.5 mmol) is added, and the contents are heated to 60° C. for 4 hrs. The reaction is cooled to r.t. 2 N HCl (3.75 mL, 7.5 mmol) is added and the pH is adjusted to ~4–6. The contents are poured into water (150 mL) and extracted with ethyl acetate (3×75 mL). The organic fractions were pooled and washed with brine (3×100 mL), dried over MgSO$_4$, filtered and reduced under vacuum to dryness. The crude material was pure enough to test as is to give the title compound. ¹H NMR (300 MHz, CDCl₃) δ 11.04 (s (broad), 1H), 7.88 (d, 1H), 7.73 (d, 1H), 7.52–7.47 (m, 2H), 7.26–7.12 (m, 3H), 7.02–6.97 (m, 1H), 6.90 (d, 1H), 4.66 (s, 2H), 4.47 (s, 2H), 3.69 (t, 2H), 3.57–3.53 (m, 2H), 2.33 (s, 3H), 2.05 (quintet, 2H). MS (ESI) 381 (M+H)⁺.

EXAMPLE 47a

Methyl 2-Methoxy-6-[4-(quinolin-2-ylmethoxy)-butoxy]-benzoate 4-(Quinolin-2-ylmethoxy)-butan-1-ol (1.62 g, 7.0 mmol) and methyl 2-hydroxy-6-methoxy-benzoate (1.72 g, 9.45 mmol, EXAMPLE 27) are dissolved in anhyd. THF (10 mL). Triphenylphosphine (2.48 g, 9.45 mmol) is added and the contents cooled to −10° C. A solution of DEAD (1.54 mL, 9.8 mmol) in anhyd. THF (2.0 mL) is added dropwise over 10 min., allowed to come to r.t. and stirred overnight. The reaction is poured into water (200 mL) and extracted with dichloromethane (3×75 mL). The organic fractions were pooled and washed with brine (2×200 mL), dried over MgSO₄, filtered and reduced under vacuum to dryness. The crude material was purified by flash chromatography (silica, 2.5% methanol in dichloromethane) to give the title compound. MS (ESI) 396 (M+H)⁺.

The following compound is prepared using essentially the same procedure used in EXAMPLE 47a, except using the cited phenol in place of methyl 2-hydroxy-6-methoxy-benzoate.

EXAMPLE 47b

Ethyl 2-Methyl-6-[4-(quinolin-2-ylmethoxy)-butoxy]-benzoate

MS (ESI) 394 (M+H)⁺. Prepared from ethyl 6-methylsalicylate (See, Hauser, Frank M., *Synthesis* 1980, 10, 814–15.

EXAMPLE 47c

Ethyl 4-Benzyloxy-2-methyl-6-[4-(quinolin-2-ylmethoxy)-butoxy]-benzoate

MS (ESI) 502 (M+H)⁺. Prepared from ethyl 4-benzyloxy-2-hydroxy-6-methyl-benzoate. The following compounds are prepared using essentially the same procedure used in the previous EXAMPLEs, except using the cited ester in place of methyl 2-methyl-6-[3-(quinolin-2-ylmethoxy)-propoxymethyl]-benzoate.

EXAMPLE 48a

2-Methoxy-6-[4-(quinolin-2-ylmethoxy)-butoxy]-benzoic Acid

¹H NMR (300 MHz, CDCl₃) δ 8.33 (d, 1H), 8.23 (d, 1H), 7.81 (d, 1H), 7.77 (t, 1H), 7.62 (d, 1H), 7.56 (t, 2H), 7.19 (t, 1H), 6.49 (t, 2H), 4.88 (s, 2H), 4.04 (t, 2H), 3.87 (s, 3H), 3.76 (t, 2H), 1.91–1.87 (m, 4H). MS (ESI) 382 (M+H)⁺. Prepared from methyl 2-methoxy-6-[4-(quinolin-2-ylmethoxy)-butoxy]-benzoate.

EXAMPLE 48b

2-Methyl-6-[4-(quinolin-2-ylmethoxy)-butoxy]-benzoic Acid

¹H NMR (300 MHz, CDCl₃) δ 8.27–8.22 (m, 2H), 7.84 (d, 1H), 7.77 (t, 1H), 7.63 (d, 1H), 7.59 (t, 1H), 7.20–7.15 (m, 1H), 6.80 (d, 1H), 6.71 (d, 1H), 4.90 (s, 2H), 4.05 (t, 2H), 3.76 (t, 2H), 2.47 (s, 3H), 1.93–1.87 (m, 4H). MS (ESI) 366 (M+H)⁺. Prepared from ethyl 2-methyl-6-[4-(quinolin-2-ylmethoxy)-butoxy]-benzoate.

EXAMPLE 48c

4-Benzyloxy-2-methyl-6-[4-(quinolin-2-ylmethoxy)-butoxy]-benzoic Acid

¹H NMR (300 MHz, CD₃OD) δ 8.32 (d, 1H), 8.00 (d, 1H), 7.90 (d, 1H), 7.75–7.58 (m, 3H), 7.41–7.33 (m, 5H), 6.45 (s, 2H), 5.05 (s, 2H), 4.77 (s, 2H), 4.02 (t, 2H), 4.69 (t, 2H), 2.28 (s, 3H), 1.95–1.85 (m, 4H). MS (ESI) 473 (M+H)⁺. Prepared from ethyl 4-benzyloxy-2-methyl-6-[4-(quinolin-2-ylmethoxy)-butoxy]-benzoate.

EXAMPLE 49

3-(2-Phenyl-oxazol-4-ylmethoxy)-propan-1-ol 1,3-Propanediol (3.6 mL, 50 mmol) is dissolved in 10% DMPU in THF and cooled to 0° C. Sodium hydride is added portionwise (60%, 400 mg, 10 mmol). The contents are stirred for 10 min at 0° C., warmed to r.t. and stirred for another 10 min. 4-Chloromethyl-2-phenyl-oxazole (2.0 g, 10 mmol, EXAMPLE 21) is added, and the contents heated to 60° C. for 4 days. The reaction is cooled to r.t., poured into water (200 mL) and extracted with ethyl acetate (2×200 mL). The organic fractions were pooled and washed with brine (2×200 mL), dried over MgSO₄, filtered and reduced under vacuum to an oil. The crude material was purified by flash chromatography (silica, 2% methanol in dichloromethane) to give the title compound. MS (ESI) 234 (M+H)⁺.

EXAMPLE 50

Isobutyl 2-Methyl-6-[3-(2-phenyl-oxazol-4-ylmethoxy)-propoxymethyl]-benzoate 3-(2-Phenyl-oxazol-4-ylmethoxy)-propan-1-ol (1.26 g, 5.4 mmol) is dissolved in 10% DMPU in THF (20 mL) and cooled to 0° C. Sodium hydride (60%, 237 mg, 5.9 mmol) is added portionwise. The contents are stirred for 10 min.at 0° C., warmed to r.t. and stirred for another 10 min. isobutyl 2-bromomethyl-6-methyl-benzoate (2.69 g, 5.4 mmol, EXAMPLE 2b) is added, allowed to come to r.t and stirred overnight. The reaction is poured into water (200 mL) and extracted with ethyl acetate (2×200 mL). The organic fractions were pooled and washed with brine (2×200 mL), dried over MgSO₄, filtered and reduced under vacuum to an oil. The crude material was purified by flash chromatography (silica, 15–20% ethyl acetate in hexane) to give the title compound (1.06 g). MS (ESI) 438 (M+H)⁺.

The following compound is prepared using essentially the same procedure used in the previous EXAMPLEs, except using the cited ester in place of methyl 2-methyl-6-[3-(quinolin-2-ylmethoxy)-propoxymethyl]-benzoate.

EXAMPLE 51

2-Methyl-6-[3-(2-phenyl-oxazol-4-ylmethoxy)-propoxymethyl]-benzoic Acid

¹H NMR (300 MHz, CDCl₃) δ 8.07–8.04 (m, 2H), 7.71 (s, 1H), 7.48–7.46 (m, 3H), 7.24–7.14 (m, 2H), 4.71 (s, 2H), 4.70 (s, 2H), 3.77 (t, 2H), 3.72 (t, 2H), 2.48 (s, 3H), 1.88 (quint, 2H). MS (ESI) 382 (M+H)⁺. Prepared from isobutyl 2-methyl-6-[3-(2-phenyl-oxazol-4-ylmethoxy)-propoxymethyl]-benzoate.

EXAMPLE 52

4-Chloromethyl-2-phenyl-oxazole

Benzamide (1.21 g, 10 mmol) is mixed with 1,3-dichloroacetone (1.26 g, 10 mmol) and the mixture heated to 130° C. and stirred at this temperature for 1 h. The resulting mixture is then cooled, diluted with ethyl acetate, washed with K$_2$CO$_3$ solution (sat.), then brine, dried over MgSO$_4$ and concentrated to give the title compound as a solid, which is used without further purification. MS (ESI) 194 (M+H, Cl pattern)$^+$.

EXAMPLE 53

2-Cyanomethoxy-3-methylbenzaldehyde

A mixture of 2-hydroxy-3-methylbenzaldehyde (10.2 g, 75.0 mmoles, Aldrich), bromoacetonitrile (5.70 mL, 82.5 mmoles), and potassium carbonate (11.4 g, 82.5 mmoles) in DMF (150 mL) is heated to 55° C. for 3 hours, cooled, then diluted with ether. The mixture is washed with distilled water, saturated NaCl solution, then the organic layer dried over MgSO$_4$ and concentrated to give the title compound as a yellow solid. $^1$H NMR (300 MHz, CDCl$_3$): δ 10.20 (s, 1H), 7.70 (d, 1H), 7.53 (d, 1H), 7.29 (m, 1H), 4.81 (s, 2H), 2.42 (s, 3H).

EXAMPLE 54

(2-Hydroxymethyl-6-methyl-phenoxy)-acetonitrile

A 2M triglyme solution of sodium borohydride (16.0 mL, 32.1 mmoles) is slowly added to a cooled (−78° C.) solution of 2-cyanomethoxy-3-methylbenzaldehyde (11.25 g, 64.2 mmoles) in THF (180 mL). After stirring for one hour, the reaction is warmed to 0° C. for two hours, then quenched with 2N HCl (16.8 mL) and diluted with ether. The organic layer is isolated and washed with twice with distilled water and brine, then dried over MgSO$_4$. The organic solution is concentrated to give the title compound as a yellow oil.

EXAMPLE 55

(2-Bromomethyl-6-methyl-phenoxy)-acetonitrile

Triphenylphosphine (15.2 g, 57.8 mmoles) is added to (2-Hydroxymethyl-6-methyl-phenoxy)-acetonitrile (9.3 g, 52.5 mmoles) in THF (175 mL). The mixture is stirred until homogeneous and cooled to 0° C., followed by addition, in three portions, of N-bromosuccinimide (10.3 g, 57.8 mmoles). After 90 minutes the reaction is concentrated and the residue purified by column chromatography (silica, 5:1 hex:EtOAc) to yield the title compound as a pale yellow crystalline solid. MS (EI) 239, 241 (M)$^+$, Br pattern.

EXAMPLE 56

(4-Chloro-2,6-dimethyl-phenoxy)-acetonitrile

4-Chloro-2,6-dimethylphenol (5.0 g, 32 mmol), bromoacetonitrile (2.2 mL, 32 mmol) and potassium carbonate (6.6 g, 48 mmol) are combined with acetone (50 mL) and heated at reflux for 18 h. The reaction is filtered, concentrated and the residue partitioned between dichloromethane and water. The organic phase is washed with 1N HCl and water and is then dried over magnesium sulfate, concentrated and purified by column chromatography (silica, 10% ethyl acetate in hexanes) to provide the title compound. MS (EI) 195 (M)$^+$, Cl pattern.

EXAMPLE 57

(2-Bromomethyl-4-chloro-6-methyl-phenoxy)-acetonitrile (4-Chloro-2,6-dimethyl-phenoxy)-acetonitrile (700 mg, 3.6 mmol), N-bromosuccinimide (510 mg, 2.9 mmol) and benzoyl peroxide (72 mg, 0.29 mmol) are heated at reflux in carbon tetrachloride (10 mL) for 16 h. The reaction is cooled, filtered and the filtrate is concentrated and purified by column chromatograpy (silica, 5% ethyl acetate in hexanes) to provide the title compound. MS (EI) 273, 275 (M)$^+$, Br pattern.

EXAMPLE 58

Methyl 6-Methoxysalicylate

A mixture of 6-methoxysalicylic acid (10.0 g, 59.5 mmol) in methanol (40 mL) and sulfuric acid (2 mL) is heated at reflux 48 h. Although some acid remains the reaction is concentrated to remove the methanol and partitioned between ethyl acetate and saturated sodium carbonate solution. The organic phase is separated and washed with sodium carbonate until no acid remains by TLC analysis. The organic phase is dried and concentrated to provide the title compound as a low melting solid.

EXAMPLE 59

Ethyl 4-Benzyloxy-2-hydroxy-6-methyl-benzoate

To a solution of ethyl-2,4-dihydroxy-6-methyl benzoate (4.22 g, 22 mmol) in acetone (80 mL) is added potassium carbonate (3.0 g, 22 mmol) and benzyl bromide (2.6 mL, 22 mmol) and this mixture is heated under reflux overnight. The cooled reaction is diluted with ethyl acetate (100 mL) and water (100 mL) and the organic layer washed with water (2×80 mL) and brine (2×80 mL). The organic layer is dried over magnesium sulfate and the solvent removed to provide the title compound without further purification. MS (EI) 286 (M)$^+$.

Solid Phase Synthesis of the Compounds of the Invention:

The following is an example of the solid phase synthesis of compounds of the invention

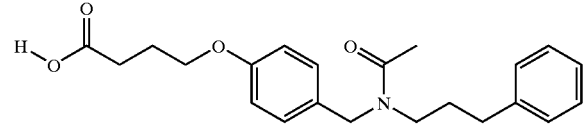

Experimental Procedures:
 1. Acid Loading:

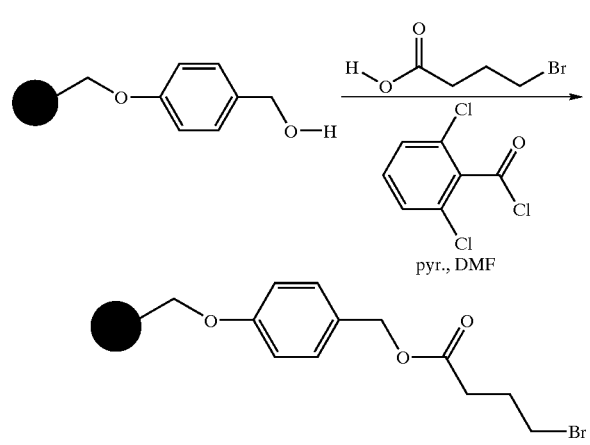

A three neck 3 L round bottom flask is charged with 4-bromobutyric acid (23.38 g, 140 mmoles) and DMF (1.5 L). The reaction flask is fitted with an overhead stirrer. After stirring for 10 min in order to dissolve the acid, the 2,6-dichlorobezoyl chloride (19.0 mL, 127 mmoles) and the pyridine (10.3 mL, 129 mmoles) are added in turn. After stirring for 2.5 hours, the MicroKANs [1456, 15 mg of Wang resin (1.7 mmole/g loading per microKAN), 25.5 micromoles/microKAN, 37.1 mmoles] are then added to the reaction flasks. The reaction is allowed to stir for 18 hours. At the end of this period, the reaction mixture is drained from the flask. DMF (1.5 L) is added to the reaction flask. The flask is allowed to stir for approximately 15 minutes and the solvent is drained. The MicroKANs are washed, stirred for 20 minutes and drained repeatedly in the following washing sequence: DMF (2×6 L), THF (3×6 L), dichloromethane (3×6 L) and ether (2×6 L). After the final washing, the MicroKANs are dried by blowing a stream of nitrogen through the flask with intermittent agitation. After sufficient drying, the MicroKANs are sorted for the next reaction.

2. Phenol Displacement:

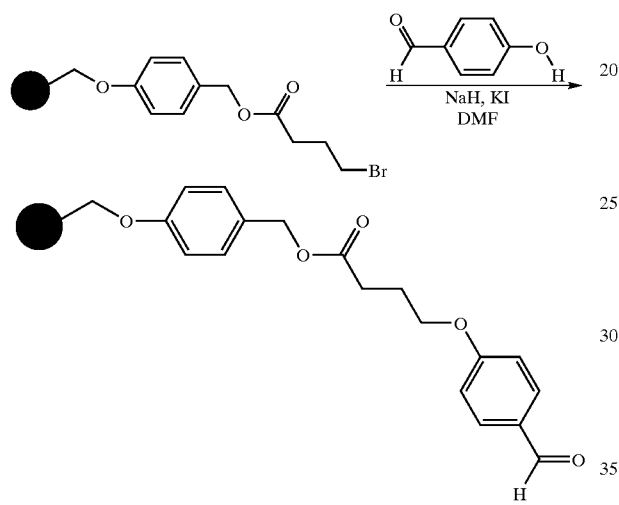

A three neck 3 L round bottom flask is charged with 4-hydroxybenzaldehyde (17.1 g, 140 mmoles) and DMF (1.5 L). The reaction flask is fitted with an overhead stirrer and immersed in an ice-water bath.

After approximately 15 minutes sodium hydride (60% dispersion in oil, 6.48 g, 180 mmoles) is carefully added. After approximately 30 minutes, the ice-water bath is removed and the reaction allowed to stir at ambient temperature for 1 hour. At the end of this time, the MicroKANs [1274, 25.5 micromoles/microKAN, 32.5 mmoles] and potassium iodide (1.0 g) are added to the reaction mixture. The reaction flask is immersed in an oil bath, which is heated to 60° C. After 14 hours, the reaction flask is removed from the oil bath and allowed to cool to ambient temperature. The reaction solvent is removed. DMF (1.2 L) is added to the reaction flask. The flask is allowed to stir for approximately 15 minutes and the solvent is drained. DMF:water (1:1, 1.2 L) is added to the reaction flask. The flask is allowed to stir for approximately 15 minutes and the solvent is drained. This sequence is repeated at least three times or until the effluent from the washing is clear. Then the reaction flask is are washed repeatedly in the following sequence: THF (2×4 L), dichloromethane (1×4 L) then methanol (1×4 L), dichloromethane (1×4 L) then methanol (1×4 L), dichloromethane (1×4 L) then methanol (1×4 L), dichloromethane (1×4 L) and ether (1×4 L). After the final washing, the MicroKANs are dried by blowing a stream of nitrogen through the flask with intermittent agitation. After sufficient drying, the MicroKANs are sorted for the next reaction.

3. Reductive Amination:

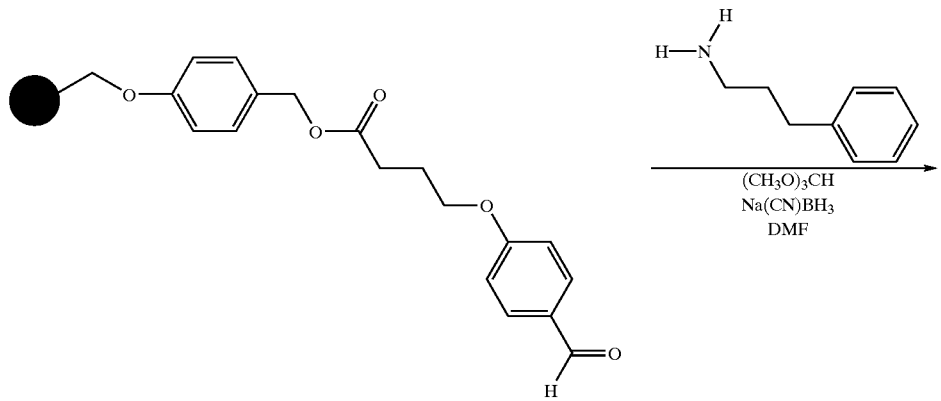

-continued

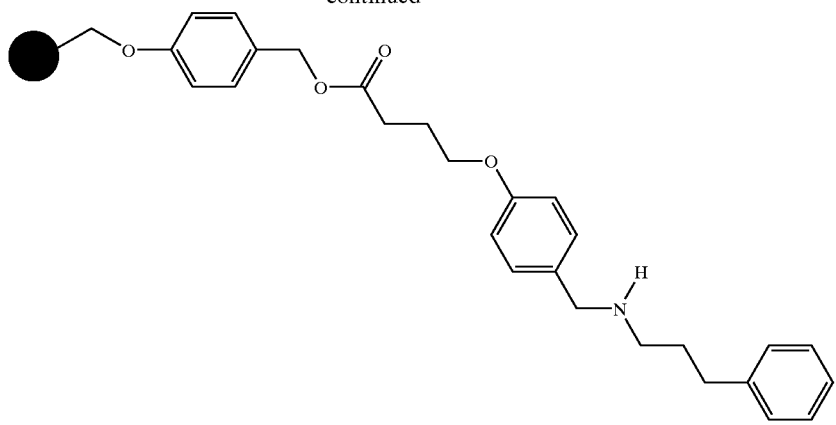

A three neck 2 L round bottom flask is charged with the MicroKANs [784, 25.5 micromoles/microKAN, 20.0 mmoles], trimethylorthoformate (850 mL) and 3-phenyl-1-propylamine (22.99 g, 170 mmoles). The reaction flask is fitted with an overhead stirrer. After 2 hours, sodium cyanoborohydride (21.37 g, 340 mmoles) is added. After approximately 10 minutes, acetic acid (17.0 mL, 297 mmoles) is added. After stirring for an additional hour, the reaction flask is drained. Methanol (800 mL) is added to the flask. After stirring for approximately 10 minutes, the flask is drained. The MicroKANs are washed in the following sequence: DMF (3×4 L), dichloromethane (1×4 L) then methanol (1×4 L), dichloromethane (1×4 L) then methanol (1×4 L), dichloromethane (1×4 L) then methanol (1×4 L), dichloromethane (1×4 L) and ether (1×4 L). After the final washing the microKANS are dried by blowing a stream of nitrogen through the flask with intermittent agitation. After sufficient drying, the MicroKANs are sorted for the next reaction.

4. Acylation:

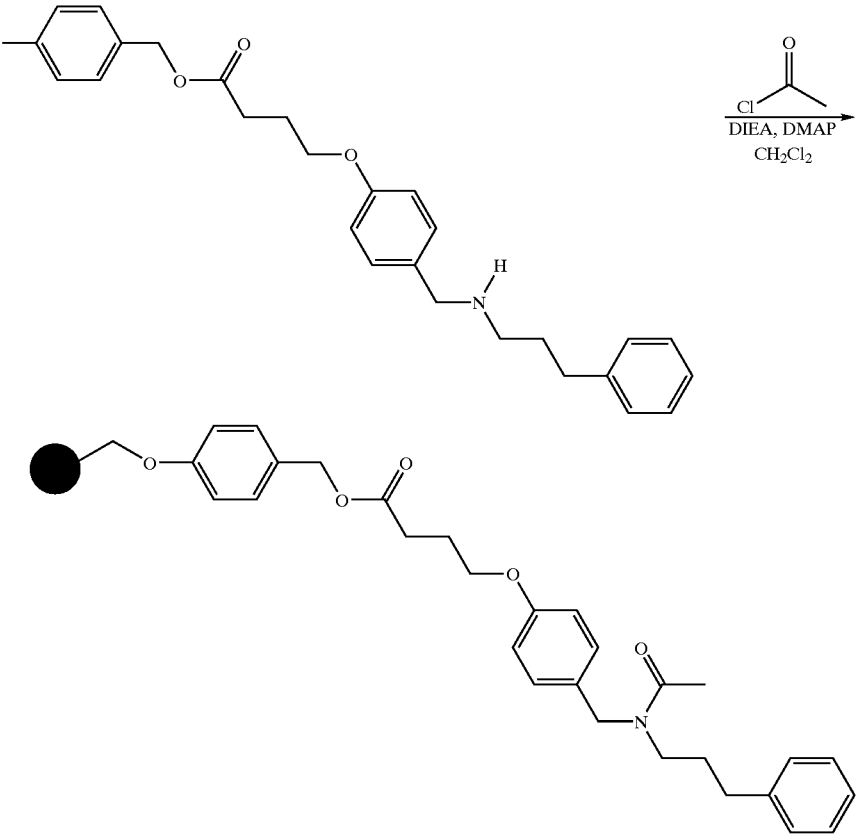

A three neck 2 L round bottom flask is charged with the MicroKANs [784, 15 mg of resin (1.7 mmole/g loading) per MicroKAN, 25.5 micromoles/microKAN, 20.0 mmoles], and dichloromethane (800 mL). The reaction flask is fitted with an overhead stirrer. N,N-diisopropylethylamine (20.9 mL, 120 mmoles) and 4-N,N-dimethylaminopyridine (195 mg, 1.6 mmoles) are added. After approximately 15 minutes, the acetyl chloride (6.3 g, 80.0 mmoles) is added. The reaction mixture is allowed to stir for 61 hours, after which the reaction flask is drained. Dichloromethane (800 mL) is added to the reaction flask. After stirring for approximately 10 minutes, the flask is drained. This is repeated. The MicroKANs from all of the acylation reactions are randomly combined into two separate large flasks and washed repeatedly in the following sequence: dichloromethane (1×4 L), THF (2×4 L), dichloromethane (1×4 L) then methanol (1×4 L), dichloromethane (1×4 L) then methanol (1×4 L), dichloromethane (1×4 L) then methanol (1×4 L), dichloromethane (1×4 L) and ether (1×4 L).

5. Cleavage:

The MicroKAN is sorted into individual wells of IRORI AccuCleave 96 cleavage stations. The well is charged with dichloromethane (600 mL) and then with a TFA:dichloromethane mixture (1:1, 600 mL). After agitating for approximately forty minutes, the reaction well is drained into 2 mL microtubes in an 96-well format. The reaction well is again charged with dichloromethane (600 mL). After manual agitation, this too is drained into the 2 mL microtubes in an 96-well format. The cleavage cocktail is removed in vacuo using a Savant Speedvac. The concentrated products from the cleavage mother plates are reconstituted with THF and transferred into two daughter plates utilizing a Packard MultiProbe liquid handler. The daughter plates are concentrated in vacuo utilizing a GenieVac.

Analytical: MS: m/z 370.2 (M+H$^+$).

Experimental Procedures:

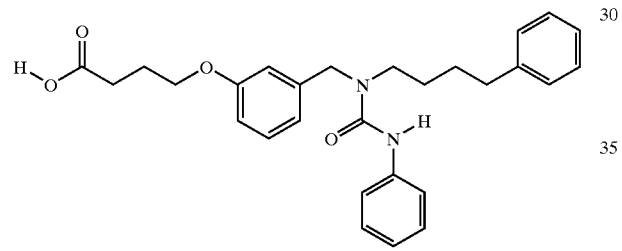

1. Acid Loading:

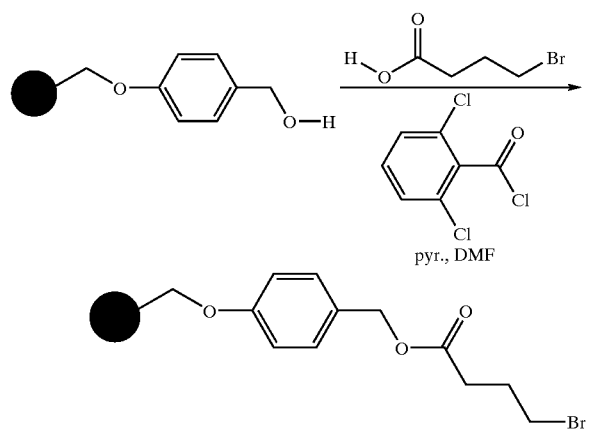

A three neck 3 L round bottom flask is charged with 4-bromobutyric acid (23.38 g, 140 mmoles) and DMF (1.5 L). The reaction flask is fitted with an overhead stirrer. After stirring for 10 min in order to dissolve the acid, the 2,6-dichlorobenzoyl chloride (19.0 mL, 127 mmoles) and the pyridine (10.3 mL, 129 mmoles) are added in turn. After stirring for 2.5 hours, the MicroKANs [1456, 15 mg of Wang resin (1.7 mmole/g loading per microKAN), 25.5 micromoles/microKAN, 37.1 mmoles] are then added to the reaction flask. The reaction is allowed to stir for 18 hours. At the end of this period, the reaction mixture is drained from the flask. DMF (1.5 L) is added to the reaction flask. The flask is allowed to stir for approximately 15 minutes, and then the solvent is drained. The MicroKANs are washed, stirred for 20 minutes and drained repeatedly in the following sequence: DMF (2×6 L), THF (3×6 L), dichloromethane (3×6 L) and ether (2×6 L). After the final washing the MicroKANs are dried by blowing a stream of nitrogen through the flask with intermittent agitation. After sufficient drying, the MicroKANs are sorted for the next reaction.

2. Phenol Displacement:

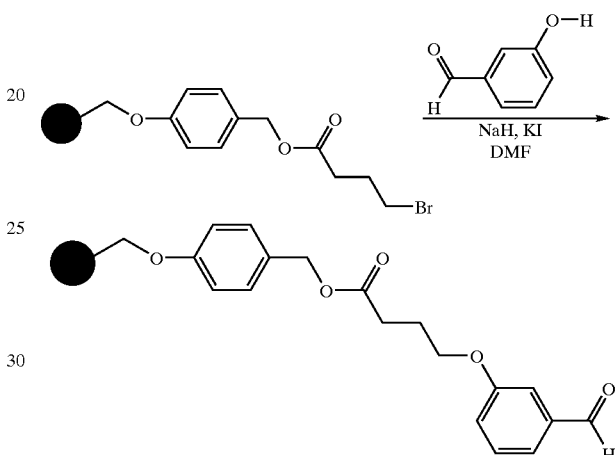

A three neck 3 L round bottom flask is charged with 3-hydroxybenzaldehyde (17.1 g, 140 mmoles) and DMF (1.5 L). The reaction flask is fitted with an overhead stirrer and immersed in an ice-water bath. After approximately 15 minutes sodium hydride (60% dispersion in oil, 6.48 g, 180 mmoles) is carefully added. After approximately 30 minutes, the ice-water bath is removed and the reaction allowed to stir at ambient temperature for 1 hour. At the end of this time, the MicroKANs [1274, 25.5 micromoles/microKAN, 32.5 mmoles] and potassium iodide (1.0 g) are added to the reaction mixture. The reaction flask is immersed into an oil bath which is heated to 60° C. After 14 hours, the reaction flask is removed from the oilbath and allowed to cool to ambient temperature. The reaction solvent is removed. DMF (1.2 L) is added to the reaction flask. The flask is allowed to stir for approximately 15 minutes and the solvent is drained. DMF:water (1:1, 1.2 L) is added to the reaction flask. The flask is allowed to stir for approximately 15 minutes, and then the solvent is drained. This sequence is repeated at least three times or until the effluent from the washing is clear. The reaction flasks are washed repeatedly in the following sequence: THF (2×4 L), dichloromethane (1×4 L) then methanol (1×4 L), dichloromethane (1×4 L) then methanol (1×4 L), dichloromethane (1×4 L) then methanol (1×4 L), dichloromethane (1×4 L) and ether (1×4 L). After the final washing, the MicroKANs are dried by blowing a stream of nitrogen through the flask with intermittent agitation. After sufficient drying, the MicroKANs are sorted for the next reaction.

3. Reductive Amination:

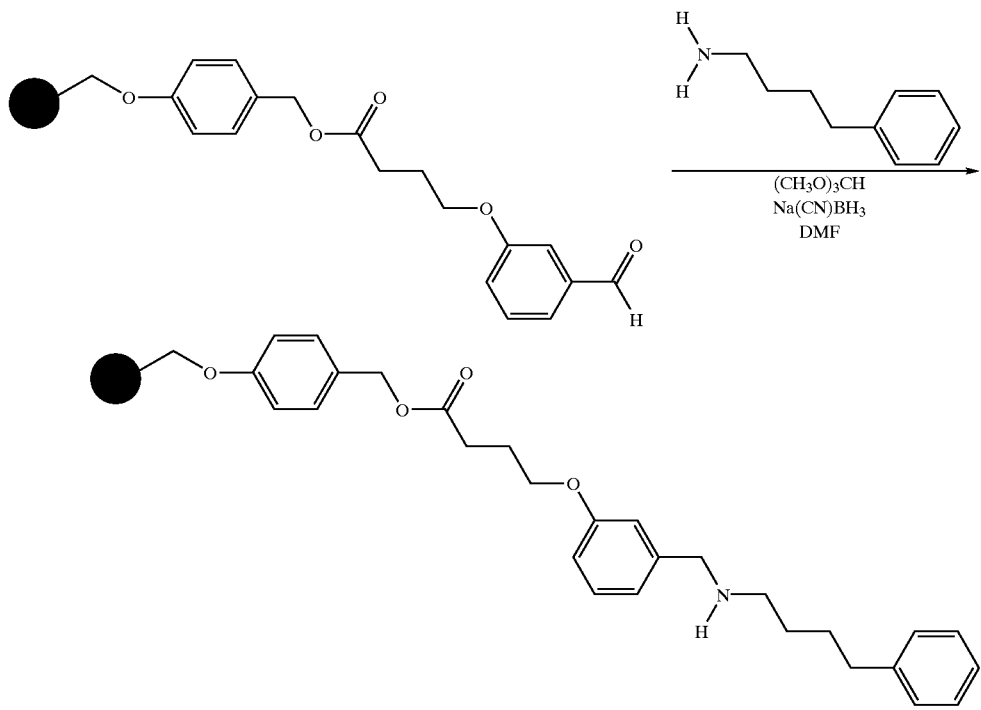

A three neck 2 L round bottom flask is charged with the MicroKANs [784, 25.5 micromoles/microKAN, 20.0 mmoles], trimethylorthoformate (850 mL) and 4-phenyl-1-butylamine (25.37 g, 170 mmoles). The reaction flask is fitted with an overhead stirrer. After 2 hours, sodium cyanoborohydride (21.37 g, 340 mmoles) is added. After approximately 10 minutes, acetic acid (17.0 mL, 297 mmoles) is added. After stirring for an additional hour, the reaction flask is drained. Methanol (800 mL) is added to the flask.

After stirring for approximately 10 minutes, the flask is drained. The MicroKANs following sequence: DMF (3×4 L), dichloromethane (1×4 L) then methanol (1×4 L), dichloromethane (1×4 L) then methanol (1×4 L), dichloromethane (1×4 L) then methanol (1×4 L), dichloromethane (1×4 L) and ether (1×4 L). After the final washing the microKANS are dried by blowing a stream of nitrogen through the flask with intermittent agitation. After sufficient drying, the MicroKANs are sorted for the next reaction.

4. Acylation:

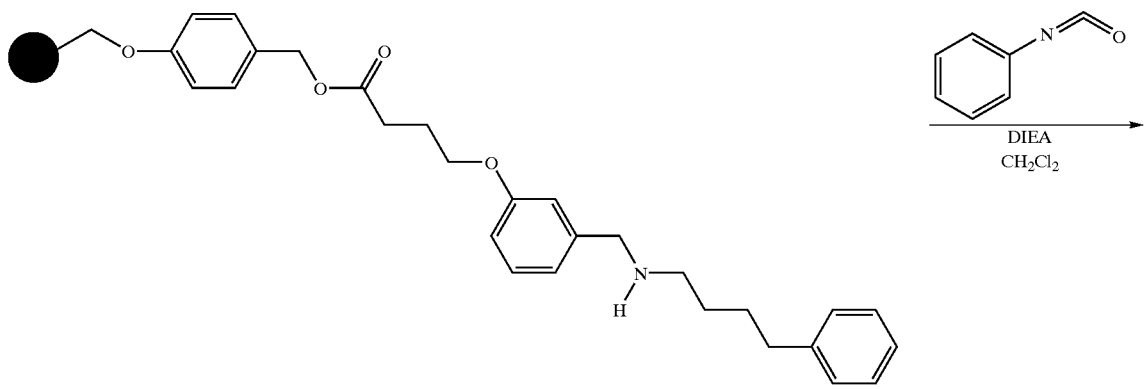

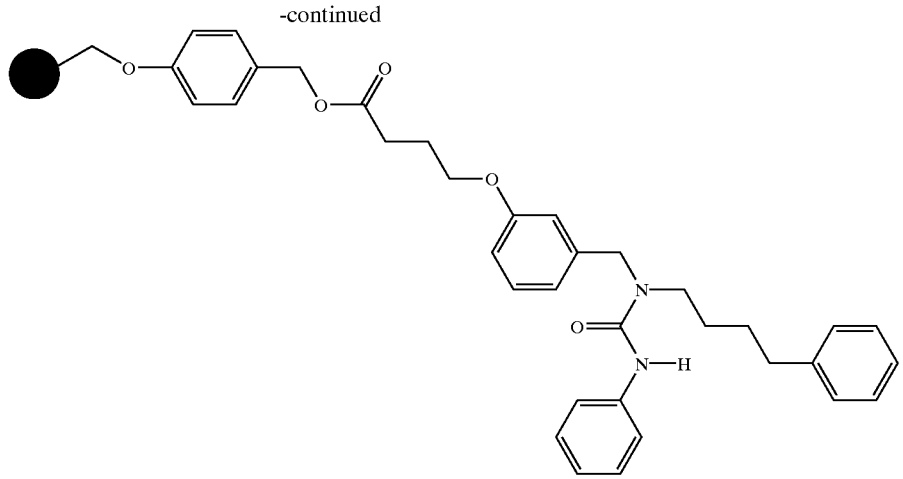

A three neck 2 L round bottom flask is charged with the MicroKANs [784, 25.5 micromoles/microKAN, 20.0 mmoles], and dichloromethane (800 mL). The reaction flask is fitted with an overhead stirrer. N,N-diisopropylethylamine (20.9 mL, 120 mmoles) is added. After approximately 15 minutes, the phenyl isocyanate (9.5 g, 80.0 mmoles) is added. The reaction mixture is allowed to stir for 61 hours, after which the reaction flask is drained. Dichloromethane (800 mL) is added to the reaction flask. After stirring for approximately 10 minutes, the flask is drained. This is repeated. The MicroKANs from all of the acylation reactions are randomly combined into two separate large flasks and washed repeatedly in the following sequence: dichloromethane (1×4 L), THF (2×4 L), dichloromethane (1×4 L) then methanol (1×4 L), dichloromethane (1×4 L) then methanol (1×4 L), dichloromethane (1×4 L) then methanol (1×4 L), dichloromethane (1×4 L) and ether (1×4 L).

5. Cleavage:

The MicroKAN is sorted into individual wells of IRORI AccuCleave 96 cleavage stations. The well is charged with dichloromethane (600 mL) and then with a TFA: dichloromethane mixture (1:1, 600 mL). After agitating for approximately forty minutes, the reaction well is drained into a 2 mL microtube in an 96-well format. The reaction well is again charged with dichloromethane (600 mL). After manual agitation, this too is drained into the 2 mL microtube in an 96-well format. The cleavage cocktail is removed in vacuo using a Savant Speedvac. The concentrated product from the cleavage mother plates is reconstituted with THF and transferred into two daughter plates utilizing a Packard MultiProbe liquid handler. The daughter plate is concentrated in vacuo utilizing a GenieVac.

Analytical: MS: m/z 461.3 (M+H$^+$).

Experimental Procedures:

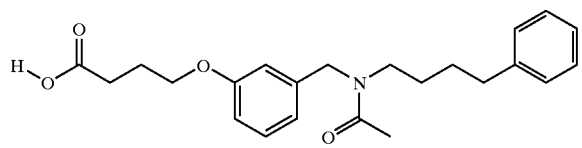

1. Acid Loading:

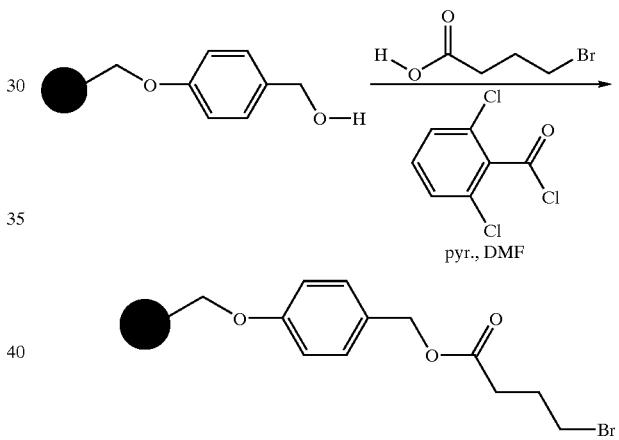

A three neck 3 L round bottom flask is charged with 4-bromobutyric acid (23.38 g, 140 mmoles) and DMF (1.5 L). The reaction flask is fitted with an overhead stirrer. After stirring for 10 min in order to dissolve the acid, the 2,6-dichlorobenzoyl chloride (19.0 mL, 127 mmoles) and the pyridine (10.3 mL, 129 mmoles) are added in turn. After stirring for 2.5 hours, the MicroKANs [1456, 15 mg of Wang resin (1.7 mmole/g loading per microKAN), 25.5 micromoles/microKAN, 37.1 mmoles] are then added to the reaction flasks. The reaction is allowed to stir for 18 hours. At the end of this period, the reaction mixture is drained from the flask. DMF (1.5 L) is added to the reaction flask. The flask is allowed to stir for approximately 15 minutes, and then the solvent is drained. The MicroKANs are washed, stirred for 20 minutes and drained repeatedly in the following sequence: DMF (2×6 L), THF (3×6 L), dichloromethane (3×6 L) and ether (2×6 L). After the final washing, the MicroKANs are dried by blowing a stream of nitrogen through the flask with intermittent agitation. After sufficient drying, the MicroKANs are sorted for the next reaction.

2. Phenol Displacement:

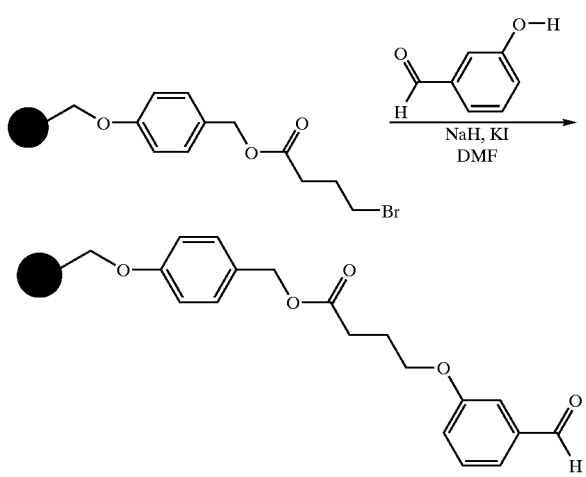

A three neck 3 L round bottom flask is charged with 3-hydroxybenzaldehyde (17.1 g, 140 mmoles) and DMF (1.5 L). The reaction flask is fitted with an overhead stirrer and immersed in an ice-water bath. After approximately 15 minutes, sodium hydride (60% dispersion in oil, 6.48 g, 180 mmoles) is carefully added. After approximately 30 minutes, the ice-water bath is removed and the reaction allowed to stir at ambient temperature for 1 hour. At the end of this time, the MicroKANs [1274, 15 mg of resin (1.7 mmole/g loading) per MicroKAN, 25.5 micromoles/microKAN, 32.5 mmoles] and potassium iodide (1.0 g) are added to the reaction mixture. The reaction flask is immersed in an oil bath, which is heated to 60° C. After 14 hours, the reaction flask is removed from the oil bath and allowed to cool to ambient temperature. The reaction solvent is removed. DMF (1.2 L) is added to the reaction flask. The flask is allowed to stir for approximately 15 minutes and the solvent is drained. DMF:water (1:1, 1.2 L) is added to the reaction flask. The flask is allowed to stir for approximately 15 minutes, and then the solvent is drained. This sequence is repeated at least three times or until the effluent from the washing is clear, the reaction flasks are washed repeatedly in the following sequence: THF (2×4 L), dichloromethane (1×4 L) then methanol (1×4 L), dichloromethane (1×4 L) then methanol (1×4 L), dichloromethane (1×4 L) then methanol (1×4 L), dichloromethane (1×4 L) and ether (1×4 L). After the final washing, the MicroKANs are dried by blowing a stream of nitrogen through the flask with intermittent agitation. After sufficient drying, the MicroKANs are sorted for the next reaction.

3. Reductive Amination:

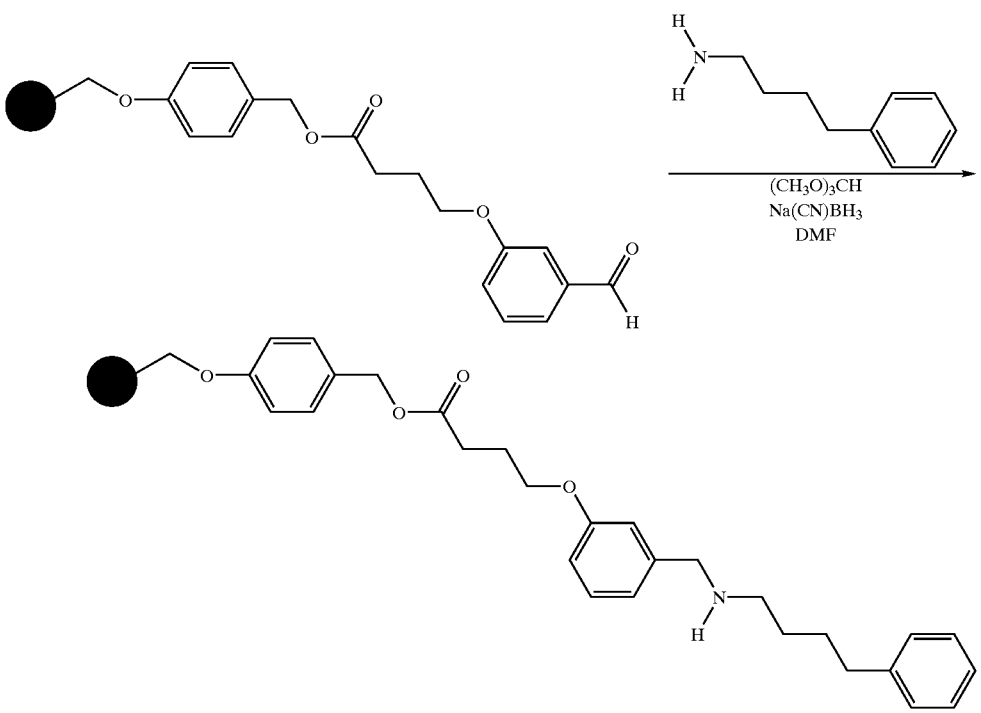

A three neck 2 L round bottom flask is charged with the MicroKANs [784, 15 mg of resin (1.7 mmole/g loading) per MicroKAN, 25.5 micromoles/microKAN, 20.0 mmoles], trimethylorthoformate (850 mL) and 4-phenyl-1-butylamine (25.37 g, 170 mmoles). The reaction flask is fitted with an overhead stirrer After 2 hours, sodium cyanoborohydride (21.37 g, 340 mmoles) is added. After approximately 10 minutes, acetic acid (17.0 mL, 297 mmoles) is added. After stirring for an additional hour, the reaction flask is drained. Methanol (800 mL) is added to the flask. After stirring for approximately 10 minutes, the flask is drained. The Micro-KANs are washed in the following sequence: DMF (3×4 L), dichloromethane (1×4 L) then methanol (1×4 L), dichloromethane (1×4 L) then methanol (1×4 L), dichloromethane (1×4 L) then methanol (1×4 L), dichloromethane (1×4 L) and ether (1×4 L). After the final washing, the microKANS are dried by blowing a stream of nitrogen through the flask with intermittent agitation. After sufficient drying, the MicroKANs are sorted for the next reaction.

4. Acylations:

romethane (1×4 L) then methanol (1×4 L), dichloromethane (1×4 L) then methanol (1×4 L), dichloromethane (1×4 L) and ether (1×4 L).

5. Cleavage:

The MicroKANs are sorted into individual wells of IRORI AccuCleave 96 cleavage stations. The well is charged with dichloromethane (600 mL) and then with a TFA:dichloromethane mixture (1:1, 600 mL). After agitating for approximately forty minutes, the reaction well is drained into 2 mL microtubes in an 96-well format. The reaction well is again charged with dichloromethane (600 mL). After manual agitation, this too is drained into the 2 mL microtubes in an 96-well format. The cleavage cocktail is removed in vacuo using a Savant Speedvac. The concentrated products from the cleavage mother plates are reconstituted with THF and transferred into two daughter plates utilizing a Packard MultiProbe liquid handler. The daughter plates are concentrated in vacuo utilizing a GenieVac.

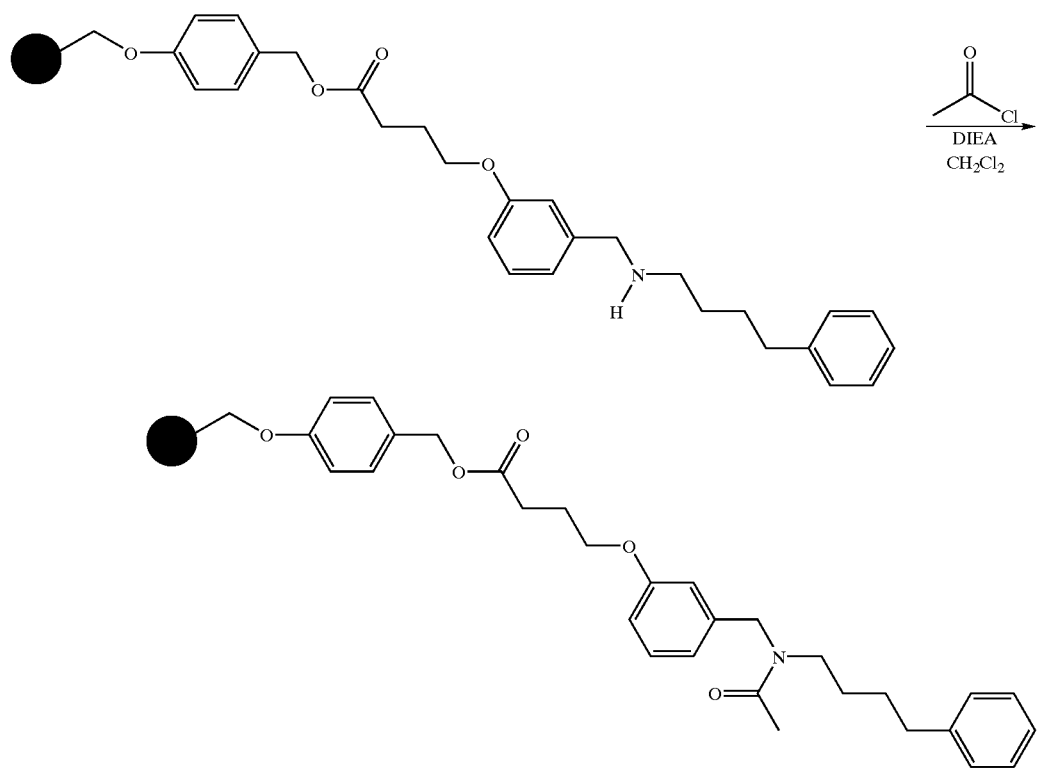

A three neck 2 L round bottom flask is charged with the MicroKANs [784, 15 mg of resin (1.7 mmole/g loading) per MicroKAN, 25.5 micromoles/microKAN, 20.0 mmoles], and dichloromethane (800 mL). The reaction flask is fitted with an overhead stirrer. N,N-diisopropylethylamine (20.9 mL, 120 mmoles) and 4-N,N-dimethylaminopyridine (195 mg, 1.6 mmoles) are added. After approximately 15 minutes, the acetyl chloride (6.3 g, 80.0 mmoles) is added. The reaction is allowed to stir for 61 hours, and then the reaction flask is drained. Dichloromethane (800 mL) is added to the reaction flask. After stirring for approximately 10 minutes, the flask is drained. This is repeated. The MicroKANs from all of the acylation reactions are randomly combined into two separate large flasks and washed repeatedly in the following sequence: dichloromethane (1×4 L), THF (2×4 L), dichloromethane (1×4 L) then methanol (1×4 L), dichlo- Analytical: MS: m/z 384.2 (M+H$^+$).

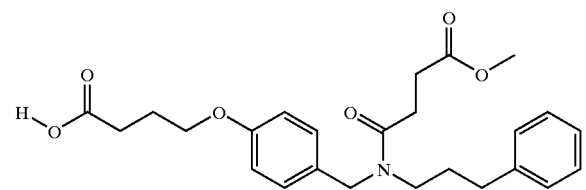

Experimental Procedures:
1. Acid Loading:

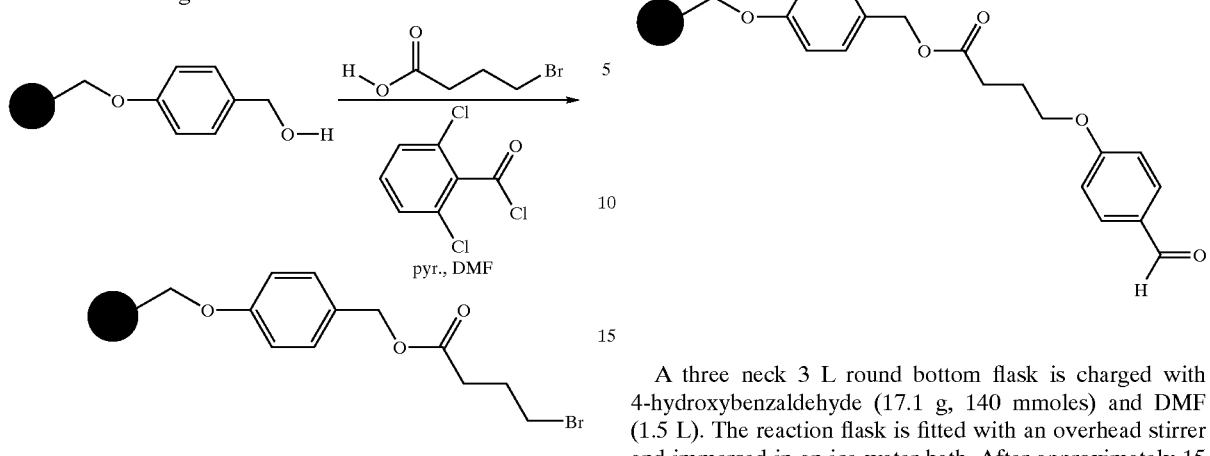

A three neck 3 L round bottom flask is charged with 4-bromobutyric acid (23.38 g, 140 mmoles) and DMF (1.5 L). The reaction flask is fitted with an overhead stirrer. After stirring for 10 min in order to dissolve the acid, the 2,6-dichlorobenzoyl chloride (19.0 mL, 127 mmoles) and the pyridine (10.3 mL, 129 mmoles) are added in turn. After stirring for 2.5 hours, the MicroKANs [1456, 15 mg of Wang resin (1.7 mmole/g loading per microKAN), 25.5 micromoles/microKAN, 37.1 mmoles] are then added to the reaction flasks. The reaction is allowed to stir for 18 hours. At the end of this period, the reaction mixture is drained from the flask. DMF (1.5 L) is added to the reaction flask. The flask is allowed to stir for approximately 15 minutes and the solvent is drained. The MicroKANs are washed, stirred for 20 minutes and drained repeatedly in the following sequence: DMF (2×6 L), THF (3×6 L), dichloromethane (3×6 L) and ether (2×6 L). After the final washing, the MicroKANs are dried by blowing a stream of nitrogen through the flask with intermittent agitation. After sufficient drying, the MicroKANs are sorted for the next reaction.

2. Phenol Displacement:

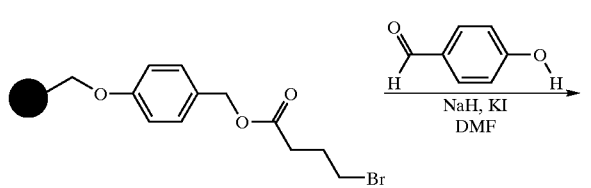

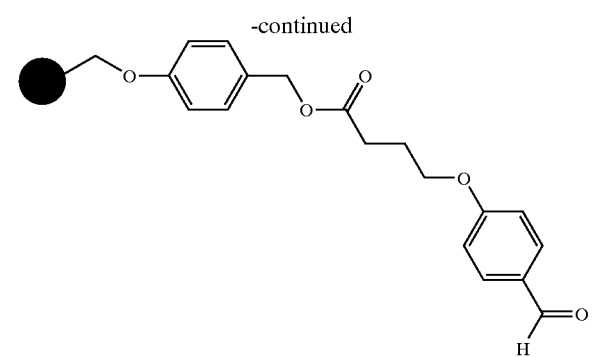

A three neck 3 L round bottom flask is charged with 4-hydroxybenzaldehyde (17.1 g, 140 mmoles) and DMF (1.5 L). The reaction flask is fitted with an overhead stirrer and immersed in an ice-water bath. After approximately 15 minutes, sodium hydride (60% dispersion in oil, 6.48 g, 180 mmoles) is carefully added. After approximately 30 minutes, the ice-water bath is removed and the reaction allowed to stir at ambient temperature for 1 hour. At the end of this time, the MicroKANs [1274, 15 mg of resin (1.7 mmole/g loading) per MicroKAN, 25.5 micromoles/microKAN, 32.5 mmoles] and potassium iodide (1.0 g) are added to the reaction mixture. The reaction flask is immersed in an oil bath, which is heated to 60° C. After 14 hours, the reaction flask is removed from the oil bath and allowed to cool to ambient temperature. The reaction solvent is removed. DMF (1.2 L) is added to the reaction flask. The flask is allowed to stir for approximately 15 minutes, and the solvent is then drained. DMF: water (1:1, 1.2 L) is added to the reaction flask. The flask is allowed to stir for approximately 15 minutes, and the solvent is then drained. This sequence is repeated at least three times or until the effluent from the washing is clear. Then the reaction flasks are washed repeatedly in the following sequence: THF (2×4 L), dichloromethane (1×4 L) then methanol (1×4 L), dichloromethane (1×4 L), then methanol (1×4 L), dichloromethane (1×4 L), then methanol (1×4 L), dichloromethane (1×4 L) and ether (1×4 L). After the final washing, the MicroKANs are dried by blowing a stream of nitrogen through the flask with intermittent agitation. After sufficient drying, the MicroKANs are sorted for the next reaction.

3. Reductive Amination:

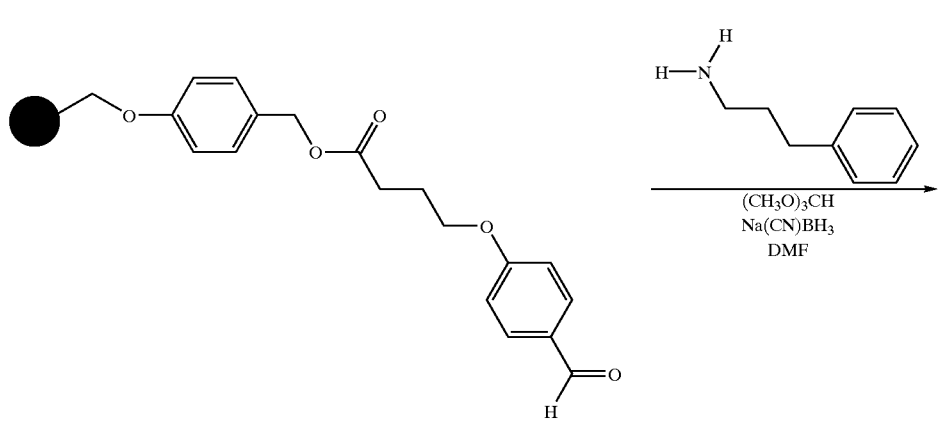

-continued

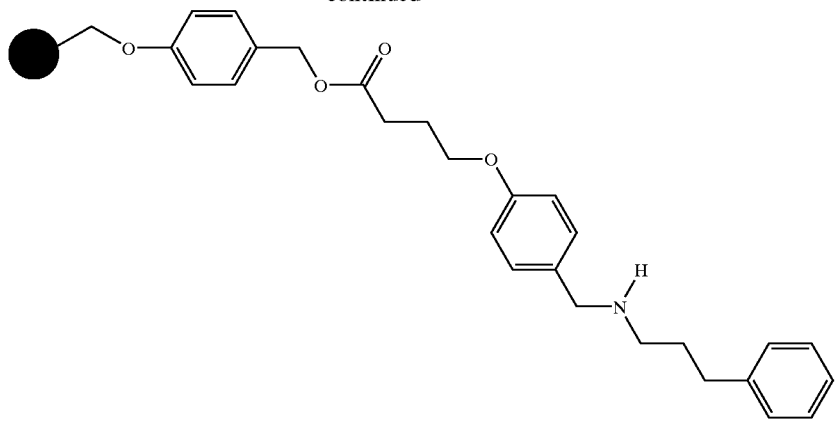

A three neck 2 L round bottom flask is charged with the MicroKANs [784, 25.5 micromoles/microKAN, 20.0 mmoles], trimethylorthoformate (850 mL) and 3-phenyl-1-propylamine (22.99 g, 170 mmoles). The reaction flask is fitted with an overhead stirrer. After 2 hours, sodium cyanoborohydride (21.37 g, 340 mmoles) is added. After approximately 10 minutes, acetic acid (17.0 mL, 297 mmoles) is added. After stirring for an additional hour, the reaction flask is drained. Methanol (800 mL) is added to the flask. After stirring for approximately 10 minutes, the flask is drained. The MicroKANs are washed in the following sequence: DMF (3×4 L), dichloromethane (1×4 L) then methanol (1×4 L), dichloromethane (1×4 L) then methanol (1×4 L), dichloromethane (1×4 L) then methanol (1×4 L), dichloromethane (1×4 L) and ether (1×4 L). After the final washing, the MicroKANS are dried by blowing a stream of nitrogen through the flask with intermittent agitation. After sufficient drying, the MicroKANs are sorted for the next reaction.

4. Acylation:

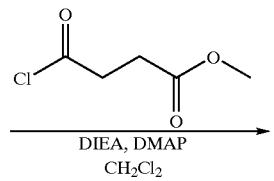

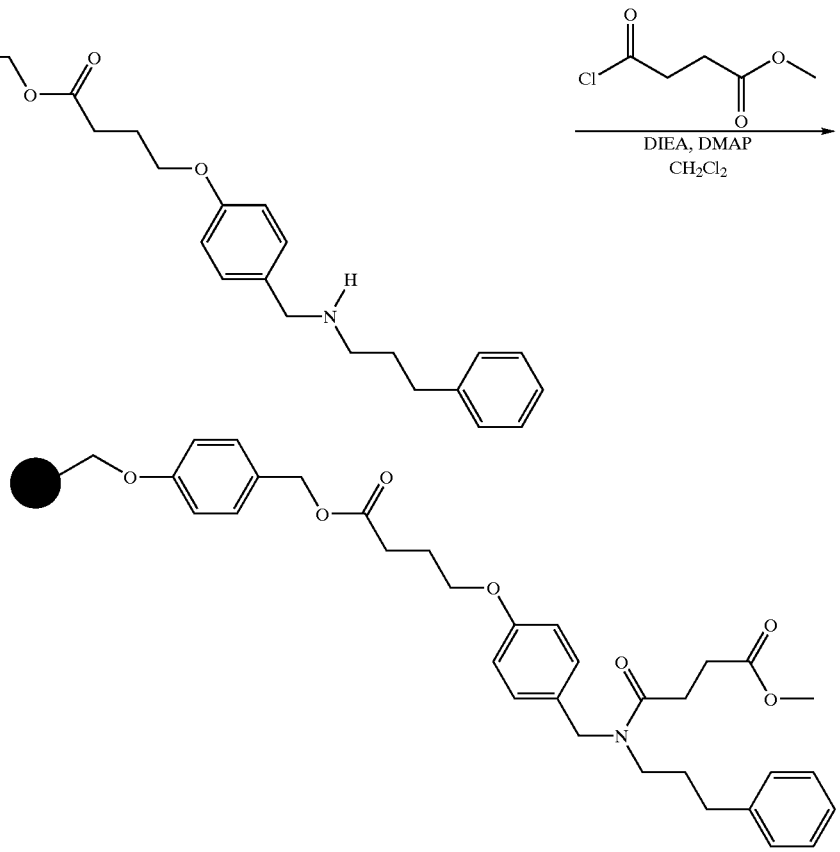

A three neck 2 L round bottom flask is charged with the MicroKANs [784, 25.5 micromoles/microKAN, 20.0 mmoles], and dichloromethane (800 mL). The reaction flask is fitted with an overhead stirrer. N,N-diisopropylethylamine (20.9 mL, 120 mmoles) and 4-N,N-dimethylaminopyridine (195 mg, 1.6 mmoles) are added. After approximately 15 minutes, the methyl 4-chloro-4-oxobutyrate (12.0 g, 80.0 mmoles) is added. The reaction is allowed to stir for 61 hours, after which the reaction flask is drained. Dichloromethane (800 mL) is added to the reaction flask. After stirring for approximately 10 minutes, the flask is drained. This is repeated. The MicroKANs from all of the acylation reactions are randomly combined into two separate large flasks and washed repeatedly in the following sequence: dichloromethane (1×4 L), THF (2×4 L), dichloromethane (1×4 L) then methanol (1×4 L), dichloromethane (1×4 L) then methanol (1×4 L), dichloromethane (1×4 L) then methanol (1×4 L), dichloromethane (1×4 L) and ether (1×4 L).

5. Cleavage:

The MicroKANs are sorted into an individual well of IRORI AccuCleave 96 cleavage station. The well is charged with dichloromethane (600 mL) and then with a ThA:dichloromethane mixture (1:1, 600 mL). After agitating for approximately forty minutes, the reaction well is drained into 2 mL microtubes in an 96-well format. The reaction well is again charged with dichloromethane (600 mL). After manual agitation, this too is drained into the 2 mL microtubes in an 96-well format. The cleavage cocktail is removed in vacuo using a Savant Speedvac. The concentrated products from the cleavage mother plates are reconstituted with THF and transferred into two daughter plates utilizing a Packard MultiProbe liquid handler. The daughter plates are concentrated in vacuo utilizing a GenieVac.

Analytical: MS: m/z 442.2 (M+H$_+$).

The methods described above are used to prepare the following compounds of this invention.

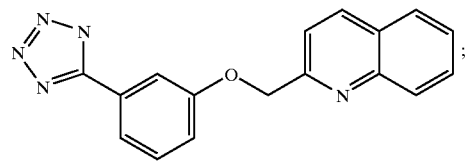

210–212° C.

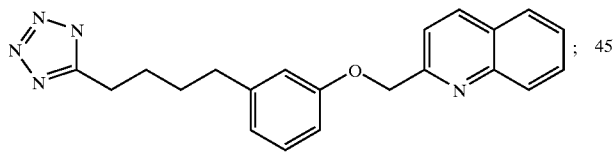

149–150° C.

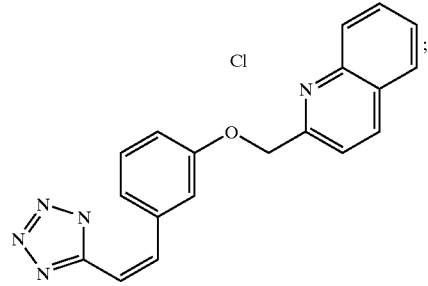

108° C.

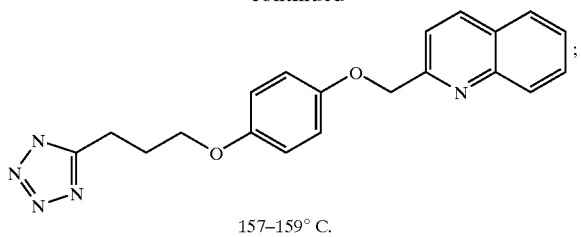

157–159° C.

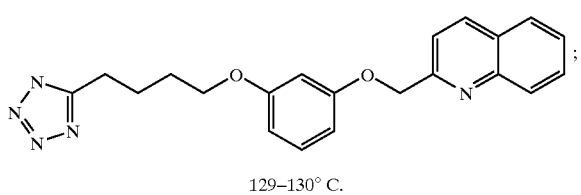

129–130° C.

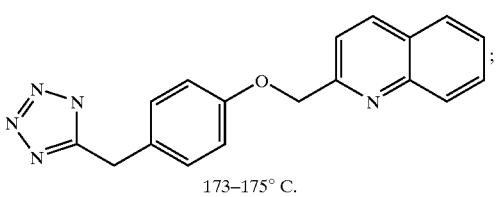

173–175° C.

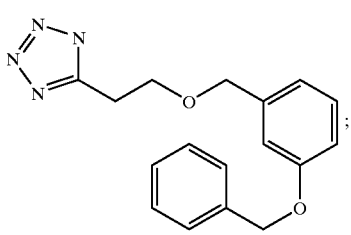

100–102° C.

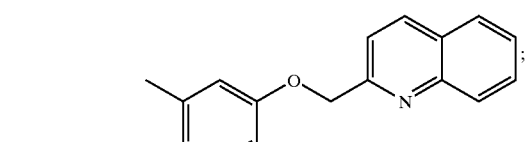

108–112° C.

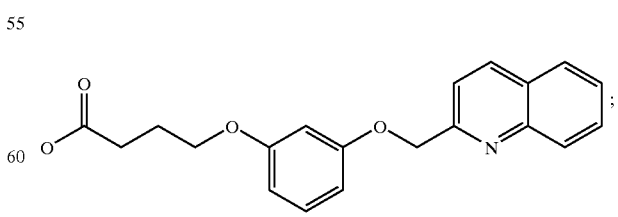

135–137° C.

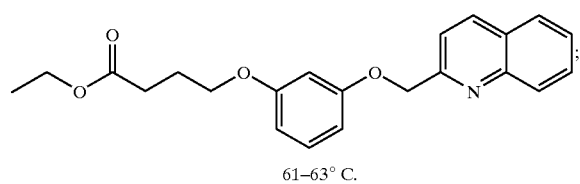
61–63° C.
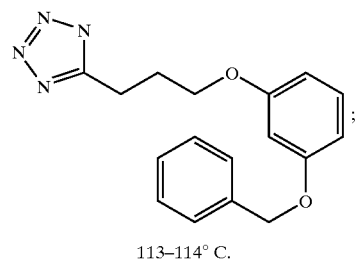
113–114° C.
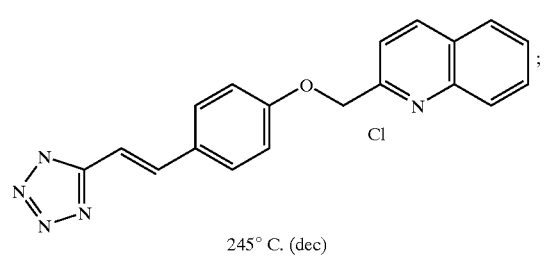
245° C. (dec)
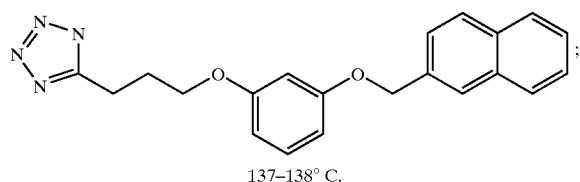
137–138° C.
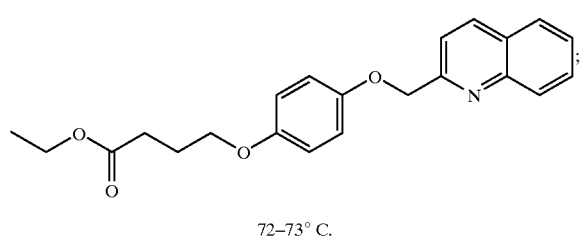
72–73° C.
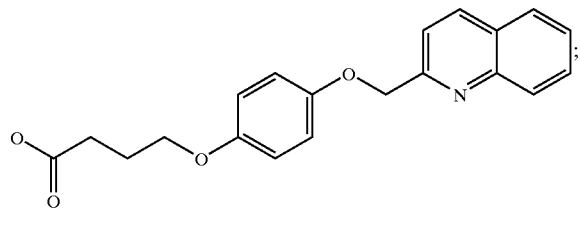
132–133° C.
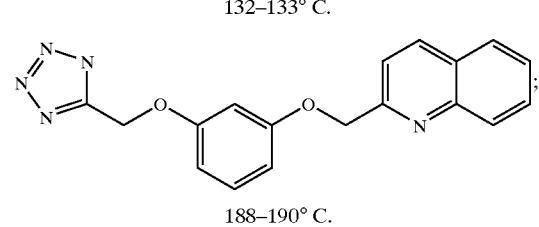
188–190° C.
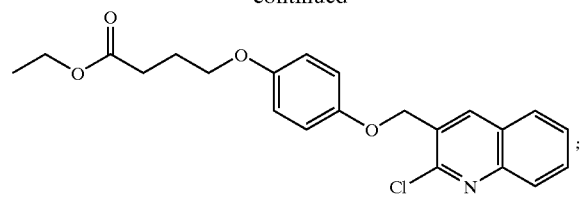
63–65° C.
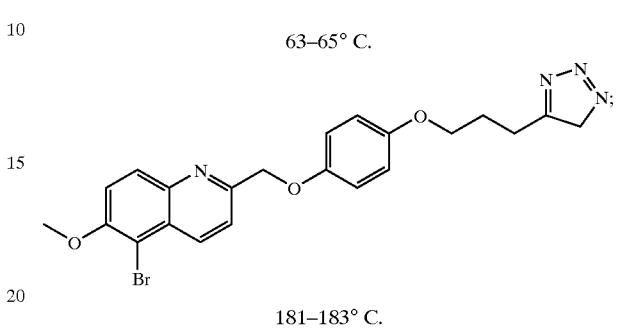
181–183° C.
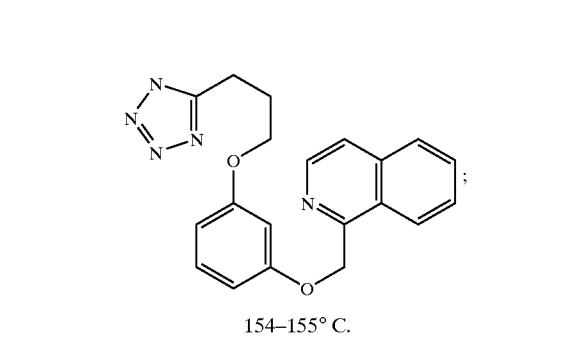
154–155° C.
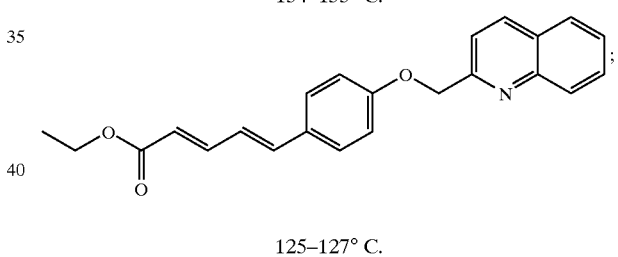
125–127° C.
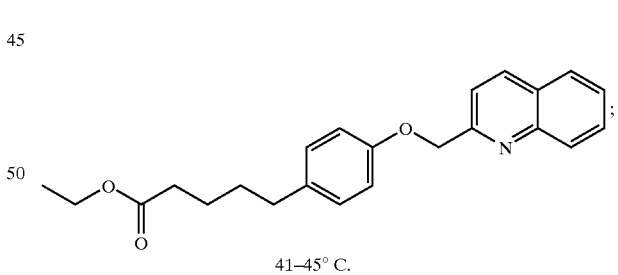
41–45° C.
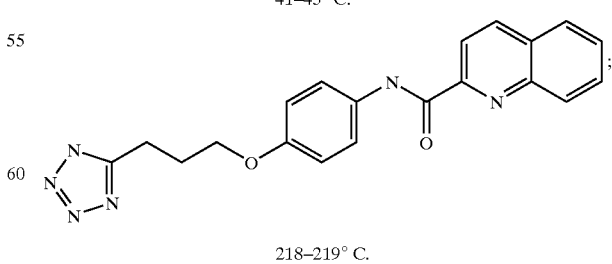
218–219° C.

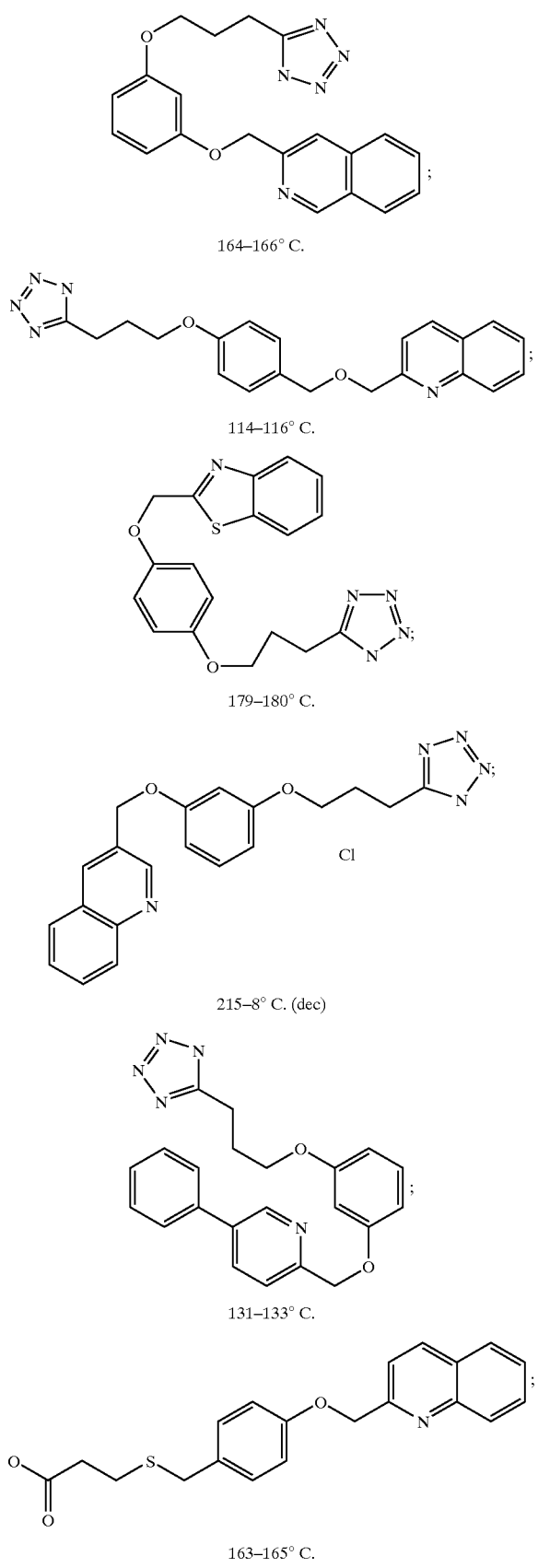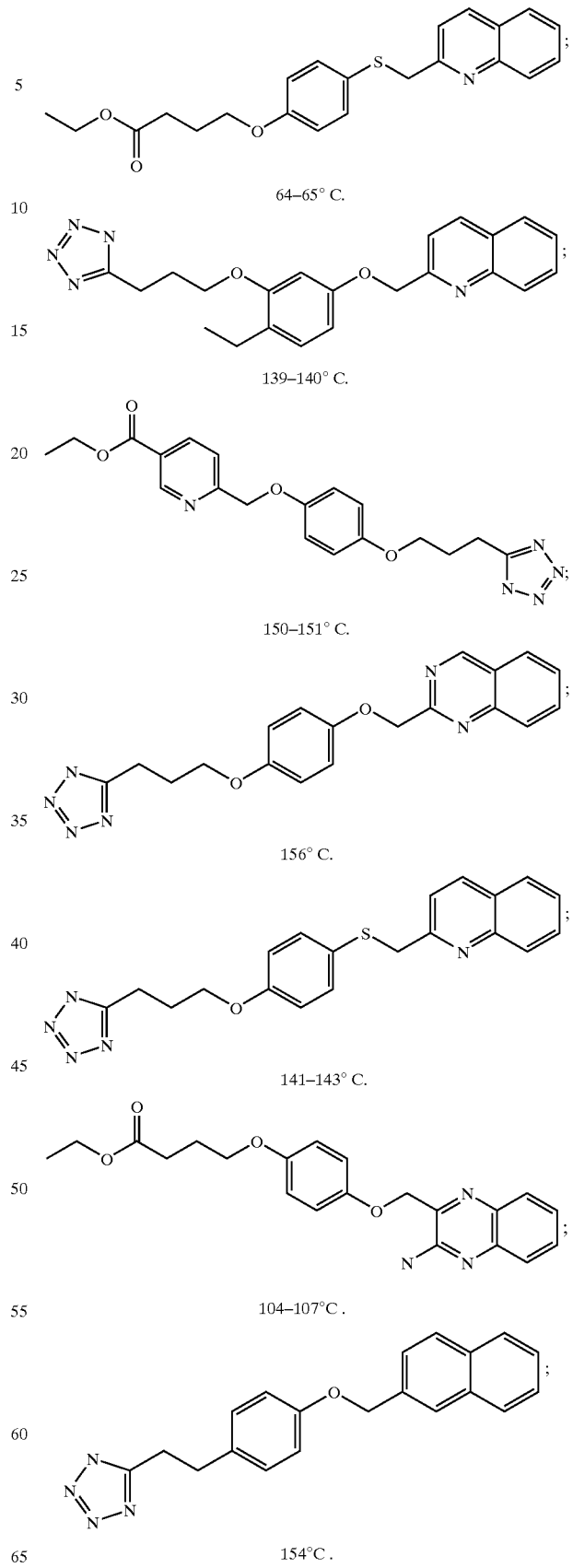

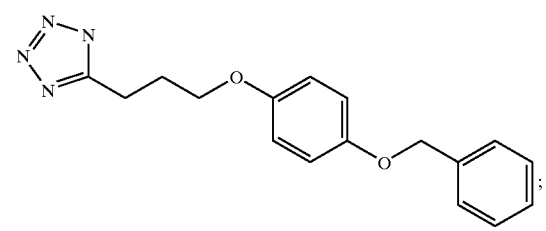
145–149°C.
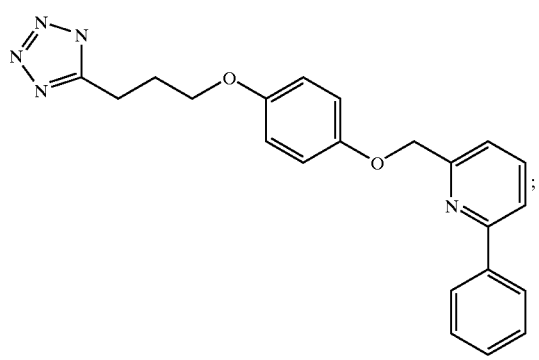
125–126°C.
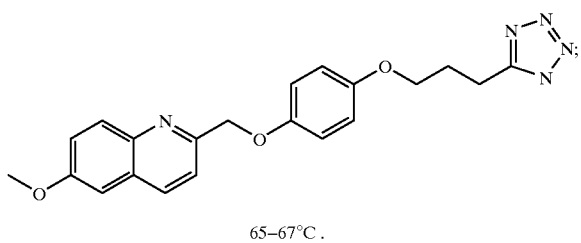
65–67°C.
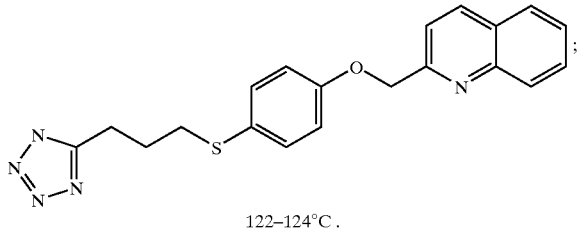
122–124°C.
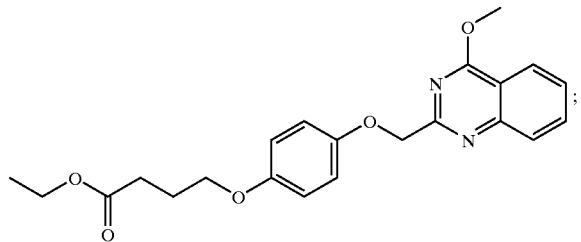
80–81° C.
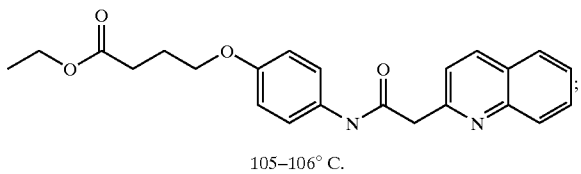
105–106° C.
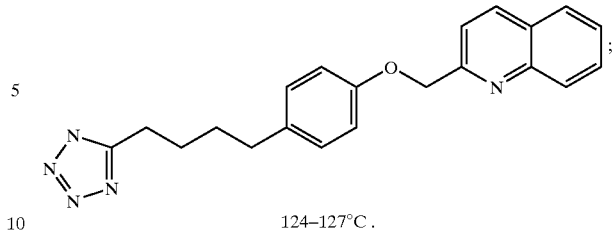
124–127°C.
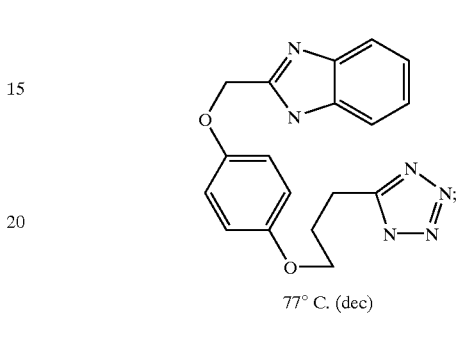
77° C. (dec)
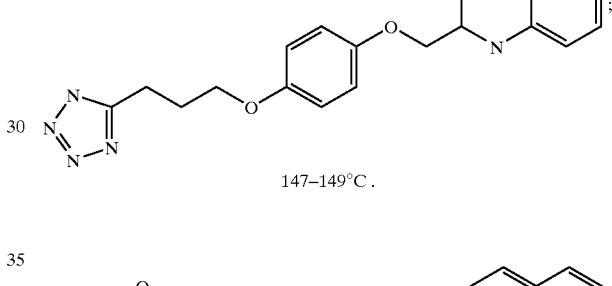
147–149°C.
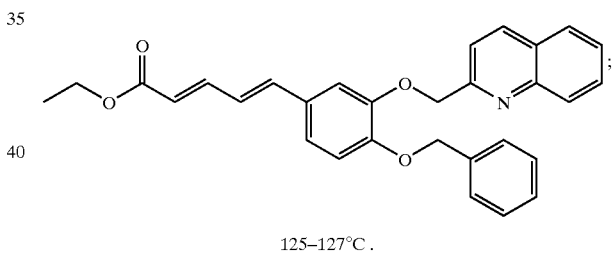
125–127°C.
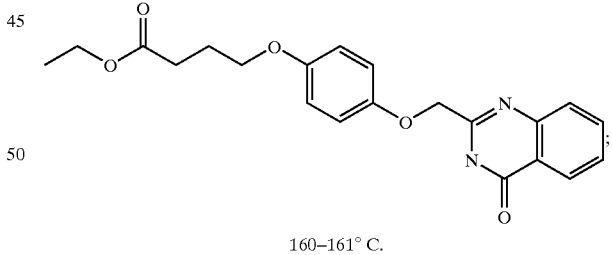
160–161° C.
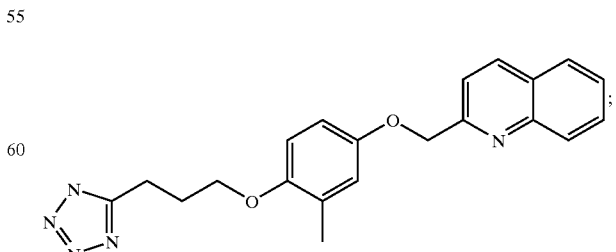
72–73° C.

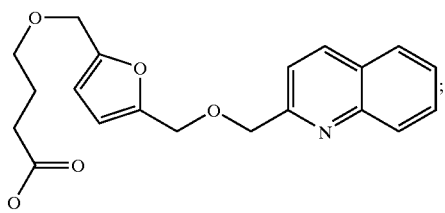
47–50° C.
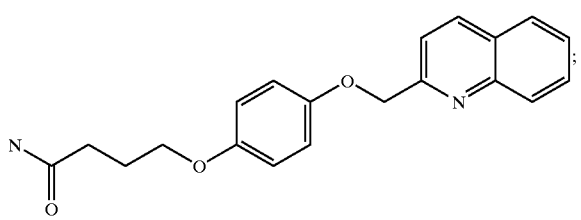
154–157° C.
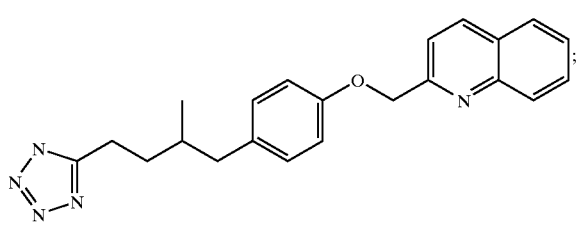
121–123° C.
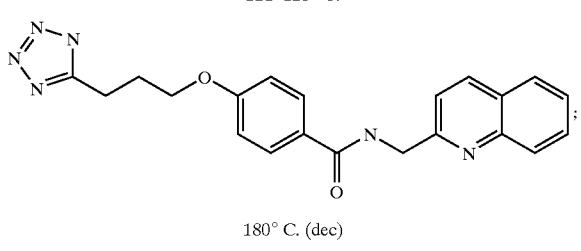
180° C. (dec)
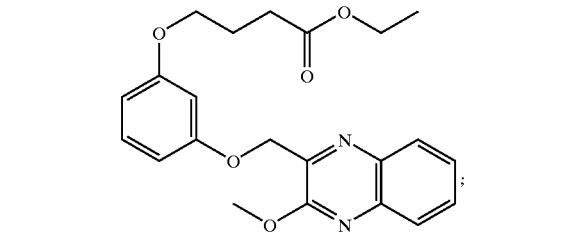
60–61° C.
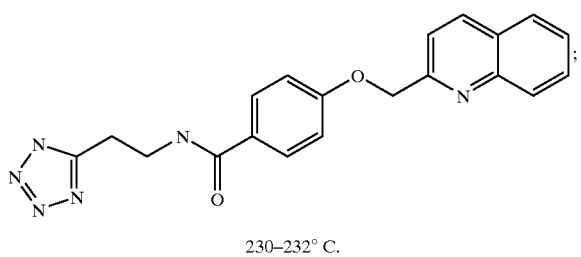
230–232° C.
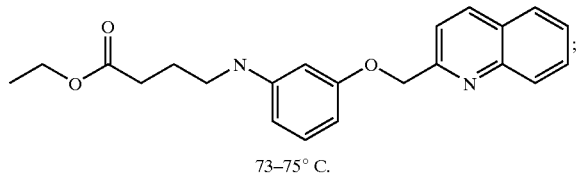
73–75° C.
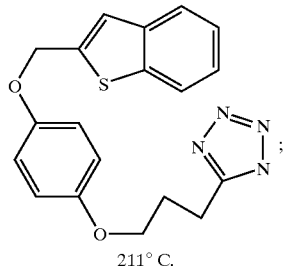
211° C.
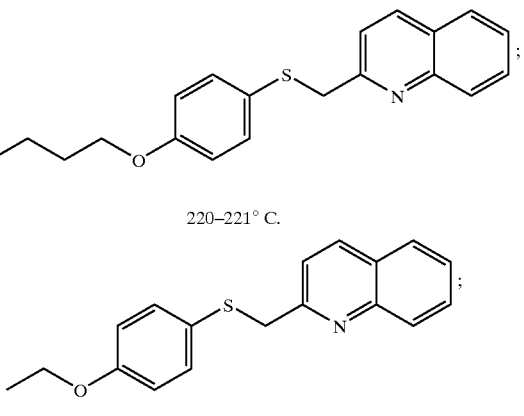
220–221° C.
65–66° C.
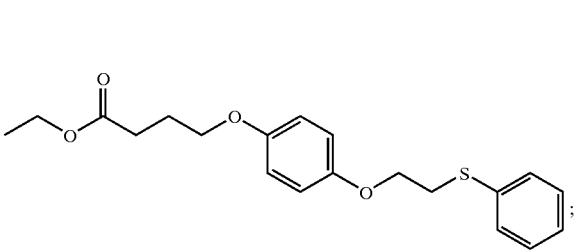
53–54° C.
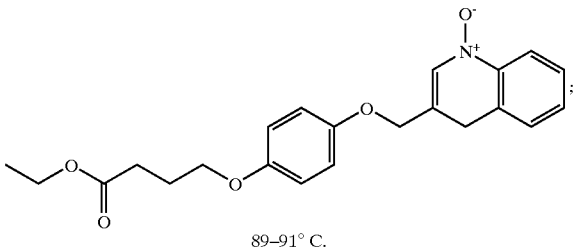
89–91° C.
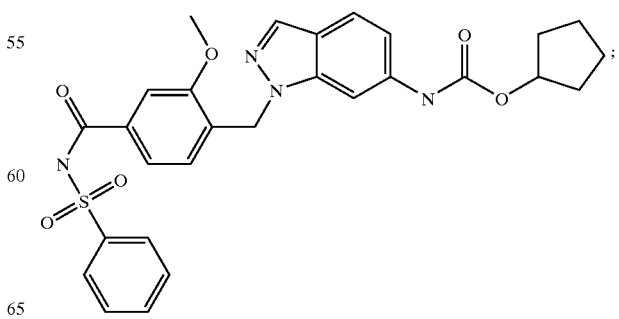
187° C.

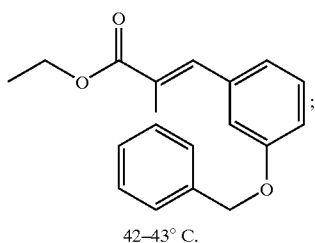
42–43° C.
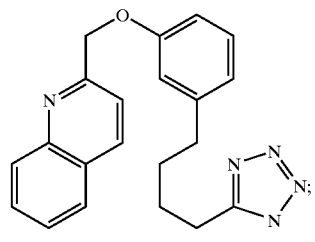
149–150° C.
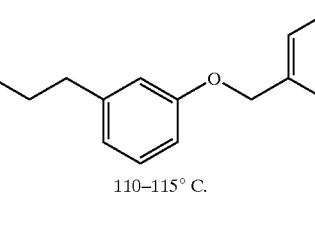
110–115° C.
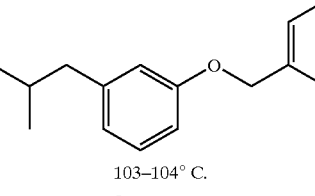
103–104° C.
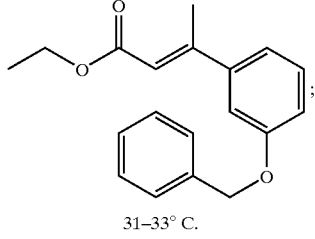
31–33° C.
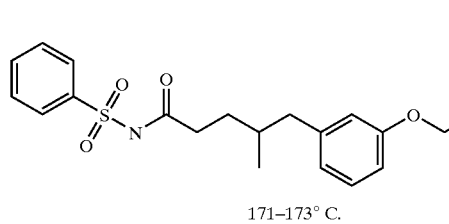
171–173° C.
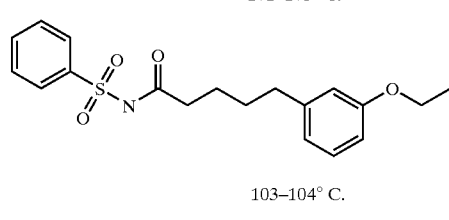
103–104° C.
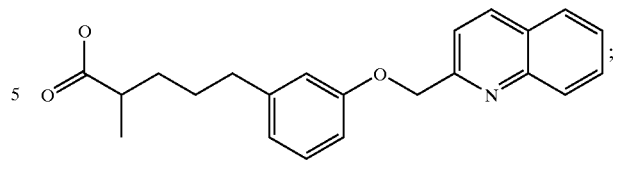
80–82° C.
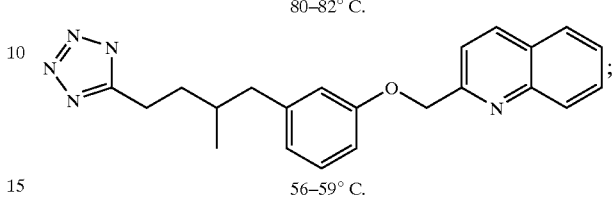
56–59° C.
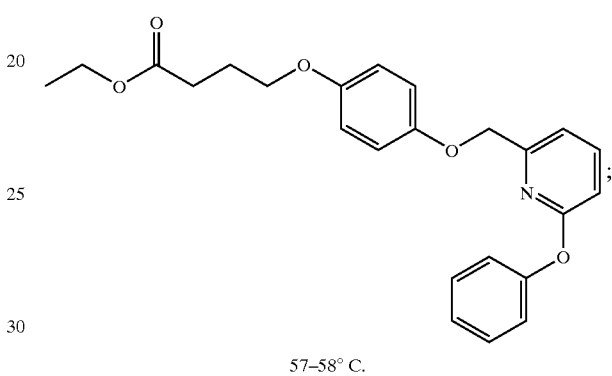
57–58° C.
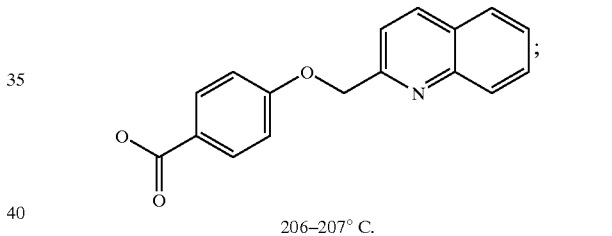
206–207° C.
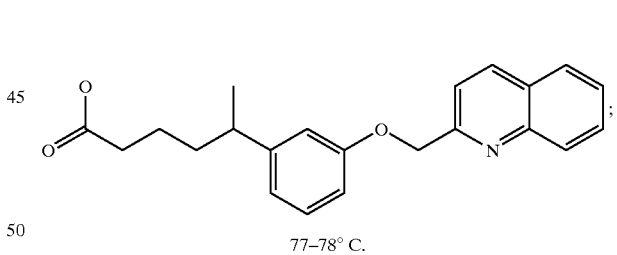
77–78° C.
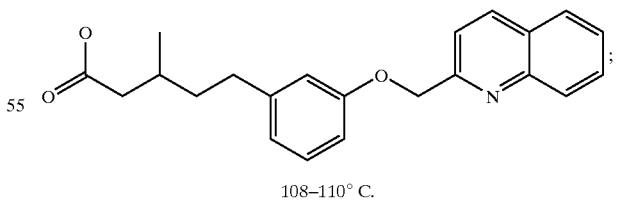
108–110° C.
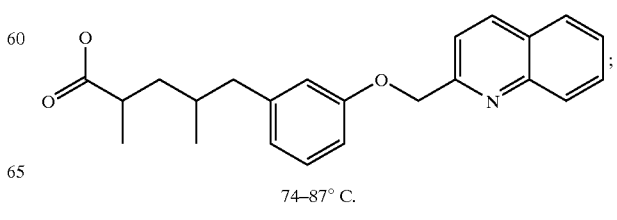
74–87° C.

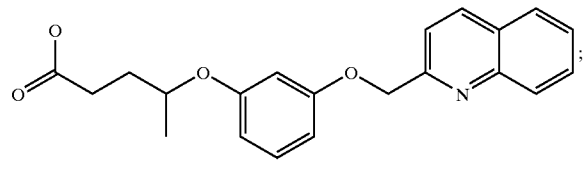
93–95° C.
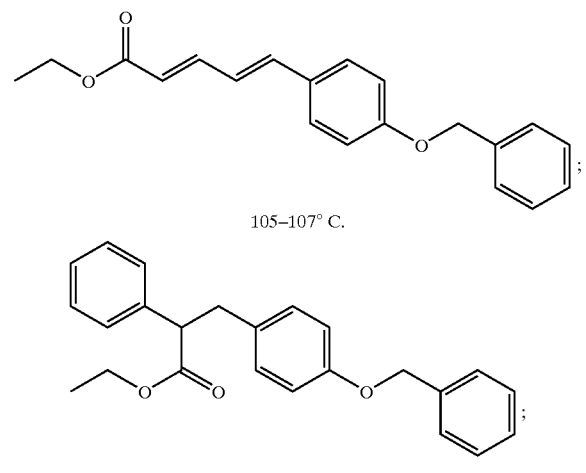
105–107° C.
49–50° C.
112–116° C.
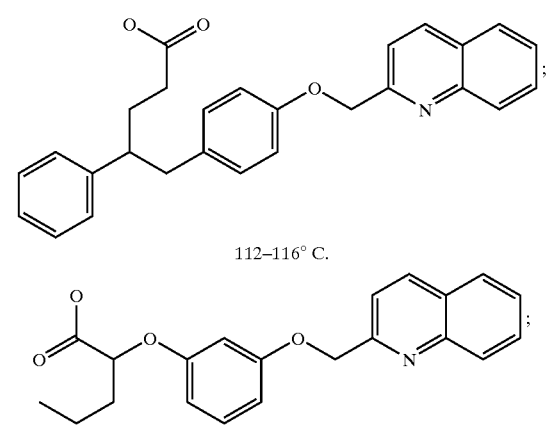
118–121° C.
90–93° C.
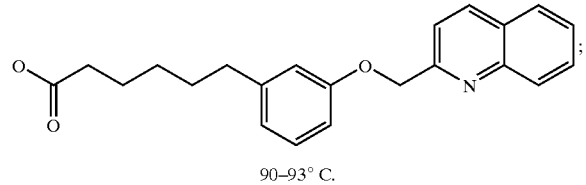
121–123° C.
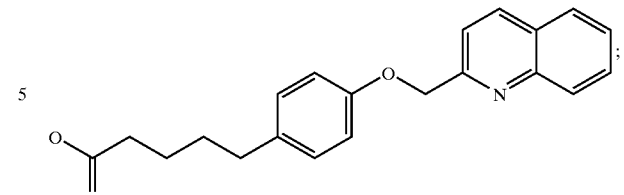
103–105° C.
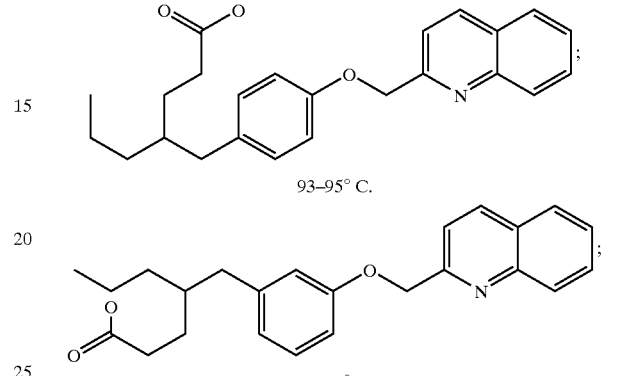
93–95° C.
96–97° C.
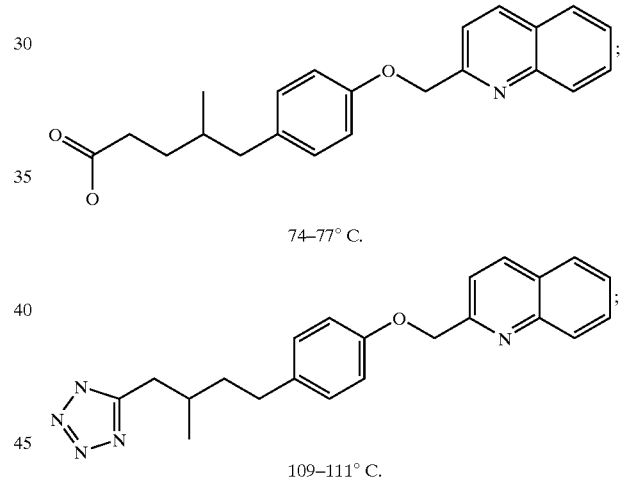
74–77° C.
109–111° C.
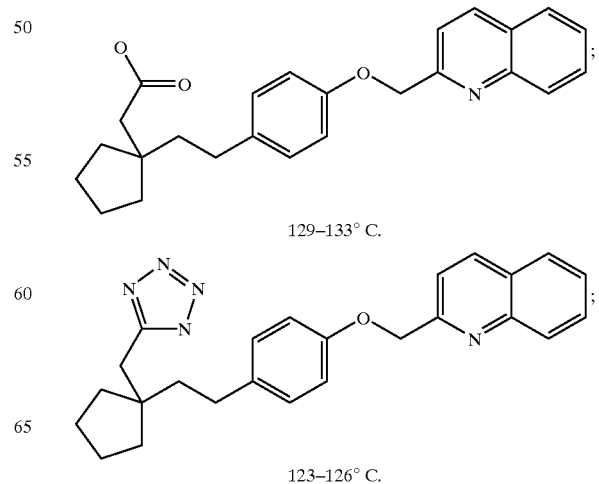
129–133° C.
123–126° C.

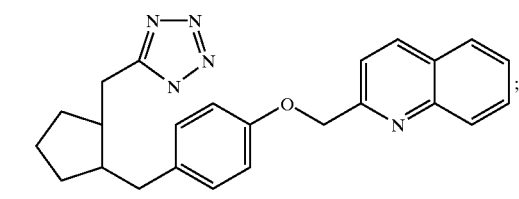
138° C.
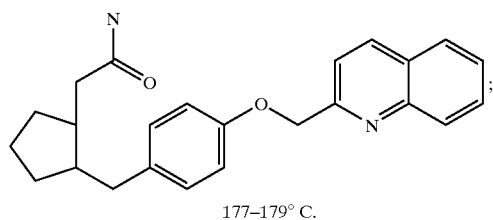
177–179° C.
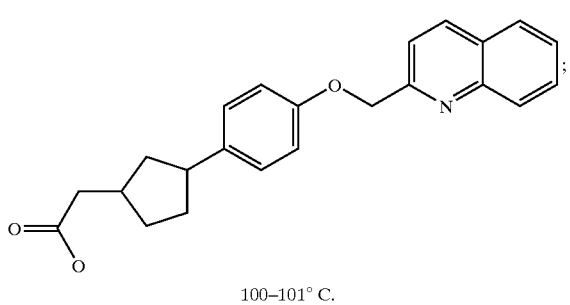
100–101° C.
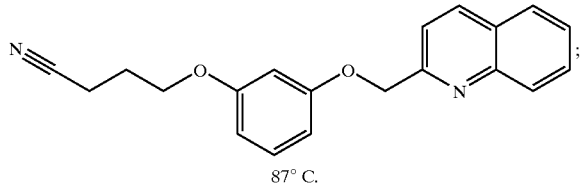
87° C.
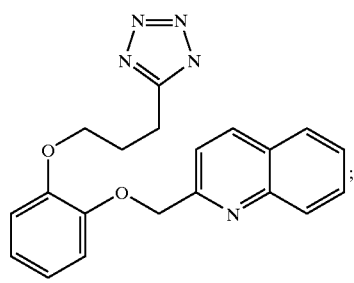
137–140° C.
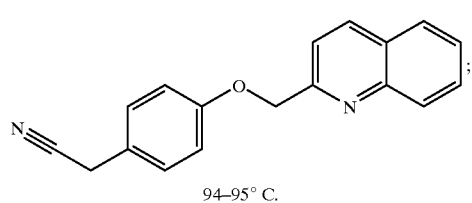
94–95° C.
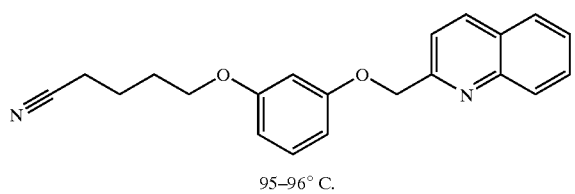
95–96° C.
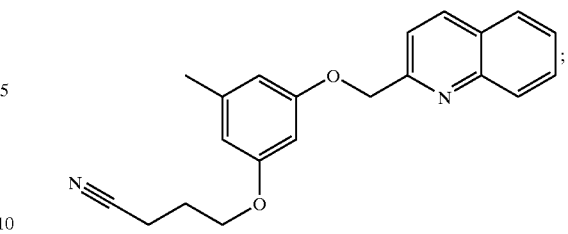
54–57° C.
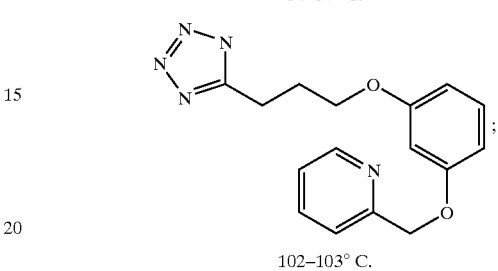
102–103° C.
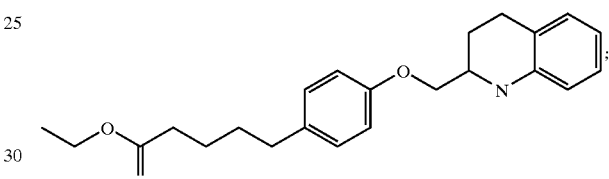
oil; CHN calc C23H29NO3: C75.17, H7.95, N3.81; found C75.02, H8.03, N4.29
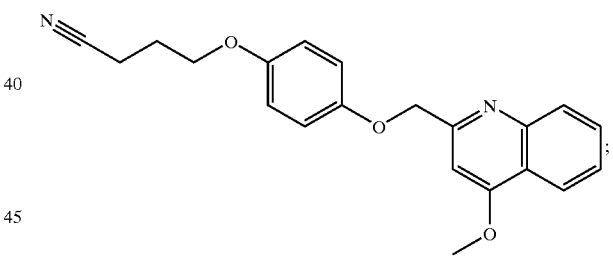
102–104° C.
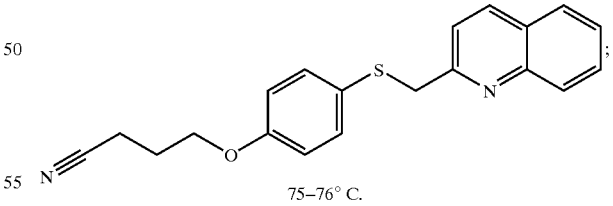
75–76° C.
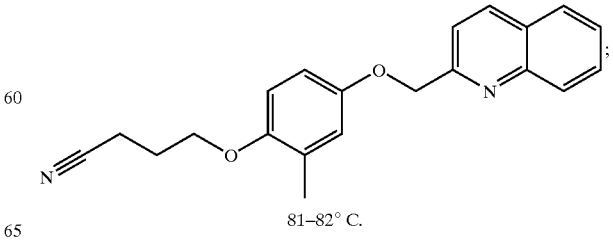
81–82° C.

80–81° C.

90–91° C.

60–62° C.

oil; CHN calc
C22H21N3O3 +
H2O; C70.00,
H5.61, N11.13;
found C70.06,
H5.84, N11.08

44–46° C.

90–91° C.

98–100° C.

114–115° C.

215° C. (dec)

262° C. (dec)

168–170° C.

91–92° C.

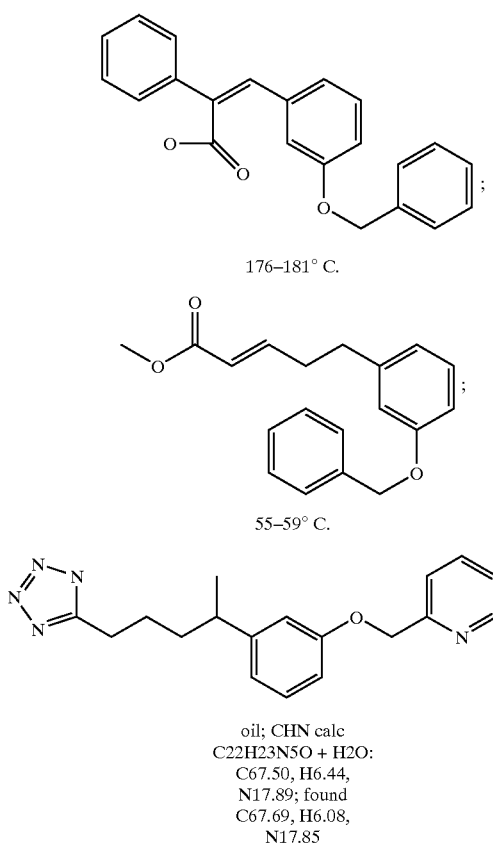
176–181° C.
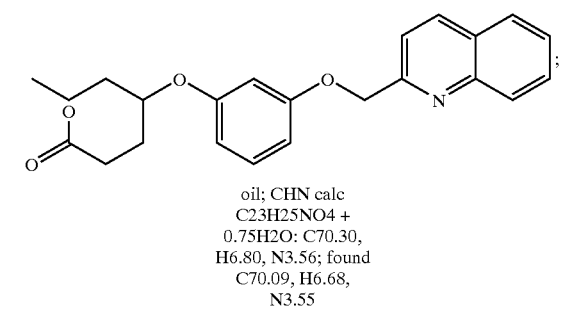
55–59° C.
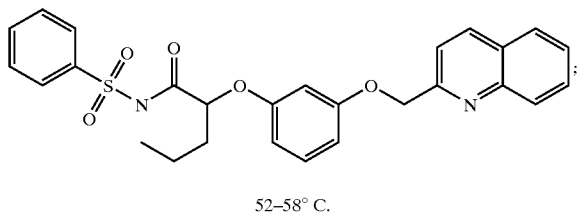
oil; CHN calc
C22H23N5O + H2O:
C67.50, H6.44,
N17.89; found
C67.69, H6.08,
N17.85
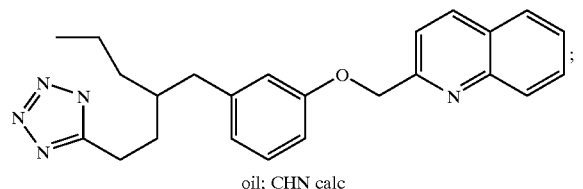
oil; CHN calc
C23H25NO4 +
0.75H2O: C70.30,
H6.80, N3.56; found
C70.09, H6.68,
N3.55
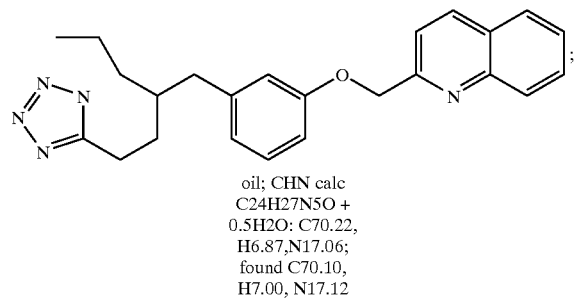
52–58° C.
oil; CHN calc
C24H27N5O +
0.5H2O: C70.22,
H6.87, N17.06;
found C70.10,
H7.00, N17.12
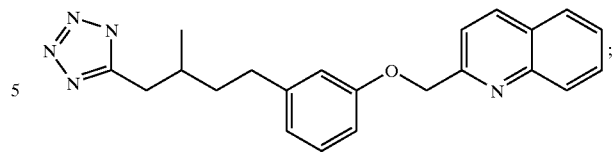
CHN calc
C22H23N5O +
0.25H2O: C69.91,
H6.27, N18.53;
found C70.00,
H6.41, N18.70
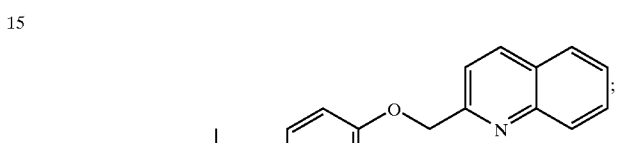
oil; CHN calc
C21H21N5O2:
C63.24, H5.96,
N17.56; found
C63.65, H6.41,
N17.16
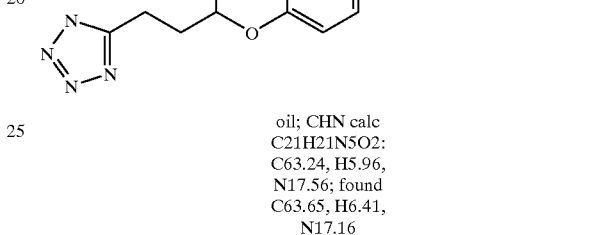
oil; CHN calc
C23H25N5O2 +
H2O: C65.54,
H6.64, N16.62;
found C65.32,
H6.72, N16.43
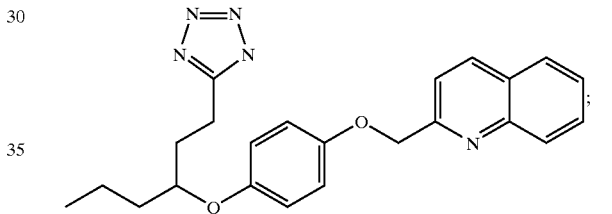
95–97° C.
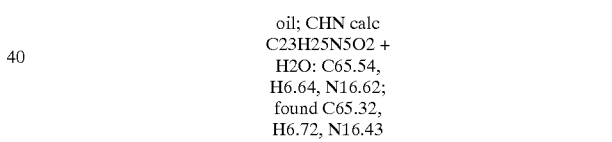
106–110° C.

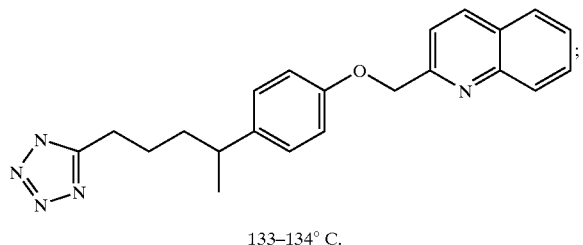
133–134° C.
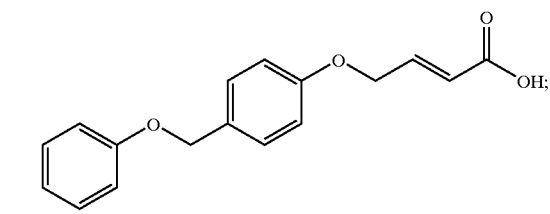
95–99° C.
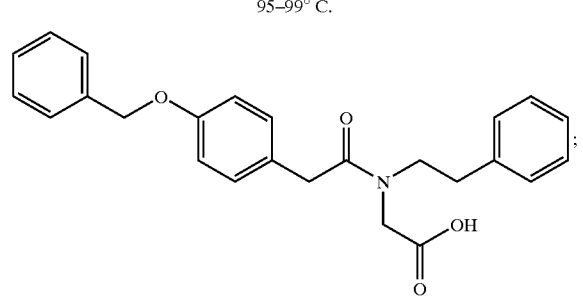
135–138° C.
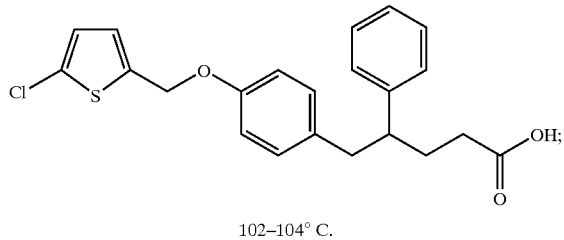
102–104° C.
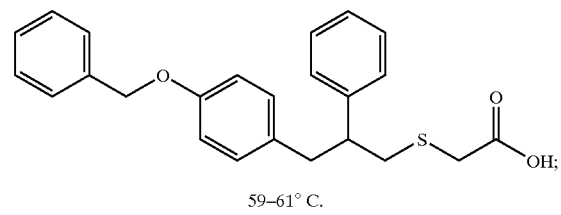
59–61° C.
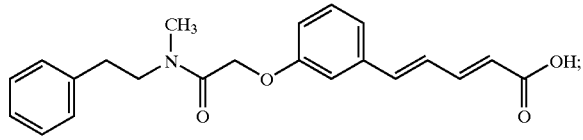
oil; CHN C22H23NO4
+ 1.6H2O, calc.
C67.02, H6.70, N3.55;
found C67.04, H6.11,
N3.41
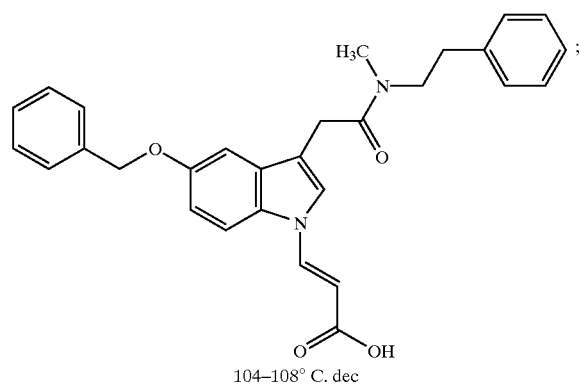
104–108° C. dec
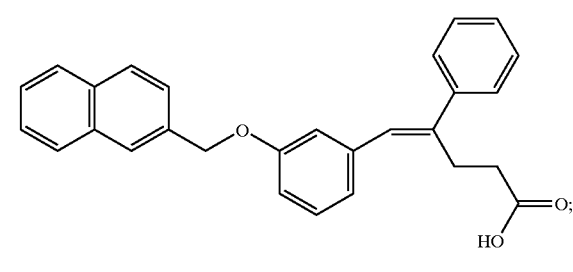
oil; CHN C28H24O3,
calc. C82.33, H5.92;
found C82.59, H5.97
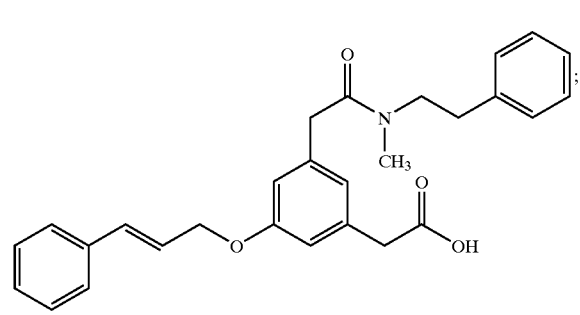
129–132° C.
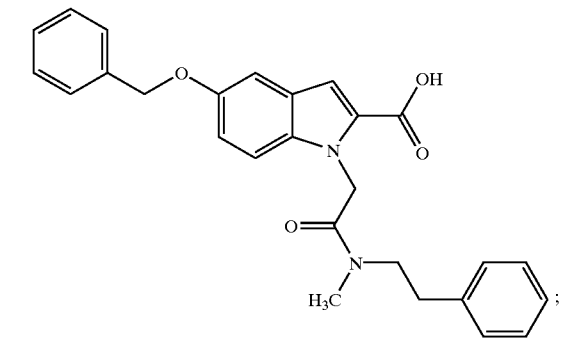
250–257° C. dec

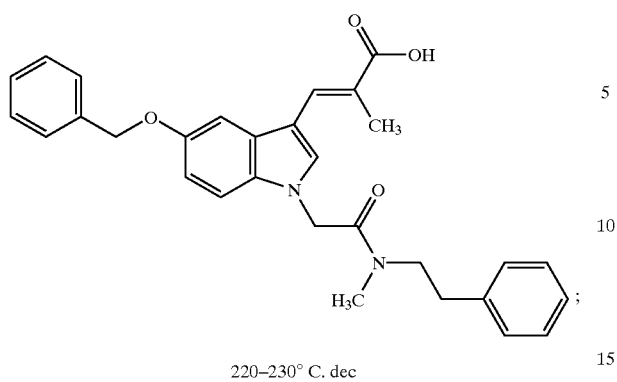
220–230° C. dec
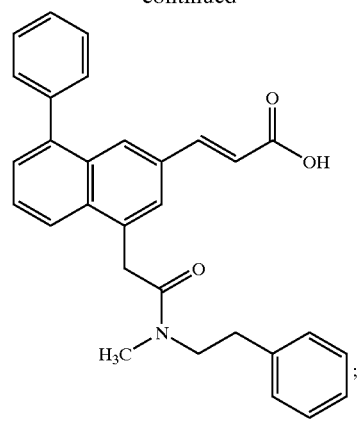
159° C. dec
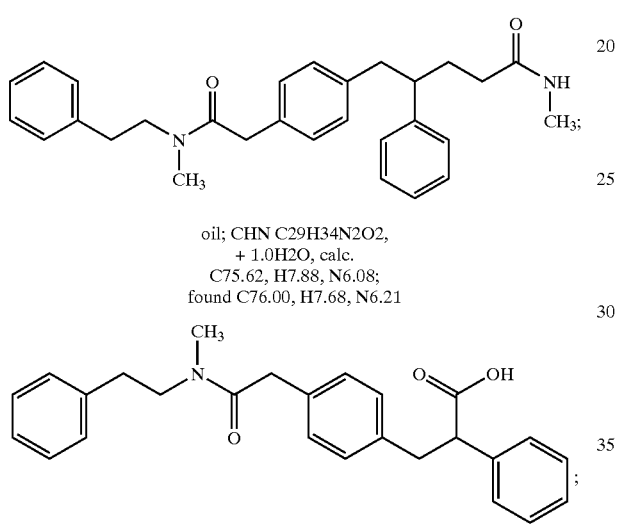
oil; CHN C29H34N2O2,
+ 1.0H2O, calc.
C75.62, H7.88, N6.08;
found C76.00, H7.68, N6.21
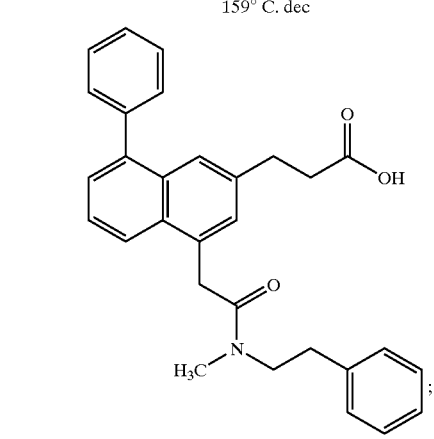
79–80° C.
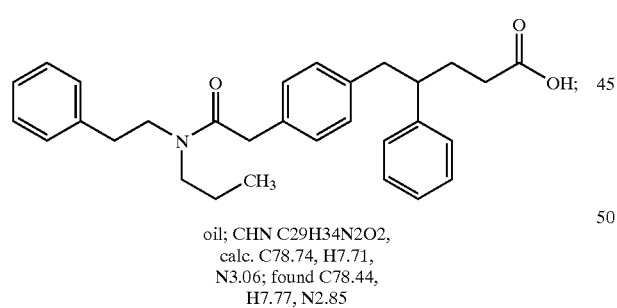
131–133° C.
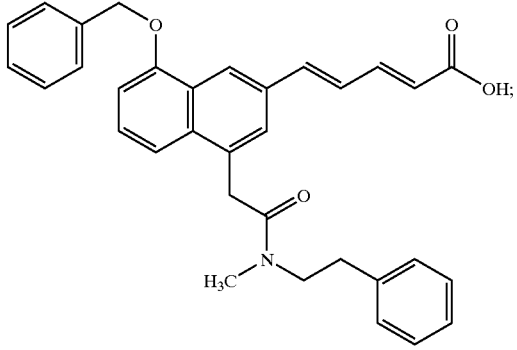
99–100° C. dec
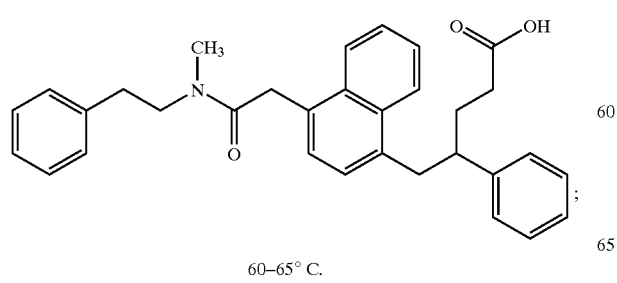
oil; CHN C29H34N2O2,
calc. C78.74, H7.71,
N3.06; found C78.44,
H7.77, N2.85
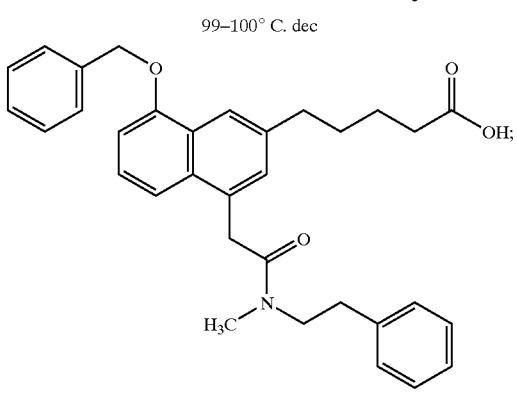
110–113° C.
60–65° C.

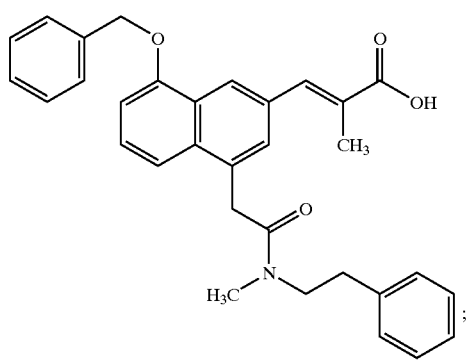
172–176° C.
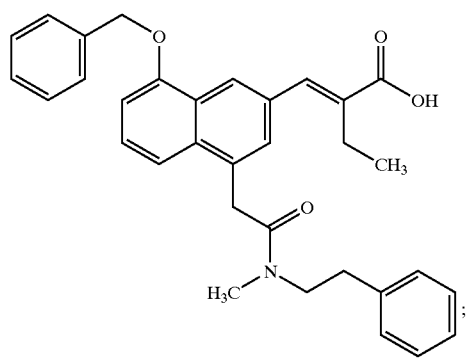
77–79° C.
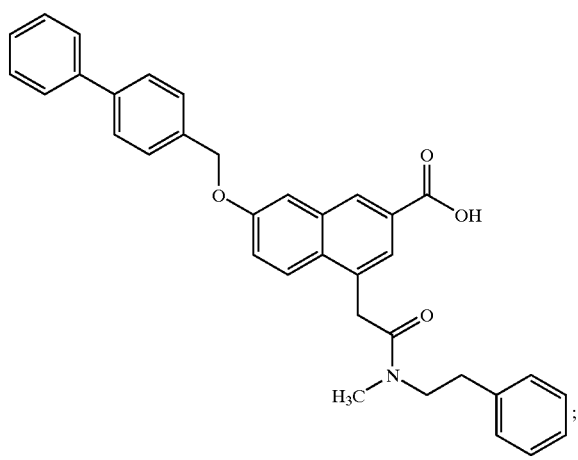
228–230° C.
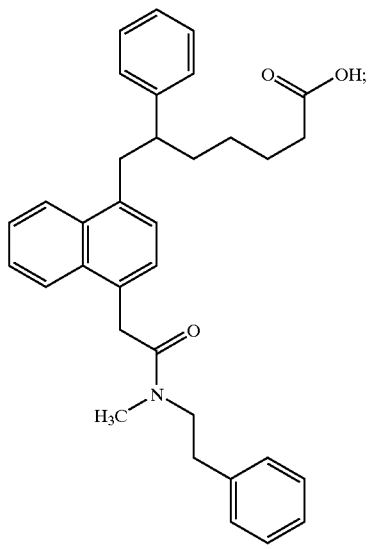
oil; CHN C34H37NO3 + 1.25H2O, calc. C77.02, H7.51, N2.64; found C77.3, H7.5, N2.6
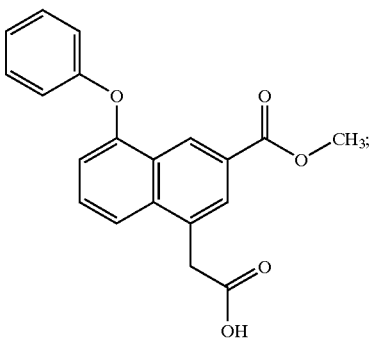
180–186° C.
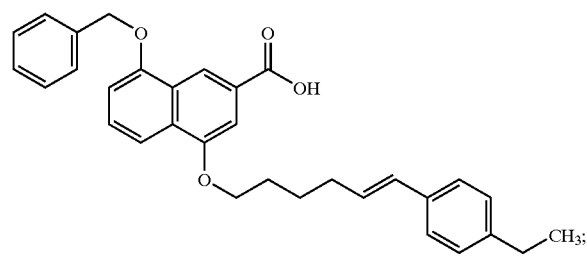
170–173° C.

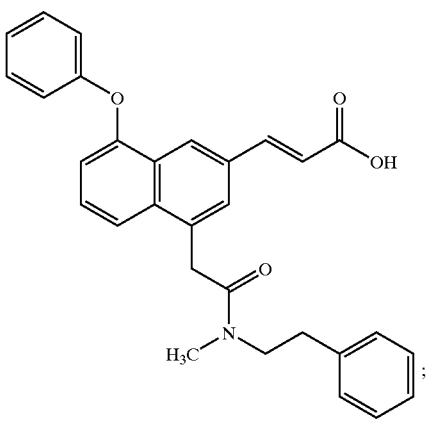

146–148° C.

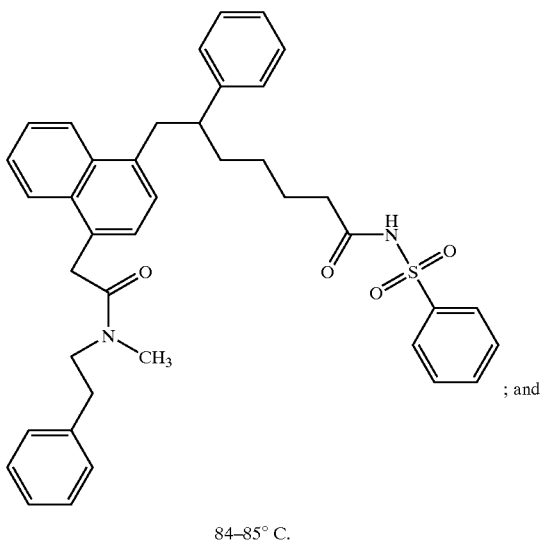

84–85° C.

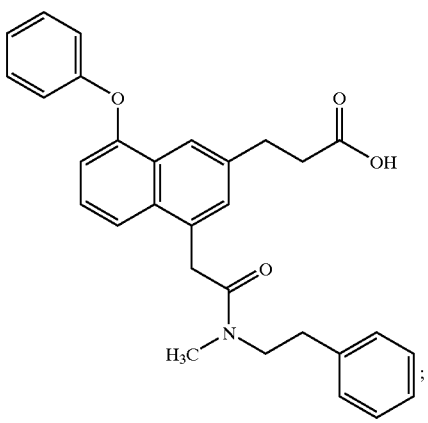

142–143° C.

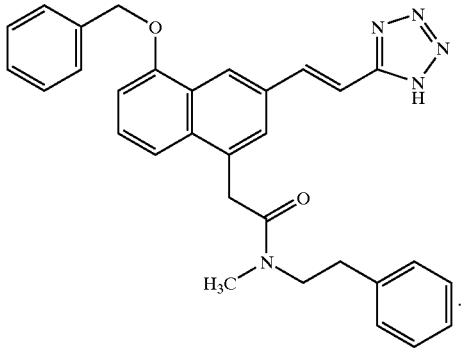

oil; CHN
C31H29N5O2 +
0.35H2O, calc. C73.0,
H5.9, N13.7: found
C73.0H5.8, N13.9

Using a combination of the above Examples, various compounds may be made within the scope of this invention.

Compounds according to the invention exhibit marked pharmacological activities according to tests described in the literature, which tests results are believed to correlate to pharmacological activity in humans and other mammals. The following pharmacological test results are typical characteristics of compounds of the present invention.

The compounds of the present invention have potent activity as PPAR ligand receptor binders and possess antidiabetic, anti-lipidemic, anti-hypertensive, and anti-arteriosclerotic activity and are also anticipated to be effective in the treatment of diabetes, obesity and other related diseases.

hPPARα Binding Assay

The activity of the compounds of the invention as PPARα modulators may be examined in several relevant in vitro and in vivo preclinical assays, for example benchmarking with a known PPARα modulator, for example, [$^3$H]-GW2331(2-(4-[2-(3-[2,4-Difluorophenyl]-1-heptylureido)-ethyl] phenoxy)-2-methylbutyric acid). (S. Kliewer, et al. Proc. Natl. Acad. Sci. USA 94 (1997).

Human Peroxime Proliferator-activated Receptor a Ligand Binding Domain(hPPARα-LBD):

A binding assay for PPARα could be carried out by the following procedure: cDNAs encoding the putative ligand binding domain of human PPARα (amino acids 167–468) (Sher, T., Yi, H.-F., McBride, O. W. & Gonzalez, F. J. (1993) *Biochemistry* 32, 5598–5604) are amplified by PCR (Polymerase Chain Reaction) and inserted in frame into the BamHI site of pGEX-2T plasmid (Pharmacia). The soluble fraction of GST-hPPARα fusion proteins or glutathione S-transferase (GST) alone are overexpressed in *E. coli* BL21(DE3)pLysS cells and purified from bacteria extracts as described in (S. Kliewer, et al. Proc. Natl. Acad. Sci. USA 94 (1997), 4318–4323).

Gel-Filtration Assays: 30 ml of 90 nM GST-hPPARα-LBD is mixed with 20 ml of 50 nM $^3$H-GW2331 with or without 5 ml of 10 mM test compounds in the binding buffer containing 10 mM Tris, 50 mM KCl, 0.05% Tween 20 and 10 mM DTT. The reaction mixtures are incubated in 96-well plates for 2 h at room temperature. 50 ml of the reaction mixtures are then loaded on a 96-well gel filtration block (following manufacture instructions)(EdgeBioSystems). The block placed on top of a clean 96-well plate is centrifuged at 1,500 rpm for 2 min. The block is discarded. 100 ml of Scintillation fluid is added to each well of the 96-well plate. After overnight equilibration, the plate is counted in the Microbeta counter (Wallac.).

Homogenous Scintillation Proximity Binding Assay.

For the Scarchard analysis, glutathione coated SPA beads (1.5 mg/ml )(Amersham) are mixed with GST-hPPARα-LBD (10 mg/ml) in the binding buffer. The resulting slurry is incubated at room temperature with agitation for 15 min. 20 ml of the slurry is then added in 30 ml of binding buffer containing various amount $^3$H-GW2331(10~500 nM). Non-specific binding is determined in the present of 100 mM of GW2331. For the competition binding assay, 20 ml of the slurry is then added in 30 ml of the binding buffer containing 75 nM of $^3$H-GW2331 and 0.03~20 mM of the test compounds. For the control experiments, the glutathione coated SPA beads (1.5 mg/ml) are coated with GST proteins (10 mg/ml). 20 ml of the slurry are mixed with 30 ml of 75 nM of $^3$H-GW2331 with or without 10 mM of GW2331. The above experiments are all performed in a 96-well plates. The sealed plates with the reaction mixtures are allowed to equilibrate for 2 h and counted in the Microbeta counter (Wallac.).

hPPARγ Binding Assay

The activity of the compounds of the invention as PPARγ modulators may be examined in several relevant in vitro and in vivo preclinical assays, for example benchmarking with a known PPARγ modulator, for example, [$^3$H]-BRL 49853 (Lehman L. J. et al, J. Biol. Chem. 270, 12953–12956; Lehman L. J. et al, J. Biol. Chem. 272, 3406–3410 (1997), and Nichols, J. S.; et al Analytical Biochemistry 257, 112–119(1998)).

Human Peroxime Proliferator-activated Receptor a Ligand Binding Domain(hPPARγ-LBD).

A binding assay for PPARγ could be carried out by the following procedure: cDNAs encoding the putative ligand binding domain of human PPARγ (amino acids 176–477) (Green, M. E. et al. Gene expression 281–299(1995)) are amplified by PCR (polymerase chain reaction) and inserted in frame into the BanmHI site of pGEX-2T plasmid (Pharmacia). The soluble fraction of GST-hPPARγ fusion proteins or glutathione S-transferase (GST) alone are over-expressed in *E. coli* BL21(DE3)pLysS cells and purified from bacteria extracts.

Binding Assay: The fusion proteins, GST-PPARγ -LBD in PBS (5 mg/110 ml/well) are incubated in the glutathione coated 96 well plates for 4 hours. Unbound proteins are then discarded and the plates are washed two times with the wash buffer (10 mM Tris, 50 mM KCl and 0.05% Tween-20). 100 ml of reaction mixtures containing 60 nM of $^3$H-BRL-49853 and 10 mM of the testing compounds (10 ml of 0.1 mM compounds from each well of the child plates) in the binding buffer (10 mM Tris, 50 mM KCl and 10 mM DTT) are then added and incubated at room temperature for 2.5 h. The reaction mixtures are discarded and the plates are washed two times with the wash buffer. 100 ml of scintillation fluid is added to each well and plates are counted on β-counter.

hPPARδ Binding Assay

The activity of the compounds of the invention as PPARδ modulators may be examined in several relevant in vitro and in vivo preclinical assays (See references WO 97/28149; Brown P. et al Chemistry & Biology, 4, 909–18, (1997)), for example benchmarking with a known PPARδ modulator, for example [$^3$H$_2$]GW2433 or [$^3$H$_2$]Compound X

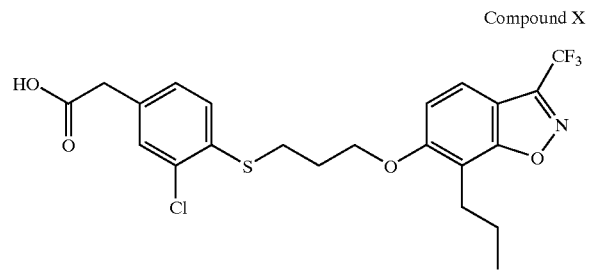

Compound X

The hPPARδ binding assay comprises the steps of:
(a) preparing multiple test samples by incubating separate aliquots of the receptor hPPARδ with a test compound in TEGM containing 5–10% COS-1 cell cytoplasmic lysate and 2.5 nM labeled ([$^3$H]Compound X, 17 Ci/mmol) for a minimum of 12 hours, and preferably for about 16 hours, at 4° C., wherein the concentration of the test compound in each test sample is different, and preparing a control sample by incubating a further separate aliquot of the receptor hPPARδ under the same conditions but without the test compound; then
(b) removing unbound ligand by adding dextran/gelatin-coated charcoal to each sample while maintaining the samples at 4° C. and allowing at least 10 minutes to pass, then
(c) subjecting each of the test samples and control sample from step (b) to centrifugation at 4° C. until the charcoal is pelleted; then
(d) counting a portion of the supernatant fraction of each of the test samples and the control sample from step (c) in a liquid scinitillation counter and analyzing the results to determine the IC$_{50}$ of the test compound.

In the hPPARδ binding assay, preferably at least four test samples of varying concentrations of a single test compound are prepared in order to determine the IC$_{50}$.

The compounds useful according to the invention can be administered to a patient in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be from about 2% to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropyl-cellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds useful according to this invention may be administered to a patient alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 100 mM/day or from about 0.1 mg to about 50 mg/kg of body weight per day, or 10 mg to about 50 mg/kg of body weight per day, or more preferably 30 mg to about 50 mg/kg of body weight per day, and higher, although it may be administered in several different dosage units. Higher dosages are required for oral administration.

The compounds useful according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

One skilled in the art will readily appreciate that the present invention is well adapted to carry out the objects of the invention and obtain the ends and advantages mentioned, as well as those inherent therein. The compounds, compositions and methods described herein are presented as representative of the preferred embodiments, or intended to be exemplary and not intended as limitations on the scope of the present invention.

What is claimed is:

1. A compound of formula (I)

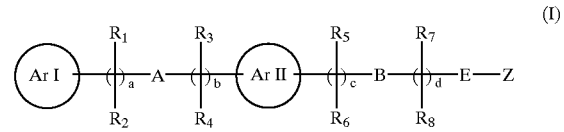

wherein:

is oxazolyl or quinolinyl, which are optionally substituted by one or more ring system substituents;

is phenyl, which is optionally substituted by one or more ring system substituents, in addition to being substituted by group Z;

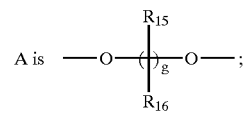

B and E are a chemical bond;

a is 1;

b is 0 or 1;

c is 0;
d is 0;
g is 1–5;
$R_1$, $R_2$, $R_3$ and $R_4$ are, independently, hydrogen, halogen or alkyl, wherein alkyl is optionally substituted by one or more alkyl group substituents;
Z is $R_{21}O_2C$—, $R_{21}OC$—, —CN, $R_{21}O_2SHNCO$—, $R_{21}O_2SHN$—, $(R_{21})_2NCO$— or $R_{21}O$—;
$R_{21}$ is independently
  hydrogen,
  alkyl, which is optionally substituted by one or more alkyl group substituents,
  aryl, which is optionally substituted by one or more ring system substituents,
  cycloalkyl, which is optionally substituted by one or more ring system substituents, or
  aralkyl, wherein the aryl portion is optionally substituted by one or more ring system substituents and the alkyl portion is optionally substituted by one or more alkyl group substituents;
$R_{15}$, $R_{16}$ are independently
  hydrogen,
  alkyl, which is optionally substituted by one or more alkyl group substituents,
  aralkyl, wherein the aryl portion is optionally substituted by one or more ring system substituents and the alkyl portion is optionally substituted by one or more alkyl group substituents, or
  alkoxycarbonyl, wherein the alkyl portion is optionally substituted by one or more alkyl group substituents;
or a pharmaceutically acceptable salt thereof, an N-oxide thereof, a hydrate thereof or a solvate thereof,
wherein
  alkyl is an aliphatic hydrocarbon group which is straight or branched having 1 to about 20 carbon atoms;
  aryl is an aromatic monocyclic or multicyclic ring system of about 6 to about 14 carbon atoms;
  a ring system substituent is halo, unsubstituted lower alkyl of 1 to about 4 carbon atoms, unsubstituted alkoxy, unsubstituted aryloxy, unsubstituted aralkyloxy or unsubstituted cycloalkylalkyloxy; and
  an alkyl group substituent is unsubstituted acyl, carboxyl, unsubstituted carboxymethyl, unsubstituted methoxycarbonylethyl, unsubstituted benzyloxycarbonylmethyl, unsubstituted pyridylmethyloxycarbonylmethyl or unsubstituted alkoxycarbonyl.

2. A compound according to claim 1 wherein a=0; $R_{15}$ and $R_{16}$ are hydrogen; g is 1, 2, 3 or 4; and b=0.

3. A compound according to claim 1 wherein Z is $R_{21}O_2SHNCO$—, and $R_{21}$ is phenyl, wherein phenyl is optionally substituted by one or more ring system substituents.

4. A comnpound according to claim 1 wherein Z is —$CO_2H$ or —CN.

5. A compound according to claim 1 wherein

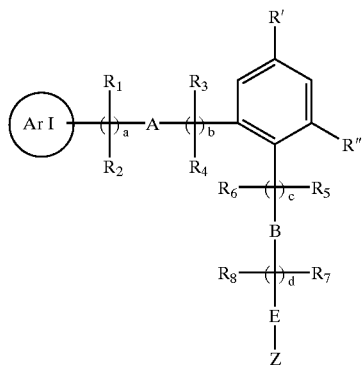

is unsubstituted quinolin-2-yl, 3-substituted quinolin-2-yl, 4-substituted quinolin-2-yl, 6-substituted quinolin-2-yl or 7 substituted quinolin-2-yl; or 2-substituted-oxazol4-yl or 2,5 disubstituted-oxazol4-yl; 4-substituted oxazol-2-yl or 4,5-disubstituted-oxazol-2-yl; wherein an indicated substituent is a ring system substituent.

6. A compound as claimed in claim 1, wherein the compound is 2-methyl-6-[3-(quniolin-2-ylmethoxy)-propoxymethyl]-benzoic acid.

7. A compound as claimed in claim 1, which is of formula

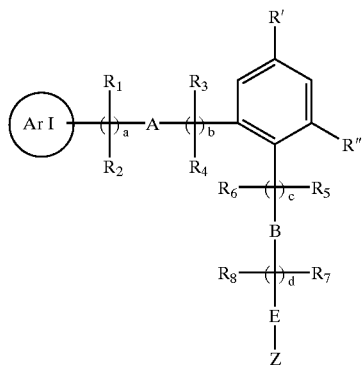

wherein
b=0;
$R_1$, $R_2$, $R_3$, $R_4$ are hydrogen
$R_{15}$, $R_{16}$ are hydrogen;
g=2, 3, 4 or 5;
Z is $R_{21}O_2C$—, $R_{21}OC$—, or $R_{21}O$—;
R' is hydrogen, halo, unsubstituted lower alkyl of 1 to about 4 carbon atoms, unsubstituted alkoxy, unsubstituted aryloxy or unsubstituted aralkyloxy; and
R" is hydrogen, halo, unsubstituted lower alkyl of 1 to about 4 carbon atoms, unsubstituted alkoxy, unsubstituted aralkyloxy or unsubstituted cycloalkylalkyloxy,
or
a pharmaceutically acceptable salt thereof, an N-oxide thereof, a hydrate thereof or a solvate thereof.

8. A compound according to claim 7, wherein Z is —$CO_2H$.

9. A compound according to claim 7, wherein R' is hydrogen; and R" is lower alkyl of 1 to about 4 carbon atoms.

10. A compound according to claim 7, wherein

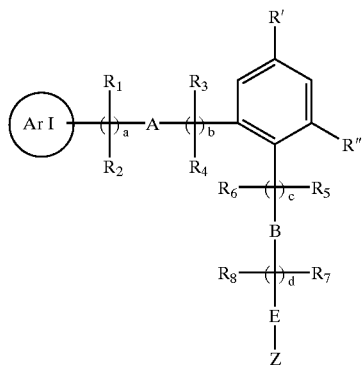

is 2-substituted-oxazol-4-yl, wherein the substituent is a ring system substituent.

11. A compound according to claim 1, wherein the compound is

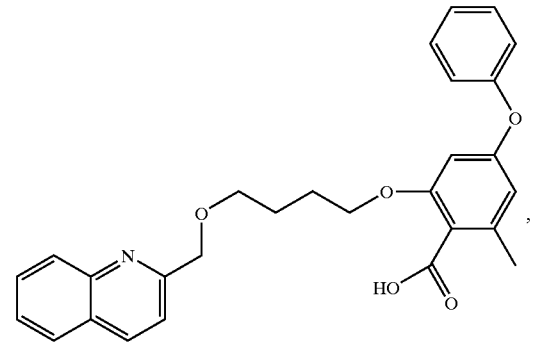

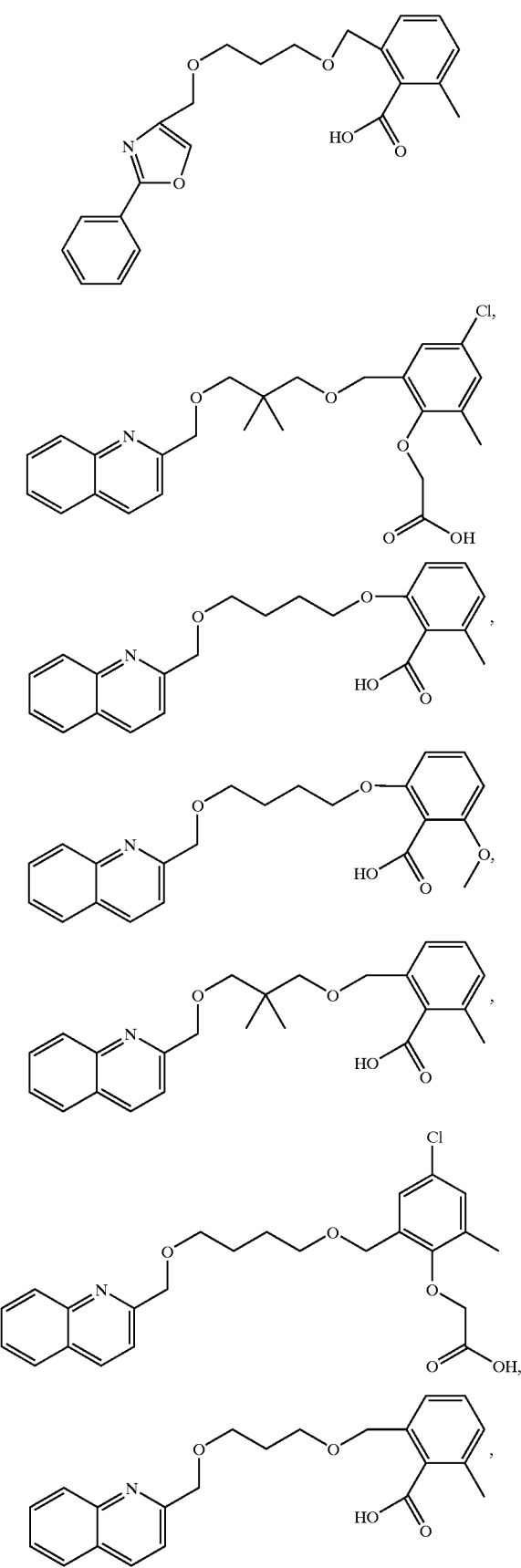
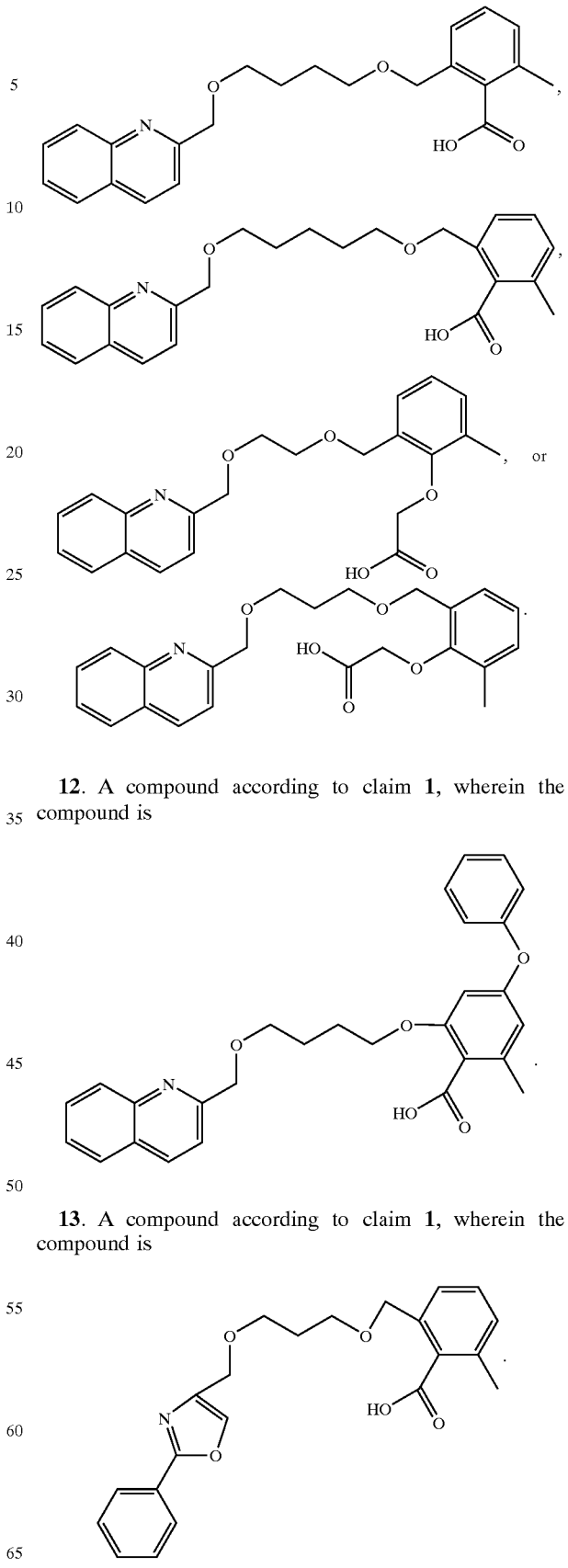
12. A compound according to claim 1, wherein the compound is
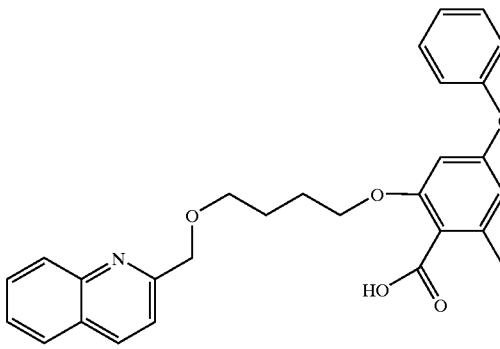
13. A compound according to claim 1, wherein the compound is
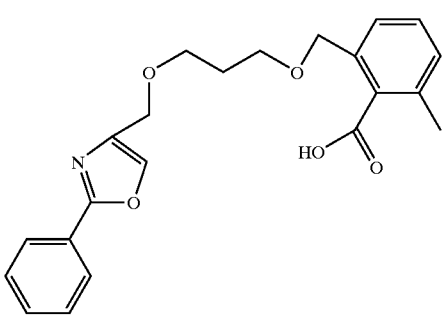

14. A pharmaceutical composition comprising a pharmaceutically acceptable amount of the compound according to claim 1 and a pharmaceutically acceptable carrier.

15. A method of treating a patient suffering from a physiological disorder capable of being modulated by a compound according to claim 1 having PPAR ligand binding activity, comprising administering to the patient a pharmaceutically effective amount of the compound wherein the disorder is associated with a physiological detrimental blood level of insulin, glucose, free fatty acids, or triglycerides.

16. A method of treating a patient suffering from a physiological disorder capable of being modulated by a compound according to claim 1 having PPAR ligand binding activity, comprising administering to the patient a pharmaceutically effective amount of the compound, wherein the physiological disorder is hyperglycemia.

17. The method according to claim 16, wherein the hyperglycemia is diabetes.

18. The method according to claim 16, where in the hyperglycemia is Type II diabetes.

19. A method of treating a patient suffering from a physiological disorder capable of being modulated by a compound according to claim 1 having PPAR ligand binding activity, comprising administering to the patient a pharmaceutically effective amount of the compound, wherein the physiological disorder is hyperinsulinism.

20. A method of treating a patient suffering from a physiological disorder capable of being modulated by a compound according to claim 1 having PPAR ligand binding activity, comprising administering to the patient a pharmaceutically effective amount of the compound, wherein the physiological disorder is insulin resistance.

21. A method of treating a patient suffering from a physiological disorder capable of being modulated by a compound according to claim 1 having PPAR ligand binding activity, comprising administering to the patient a pharmaceutically effective amount of the compound, wherein the physiological disorder is a cardiovascular condition.

22. The method according to claim 21, wherein the cardiovascular condition is atherosclerosis.

23. A method of treating a patient suffering from a physiological disorder capable of being modulated by a compound according to claim 1 having PPAR ligand binding activity, comprising administering to the patient a pharmaceutically effective amount of the compound, wherein the physiological disorder is hyperlipidemia.

24. A method of treating a patient suffering from a physiological disorder capable of being modulated by a compound according to claim 1 having PPAR ligand binding activity, comprising administering to the patient a pharmaceutically effective amount of the compound, wherein the physiological disorder is hypertension.

25. A method of treating a patient suffering from a physiological disorder capable of being modulated by a compound according to claim 1 having PPAR ligand binding activity, comprising administering to the patient a pharmaceutically effective amount of the compound, wherein the physiological disorder is an eating disorder.

* * * * *

UNITED STATES PATENT AND TRADEMARK OFFICE
CERTIFICATE OF CORRECTION

PATENT NO. : 6,635,655 B1 Page 1 of 1
DATED : October 21, 2003
INVENTOR(S) : Zaid Jayyosi et al.

It is certified that error appears in the above-identified patent and that said Letters Patent is hereby corrected as shown below:

Title page,
Item [75], Inventors, "Collegeville, PA" should read -- Flemington, NJ --.

Column 165,
Lines 64-65, "2-substituted-oxazol4-yl or 2,5 disubstituted-oxazol4-yl;" should read -- 2-substituted-oxazol-4-yl or 2,5 disubstituted-oxazol-4-yl; --.

Column 169,
Line 19, "where in" should read -- wherein --.

Signed and Sealed this

Eighteenth Day of May, 2004

JON W. DUDAS
*Acting Director of the United States Patent and Trademark Office*